(12) United States Patent  
Strozier

(10) Patent No.: US 12,109,263 B2  
(45) Date of Patent: Oct. 8, 2024

(54) INTEGRIN AGONISTS OR ACTIVATING COMPOUNDS AND METHODS FOR MAKING AND USING SAME

(71) Applicant: 7 Hills Pharma LLC, Houston, TX (US)

(72) Inventor: Robert W Strozier, Houston, TX (US)

(*) Notice: Subject to any disclaimer, the term of this patent is extended or adjusted under 35 U.S.C. 154(b) by 0 days.

(21) Appl. No.: 17/471,922

(22) Filed: Sep. 10, 2021

(65) Prior Publication Data

US 2022/0118086 A1    Apr. 21, 2022

Related U.S. Application Data

(60) Provisional application No. 63/076,595, filed on Sep. 10, 2020.

(51) Int. Cl.

| | |
|---|---|
| *A61K 39/39* | (2006.01) |
| *A61K 31/16* | (2006.01) |
| *A61K 31/381* | (2006.01) |
| *A61K 31/404* | (2006.01) |
| *A61K 31/44* | (2006.01) |
| *A61K 31/4436* | (2006.01) |
| *A61K 31/4439* | (2006.01) |
| *A61K 39/00* | (2006.01) |
| *A61K 47/60* | (2017.01) |
| *A61P 37/04* | (2006.01) |

(52) U.S. Cl.
CPC ............. *A61K 39/39* (2013.01); *A61K 31/16* (2013.01); *A61K 31/381* (2013.01); *A61K 31/404* (2013.01); *A61K 31/44* (2013.01); *A61K 31/4436* (2013.01); *A61K 31/4439* (2013.01); *A61K 39/0011* (2013.01); *A61K 47/60* (2017.08); *A61P 37/04* (2018.01); *A61K 2039/55511* (2013.01)

(58) Field of Classification Search
CPC ...... A61K 39/39; A61K 31/16; A61K 31/381; A61K 31/404; A61K 31/44; A61K 31/4436; A61K 31/4439; A61K 39/0011; A61K 47/60; A61K 2039/55511; A61P 37/04; A61P 35/00

See application file for complete search history.

(56) References Cited

U.S. PATENT DOCUMENTS

| | | | |
|---|---|---|---|
| 10,709,780 B2* | 7/2020 | Woodside | A61K 39/0011 |
| 10,716,849 B2* | 7/2020 | Woodside | A61P 43/00 |
| 11,311,619 B2* | 4/2022 | Woodside | A61K 31/381 |
| 2016/0339098 A1* | 11/2016 | Woodside | A61K 31/16 |

FOREIGN PATENT DOCUMENTS

WO    WO-2012068251 A2 *    5/2012    ............. A61K 35/12

* cited by examiner

*Primary Examiner* — Robert H Havlin  
*Assistant Examiner* — Lauren Wells  
(74) *Attorney, Agent, or Firm* — Robert W. Strozier

(57) ABSTRACT

Small molecule integrin agonists or integrin activating compounds including at least one di-alkylaryl amine end group and at least one alkyl or alkenoxy linking group including at least one protonatable moiety, wherein the compounds enhance vaccine efficacies, enhance adoptive cell therapy efficacies, enhance immunotherapy efficacies, enhance therapeutic antibody therapy efficacies, enhance checkpoint inhibitor therapy efficacies, enhance effector cell therapy efficacies, and enhanced cell based transplant efficacies and wherein at protonatable moiety either protonate at biological pHs or bears a charge with associated pharmaceutically acceptable counterion making the compound water soluble to improve bioavailability and methods for making and using same.

13 Claims, 27 Drawing Sheets

Ar¹ and Ar² are independently 3-methoxy benzyl, 4-methoxy benzyl, 4-dimethylamino phenyl, or methylthienyl $Ar^1$ and $Ar^2$ are independently 3-methoxy benzyl, 4-methoxy benzyl, 4-dimethylamino phenyl, or methylthienyl

INTEGRIN AGONISTS OR ACTIVATING COMPOUNDS AND METHODS FOR MAKING AND USING SAME

RELATED APPLICATIONS

The present application claims priority to and the benefit of U.S. Provisional Patent Application Ser. No. 63/076,595 filed Sep. 10, 2020.

BACKGROUND OF THE DISCLOSURE

1. Field of the Disclosure

Embodiments of this disclosure relate to integrin agonists or integrin activating compounds including end groups that interact with cell surface integrins and at least one moiety that protonates at biological pHs or bears a charge with associated counterion. The embodiments also relate to methods for making and using such integrin agonist compounds.

In particular, embodiments of this disclosure relate to integrin agonists or integrin activating compounds including end groups that interact with cell surface integrins and at least one moiety that protonates at biological pHs or bears a charge with associated counterion, wherein the integrin agonist compounds: (1) convert surface integrins from an inactive state to an active state; (2) enhance integrin-ligand interactions; (3) enhance homing, migration, infiltration, and grafting of stem cells such as hematopoietic stem cells (HSCs); (4) enhance vaccine efficacies; (5) enhance radiation-induced antigen immune responses; (6) enhance immune responses to antigens; (7) enhance antigen presentation, B cell priming, and nascent T cell activation; (8) enhance T-cells homing, migration, and infiltration into solid tumors, and cancer cell elimination in the solid tumors; (9) enhance adoptive cell therapies; (10) have single molecular anti-tumor activity; (11) enhance checkpoint inhibitor activity; (12) enhance therapeutic antibody activity; and/or (13) enhance the efficacy of other treatments involving integrins. The methods including administering to a subject or host an effective amount of one or more integrin agonist compounds, administering or co-administering one or more integrin agonist compounds and treated and/or untreated cells, administering or co-administering one or more integrin agonist compounds and one or more checkpoint inhibitors, administering or co-administering one or more integrin agonist compounds and one or more therapeutic antibodies, administering or co-administering one or more integrin agonist compounds and one or more antigens, irradiating and co-administering one or more integrin agonist compounds, and/or combinations thereof. The methods of making integrin agonist compounds include contacting one or more precursors under appropriate conditions to prepare each desired class of integrin agonist compounds.

2. Description of the Related Art

There is a major need in the art for compounds to enhance vaccine efficacies, to enhance adoptive cell therapies, to enhance antitumor therapies, to enhance therapeutic checkpoint inhibitor therapies, to enhance therapeutic antibody therapies, or any other therapeutic therapy in which integrins are involved and for which integrin agonists are effective in promoting integrin-ligand interactions, cell-cell adhesion, cell homing, migration, and infiltration, and integrin mediated therapeutic activity. Additional information on integrin activating compounds, their uses, syntheses, and testing may be found in U.S. Pat. Nos. 10,287,264; 10,071,980; 10,035,784; 9,512,109; 10,709,781; 10,716,849; 10,709,780; 10,342,866; and 10,342,866, and in United States Patent Application Nos.: 20150250883; 20160000755; 20160000755; and 20200054600, incorporated by reference by operation of the closing paragraph.

SUMMARY OF THE DISCLOSURE

Embodiments of this disclosure provide small molecule integrin agonists or integrin activating compounds designed to interact with integrins on the surface of cells binding to the integrin subunits, which is believed to result in a change in a conformation of the integrin from a compact inactive state to an elongated or extended active state. In the active state, the integrin is configured to interact efficiently with a conjugate ligand of another cell. As the agonists are not tightly bound to the integrins, they are believed to be released upon ligand binding. Thus, the agonists operate to transition an integrin from an inactive state to an active state via a displaceable binding process. In certain embodiments, the small molecule integrin agonists have a molecular weight below about 2,000 grams per mole. In other embodiments, the small molecule integrin agonists have a molecular weight below about 1,500 grams per mole. In other embodiments, the small molecule integrin agonists have a molecular weight below about 1,000 grams per mole.

Embodiments of this disclosure provide small molecule integrin agonists or integrin activating compounds including one or more chemical compounds of the general Formula (I):

$$Q^1\text{-}R^a\text{---}Z\text{---}R^b\text{-}Q^2 \tag{I}$$

wherein:
the $Q^1$ and $Q^2$ groups may independently be an $R^1R^2N$— group, an $R^1R^2NC(\!=\!O)$— group, an $R^1R^2NC(\!=\!O)N(R^3)$— group, an $R^1R^2NC(\!=\!O)O$— group, or an $R^1R^2NSO_2$— group,
the $R^1$ and $R^2$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof, and
the $R^3$ group may be a hydrocarbyl group or a heterohydrocarbyl group;
the $R^a$ and $R^b$ groups may independently be a hydrocarbenyl linking group, wherein one or more carbon atoms may be replaced by oxygen atoms, e.g., an alkyleneoxide linking group such as a methlyeneoxide containing linking group or an ethyleneoxide containing linking group; and
the Z group may be a hydrocarbenyl linking group or a heterohydrocarbenyl linking group and includes one or more protonatable moieties.

In certain embodiments, the one or more protonatable moieties become protonated at biological pHs and/or are protonated and include pharmaceutically acceptable counterions.

In certain embodiments, the $R^1$ and $R^2$ groups are selected from the groups consisting of an 2-thienylalkyl group, an 3-alkoxybenzyl group, an 4-alkoxybenzyl group, an pyridin-2-ylalkyl, pyridin-4-ylalkyl group, an pyridin-4-ylalkyl group, an 4-dialkylaminobenzyl group, an 3-dialkylaminobenzyl group, and mixture or combinations thereof, where the alkyl or alkoxy groups independently include 1 to 6 carbon atoms. In other embodiments, the $R^1$ and $R^2$ groups are selected from the groups consisting of an 2-thienylmethyl group, an 2-(2-thienyl)ethyl group, an 3-methoxybenzyl group, an 4-methoxybenzyl group, an pyridin-2-ylmethyl group, an pyridin-4-ylmethyl group, an pyridin-4-ylmethyl group, an 4-dimethylaminobenzyl group, an 3-dimethylaminobenzyl, carbazole, 3,6-dimethoxycarbazole, and mixture or combinations thereof.

In certain embodiments, the $R^a$ and $R^b$ groups may independently be an —O($R^cO)_n$—, —$R^dO(R^cO)_n$— group, an —O($R^cO)_nR^e$— group, an —$R^dO(R^cO)_nR^e$— group, or an $R^{aa}$ group, wherein $R^c$, $R^d$, $R^e$, and $R^{aa}$ may independently be hydrocarbyl linking groups, and each n is independently an integer having a value of 1 to 6. In other embodiments, the $R^a$ and $R^b$ groups may independently be —O(($CH_2)_mO)_n$—, where m is an integer having a value of 1 to 3 and n an integer having a value or 1 to 6. In other embodiments, the $R^a$ and $R^b$ groups may independently be an —O(($CH_2)_{m1}1)((CH_2)_{m2}O)_n(CH_2)_{m3}$— group, where m1, m2 and m3 are integers having values of 1 to 3 and n an integer having a value of 1 to 8. In other embodiments, the $R^a$ and $R^b$ groups may independently be an —(($CH_2)_{m1})((CH_2)_{m2}O)_n(CH_2)_{m3}$— group or —($CH_2)_{m1}$—, where m1, m2 and m3 are integers having values of 1 to 3 and n an integer having a value of 1 to 6. Illustrative examples include, without limitation, an —O($CH_2)_n$— group, an —O($CH_2CH_2O)_n$— group, an —O($CH_2CH_2CH_2O)_n$— group, an —$CH_2O(CH_2O)_n$— group, an —O($CH_2O)_nCH_2$— group, an —$CH_2O(CH_2O)_nCH_2$— group, an —$CH_2O(CH_2CH_2O)_n$— group, an —O($CH_2CH_2O)_nCH_2$— group, an —$CH_2O(CH_2CH_2O)_nCH_2$— group, an —$CH_2CH_2O(CH_2CH_2O)_n$— group, an —O($CH_2CH_2O)_nCH_2CH_2$— group, an —$CH_2CH_2O(CH_2CH_2O)_nCH_2CH_2$— group, or higher analogs, or —($CH_2)_n$— group, wherein n is an integer having a value between 1 and 6. It should be recognized that the choice of $R^a$ and $R^b$ will depend on the choice of $Q^1$ and $Q^2$ so that the agonists do not include certain moieties such as an —C—N—O— moiety, an —O—O— moiety, or other linkages that are unstable or breakdown into undesirable by products.

In certain embodiments, the Z group may be an —$R^fN(R^4)R^g$— group, an —$R^fN^+(R^4R^5A^-)R^g$— group, an —$R^fC(R^6)(N(R^4R^5))R^g$— group, an —$R^fC(R^6)(N(R^4R^5R^7A^-))R^g$— group, an —$R^fC(R^6)(R^hN(R^4R^5))R^g$— group, or an —$R^fC(R^6)(R^hN(R^4R^5R^7A^-))R^g$— group, wherein (a) the $R^4$, $R^5$, $R^6$, and $R^1$ groups are independently hydrocarbyl groups or heterohydrocarbyl groups, (b) the $R^f$ and $R^g$ groups are independently $C_1$-$C_3$ alkenyl linking group, and (c) the $A^-$ groups are independently counterions. In other embodiments, the Z group comprises an -$G^1$-J-$G^2$-group, wherein (a) the J group comprises an arylene group or a heteroarylene group; (b) the $G^1$ and $G^2$ groups are independently an —$R^f$—($R^8$)N— group, an —$R^f$—($R^8$)N—$R^g$— group, an —$R^f$—O— group, an —$R^f$—O—$R^g$— group, an —C(=O)— group, an —C(=O)—$R^g$— group, an —C(=O)N($R^8$)— group, an —C(=O)N($R^8$)—$R^g$— group, an —C(=O)O— group, an —C(=O)O—$R^g$— group, an —$R^f$—($R^8$)NC(=O)— group, an —$R^f$—($R^8$)NC(=O)—$R^g$— group, an —$R^f$—($R^8$)NC(=O)N($R^8$)— group, an —$R^f$—($R^8$)NC(=O)N($R^8$)—$R^g$— group, an —$R^f$—($R^8$)NC(=O)O— group, an —$R^f$—($R^8$)NC(=O)O—$R^g$— group, an —$R^f$—OC(=O)— group, an —$R^f$—OC(=O)—$R^g$— group, an —$R^f$—OC(=O)N($R^8$)— group, an —$R^f$—OC(=O)N($R^8$)—$R^g$— group, an —$R^f$—OC(=O)O— group, or an —$R^f$OC(=O)O—$R^g$— group; (c) the $R^f$ and $R^g$ groups are independently $C_1$-$C_3$ alkenyl linking group, (d) the $R^8$ groups are independently a hydrogen atom or a $C_1$-$C_8$ hydrocarbyl group, and (e) the $A^-$ groups independently comprise counterions.

In certain embodiments, the Z group may include a hydrocarbyl or a heterohydrocarbyl linking group including any of the hydrocarbyl or a heterohydrocarbyl linking group disclosed herein.

In other embodiments, the Z group may include a hydrocarbyl or a heterohydrocarbyl group, wherein the hydrocarbyl or a heterohydrocarbyl group includes one or more moieties that protonate at biological pHs and/or bear a charge in association with an acceptable counterion. Illustrative examples of Z groups comprising a hydrocarbyl group or a heterohydrocarbyl group including at least one moiety that protonates at biological pHs and/or bears a charge in association with an acceptable counterion include, without limitation, groups derived from pyrrole, pyrrole-2,3-dicarboxylic acid, pyridine, pyridine-2,3-dicarboxylic acid, pyridine-2,4-dicarboxylic acid, pyridine-2,5-dicarboxylic acid, pyridine-3,4-dicarboxylic acid, pyridine-2,4-dicarboxylic acid, pyridine-2,5-dicarboxylic acid, pyridine-2,6-dicarboxylic acid, pyridine-3,4-dicarboxylic acid, pyridine-3,5-dicarboxylic acid, or other heterohydrocarbyl groups. In other embodiments, the Z group may be derived from a hydrocarbyl group include, without limitation, 1-amino-benzene-2,4-dicarboxylic acid, 1-amino-benzene-2,5-dicarboxylic acid, 1-amino-benzene-2,6-dicarboxylic acid, 1-amino-benzene-3,4-dicarboxylic acid, 1-amino-benzene-3,5-dicarboxylic acid, 1,2,3-trihydroxybenzene, 1,2,4-trihydroxybenzene, 1,2,5-trihydroxybenzene, 1,3,4-trihydroxybenzene, 1,3,5-trihydroxybenzene, 1-amino-2,3-dihydroxybenzene, 1-amino-2,4-dihydroxybenzene, 1-amino-2,5-dihydroxybenzene, 1-amino-3,4-dihydroxybenzene, 1-amino-3,5-dihydroxybenzene, orthoformic acid, glycerol, 2-amino-1,3-dihydroxypropane, diethanolamine, N-methyldiethanolamine, dipropanolamine, N-methyldipropanolamine, diisopropanolamine, N-methyldiisopropanolamine, higher dialkanolamines, higher N-methyl dialkanolamines, or other hydrocarbyl groups.

In certain embodiments, when present and not a hydrogen atom, the $R^1$, $R^2$, $R^3$, $R^4$, $R^5$, $R^6$, $R^7$, and $R^8$ groups may independently be either unsubstituted or substituted with one or more substituents selected from the group consisting of an alkyl group, an aryl group, an aralkyl group, a cycloalkyl group, a cycloalkylalkyl group, a heterocyclyl group, a heterocyclylalkyl group, a heterocyclylaryl group, a hydroxy group, an alkoxy group, an azido group, a haloalkoxy group, a hydroxyalkyl group, an aryloxy group, a hydroxyaryl group, an alkoxyaryl group, a halogen atom, a haloalkyl group, a haloaryl group, an amino group, an alkylamino group, a dialkylamino group, an arylamino group, a diarylamino group, an —NHC(=O)(alkyl) group, an —NHC(=O)(aryl) group, an —NHC(=O)(aralkyl) group, an —NHC(=O)(haloalkyl) group, an —$NHSO_2$(alkyl) group, an —$NHSO_2$(aryl) group, an —$NHSO_2$(aralkyl) group, an alkoxycarbonyl group, an alkoxycarbonylalkyl group, an —OC(=O)(alkylamino) group, and an —OC(=O)(dialkylamino) group.

Embodiments of the present disclosure provide methods including administering one or more small molecule integrin agonists or integrin activating compounds to an animal, mammal or human in an amount sufficient to reduce solid tumor growth, to enhance effector cell therapies, to enhance antibody therapies, to enhance check point inhibitor therapies, to enhance efficacies of vaccines, to increase immune responses to antigens, to increase immune responses due to in situ generated antigens, to increase immune responses due to radiation generated antigens or inflammation, to enhance radiation anti-cancer therapies, and/or to enhance the efficacies of any other therapy that involves integrin activation, where the integrin participate in the therapy.

In certain embodiments, the integrins targeted by these compounds include, but are not limited to, α4β1, α4β7, α5β1, αLβ2 and/or αVβ3. In various embodiments, the ligands that bind to the active state of the integrins include, but are not limited to, VCAM-1, fibronectin, MAdCAM-1, ICAM-1, ICAM-2, and/or vitronectin.

BRIEF DESCRIPTION OF THE DRAWINGS OF THE DISCLOSURE

The disclosure can be better understood with reference to the following detailed description together with the appended illustrative drawings in which like elements are numbered the same:

Figure 8A:
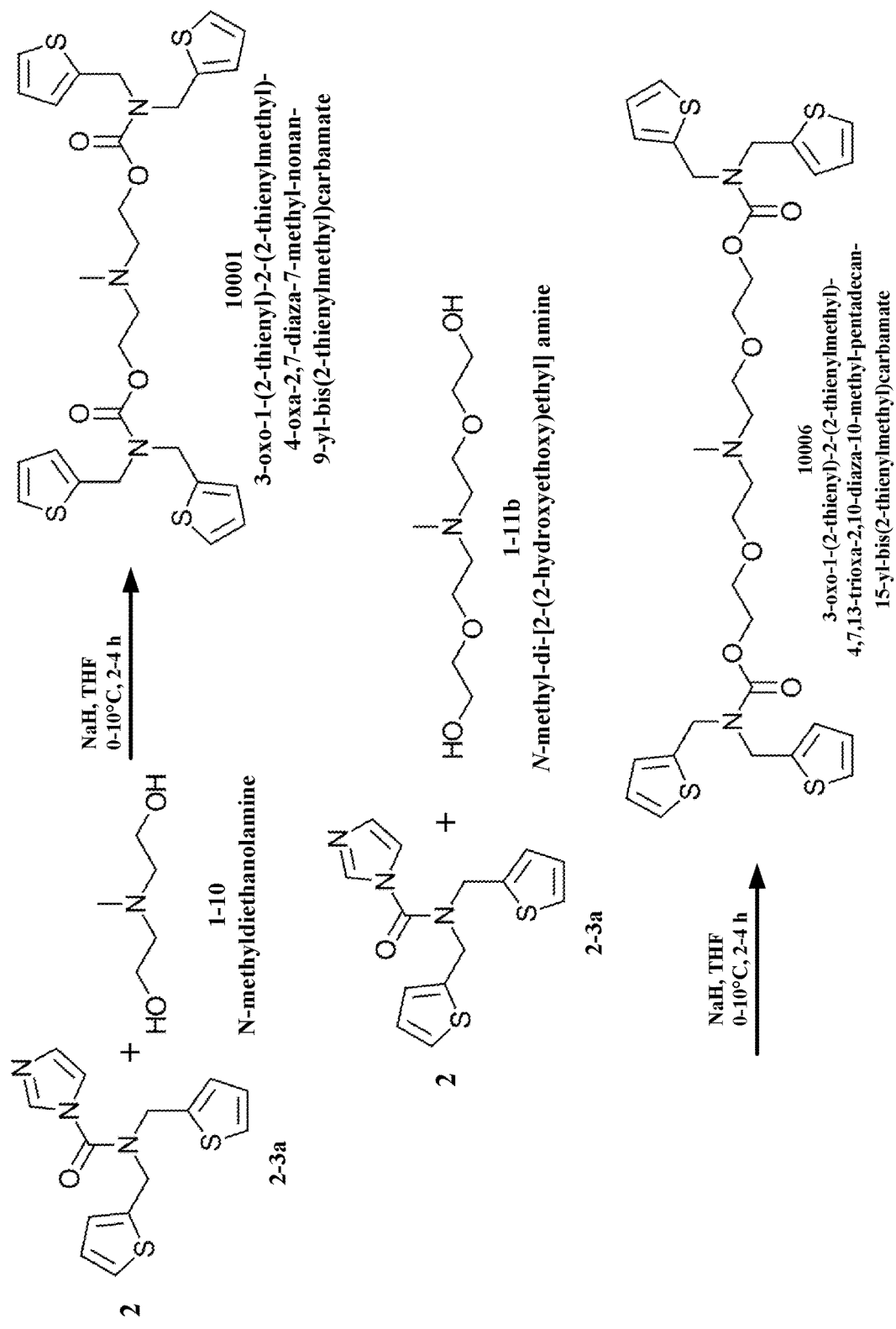
Figure 8B:
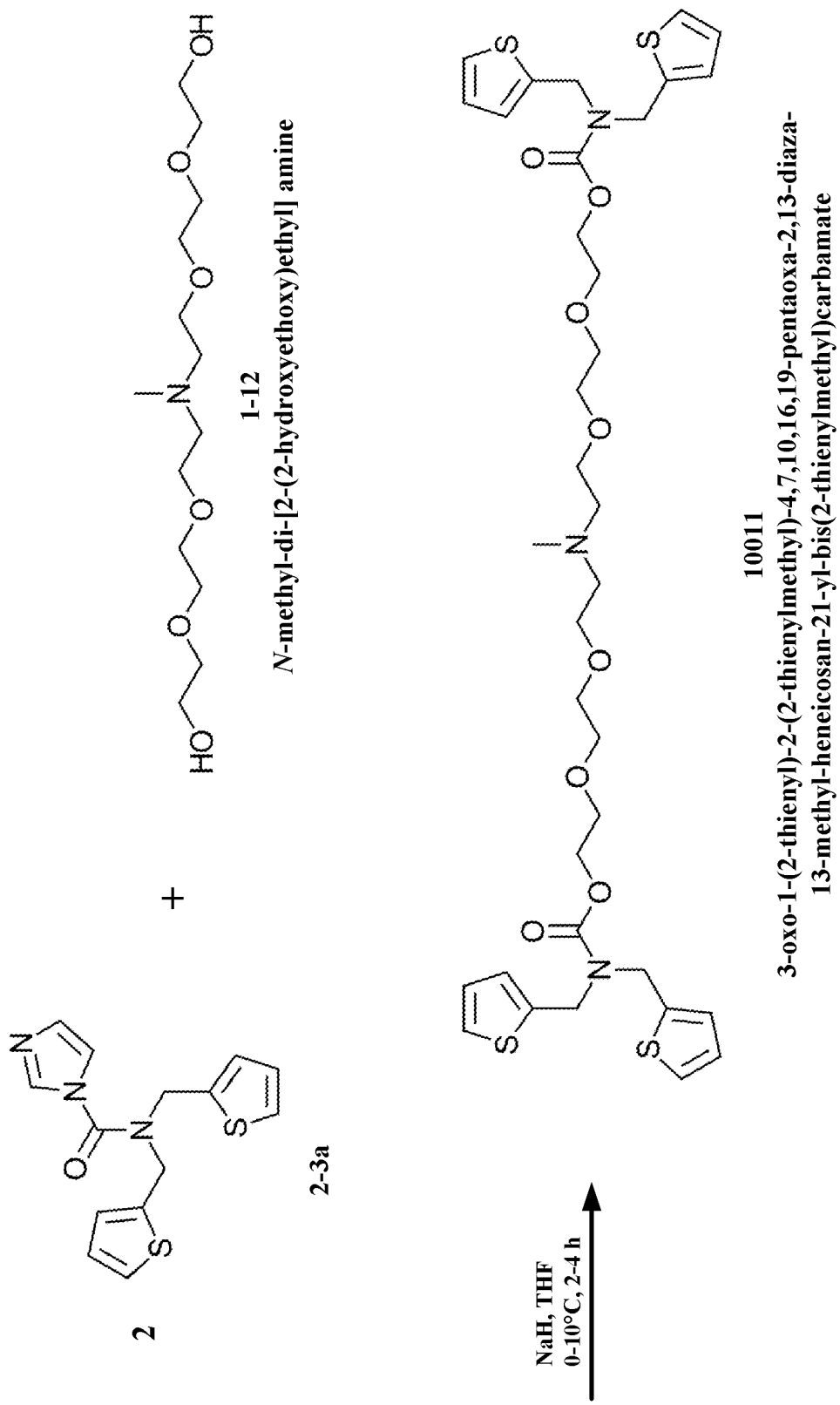

FIGS. 8A&B depicts the syntheses of integrin activators 10001, 10006, and 10011.

Figure 9A:
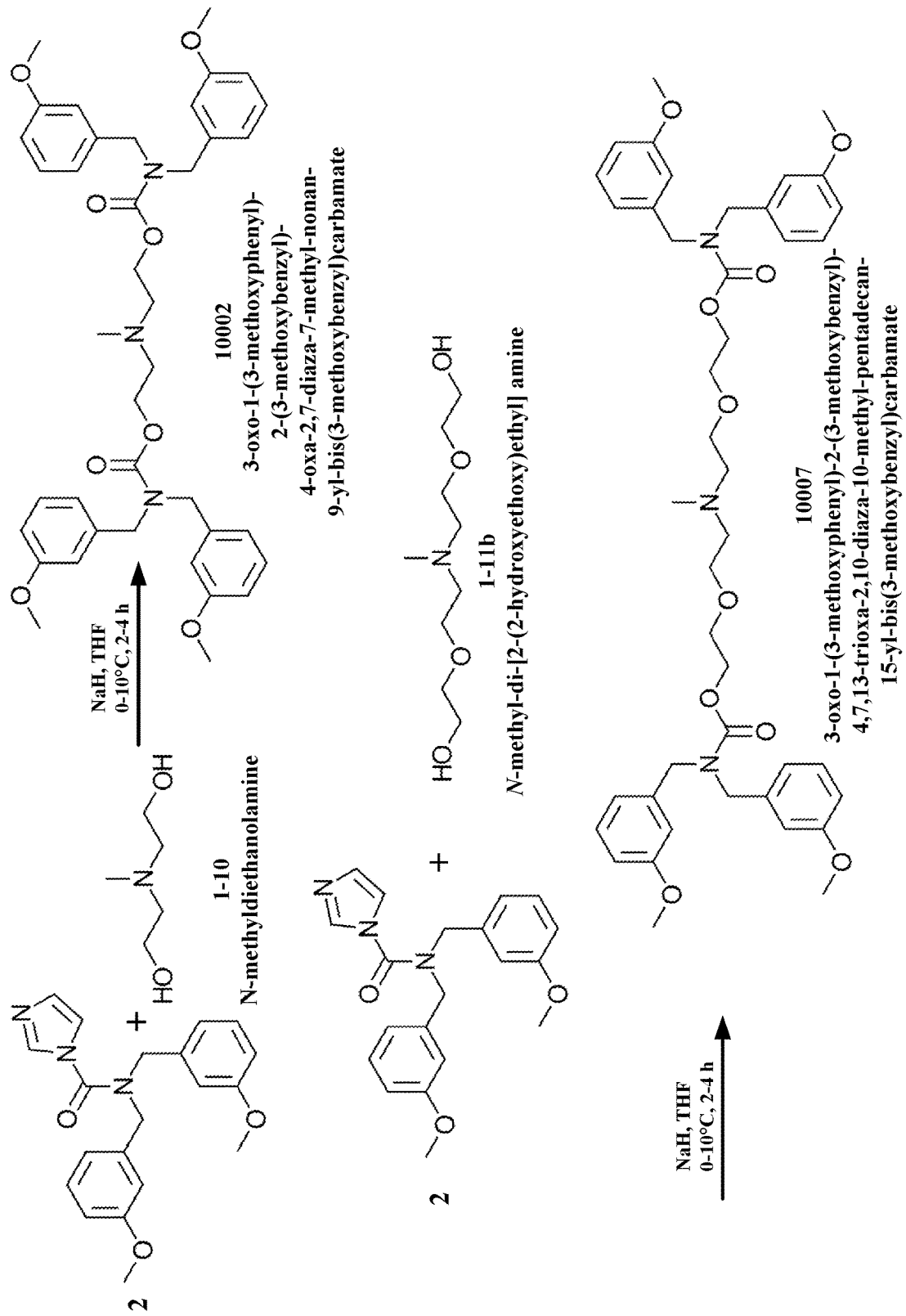
Figure 9B:
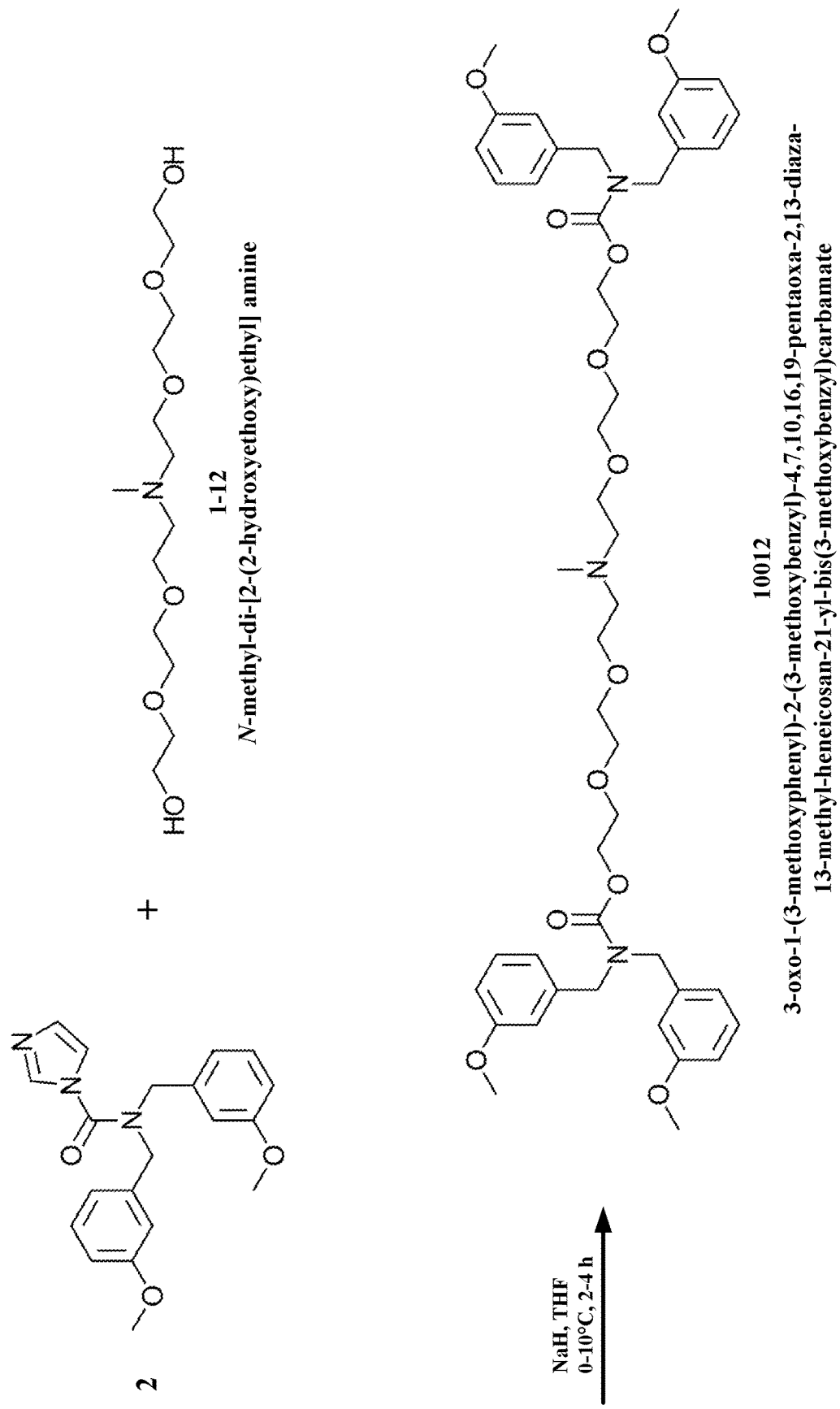

FIGS. 9A&B depicts the syntheses of integrin activators 10002, 10007, and 10012.

Figure 10A:
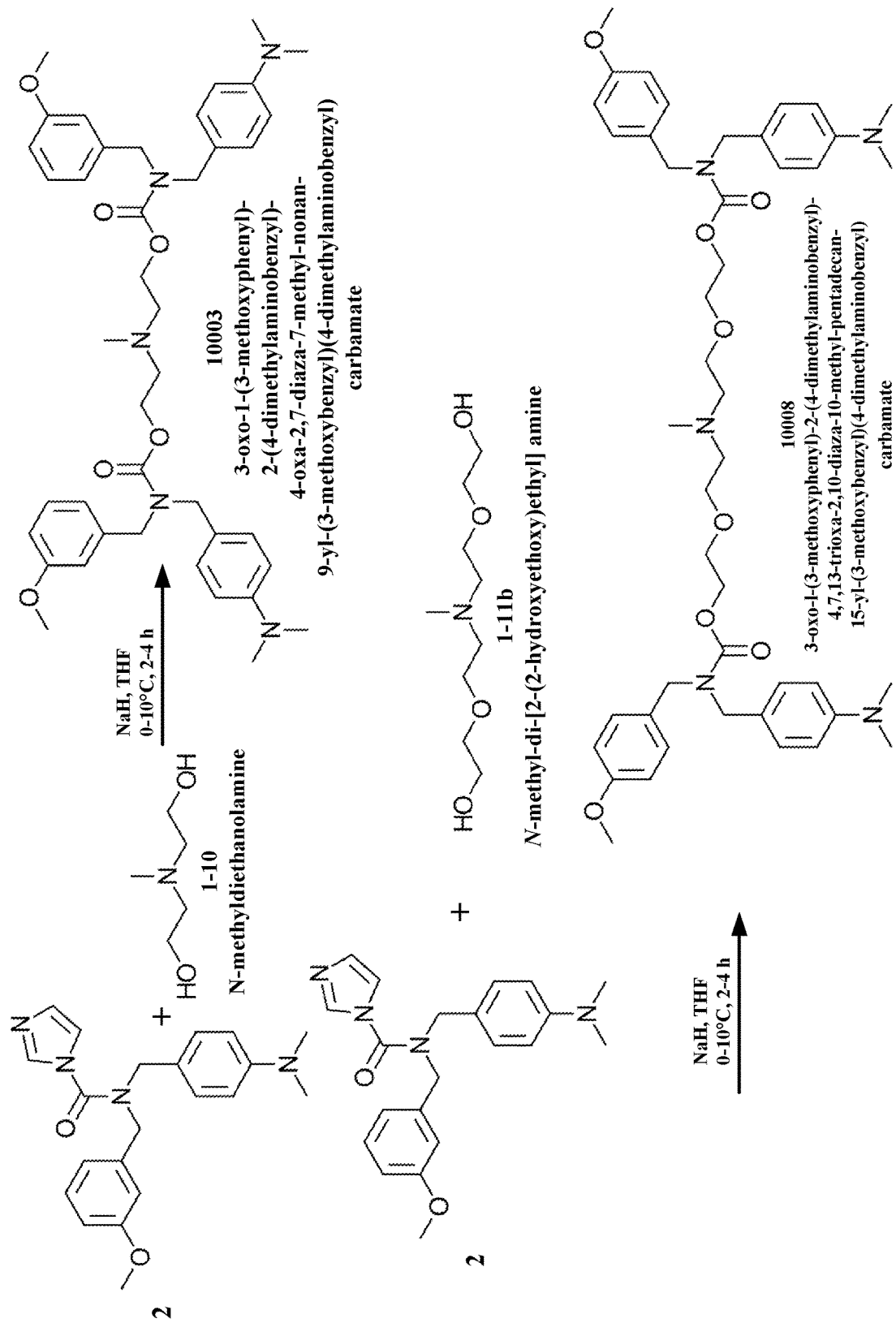
Figure 10B:
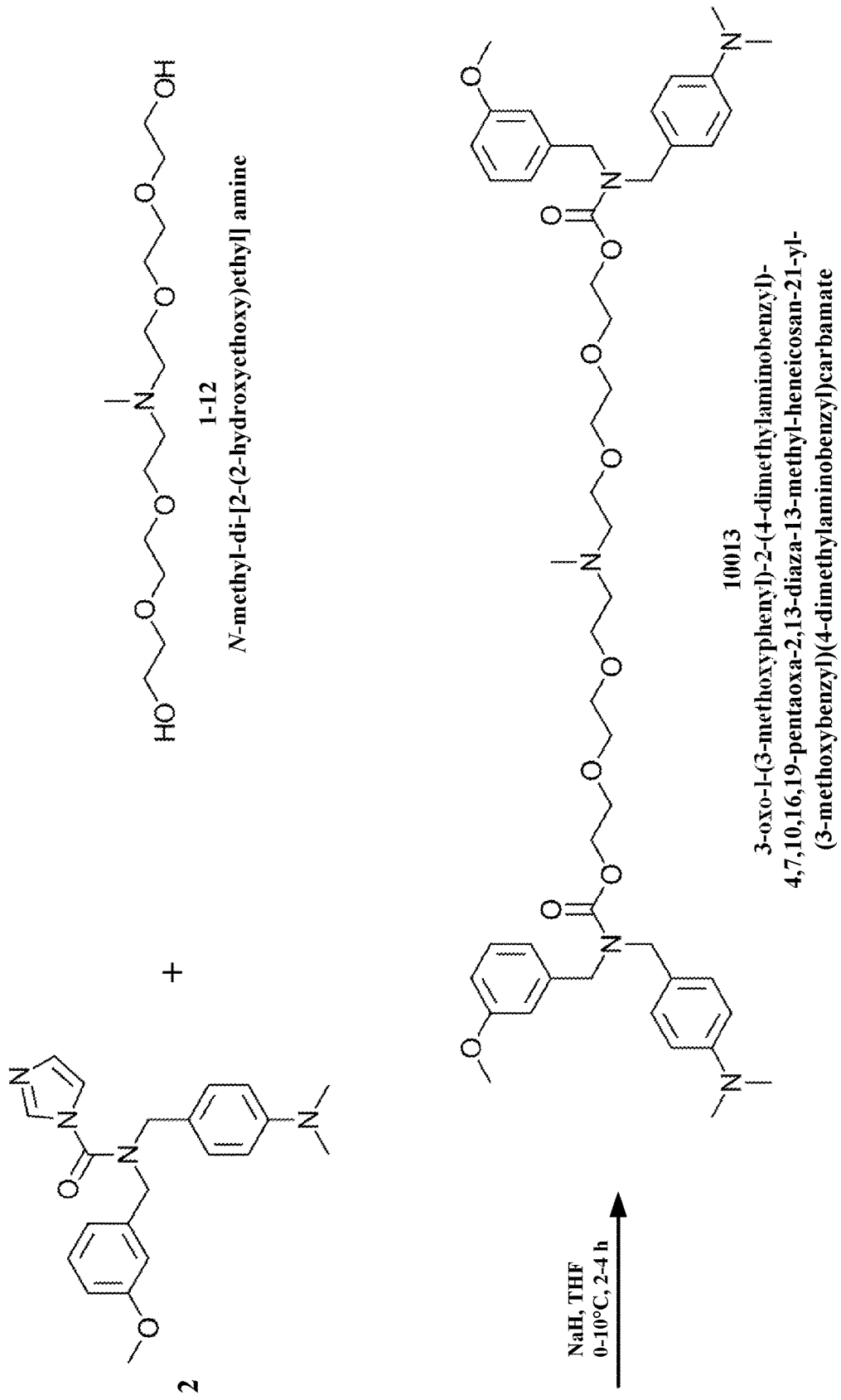

FIGS. 10A&B depicts the syntheses of integrin activators 10003, 10008, and 10013.

Figure 11A:
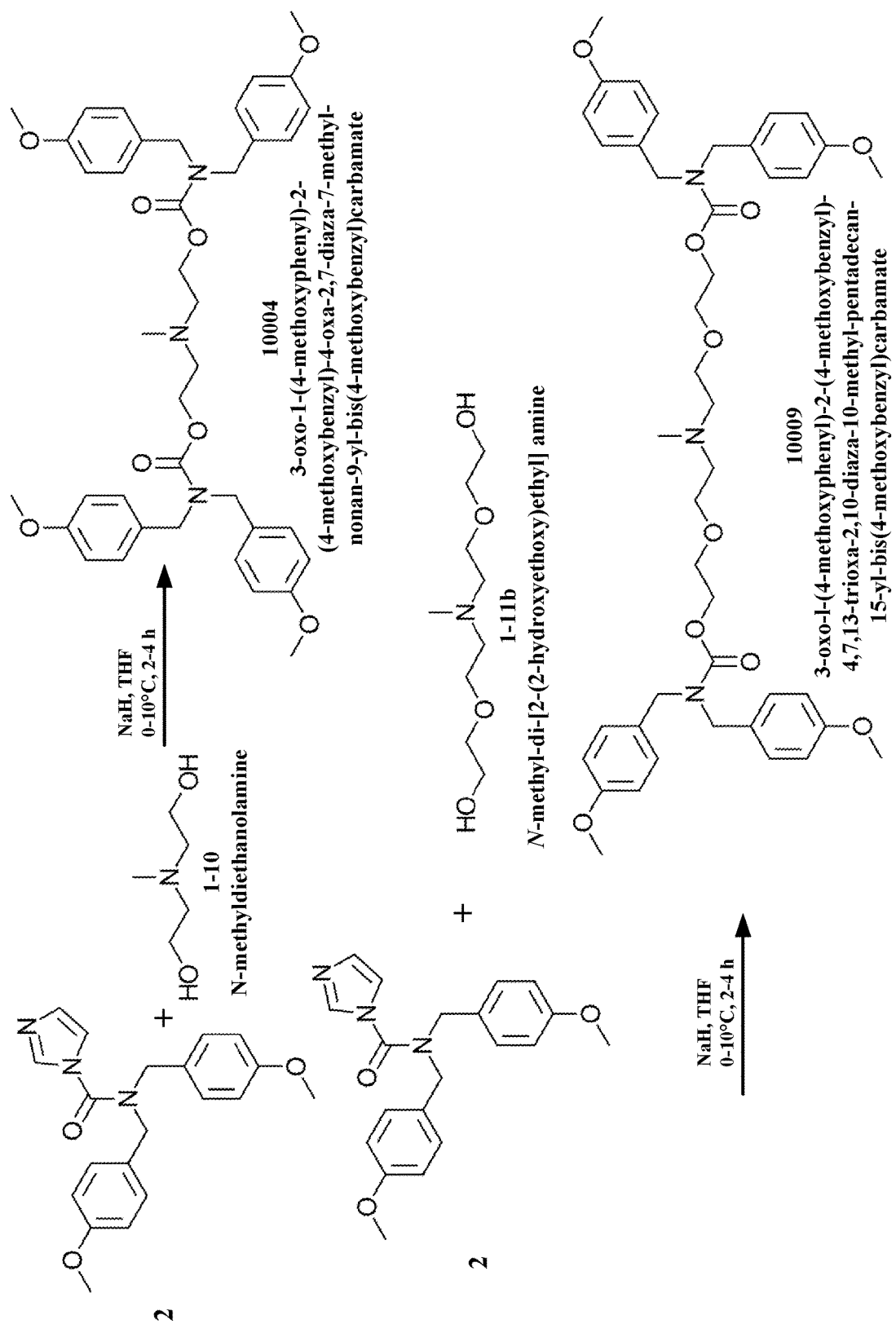
Figure 11B:
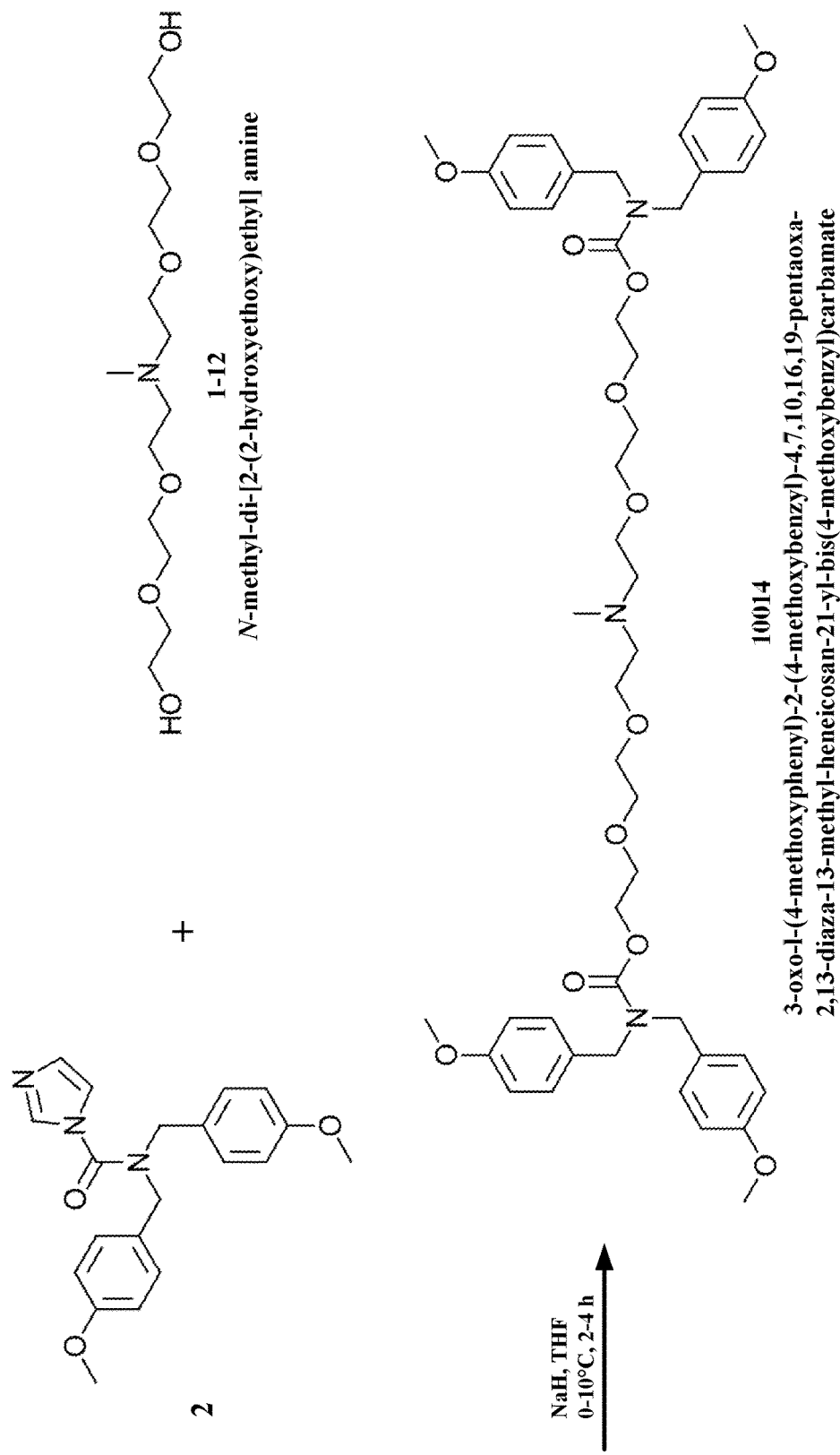

FIGS. 11A&B depicts the syntheses of integrin activators 10004, 10009, and 10014.

Figure 12A:
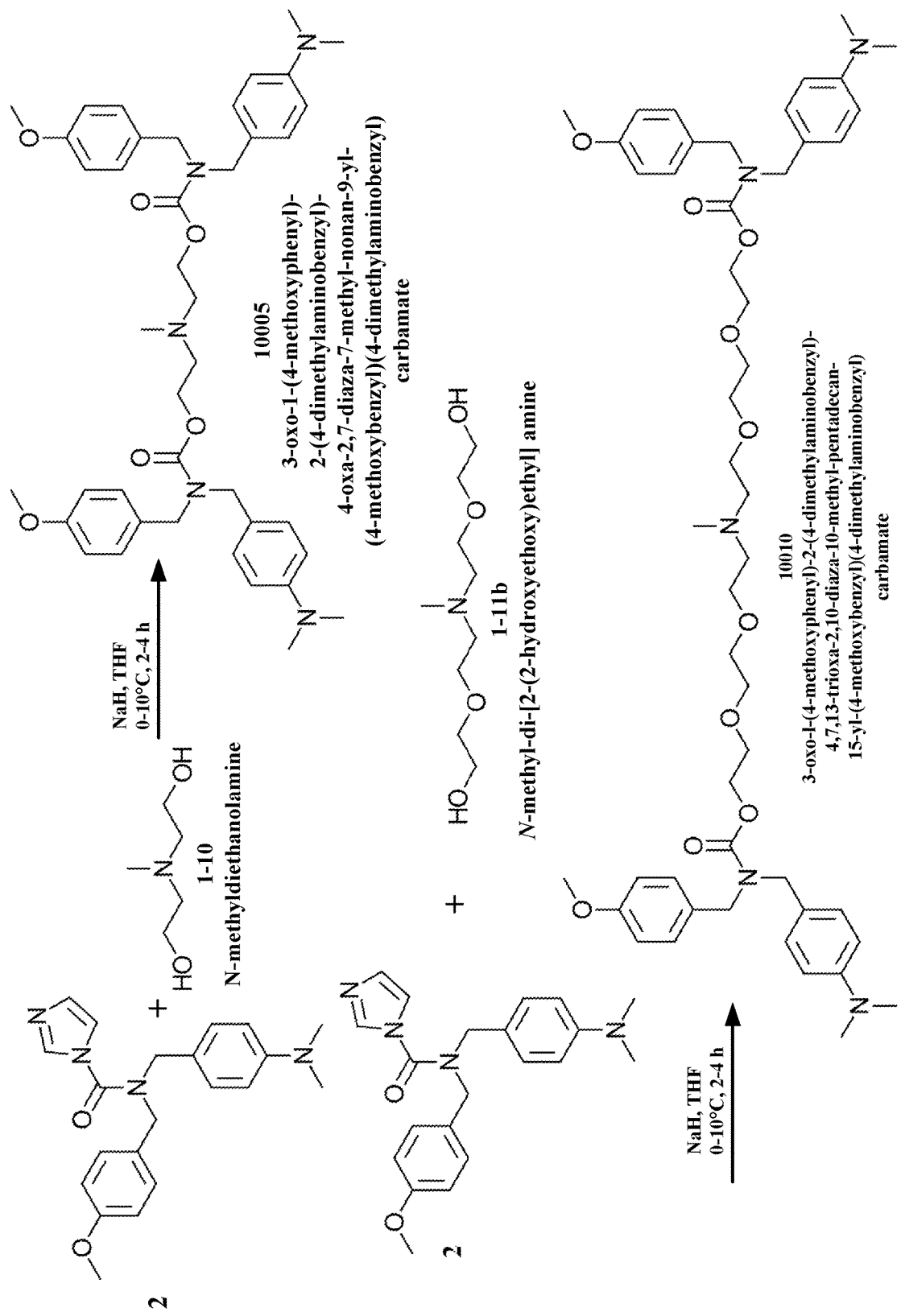
Figure 12B:
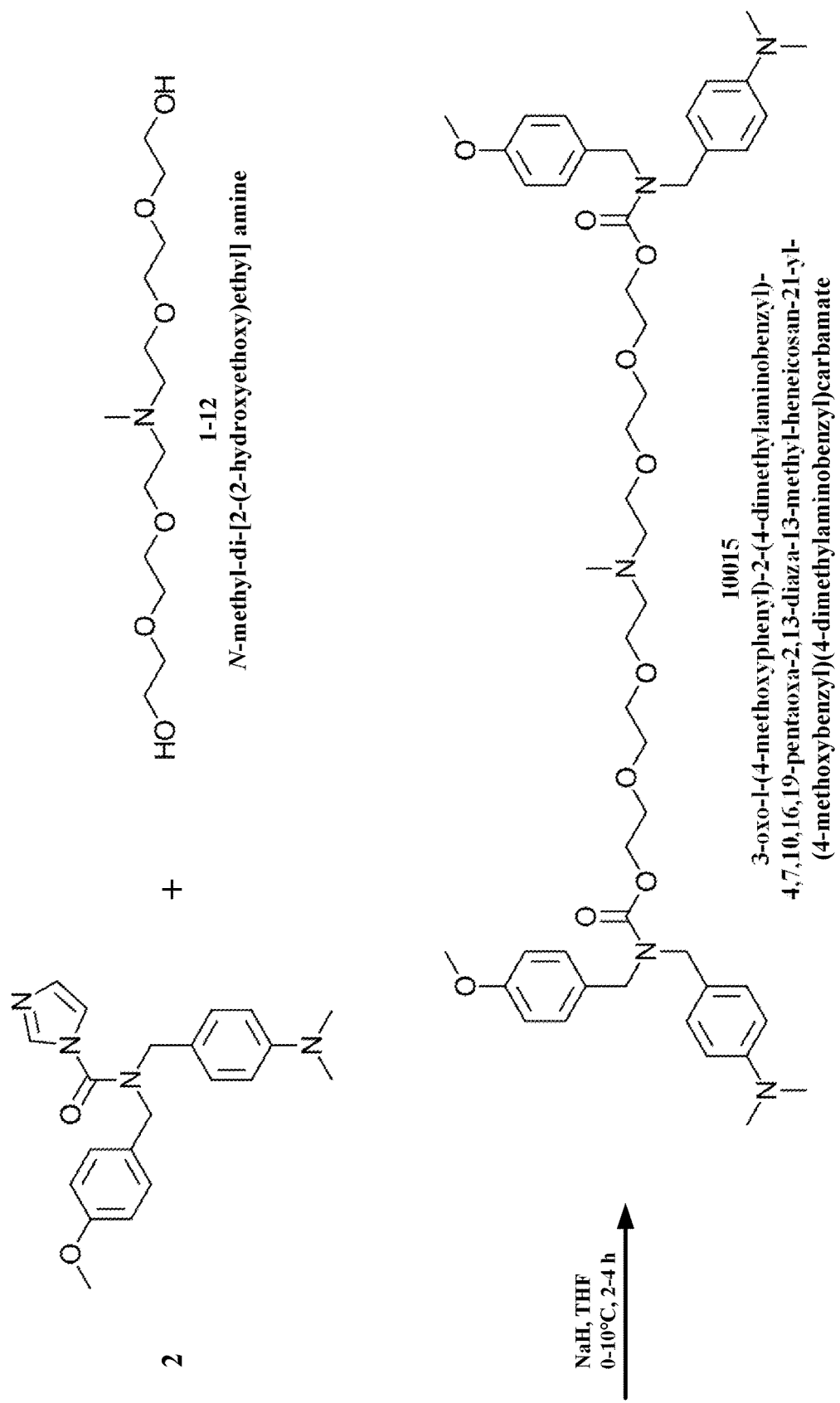

FIGS. 12A&B depicts the syntheses of integrin activators 10005, 10010, and 10015.

Figure 13A:
Figure 13B:
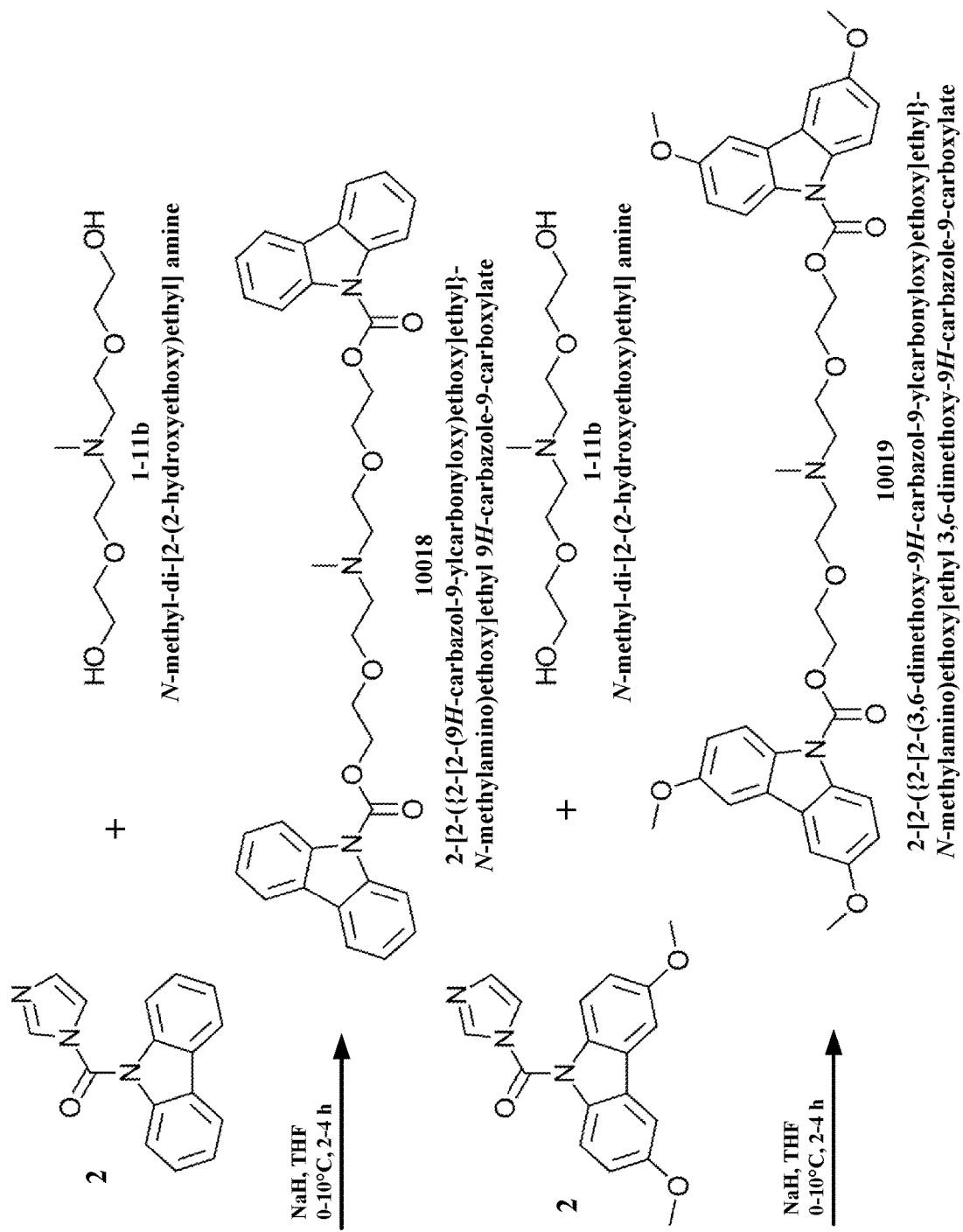
Figure 13C:
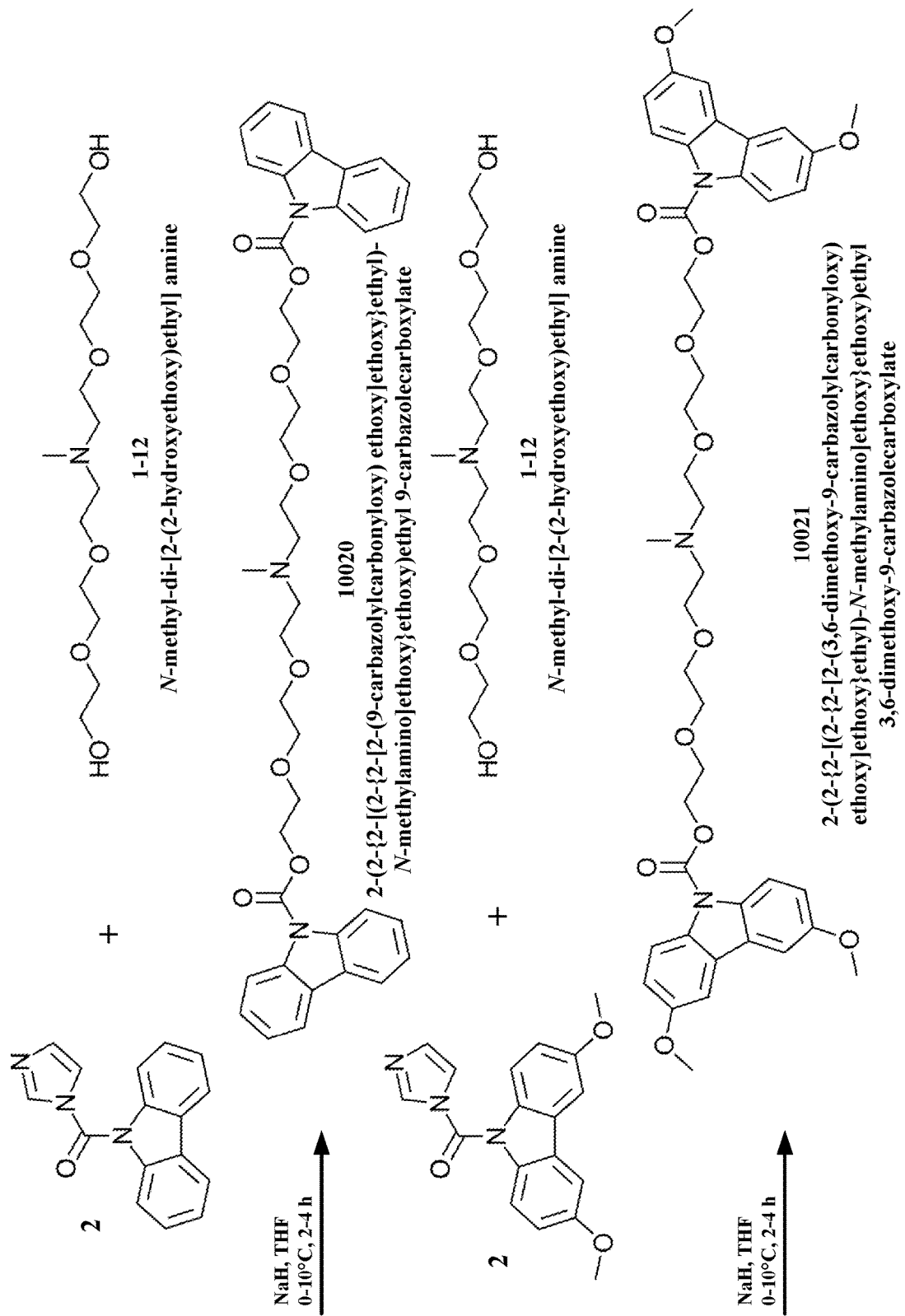

FIG. 13A-C depicts the syntheses of integrin activators 10016, 10017, 10018, 10019, 10020, and 10021.

Figure 14:
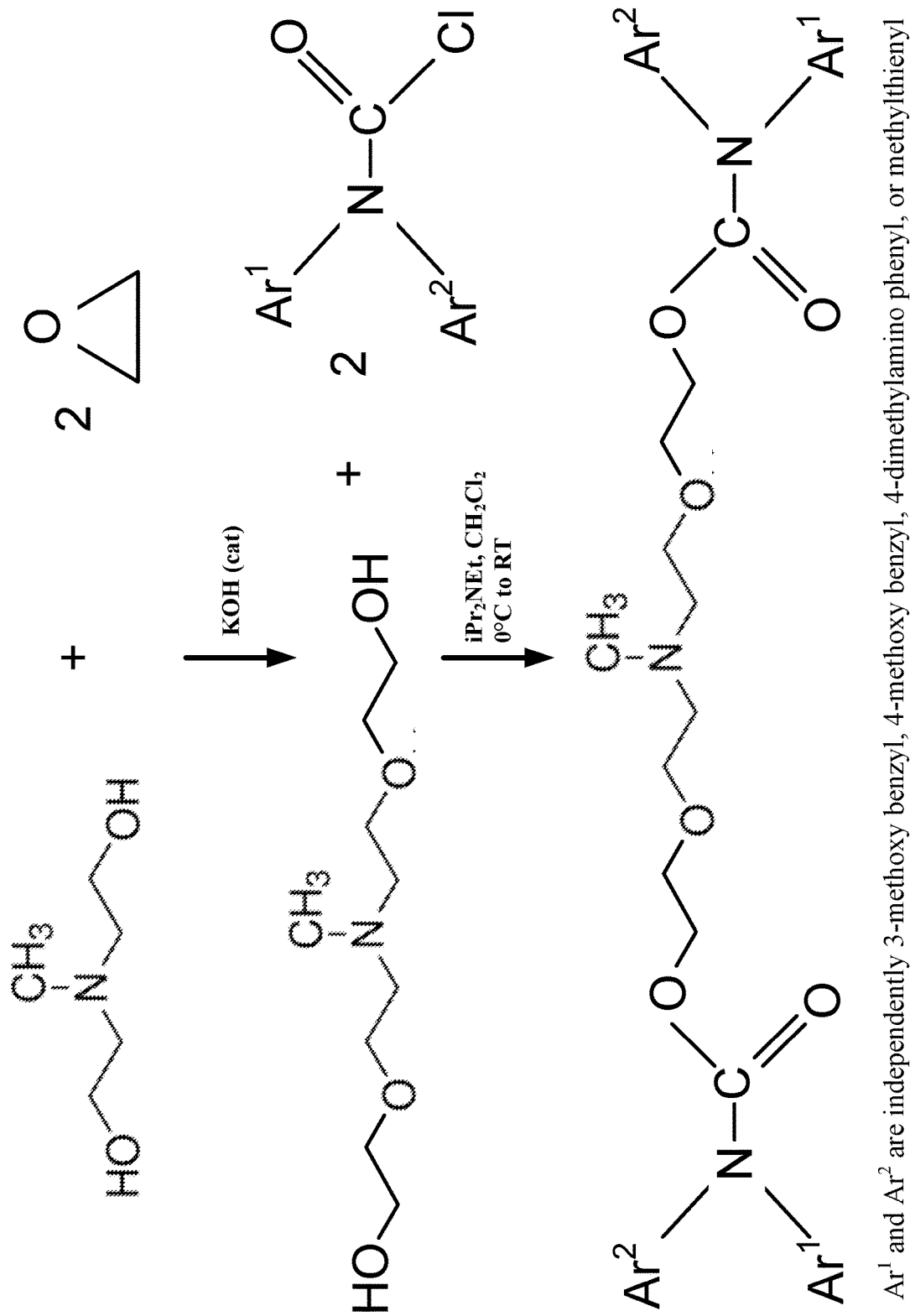

FIG. 14 depicts a general synthetic scheme for preparing ethoxylated integrin activating compounds of Formula (II).

Figure 15:
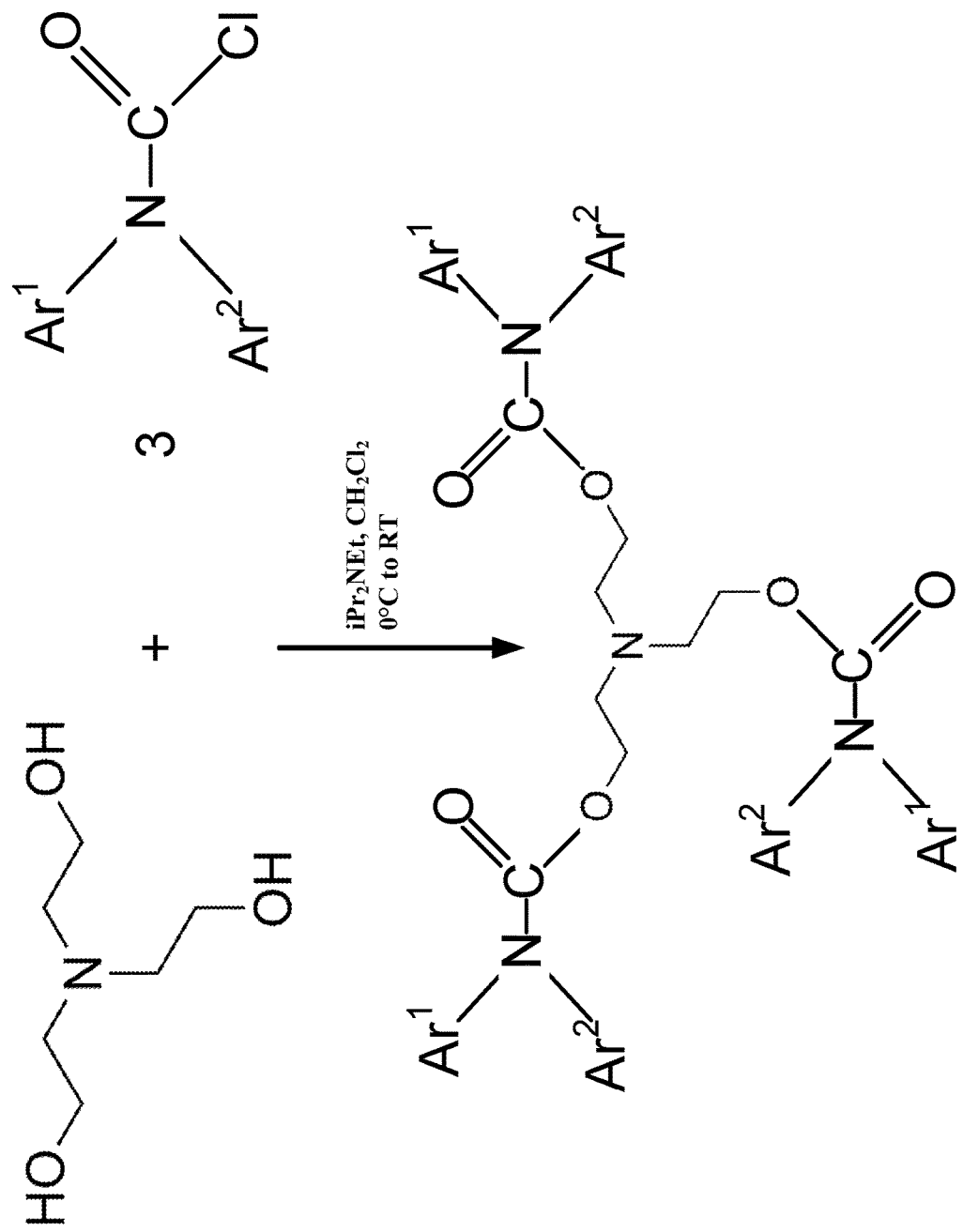

FIG. 15 depicts a general synthetic scheme for preparing integrin activating compounds derived from triethanolamine.

Figure 16:
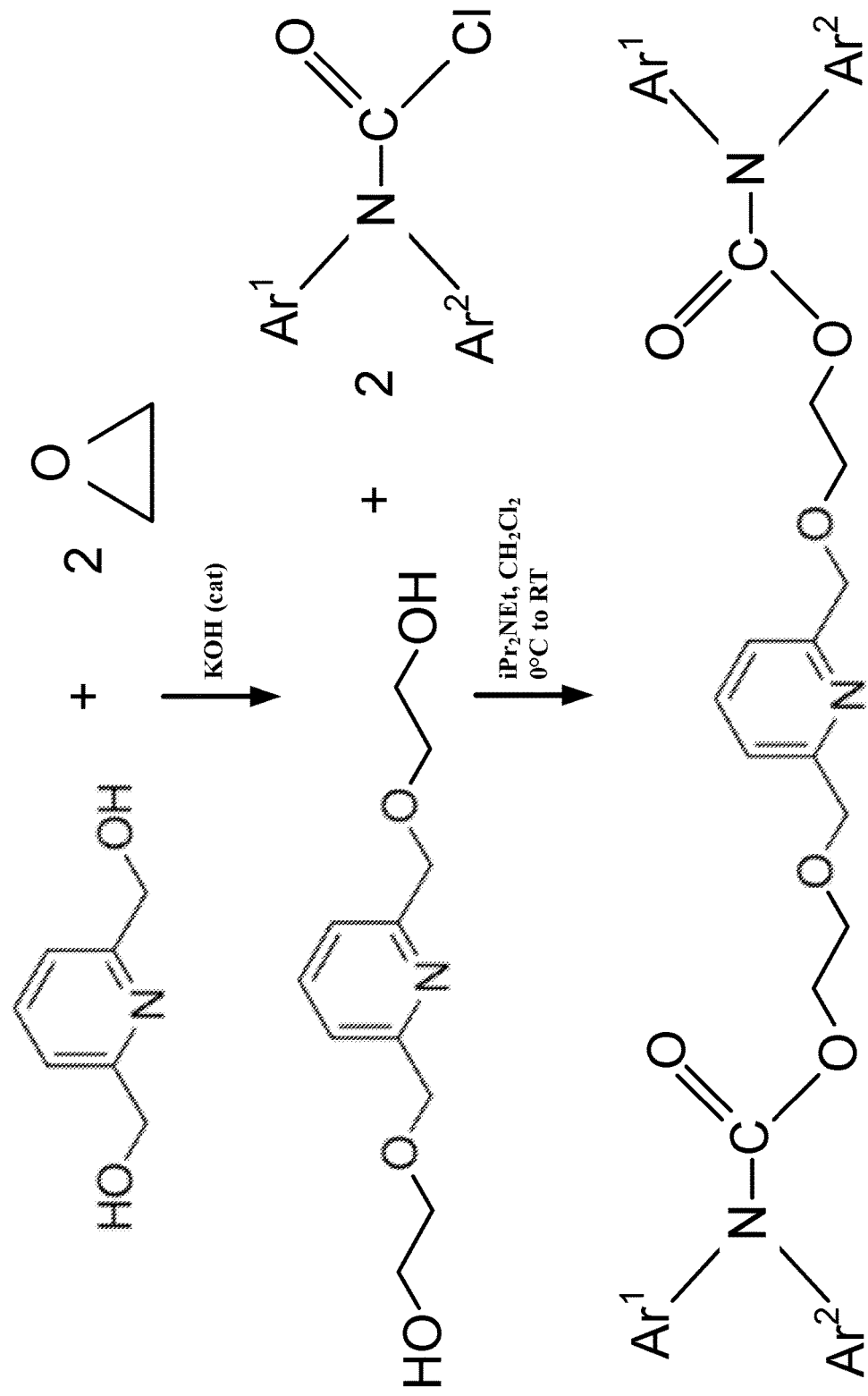

FIG. 16 depicts a general synthetic scheme for preparing ethoxylated integrin activating compounds of Formula (IV).

Figure 17:
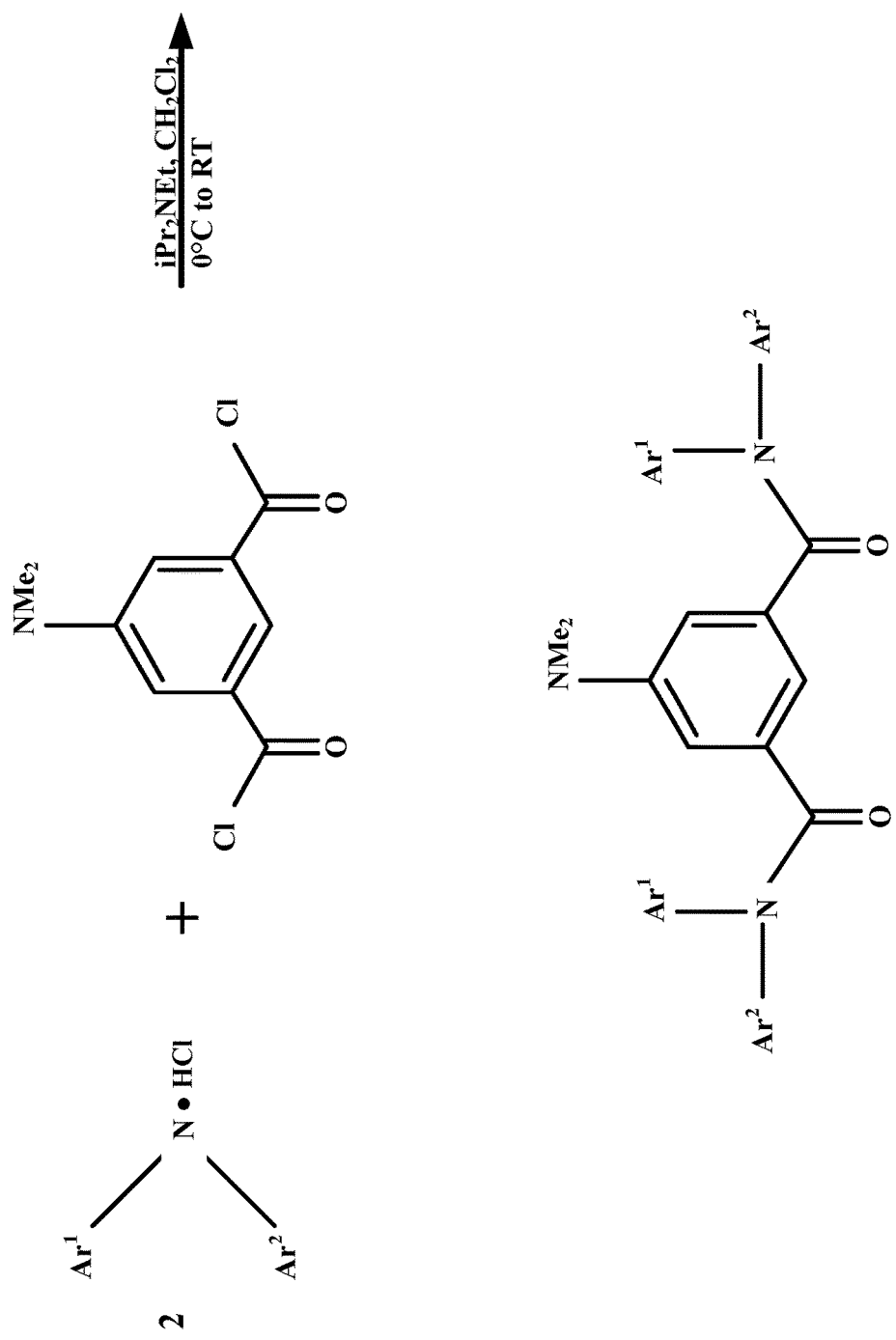

FIG. 17 depicts a general synthetic scheme for preparing integrin activating compounds derived from 3,5-aniline dicarboxylic acid chloride.

Figure 18:
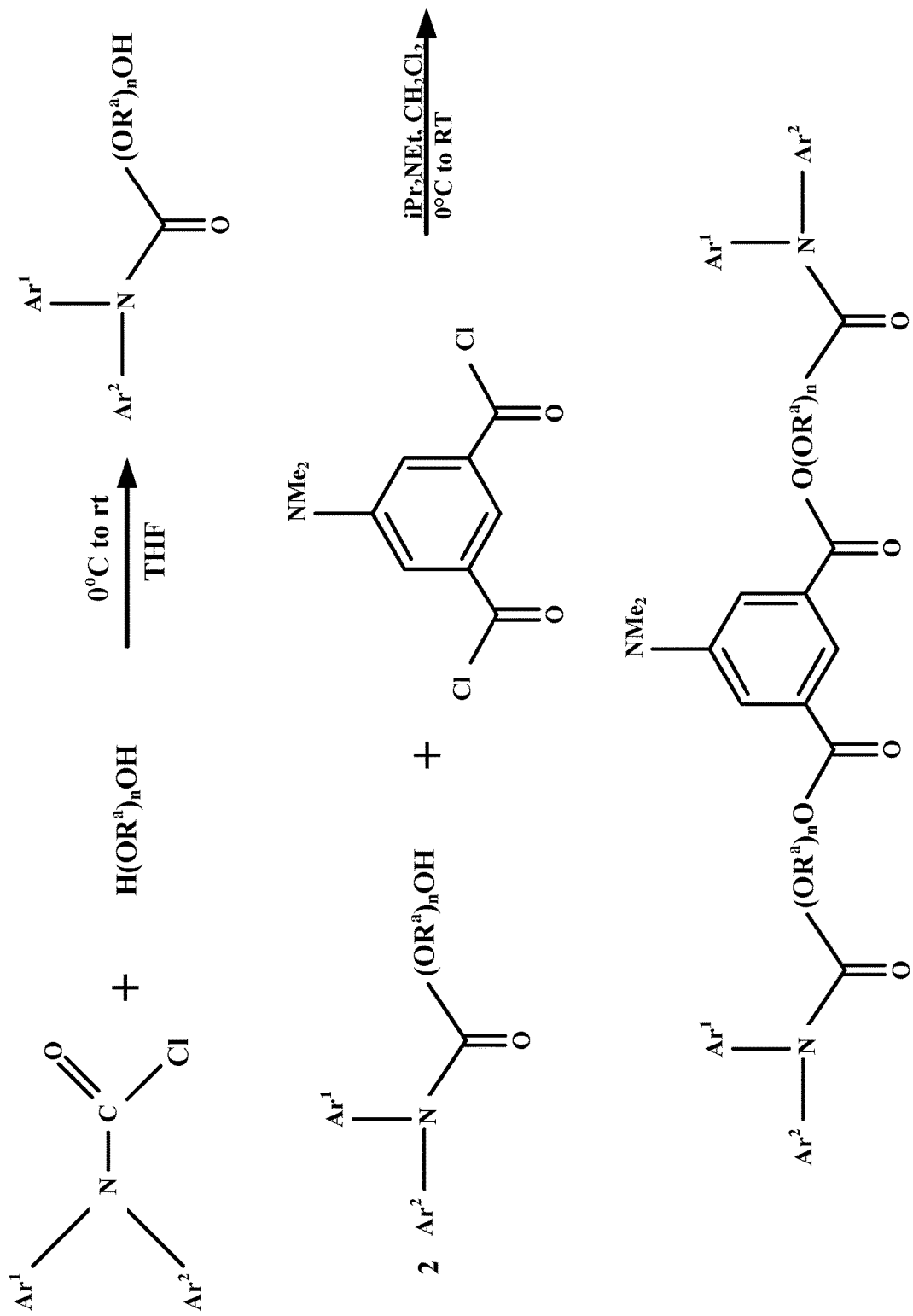

FIG. 18 depicts a general synthetic scheme for preparing integrin activating compounds derived from 3,5-aniline dicarboxylic acid chloride, where $R^a$ is a 1-3 carbon chain and n is 1 to 6.

Figure 19:
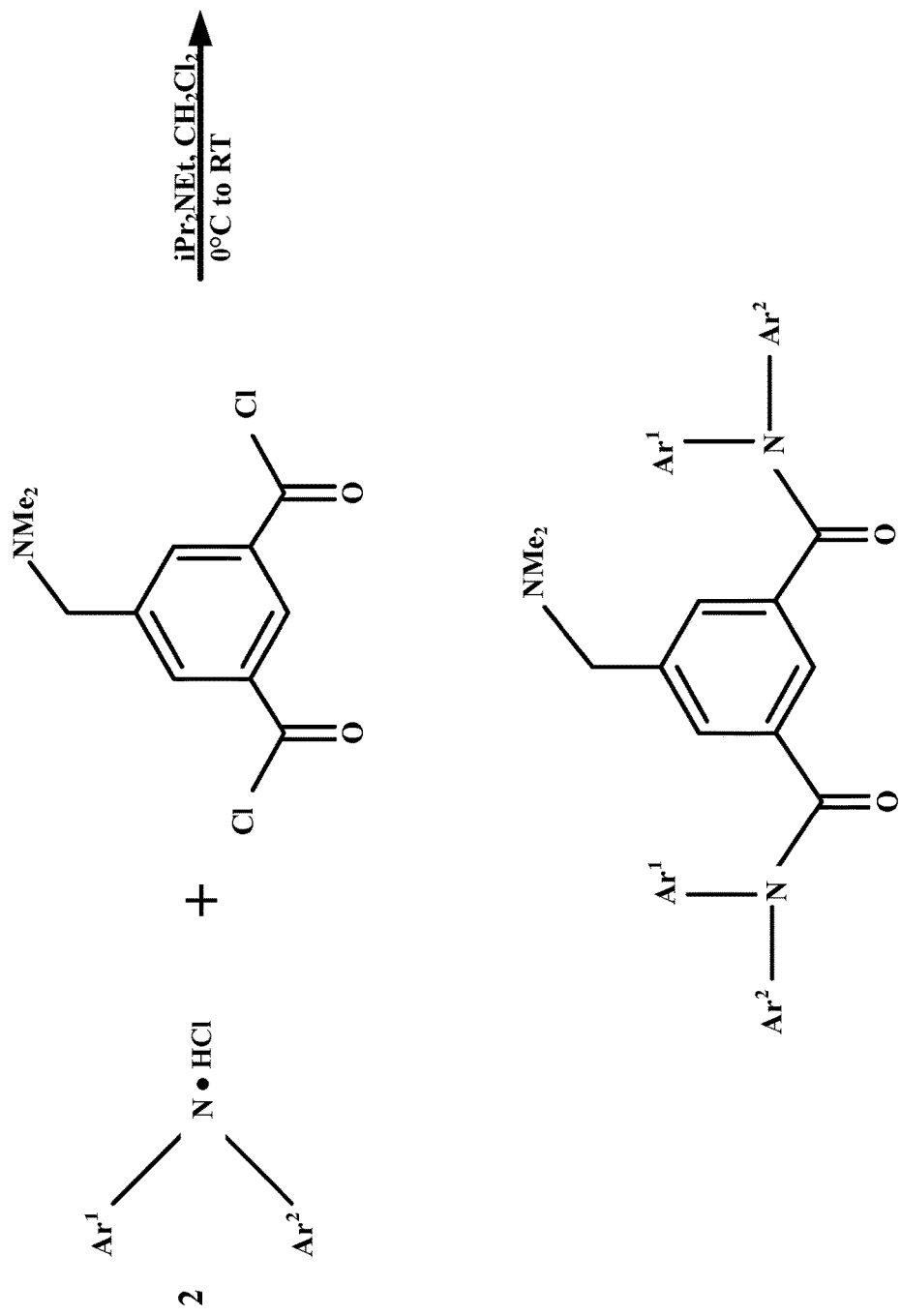

FIG. 19 depicts a general synthetic scheme for preparing integrin activating compounds derived from 3,5-benylamine dicarboxylic acid chloride.

Figure 20:

FIG. 20 depicts a general synthetic scheme for preparing integrin activating compounds derived from 3,5-benylamine dicarboxylic acid chloride, where $R^a$ is a 1-3 carbon chain and n is 1 to 6.

DEFINITIONS USED IN THE DISCLOSURE

In addition to having their customary and usual meaning, the following definitions apply where the context permits in the specification and claims:

The term "pharmaceutical composition" means a composition including one or more chemical compounds and/or one or more acceptable salts thereof, with or without a pharmaceutically acceptable carrier, where the composition is suitable for administration to an animal, a mammal, or a human.

The term "cell therapeutic" means a composition including one or more cell types, one or more chemical compounds and/or pharmaceutically acceptable salts thereof, with or without a pharmaceutically acceptable carrier, where the composition is suitable for administration to an animal, a mammal, or a human.

The term "therapeutically effective amount" means an amount of a therapeutic composition sufficient to elicit a desired therapeutic response or to reduce or ameliorate one or more of the symptoms of a disorder or disease or prolong the survival of a subject to which the composition is being administered.

The term "therapeutically ineffective amount" means an amount of a therapeutic composition insufficient to elicit a desired therapeutic response or to reduce or ameliorate one or more of the symptoms of a disorder or disease or prolong the survival of a subject to which the composition is being administered.

The term "intrinsic resistance" means the innate ability of a cell or organism to resist activity of a particular agent through its inherent structural or functional characteristics, which allow tolerance of a particular drug or drug class.

The term "acquired resistance" is the adaptive ability of a cell or organism to resist activity of a particular agent through induction of inherent structural or functional characteristics, which allow tolerance of a particular drug or drug class.

With respect to a disease or disorder, the term "treatment" means preventing, reducing, or deterring the occurrence of a disease or disorder, arresting, regressing, or providing relief from symptoms or side effects of the disease or disorder and/or prolonging the survival of the subject being treated.

The term "carbyl group" or "hydrocarbyl group" means a linear, branched, cyclic, or aromatic group including 1 to 40 carbon atoms with sufficient hydrogen atoms to satisfy the valency of the structure, where one or more hydrogen atoms may be replaced by F, Cl, C(=O)NRR', or other relatively inert groups (groups that do not significantly change the biological behavior of the compound), where R and R' may be independently hydrocarbyl groups. Hydrocarbyl groups include, without limitation, alkyl groups, alkenyl groups, alkynyl groups, cycloalkyl groups, cycloalkenyl groups, haloalkyl groups, alkoxy groups, alkenoxy groups, alkynoxy groups, carboxyl groups, thioalkoxy groups, carboxaldehyde groups, carboxamide groups, alkoxyalkoxy groups, alkylamino groups, alkynylamino groups, dialkylamino groups, alkoxycarbonyl groups, aryl groups, aromatic groups, arylene groups, arylalkyl groups, alkylaryl groups, aralkyl groups, aralkenyl groups, arylamino groups, biaryl groups, thioaryl groups, aroyl groups, heterocyclyl groups, alkylheterocyclyl groups, heterocyclylalkyl groups, aminal groups, electron-withdrawing groups, or electron-donating groups, where the alkyl moieties of the groups may be linear or branched.

The term "heterocarbyl group" or "heterohydrocarbyl group" means a linear, branched, cyclic, or aromatic group including 1 to 40 carbon atoms with sufficient hydrogen atoms to satisfy the valency of the structure, where one or more carbon atoms may be replaced by a heteroatom and one or more hydrogen atoms may be replaced by F, Cl, C(=O)NRR', or other relatively inert groups (groups that do not significantly change the biological behavior of the compound), where R and R' may be independently hydrocarbyl groups. Hydrocarbyl groups include, without limitation, alkyl groups, alkenyl groups, alkynyl groups, cycloalkyl groups, cycloalkenyl groups, haloalkyl groups, alkoxy groups, alkenoxy groups, alkynoxy groups, carboxyl groups, thioalkoxy groups, carboxaldehyde groups, carboxamide groups, alkoxyalkoxy groups, alkylamino groups, alkynylamino groups, dialkylamino groups, alkoxycarbonyl groups, aryl groups, aromatic groups, arylene groups, arylalkyl groups, alkylaryl groups, aralkyl groups, aralkenyl groups, arylamino groups, biaryl groups, thioaryl groups, aroyl groups, heterocyclyl groups, alkylheterocyclyl groups, heterocyclylalkyl groups, aminal groups, electron-withdrawing groups, or electron-donating groups, where the alkyl moieties of the groups may be linear or branched.

The term "carbenyl linking group" or "hydrocarbenyl linking group" means a linear, branched, cyclic, or aromatic group including 1 to 40 carbon atoms with sufficient hydrogen atoms to satisfy the valency of the structure and including two (2) sites to which other groups are attached, where one or more hydrogen atoms may be replaced by F, Cl, C(=O)NRR', or other relatively inert groups (groups that do not significantly change the biological behavior of the compound), where R and R' may be independently hydrocarbyl groups.

The term "heterocarbenyl linking group" or "heterohydrocarbenyl linking group" means a linear, branched, cyclic, or aromatic group including 1 to 40 carbon atoms with sufficient hydrogen atoms to satisfy the valency of the structure and including two (2) sites to which other groups are attached, where one or more carbon atoms may be replaced by a heteroatom and one or more hydrogen atoms may be replaced by F, Cl, C(=O)NRR', or other relatively inert groups (groups that do not significantly change the biological behavior of the compound), where R and R' may be independently hydrocarbyl groups.

The term "alkyl" as used herein alone or in combination means $C_1$-$C_{12}$ straight or branched, substituted or unsubstituted saturated chain radicals derived from saturated hydrocarbons by the removal of one hydrogen atom. Representative examples of alkyl groups include methyl, ethyl, n-propyl, iso-propyl, n-butyl, sec-butyl, iso-butyl, and tert-butyl among others.

The term "alkenyl", alone or in combination means a substituted or unsubstituted straight-chain or substituted or unsubstituted branched-chain alkenyl radical containing from 2 to 10 carbon atoms. Examples of such radicals include, but are not limited to, ethenyl, E- and Z-pentenyl, decenyl and the like.

The term "alkynyl", alone or in combination means a substituted or unsubstituted straight or substituted or unsubstituted branched chain alkynyl radical containing from 2 to 10 carbon atoms. Examples of such radicals include, but are not limited to ethynyl, propynyl, propargyl, butynyl, hexynyl, decynyl and the like.

The term "lower" modifying "alkyl", "alkenyl", "alkynyl" or "alkoxy" means a $C_1$-$C_6$ unit for a particular functionality. For example, lower alkyl means $C_1$-$C_6$ alkyl.

The term "cycloalkyl" alone or in combination means a substituted or unsubstituted aliphatic ring system having 3 to 10 carbon atoms and 1 to 3 rings, including, but not limited to cyclopropyl, cyclopentyl, cyclohexyl, norbornyl, and adamantyl among others. Cycloalkyl groups can be unsubstituted or substituted with one, two or three substituents independently selected from lower alkyl, haloalkyl, alkoxy, thioalkoxy, amino, alkylamino, dialkylamino, hydroxy, halo, mercapto, nitro, carboxaldehyde, carboxy, alkoxycarbonyl and carboxamide. This term is meant to encompass cycloalkenyl and cycloalkynyl groups. "Cycloalkyl" includes cis or trans forms. Furthermore, the substituents may either be in endo or exo positions in the bridged bicyclic systems.

The term "cycloalkenyl" alone or in combination means a cyclic carbocycle containing from 4 to 8 carbon atoms and one or more double bonds. Examples of such cycloalkenyl radicals include, but are not limited to, cyclopentenyl, cyclohexenyl, cyclopentadienyl and the like.

The term "cycloalkylalkyl" means a cycloalkyl group appended to a lower alkyl radical, including, but not limited to cyclohexyl methyl.

The term "halo" or "halogen" means I, Br, Cl or F.

The term "haloalkyl" means a lower alkyl radical, to which is appended at least one halogen substituent, for example chloromethyl, fluoroethyl, trifluoromethyl and pentafluoroethyl among others.

The term "alkoxy" alone or in combination means an alkyl ether radical, group or moiety, wherein the term "alkyl" is as defined above. Examples of suitable alkyl ether radicals include, but are not limited to, methoxy, ethoxy, n-propoxy, iso-propoxy, n-butoxy, iso-butoxy, sec-butoxy, tert-butoxy and the like.

The term "alkenoxy" alone or in combination means a radical, group or moiety of formula alkenyl-O—, provided that the radical is not an enol ether, wherein the term "alkenyl" is as defined above. Examples of suitable alkenoxy radicals include, but are not limited to, allyloxy, E- and Z-3-methyl-2-propenoxy and the like.

The term "alkynoxy" alone or in combination means a radical, group or moiety of formula alkynyl-O—, provided that the radical is not an -ynol ether. Examples of suitable alkynoxy radicals include, but are not limited to, propargyloxy, 2-butynyloxy and the like.

The term "carboxyl" means an —$CO_2H$ group.

The term "thioalkoxy" means a thioether radical, group or moiety of formula alkyl-S—, wherein "alkyl" is as defined above.

The term "carboxaldehyde" means —C(=O)R, wherein R is hydrogen.

The term "carboxamide" means —C(=O)$NR_2$, wherein R is hydrogen, alkyl or any other suitable substituent.

The term "alkoxyalkoxy" means R"O—R*O—, wherein R" is lower alkyl as defined above and R* is alkylene linking group wherein alkylene is an —$(CH_2)_{n'}$— group, wherein n' is an integer from 1 to 6. Representative examples of alkoxyalkoxy groups include methoxymethoxy, ethoxymethoxy, and t-butoxymethoxy among others.

The term "alkylamino" means R"NH—, wherein R" is a lower alkyl group, for example, ethylamino, butylamino, among others.

The term "alkenylamino" alone or in combination means a radical, group, or moeity of formula alkenyl-NH— or (alkenyl)$_2$N—, wherein the term "alkenyl" is as defined above, provided that the radical is not an enamine. An example of such alkenylamino radicals is the allylamino radical.

The term "alkynylamino" alone or in combination means a radical, group, or moeity of formula alkynyl-NH— or (alkynyl)$_2$-, wherein the term "alkynyl" is as defined above, provided that the radical is not an amine. An example of such alkynylamino radicals is the propargyl amino radical.

The term "dialkylamino" means R'R"N—, wherein R' and R" are independently selected from lower alkyl, for example diethylamino, and methyl propylamino, among others.

The term "amino" means H$_2$N—.

The term "alkoxycarbonyl" means an alkoxyl group as previously defined appended to the parent molecular moiety through a carbonyl group. Examples of alkoxycarbonyl include methoxycarbonyl, ethoxycarbonyl, and isopropoxycarbonyl among others.

The term "aryl" or "aromatic" alone or in combination means a substituted or unsubstituted carbocyclic aromatic group having about 6 to 12 carbon atoms such as phenyl, naphthyl, indenyl, indanyl, azulenyl, fluorenyl and anthracenyl; or a heterocyclic aromatic group selected from the group consisting of furyl, thienyl, pyridyl, pyrrolyl, oxazolyl, thiazolyl, imidazolyl, pyrazolyl, 2-pyrazolinyl, pyrazolidinyl, isoxazolyl, isothiazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, 2,3-dihydrobenzofuranyl, benzo[b]thiophenyl, 1H-indazolyl, benzimidazolyl, benzthiazolyl, purinyl, 4H-quinolizinyl, isoquinolinyl, cinnolinyl, phthalazinyl, quinazolinyl, quinoxalinyl, 1,8-naphthridinyl, pteridinyl, carbazolyl, acridinyl, phenazinyl, phenothiazinyl, phenoxyazinyl, pyrazolo[1,5-c]triazinyl and the like. "Arylalkyl" and "alkylaryl" employ the term "alkyl" as defined above. Rings may be multiply substituted. Aromatic rings may be fused with other aromatic or non-aromatic rings to form multicyclic rings, and are also encompassed by the term "aromatic," as used herein.

The term "arylene" means aryl group used as linking group and alone or in combination refers to a substituted or unsubstituted carbocyclic aromatic group having about 6 to 12 carbon atoms such as phenyl, naphthyl, indenyl, indanyl, azulenyl, fluorenyl and anthracenyl; or a heterocyclic aromatic group selected from the group consisting of furyl, thienyl, pyridyl, pyrrolyl, oxazolyl, thiazolyl, imidazolyl, pyrazolyl, 2-pyrazolinyl, pyrazolidinyl, isoxazolyl, isothiazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, 2,3-dihydrobenzofuranyl, benzo[b]thiophenyl, 1H-indazolyl, benzimidazolyl, benzthiazolyl, purinyl, 4H-quinolizinyl, isoquinolinyl, cinnolinyl, phthalazinyl, quinazolinyl, quinoxalinyl, 1,8-naphthridinyl, pteridinyl, carbazolyl, acridinyl, phenazinyl, phenothiazinyl, phenoxyazinyl, pyrazolo[1,5-c]triazinyl and the like. "Arylalkyl" and "alkylaryl" employ the term "alkyl" as defined above. Rings may be multiply substituted. Aromatic rings may be fused with other aromatic or non-aromatic rings to form multicyclic rings, and are also encompassed by the term "aromatic," as used herein.

The term "aralkyl" alone or in combination means an aryl substituted alkyl radical, wherein the terms "alkyl" and "aryl" are as defined above. Examples of suitable aralkyl radicals include, but are not limited to, phenylmethyl, phenethyl, phenylhexyl, diphenylmethyl, pyridylmethyl, tetrazolyl methyl, furylmethyl, imidazolyl methyl, indolylmethyl, thienylpropyl and the like.

The term "aralkenyl" alone or in combination means an aryl substituted alkenyl radical, wherein the terms "aryl" and "alkenyl" are as defined above.

The term "arylamino", alone or in combination means a radical, group, or moeity of formula aryl-NR—, wherein "aryl" is as defined above. R may be selected from the group consisting of H, lower alkyl, aryl and aralkyl among others. Examples of arylamino radicals include, but are not limited to, phenylamino(anilido), naphthlamino, 2-, 3-, and 4-pyridylamino and the like.

The term "biaryl" alone or in combination means a radical, group, or moeity of formula aryl-aryl, wherein the term "aryl" is as defined above.

The term "thioaryl" alone or in combination means a radical, group, or moeity of formula aryl-S—, wherein the term "aryl" is as defined above. An example of a thioaryl radical is the thiophenyl radical.

The term "aroyl" alone or in combination means a radical, group, or moeity of formula aryl-CO—, wherein the term "aryl" is as defined above. Examples of suitable aromatic acyl radicals include, but are not limited to, benzoyl, 4-halobenzoyl, 4-carboxybenzoyl, naphthoyl, pyridylcarbonyl and the like.

The term "heterocyclyl" alone or in combination means a non-aromatic 3- to 10-membered ring containing at least one endocyclic N, O, or S atom. The heterocycle may be optionally aryl-fused. The heterocycle may also optionally be substituted with at least one substituent which is independently selected from the group consisting of hydrogen, halogen, hydroxyl, amino, nitro, trifluoromethyl, trifluoromethoxy, alkyl, aralkyl, alkenyl, alkynyl, aryl, cyano, carboxyl, alkoxycarbonyl, carboxyalkyl, oxo, arylsulfonyl and aralkylaminocarbonyl among others.

The term "alkylheterocyclyl" means an alkyl group as previously defined appended to the parent molecular moiety through a heterocyclyl group.

The term "heterocyclylalkyl" means a heterocyclyl group as previously defined appended to the parent molecular moiety through an alkyl group.

The term "higher analogs" means a compound having the same general features, but having a high carbon atom count. For example, higher analogs of $C_1$-$C_{12}$ alkanes, would be alkanes having a up to 10 additional carbons or hetero atoms. In certain embodiment, the terms refers to analogs having up to 5 additional carbons or hetero atoms. In other embodiment, the terms refers to analogs having up to 3 additional carbons or hetero atoms. In certain embodiment, the terms refers to analogs having up to 2 additional carbons or hetero atoms.

The term "aminal" means a hemi-acetal of the structure RCH(NH$_2$)(OH).

The terms "electron-withdrawing" or "electron-donating" means the ability of a substituent to withdraw or donate electrons relative to that of hydrogen if hydrogen occupied the same position in the molecule. These terms are well-understood by one skilled in the art and are discussed in Advanced Organic Chemistry by J. March, 1985, pp. 16-18, incorporated herein by reference. Electron withdrawing groups include halo, nitro, carboxyl, lower alkenyl, lower alkynyl, carboxaldehyde, carboxyamido, aryl, quaternary ammonium, trifluoromethyl, and aryl lower alkanoyl among others. Electron donating groups include such groups as hydroxy, lower alkyl, amino, lower alkylamino, di(lower alkyl)amino, aryloxy, mercapto, lower alkylthio, lower alkylmercapto, and disulfide among others. One skilled in the art will appreciate that the afore mentioned substituents may have electron donating or electron withdrawing properties under different chemical conditions. Moreover, the present disclosure contemplates any combination of substituents selected from the above-identified groups.

Exemplary examples of electron donating or electron withdrawing substituents are halo, nitro, alkanoyl, carboxaldehyde, arylalkanoyl, aryloxy, carboxyl, carboxamide, cyano, sulfonyl, sulfoxide, heterocyclyl, guanidine, quaternary ammonium, lower alkenyl, lower alkynyl, sulfonium salts, hydroxy, lower alkoxy, lower alkyl, amino, lower alkylamino, di(lower alkyl)amino, amine lower alkyl mercapto, mercaptoalkyl, alkylthio and alkyldithio.

Use of the above terms is meant to encompass substituted and unsubstituted moieties. Substitution may be by one or more groups such as alcohols, ethers, esters, amides, sulfones, sulfides, hydroxyl, nitro, cyano, carboxy, amines, heteroatoms, lower alkyl, lower alkoxy, lower alkoxycarbonyl, alkoxyalkoxy, acyloxy, halogens, trifluoromethoxy, trifluoromethyl, alkyl, aralkyl, alkenyl, alkynyl, aryl, cyano, carboxy, carboalkoxy, carboxyalkyl, cycloalkyl, cycloalkylalkyl, heterocyclyl, alkylheterocyclyl, heterocyclylalkyl, oxo, arylsulfonyl and aralkylaminocarbonyl or any of the substituents of the preceding paragraphs or any of those substituents either attached directly or by suitable linkers. The linkers are typically short chains of 1-3 atoms containing any combination of —C—, —C(=O)—, —NH—, —S—, —S(O)—, —O—, —C(=O)O— or —S(=O)O—. Rings may be substituted multiple times.

The term "heteroatom" means nitrogen, sulfur and oxygen.

The term "alpha" means the position immediately adjacent to the position described.

The term "inactive ingredient" means a harmless drug that is ordinarily used as an inactive ingredient, such as a coloring, emulsifier, excipient, flavoring, lubricant, preservative, or solvent, in the preparation of other drugs shall be exempt from section 502(f)(1) of the act (21 CFR 201.117).

The term "excipient" means any substance other than the active drug or product which has been appropriately evaluated for safety and is included in a drug delivery system to either aid the processing of the drug delivery system during its manufacture; protect, support, or enhance stability, bioavailability, or patient acceptability; assist in product identification; or enhance any other attribute of the overall safety and effectiveness of the drug delivery system during storage or use (40 CFR 63.1251).

The term "vaccine" means a composition administered to an animal, mammal, or human to affect an immune response to one or more antigens sufficient to immunize the animal, mammal, or human against a particular disease, bacteria, virus, cancer, etc. The term also refers to all type of vaccine types including, without limitation, live-attenuated vaccines, inactivated vaccines, subunit, recombinant, polysaccharide, and conjugate vaccines, and toxoid vaccines.

The term "antigen" means any material, compound, and/or composition capable inducing an immune response when administered to an animal, mammal, or human in an amount sufficient to immunize the animal, mammal, or human against a particular disease, bacteria, virus, cancer, allergen, etc. An antigen may be a compound, a protein, a purified protein, a peptide, a purified peptide, an RNA segment, a DNA segment, a cellular segment, a cell, a cell lysate, a live-attenuated microorganism or virus, an inactivated microorganism or virus, subunit, recombinant, polysaccharide, and conjugate derived from a microorganism or virus vaccines, toxoids such as animal toxins, bacterial toxins, insect toxins, etc., allergens, and/or any other material that induces an immune response when administered to an animal, mammal, or human.

The term "effector cell" means a cell that can bind to and either engulf or induce cytolysis of a target cell. Effector cell types may include, but are not limited to: (1) cytotoxic T-lymphocytes that bind to target cells and are activated by an antigen specific T cell receptor, (2) monocytes, macrophage, natural killer (NK) cells, and neutrophils that bind to and lyse target cells through interactions of fragment crystallizable (Fc) receptors and monoclonal antibody opsonized target cells, (3) NK and NK-variants that bind to and lyse target cells independent of antigen specificity, (4) Tumor Infiltrating Lymphocytes (TILs) which are lymphocytes isolated from tumors and expanded ex vivo that express cell surface markers including, but not limited to, CD3, CD8, and/or CD4, (5) T cells genetically engineered with tumor specific T cell receptors or chimeric antigen receptors that possess cell surface markers including but not limited to CD3, CD8, and/or CD4, (6) T cells including, but not limited to, CD3, CD8, and/or CD4, (7) radiation induced T cells including, but not limited to, CD3, CD8, and/or CD4, and/or (8) any other effector cell suitable for use in adaptive or adoptive cell therapies.

The term "adoptive T cell" means a effector cell that is derived from a naive T cell or activated T cell capable of effector functions.

The term "solid tumor" means an abnormal mass of tissue that usually does not contain cysts or liquid areas. Solid tumors may be benign (not cancer), or malignant (cancer). Different types of solid tumors are named for the type of cells that form them. Examples of solid tumors are sarcomas, carcinomas, and lymphomas.

The term "small molecule integrin activating compounds" or "small molecule integrin agonist" means an integrin agonist, a chemical compound, having a molecular weight less than or equal to (≤) 5,000 g/mole that are capable of reversibly binding to integrins on the surface of cells changing a conformation of the integrins from inactive compact conformations or elongated active conformation to facilitate integrin-ligand interactions. In other embodiments, the small molecule agonist have a molecular weight less than or equal to (≤) 4,000 g/mole that facilitate integrin-ligand interactions. In other embodiments, the small molecule agonist have a molecular weight less than or equal to (≤) 3,000 g/mole that facilitate integrin-ligand interactions. In other embodiments, the small molecule agonist have a molecular weight less than or equal to (≤) 2,000 g/mole that facilitate integrin-ligand interactions. In other embodiments, the small molecule agonist have a molecular weight less than or equal to (≤) 1,000 g/mole that facilitate integrin-ligand interactions.

In this disclose, all ranges are inclusive—include the end points. All ranges include all subranges and all values between the ranges. For example, a range between 1 and 10 includes all subranges such as between 2 and 8, between 1.1 and 9.9, etc.

In this disclose, all values that state "less than" means all values less than a specific value. All values that state "greater than" means all values greater than a specific value. All values that state "less than or equal to" means all values less than a specific value including the specific values. All values that state "greater than or equal to" means all values greater than a specific value including the specific value.

The term "at least one" means one or more or one or a plurality, additionally, these three terms may be used interchangeably within this application. For example, at least one device means one or more devices or one device and a plurality of devices.

The term "one or a plurality" means one item or a plurality of items.

The term "about" means that a value of a given quantity is within ±20% of the stated value. In other embodiments, the value is within ±15% of the stated value. In other embodiments, the value is within ±10% of the stated value. In other embodiments, the value is within ±5% of the stated value. In other embodiments, the value is within ±2.5% of the stated value. In other embodiments, the value is within ±1% of the stated value.

The term "substantially" or "essentially" means that a value of a given quantity is within ±5% of the stated value. In other embodiments, the value is within ±2.5% of the stated value. In other embodiments, the value is within ±2% of the stated value. In other embodiments, the value is within ±1% of the stated value. In other embodiments, the value is within ±0.1% of the stated value.

ABBREVIATIONS USED IN THE DISCLOSURE

The following abbreviations are used herein: Ac is acetyl, AcOH is acetic acid, ADCC is antibody dependent cellular cytotoxicity, 6-Ahx-OH is 6-aminohexanoic acid, APC is antigen presenting cell, BATDA is bis(acetoxymethyl) 2,2': 6',2"-terpyridine-6,6"-dicarboxylate, BCG is bacillus calmette-guérin, Bz is benzyl, Boc is tert-butyloxycarbonyl, nBu is n-butyl, nBuLi is n-butyllithium, 1.6M in hexanes (unless other concentration noted), Cbz is benzyloxycarbonyl, CD is cluster of differentiation, CDI is N,N'-carbonyldiimidazole, COMU is (1-cyano-2-ethoxy-2-oxoethylidenaminooxy)dimethylamino-morpholino-carbenium hexafluorophosphate, CTL is cytotoxic T lymphocyte, CTLA-4 is cytotoxic T lymphocyte-associated antigen-4, Dab is 2,4-diaminobutyryl, DBU is 1,8-diazabicyclo[5.4.0]undec-7-ene, DCE is 1,2-dichloroethane, DCHA is dicyclohexylamine, DCM is dichloromethane (methlyene chloride), dioxane is 1,4-dioxane, DIPEA is N,N-diisopropylethylamine, DMED is N,N'-dimethylethylene diamine, DMF is N,N-dimethylformamide, DMSO is dimethylsulfoxide, Me is methyl, MeOH is methanol, Et is ethyl, EtOH is ethanol, FBS is fetal bovine serum, Fc is fragment crystallizable, FGF is fibroblast growth factor, Fmoc is 9H-fluoren-9-ylmethoxycarbonyl, G-CSF is granulocyte colony stimulating factor, Glu is glutamic acid, Gly is glycine, HBTU is O-(Benzotriazol-1-yl)-N,N,N',N'-tetramethyluronium hexafluorophosphate, HMDS is hexamethyldisilazane, ICAM-1 is intercellular adhesion molecule-1, IDO is indoleamine 2,3-dioxygenase, iNKT is invariant natural killer T cell, iPr is isopropyl, KHMDS is potassium bis(trimethylsilyl)amide, LFA is lymphocyte function-associated antigen where LFA-1 is the integrin αLβ2, Lys is lysine, LHMDS is lithium bis(trimethylsilyl)amide, MAdCAM-1 is mucosal addressin cell adhesion molecule-1, Me is methyl, MeOH is methanol, MHC is major histocompatibility complex, NK is natural killer, Nle is norleucine, NMM is 4-methylmorpholine, NSMC is N-succinimidyl-N-methyl-carbamate, OAc is acetate, Orn is Ornithine, PBS is phosphate buffered saline, PD1 is programmed death 1, PDL1 is programmed death ligand 1, pTsOH is para-toluenesulfonic acid, Ph is phenyl, RT is room temperature, SDF1α is stromal cell derived factor-1α, tBu is tert-butyl, TBS is tris-buffered saline, TDA is 2,2':6',2"-terpyridine-6,6"-dicarboxylic acid, TEA is triethylamine, TIL is tumor infiltrating lymphocyte, Tfa is trifluoroacetyl, Th1 is T helper 1, Th2 is T helper 2, THF is tetrahydrofuran, Tol is toluene, Tyr is tyrosine, VCAM-1 is vascular cell adhesion molecule-1, Veh is vehicle, VLA is very late activation antigen, VLA-4 is the integrin α4β1 and VLA-5 is the integrin α5β1, and Z is benzyloxycarbonyl.

DETAILED DESCRIPTION OF THE DISCLOSURE

General

The inventor has also found that small molecule integrin agonists or integrin activating compounds including at least one di-alkylaryl amine end group and at least one alkyl or alkenoxy linking group including at least one protonatable moiety, wherein the compounds enhance vaccine efficacies, enhance adoptive cell therapy efficacies, enhance immunotherapy efficacies, enhance therapeutic antibody therapy efficacies, enhance checkpoint inhibitor therapy efficacies, enhance effector cell therapy efficacies, and enhanced cell based transplant efficacies and wherein at protonatable moiety either protonate at biological pHs or bears a charge with associated pharmaceutically acceptable counterion making the compound water soluble to improve bioavailability and methods for making and using same. The inventor has found that small molecule compounds may be prepared that enhance therapies that involve integrin-mediated interactions such as integrin-ligand interactions, cell-cell adhesion, activity of therapeutic agents, efficacy of antigen immune responses and vaccines, and other type of therapies that are dependent on integrins. The inventor has found that these small molecules act as integrin agonists or activators and are capable of reversibly binding to integrin subunits to affect a transition of the integrin from an inactive or less active state to an active or more active state. The inventor has also found that the transition is the result of a conformational change in the integrin from a compact low active state or inactive state or low active conformation to an elongated active state or active conformation that facilitates integrin-ligand binding and is released upon ligand binding. The inventor has also found that the agonists may be synthesized with one or more moieties in the main body of the molecular structure that protonate at biological pHs and/or bear a charge balanced by a therapeutically counterion to improve bioavailability and aqueous solubility. The inventor has also found that the agonists enhance the amelioration or abatement of disease or malady symptoms, directly treat solid tumors or other cancerous growths, enhance cell-based therapies, enhance antibody activities, enhance check point inhibitor activities, enhance antigen presentation, enhance antigen immune responses, enhance vaccine efficacies, and/or enhance the activity of any therapy in which integrins place a role. The inventor has also found that the small molecule compounds may include end moieties that reversibly bind to integrin subunits and include at least one moiety in the body of the molecular structure that protonates at biological pHs or bears a charge balanced by a therapeutically counterion. The inventor has also found that the agonists of Formula (I) do not appear to affect the expression of the integrin like other agonists that must be absorbed into the cell causing the cell to up regulate production of surface integrins such as α4β1, α4β7, α5β1, αLβ2 and/or αVβ3 integrins, but again the agonists of Formula (I) act to active existing surface integrins. The inventor believes that the present agonists could be used in conjunction with agonists that up regulate integrin expression so that the agonists of Formula (I) would activate present and newly expressed integrins. The inventor believes that the small molecules small molecule integrin agonists of Formula (I) are capable of acting as integrin ligand mimics that facilitate integrin-ligand interactions and are designed to have increased aqueous solubility and bioavailability for use in vaccines, antibody therapies, antibody dependent cellular cytotoxicity (ADCC) therapies, checkpoint inhibitor therapies, adoptive or adaptive cell therapies, and immunotherapies, and a variety of other conditions and thereby enhance the efficacy of vaccines, antibody therapies, antibody dependent cellular cytotoxicity (ADCC) therapies, checkpoint inhibitor therapies, adoptive or adaptive cell therapies, and immunotherapies, and a variety of other conditions.

Communication between a variety of cell types must occur through direct cell-to-cell contact for a productive immune response to follow an antigenic challenge. Direct cell-to-cell contacts are mediated by a family of cell adhesion molecules also referred to as integrins. Integrin cell adhesion molecules or integrins are cell surface glycoproteins comprised on non-covalently associated α and β heterodimers. One of eighteen different α-monomers combine with one of eight different β-monomers to form 24 different αβ pairs. On leukocytes, integrins are intimately involved in the adhesion cascade, which governs leukocyte trafficking to sites of inflammation or injury. Integrins are also key components in the generation of an adaptive immune response, which is easily observed during the process of vaccination.

In certain embodiments, the agonists interact with integrins including, but are not limited to, α4β1, α4β7, α5β1, αLβ2 and/or αVβ3. In certain embodiments, the agonist activated integrins interact with ligands including, but are not limited to, VCAM-1, fibronectin, MAdCAM-1, ICAM-1, ICAM-2, and/or vitronectin.

In certain embodiments, the compositions include an effective amount of one or more integrin agonists or integrin activating compounds or integrin activators, where the activator comprise one or more chemical compounds of the general Formula (I):

$$Q^1\text{-}R^a\text{—}Z\text{—}R^b\text{-}Q^2 \qquad (I)$$

wherein:
the $Q^1$ and $Q^2$ groups may independently be an $R^1R^2N$— group, an $R^1R^2NC(=O)$— group, an $R^1R^2NC(=O)N(R^3)$— group, an $R^1R^2NC(=O)O$— group, or an $R^1R^2NSO_2$— group,
the $R^1$ and $R^2$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof, and
the $R^3$ group may be a hydrocarbyl group or a heterohydrocarbyl group;
the $R^a$ and $R^b$ groups may independently be a hydrocarbenyl linking group, wherein one or more carbon atoms may be replaced by oxygen atoms, e.g., an alkyleneoxide linking group such as a methyleneoxide containing linking group or an ethyleneoxide containing linking group; and
the Z group may be a hydrocarbenyl linking group or a heterohydrocarbenyl linking group and includes one or more protonatable moieties.

In certain embodiments, the one or more protonatable moieties become protonated at biological pHs and/or are protonated and include pharmaceutically acceptable counterions.

In certain embodiments, the one or more integrin activating compounds or agonist comprise compounds of the general Formula (II):

$$Q\text{-}R^a\text{-}Z\text{—}R^a\text{-}Q \qquad (II)$$

wherein:
the Q groups independently comprise $R^1R^2NC(=O)$—;
the $R^1$ and $R^2$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof;
the $R^a$ groups independently comprise $(OCH_2)_n$ or $(OCH_2CH_2)_n$;
n independently is an integer having a value between 1 and 6;
the Z group is N(R); and
the R group comprises a hydrocarbyl group or a heterohydrocarbyl group.

In certain embodiments, the one or more integrin activating compounds or agonist comprise compounds of the general Formula (III):

$$Q\text{-}R^a\text{—}Z\text{—}R^a\text{-}Q \qquad (III)$$

wherein:
the Q groups independently comprise $R^1R^2NC(=O)$—;
the $R^1$ and $R^2$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof;
the $R^a$ groups independently comprise $(OCH_2)_n$ or $(OCH_2CH_2)_n$;
n independently is an integer having a value between 0 and 6; and
the Z group is derived from 2,6-dihydroxypyridine; and.

In certain embodiments, the one or more integrin activating compounds or agonist comprise compounds of the general Formula (IV):

$$Q\text{-}R^a\text{—}Z\text{—}R^a\text{-}Q \qquad (IV)$$

wherein:
the Q groups independently comprise $R^1R^2NC(=O)$—,
the $R^1$ and $R^2$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof;
the $R^a$ groups independently comprise $(OCH_2)_n$ or $(OCH_2CH_2)_n$;
n independently is an integer having a value between 0 and 6; and
the Z group is derived 2,6-dimethanolpyridine.

In certain embodiments, the one or more integrin activating compounds or agonist comprise compounds of the general Formula (V):

$$Q\text{-}R^a\text{—}Z\text{—}R^a\text{-}Q \qquad (V)$$

wherein:
the Q groups independently comprise $R^1R^2NC(=O)-$,
the $R^1$ and $R^2$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof;
the $R^a$ groups independently comprise $(OCH_2)_n$ or $(OCH_2CH_2)_n$;
n independently is an integer having a value between 0 and 6; and
the Z group is derived 3,5-dihydroxypyridine.

In certain embodiments, the one or more integrin activating compounds or agonist comprise compounds of the general Formula (VI):

$$Q-R^a-Z-R^a-Q \qquad (VI)$$

wherein:
the Q groups independently comprise $R^1R^2NC(=O)-$,
the $R^1$ and $R^2$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof;
the $R^a$ groups independently comprise $(OCH_2)_n$ or $(OCH_2CH_2)_n$;
n independently is an integer having a value between 0 and 6; and
the Z group is derived 3,5-dimethanolpyridine.

In certain embodiments, the one or more integrin activating compounds or agonist comprise compounds of the general Formula (VII):

$$Q-R^a-Z-R^a-Q \qquad (VII)$$

wherein:
the Q groups independently comprise $R^1R^2NC(=O)-$,
the $R^1$ and $R^2$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof;
the $R^a$ groups independently comprise $(OCH_2)_n$ or $(OCH_2CH_2)_n$; and
n independently is an integer having a value between 0 and 6; and
the Z group is derived dimethyl-3,5-dihydroxy aniline.

In certain embodiments, the one or more integrin activating compounds or agonist comprise compounds of the general Formula (VIII):

$$Q-R^a-Z-R^a-Q \qquad (VIII)$$

wherein:
the Q groups independently comprise $R^1R^2NC(=O)-$,
the $R^1$ and $R^2$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof;
the $R^a$ groups independently comprise $(OCH_2)_n$ or $(OCH_2CH_2)_n$;
n independently is an integer having a value between 0 and 6; and
the Z group is derived 3,5-dihydroxy-dimethyl benzylamine.

In certain embodiments, the one or more integrin activating compounds or agonist comprise compounds of the general Formula (IXa&b):

$$Q-R^a-Z-R^a-Q \qquad (IXa)$$

wherein:
the Q groups independently comprise $R^1R^2NC(=O)-$,
the $R^1$ and $R^2$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof;
the $R^a$ groups independently comprise $(OCH_2)_n$ or $(OCH_2CH_2)_n$
n independently is an integer having a value between 0 and 6; and
the Z group is derived 2,6-pyridine dicarboxylic acid.

In certain embodiments, the one or more integrin activating compounds or agonist comprise compounds of the general Formula (Xa&b):

$$Q-R^a-Z-R^a-Q \qquad (Xa)$$

wherein:
the Q groups independently comprise $R^1R^2NC(=O)-$,
the $R^1$ and $R^2$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof;
the $R^a$ groups independently comprise $(OCH_2)_n$ or $(OCH_2CH_2)_n$;
n independently is an integer having a value between 0 and 6
the Z group is derived 3,5-pyridine dicarboxylic acid.

In certain embodiments, the one or more integrin activating compounds or agonist comprise compounds of the general Formula (XIa&b):

$$Q-R^a-Z-R^a-Q \qquad (XIa)$$

wherein:
the Q groups independently comprise $R^1R^2NC(=O)-$,
the $R^1$ and $R^2$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof;
the $R^a$ groups independently comprise $(OCH_2)_n$ or $(OCH_2CH_2)_n$;
n independently is an integer having a value between 0 and 6; and
the Z group is derived 3-dimethylamino-1,5-pentanediol.

In certain embodiments, the one or more integrin activating compounds or agonist comprise compounds of the general Formula (XII):

Q-R$^a$—Z wherein:
the Q group comprises R$^1$R$^2$NC(=O)—,
the R$^1$ and R$^2$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof;
the R$^a$ group comprises (OCH$_2$)$_n$ or (OCH$_2$CH$_2$)$_n$;
n is an integer having a value between 2 and 6; and
the Z group comprises derived PEGn-omega-dimethylamine group.

In certain embodiments, the R$^1$ and R$^2$ group are selected from the groups consisting of an 2-thienylalkyl group, an 3-alkoxybenzyl group, an 4-alkoxybenzyl group, an pyridin-2-ylalkyl, pyridin-4-ylalkyl group, an pyridin-4-ylalkyl group, an 4-dialkylaminobenzyl group, an 3-dialkylaminobenzyl group, carbazole, 3,6-dimethoxycarbazole, and mixture or combinations thereof, where the alkyl groups independently have 1 to 6 carbon atoms. In other embodiments, the R$^1$ and R$^2$ groups are selected from the groups consisting of an 2-thienylmethyl group, an 2-(2-thienyl)ethyl group, an 3-methoxybenzyl group, an 4-methoxybenzyl group, an pyridin-2-ylmethyl group, an pyridin-4-ylmethyl group, an pyridin-4-ylmethyl group, an 4-dimethylaminobenzyl group, an 3-dimethylaminobenzyl group, carbazole, 3,6-dimethoxycarbazole, and mixture or combinations thereof, where the alkyl groups independently have 1 to 2 carbon atoms.

In certain embodiments, the R$^a$ and R$^b$ groups may independently be an —O(R$^b$O)$_n$—, —R$^c$O(R$^b$O)$_n$— group, an —O(R$^b$O)$_n$R$^d$— group, an —R$^c$O(R$^b$O)$_n$R$^d$— group, or a R$^{aa}$ group, wherein R$^b$, R$^c$, R$^d$, and R$^{aa}$ may independently be hydrocarbyl linking groups, and each n is independently an integer having a value of 1 to 8. In other embodiments, the R$^a$ and R$^b$ groups may independently be an —O((CH$_2$)$_m$O)$_n$— group, where m is an integer having a value of 1 to 3 and n an integer having a value or 1 to 8. In other embodiments, the R$^a$ and R$^b$ groups may independently be an —O((CH$_2$)$_{m1}$)((CH$_2$)$_{m2}$O)$_n$(CH$_2$)$_{m3}$— group, wherein m1, m2 and m3 are integers having values of 1 to 3 and n an integer having a value of 1 to 8. In other embodiments, the R$^a$ and R$^b$ groups may independently be an —((CH$_2$)$_{m1}$)((CH$_2$)$_{m2}$O)$_n$(CH$_2$)$_{m3}$— group, wherein m1, m2 and m3 are integers having values of 1 to 3 and n an integer having a value of 1 to 8. Exemplary examples include, without limitation, an —O(CH$_2$O)$_n$— group, an —O(CH$_2$CH$_2$O)$_n$— group, an —O(CH$_2$CH$_2$CH$_2$O)$_n$— group, an —CH$_2$O(CH$_2$O)$_n$— group, an —O(CH$_2$O)$_n$CH$_2$— group, an —CH$_2$O(CH$_2$O)$_n$CH$_2$— group, an —CH$_2$O(CH$_2$CH$_2$O)$_n$— group, an —O(CH$_2$CH$_2$O)$_n$CH$_2$— group, an —CH$_2$O(CH$_2$CH$_2$O)$_n$CH$_2$— group, an —CH$_2$CH$_2$O(CH$_2$CH$_2$O)$_n$— group, an —O(CH$_2$CH$_2$O)$_n$CH$_2$CH$_2$— group, an —CH$_2$CH$_2$O(CH$_2$CH$_2$O)$_n$CH$_2$CH$_2$— group, or higher analogs, or —(CH$_2$)$_n$— group, wherein n is an integer having a value between 1 and 8.

In certain embodiments, the linking group —O(R$^c$O)$_n$—, —R$^d$O(R$^c$O)$_n$—, —O(R$^c$O)$_n$R$^e$—, and —R$^d$O(R$^c$O)$_n$R$^e$— may be selected from the group consisting of: (a) C$_2$ oxygen-containing linking groups include: 1-oxaethenyl (—OCH$_2$—), and 2-oxaethenyl (—CH$_2$O—); (b) C$_3$ oxygen-containing linking groups include: 1-oxapropenyl (—O(CH$_2$)$_2$—), 2-oxapropenyl (—CH$_2$OCH$_2$—), 3-oxapropenyl (—(CH$_2$)$_2$O—), and 1,3-dioxapropenyl (—OCH$_2$O—); (c) C$_4$ oxygen-containing linking groups include: 1-oxabutenyl (—(CH$_2$)$_3$O—), 2-oxabutenyl (—CH$_2$O(CH$_2$)$_2$—), 3-oxabutenyl (—(CH$_2$)$_2$OCH$_2$—), 4-oxabutenyl (—(CH$_2$)$_3$O—), 1,3-dioxabutenyl (—OCH$_2$OCH$_2$—), 1,4-dioxabutenyl (—O(CH$_2$)$_2$O—), and 2-4-dioxabutenyl (—CH$_2$OCH$_2$O—); (d) C$_5$ oxygen-containing linking groups include: 1-oxapentenyl (—O(CH$_2$)$_4$—), 2-oxapentenyl (—CH$_2$O(CH$_2$)$_3$—), 3-oxapentenyl (—(CH$_2$)$_2$O(CH$_2$)$_2$—), 4-oxapentenyl (—(CH$_2$)$_3$OCH$_2$—), 5-oxapentenyl (—(CH$_2$)$_4$O—), 1,3-dioxapentenyl (—OCH$_2$O(CH$_2$)$_2$—), 1,4-dioxapentenyl (—O(CH$_2$)$_2$OCH$_2$—), 1,5-dioxapentenyl (—O(CH$_2$)$_3$O—), 2-4-dioxapentenyl (—CH$_2$OCH$_2$OCH$_2$—), 2,5-dioxapentenyl (—CH$_2$O(CH$_2$)$_2$O—), 3,5-dioxapentenyl (—(CH$_2$)$_2$OCH$_2$O—), and 1,3,5-trioxapentenyl (—OCH$_2$OCH$_2$O—); (e) C$_6$ oxygen-containing linking groups include: 1-oxahexenyl(—O(CH$_2$)$_5$—), 2-oxahexenyl(—CH$_2$O(CH$_2$)$_4$—), 3-oxahexenyl (—(CH$_2$)$_2$O(CH$_2$)$_3$—), 4-oxahexenyl (—(CH$_2$)$_3$O(CH$_2$)$_2$—), 5-oxahexenyl(—(CH$_2$)$_4$OCH$_2$—), 6-oxahexenyl (—(CH$_2$)$_5$O—), 1,3-dioxahexenyl (—OCH$_2$O(CH$_2$)$_3$—), 1,4-dioxahexenyl (—O(CH$_2$)$_2$O(CH$_2$)$_2$—), 1,5-dioxahexenyl (—O(CH$_2$)$_3$OCH$_2$—), 1,6-dioxahexenyl (—O(CH$_2$)$_4$O—), 2,4-dioxahexenyl (—CH$_2$OCH$_2$O(CH$_2$)$_2$—), 2,5-dioxahexenyl (—CH$_2$O(CH$_2$)$_2$OCH$_2$—), 2,6-dioxahexenyl (—CH$_2$O(CH$_2$)$_3$O—), 3,5-dioxahexenyl (—(CH$_2$)$_2$OCH$_2$OCH$_2$—), 3,6-dioxahexenyl (—(CH$_2$)$_2$O(CH$_2$)$_2$O—), 4,6-dioxahexenyl (—(CH$_2$)$_3$OCH$_2$O—), 1,3,5-trioxahexenyl (—OCH$_2$OCH$_2$OCH$_2$—), 1,3,6-trioxahexenyl (—OCH$_2$O(CH$_2$)$_2$—), 1,4,6-trioxahexenyl (—O(CH$_2$)$_2$OCH$_2$O—), and 2,4,6-trioxahexenyl (—CH$_2$OCH$_2$OCH$_2$O—); (f) C$_7$ oxygen-containing linking groups include: 1-oxaheptenyl(—O(CH$_2$)$_6$—), 2-oxaheptenyl (—CH$_2$O(CH$_2$)$_5$—), 3-oxaheptenyl (—(CH$_2$)$_2$O(CH$_2$)$_4$—), 4-oxaheptenyl (—(CH$_2$)$_3$O(CH$_2$)$_3$—), 5-oxaheptenyl (—(CH$_2$)$_4$O(CH$_2$)$_2$—), 6-oxaheptenyl (—(CH$_2$)$_5$OCH$_2$—), 7-oxaheptenyl (—(CH$_2$)$_6$O—), 1,3-dioxaheptenyl (—OCH$_2$O(CH$_2$)$_4$—), 1,4-dioxaheptenyl (—O(CH$_2$)$_2$O(CH$_2$)$_3$—), 1,5-dioxaheptenyl(—O(CH$_2$)$_3$O(CH$_2$)$_2$—), 1,6-dioxaheptenyl(—O(CH$_2$)$_4$OCH$_2$—), 1,7-dioxaheptenyl (—O(CH$_2$)$_5$O—), 2,4-dioxaheptenyl (—CH$_2$OCH$_2$O(CH$_2$)$_3$—), 2,5-dioxaheptenyl (—CH$_2$O(CH$_2$)$_2$O(CH$_2$)$_2$—), 2,6-dioxaheptenyl (—CH$_2$O(CH$_2$)$_3$OCH$_2$—), 2,7-dioxaheptenyl (—CH$_2$O(CH$_2$)$_4$O—), 3,5-dioxaheptenyl (—(CH$_2$)$_2$OCH$_2$O(CH$_2$)$_2$—), 3,6-dioxaheptenyl (—(CH$_2$)$_2$O(CH$_2$)$_2$OCH$_2$—), 3,7-dioxaheptenyl (—(CH$_2$)$_2$O(CH$_2$)$_3$O—), 4,6-dioxaheptenyl (—(CH$_2$)$_3$OCH$_2$OCH$_2$—), 4,7-dioxaheptenyl (—(CH$_2$)$_3$O(CH$_2$)$_2$O—), 5,7-dioxaheptenyl (—(CH$_2$)$_4$OCH$_2$O—), 1,3,5-trioxaheptenyl (—OCH$_2$OCH$_2$O(CH$_2$)$_2$—), 1,3,6-trioxaheptenyl (—OCH$_2$O(CH$_2$)$_2$OCH$_2$—), 1,3,7-trioxaheptenyl (—OCH$_2$O(CH$_2$)$_3$O—), 1,4,6-trioxaheptenyl (—O(CH$_2$)$_2$OCH$_2$OCH$_2$—), 1,4,7-trioxaheptenyl (—O(CH$_2$)$_2$O(CH$_2$)$_2$O—), 1,5,7-trioxaheptenyl (—O(CH$_2$)$_3$OCH$_2$O—), 2,4,6-trioxaheptenyl (—CH$_2$OCH$_2$OCH$_2$OCH$_2$—), 2,4,7-trioxaheptenyl (—CH$_2$OCH$_2$O(CH$_2$)$_2$O—), 2,5,7-trioxaheptenyl (—CH$_2$O(CH$_2$)$_2$OCH$_2$O—), 3,5,7-trioxaheptenyl (—(CH$_2$)$_2$OCH$_2$OCH$_2$O—), and 1,3,5,7-tetraoxaheptenyl (—OCH$_2$OCH$_2$OCH$_2$O—); (g) C$_8$ oxygen-containing linking groups include: 1-oxaoctenyl (—O(CH$_2$)$_7$—), 2-oxaoctenyl (—CH$_2$O(CH$_2$)$_6$—), 3-oxaoctenyl(—(CH$_2$)$_2$O(CH$_2$)$_5$—), 4-oxaoctenyl(—(CH$_2$)$_3$O(CH$_2$)$_4$—), 5-oxaoctenyl(—(CH$_2$)$_4$O(CH$_2$)$_3$—), 6-oxaoctenyl (—(CH$_2$)$_5$O(CH$_2$)$_2$—), 7-oxaoctenyl (—(CH$_2$)$_6$OCH$_2$—), 8-oxaoctenyl (—(CH$_2$)$_7$O—), 1,3-dioxaoctenyl (—OCH$_2$O(CH$_2$)$_5$—), 1,4-dioxaoctenyl (—O(CH$_2$)$_2$O(CH$_2$)$_4$—), 1,5-dioxaoctenyl (—O(CH$_2$)$_3$O(CH$_2$)$_3$—), 1,6-dioxaoctenyl(—O(CH$_2$)$_4$O (CH$_2$)$_2$—), 1,7-dioxaoctenyl(—O(CH$_2$)$_5$OCH$_2$—), 1,8-dioxaoctenyl (—O(CH$_2$)$_6$O—), 2,4-dioxaoctenyl (—CH$_2$OCH$_2$O(CH$_2$)$_4$—), 2,5-dioxaoctenyl (—CH$_2$O (CH$_2$)$_2$O(CH$_2$)$_3$—), 2,6-dioxaoctenyl (—CH$_2$O(CH$_2$)$_3$O (CH$_2$)$_2$—), 2,7-dioxaoctenyl (—CH$_2$O(CH$_2$)$_4$OCH$_2$—), 2,8-dioxaoctenyl (—CH$_2$O(CH$_2$)$_5$O—), 3,5-dioxaoctenyl (—(CH$_2$)$_2$OCH$_2$O(CH$_2$)$_3$—), 3,6-dioxaoctenyl (—(CH$_2$)$_2$O (CH$_2$)$_2$O(CH$_2$)$_2$—), 3,7-dioxaoctenyl (—(CH$_2$)$_2$O(CH$_2$)$_3$ OCH$_2$—), 3,8-dioxaoctenyl (—(CH$_2$)$_2$O(CH$_2$)$_4$O—), 4,6-dioxaoctenyl (—(CH$_2$)$_3$OCH$_2$O(CH$_2$)$_2$—), 4,7-dioxaoctenyl (—(CH$_2$)$_3$O(CH$_2$)$_2$OCH$_2$—), 4,8-dioxaoctenyl (—(CH$_2$)$_3$O(CH$_2$)$_3$O—), 5,7-dioxaoctenyl (—(CH$_2$)$_4$ OCH$_2$OCH$_2$—), 5,8-dioxaoctenyl (—(CH$_2$)$_4$O(CH$_2$)$_2$O—), 6,8-dioxaoctenyl (—(CH$_2$)$_5$OCH$_2$O—), 1,3,5-trioxaoctenyl (—OCH$_2$OCH$_2$O(CH$_2$)$_3$—), 1,3,6-trioxaoctenyl (—OCH$_2$ O(CH$_2$)$_2$O(CH$_2$)$_2$—), 1,3,7-trioxaoctenyl (—OCH$_2$O(CH$_2$)$_3$OCH$_2$—), 1,3,8-trioxaoctenyl (—OCH$_2$O(CH$_2$)$_4$O—), 1,4,6-trioxaoctenyl (—O(CH$_2$)$_2$ OCH$_2$O(CH$_2$)$_2$—), 1,4,7-trioxaoctenyl (—O(CH$_2$)$_2$O(CH$_2$)$_2$ OCH$_2$—), 1,4,8-trioxaoctenyl (—O(CH$_2$)$_2$O(CH$_2$)$_3$ O—), 1,5,7-trioxaoctenyl (—O(CH$_2$)$_3$OCH$_2$OCH$_2$—), 1,5,8-trioxaoctenyl (—O(CH$_2$)$_3$O(CH$_2$)$_2$O—), 1,6,8-trioxaoctenyl (—O(CH$_2$)$_4$OCH$_2$O—), 2,4,6-trioxaoctenyl (—CH$_2$OCH$_2$OCH$_2$O(CH$_2$)$_2$—), 2,4,7-trioxaoctenyl (—CH$_2$OCH$_2$O(CH$_2$)$_2$OCH$_2$—), 2,4,8-trioxaoctenyl (—CH$_2$OCH$_2$O(CH$_2$)$_3$O—), 2,5,7-trioxaoctenyl (—CH$_2$O (CH$_2$)$_2$OCH$_2$OCH$_2$—), 2,5,8-trioxaoctenyl (—CH$_2$O (CH$_2$)$_2$ O(CH$_2$)$_2$O—), 2,6,8-trioxaoctenyl (—CH$_2$O(CH$_2$)$_3$ OCH$_2$O—), 3,5,7-trioxaoctenyl (—(CH$_2$)$_2$ OCH$_2$OCH$_2$OCH$_2$—), 3,5,8-trioxaoctenyl (—(CH$_2$)$_2$ OCH$_2$O(CH$_2$)$_2$O—), 4,6,8-trioxaoctenyl (—(CH$_2$)$_3$ OCH$_2$OCH$_2$O—), 1,3,5,7-tetraoxaoctenyl (—OCH$_2$ OCH$_2$OCH$_2$OCH$_2$—), 1,3,5,8-tetraoxaoctenyl(—OCH$_2$ OCH$_2$OCH$_2$)$_2$O—), 1,4,6,8-tetraoxaoctenyl(—O(CH$_2$)$_2$ OCH$_2$OCH$_2$O—), and 2,4,6,8-tetraoxaoctenyl (—CH$_2$OCH$_2$OCH$_2$OCH$_2$O—); (h) higher alkenyloxy linking groups, and/or (i) mixtures and combinations thereof.

In certain embodiments, the Z group may be a —R$^f$N(R$^4$) R$^g$— group, a —R$^f$N$^+$(R$^4$R$^5$A$^-$)R$^g$— group, an —R$^f$C(R$^6$) (N(R$^4$R$^5$))R$^g$— group, an —R$^f$C(R$^6$)(N(R$^4$R$^5$R$^7$A$^-$))R$^g$— group, an —R$^f$C(R$^6$)(R$^h$N(R$^4$R$^5$))R$^g$— group, or an —R$^f$C (R$^6$)(R$^h$N(R$^4$R$^5$R$^7$A$^-$))R$^g$— group, wherein (a) the R$^4$, R$^5$, R$^6$, and R$^7$ groups are independently hydrocarbyl groups or heterohydrocarbyl group, (b) the R$^f$ and R$^g$ groups may independently be C$_1$-C$_3$ alkenyl linking group, and (c) the A$^-$ group is an acceptable counterion. In other embodiments, the Z group may be is a -G$^1$-J-G$^2$-group, wherein (a) the J group may be an arylene group or a heteroarylene group, (b) the G$^1$ and G$^2$ groups may independently be an —R$^g$—(R$^8$) N— group, an —R$^f$—(R$^8$)N—R$^g$— group, an —R$^f$—O— group, an —R$^f$—O—R$^g$— group, an —C(=O)— group, an —C(=O)—R$^g$— group, an —C(=O)N(R$^8$)— group, an —C(=O)N(R$^8$)—R$^g$— group, an —C(=O)O— group, an —C(=O)O—R$^g$— group, an —R$^f$(R$^8$)NC(=O)— group, an —R$^f$—(R$^8$)NC(=O)—R$^g$— group, an —R$^f$—(R$^8$)NC (=O)N(R$^8$)— group, an —R$^f$—(R$^8$)NC(=O)N(R$^8$)—R$^g$— group, an —R$^f$—(R$^8$)NC(=O)O— group, an —R$^f$—(R$^8$) NC(=O)O—R$^g$— group, an —R$^f$—OC(=O)— group, an —R$^f$—OC(=O)—R$^g$— group, an —R$^f$—OC(=O)N(R$^8$)— group, an —R$^f$—OC(=O)N(R$^8$)—R$^g$— group, an —R$^f$— OC(=O)O— group, or an —R$^f$—OC(=O)O—R$^g$— group, (c) the R$^f$ and R$^g$ groups may independently be C$_1$-C$_3$ alkenyl linking group, (d) the R$^8$ group may a hydrogen atom or a C$_1$-C$_8$ hydrocarbyl group, and (e) the A$^-$ group is an acceptable counterion.

In other embodiments, the Z group may be derived from a heterohydrocarbyl group include, without limitation, pyrrole-2,3-dicarboxylic acid, pyridine-2,3-dicarboxylic acid, pyridine-2,4-dicarboxylic acid, pyridine-2,5-dicarboxylic acid, pyridine-3,4-dicarboxylic acid, pyridine-2,4-dicarboxylic acid, pyridine-2,5-dicarboxylic acid, pyridine-2,6-dicarboxylic acid, pyridine-3,4-dicarboxylic acid, pyridine-3,5-dicarboxylic acid, or other heterohydrocarbyl groups. In other embodiments, the Z group may be derived from a hydrocarbyl group include, without limitation, 1-amino-benzene-2,4-dicarboxylic acid, 1-amino-benzene-2,5-dicarboxylic acid, 1-amino-benzene-2,6-dicarboxylic acid, 1-amino-benzene-3,4-dicarboxylic acid, 1-amino-benzene-3,5-dicarboxylic acid, 1,2,3-trihydroxybenzene, 1,2,4-trihydroxybenzene, 1,2,5-trihydroxybenzene, 1,3,4-trihydroxybenzene, 1,3,5-trihydroxybenzene, 1-amino-2,3-dihydroxybenzene, 1-amino-2,4-dihydroxybenzene, 1-amino-2,5-dihydroxybenzene, 1-amino-3,4-dihydroxybenzene, 1-amino-3,5-dihydroxybenzene, orthoformic acid, glycerol, 2-amino-1,3-dihydroxypropane, diethanolamine, N-methyldiethanolamine, dipropanolamine, N-methyldipropanolamine, diisopropanolamine, N-methyldiisopropanolamine, higher dialkanolamines, higher N-methyl dialkanolamines, or other hydrocarbyl groups.

In certain embodiments, when present and not a hydrogen atom, the R$^1$, R$^2$, R$^3$, R$^4$, R$^5$, R$^6$, R$^7$, and R$^8$ group may independently be either unsubstituted or substituted with one or more substituents selected from the group consisting of an alkyl group, an aryl group, an aralkyl group, a cycloalkyl group, a cycloalkylalkyl group, a heterocyclyl group, a heterocyclylalkyl group, a heterocyclylaryl group, a hydroxy group, an alkoxy group, an azido group, a haloalkoxy group, a hydroxyalkyl group, an aryloxy group, a hydroxyaryl group, an alkoxyaryl group, a halogen atom, a haloalkyl group, a haloaryl group, an amino group, an alkylamino group, a dialkylamino group, an arylamino group, a diarylamino group, an —NHC(=O)(alkyl) group, an —NHC(=O)(aryl) group, an —NHC(=O)(aralkyl) group, an —NHC(=O)(haloalkyl) group, an —NHSO$_2$ (alkyl) group, an —NHSO$_2$(aryl) group, an —NHSO$_2$(aralkyl) group, an alkoxycarbonyl group, an alkoxycarbonylalkyl group, an —OC(=O)(alkylamino) group, and an —OC (=O)(dialkylamino) group.

Specific Integrin Activating Compounds or Agonists Classes R$^a$ZR$^b$=(OCH$_2$)$_n$N(CH$_3$)(CH$_2$O) Class Agonists In certain embodiments, the integrin activating compounds comprise one or more compound of Formula (I), wherein the R$^a$ZR$^b$ group comprises —(OCH$_2$)$_n$N(CH$_3$) (CH$_2$O)$_n$—, wherein n is an integer between 1 and 6. In other embodiments, the integrin activating compounds comprise one or more of the following integrin activating compound: (a) 3-oxo-1-(2-thienyl)-2-(2-thienylmethyl)-4-oxa-2,6-diaza-6-methyl-heptan-7-yl-bis(2-thienylmethyl) carbamate or 3,9-dioxo-1,11-bis(2-thienyl)-2,10-bis(2-thienylmethyl)-4,8-dioxa-2,6,10-triaza-6-methyl-undecane, (b) 3-oxo-1-(2-thienyl)-2-(2-thienylmethyl)-4,6,10-trioxa-2,8-diaza-8-methyl-undecan-11-yl-bis(2-thienylmethyl)carbamate or 3,13-dioxo-1,15-bis(2-thienyl)-2,14-bis(2-thienylmethyl)-4,6,10,12-tetraoxa-2,8,14-triaza-8-methyl-pentadecane, (c) 3-oxo-1-(2-thienyl)-2-(2-thienylmethyl)-4,6,8,12, 14-pentaoxa-2,10-diaza-10-methyl-pentadecan-15-yl-bis(2-thienylmethyl)carbamate or 3,17-dioxo-1,19-bis(2-thienyl)-2,18-bis(2-thienylmethyl)-4,6,8,12,14,16-hexaoxa-2,10,18-triaza-10-methyl-nonadecane, (d) 3-oxo-1-(3-methoxyphenyl)-2-(3-methoxybenzyl)-4-oxa-2,6-diaza-6-methyl-heptan-7-yl-bis(3-methoxybenzyl)carbamate or 3,9-dioxo-1,11-bis(3-methoxyphenyl)-2,10-bis(3-methoxybenzyl)-4,8-dioxa-2,6,10-triaza-6-methyl-undecane, (e) 3-oxo-1-(3-methoxyphenyl)-2-(3-methoxybenzyl)-4,6,10-trioxa-2,8-diaza-8-methyl-undecan-11-yl-bis(3-methoxybenzyl)carbamate or 3,13-dioxo-1,15-bis(3-methoxyphenyl)-2,14-bis(3-methoxybenzyl)-4,6,10,12-tetraoxa-2,8,14-triaza-8-methyl-pentadecane, (f) 3-oxo-1-(3-methoxyphenyl)-2-(3-methoxybenzyl)-4,6,8,12,14-pentaoxa-2,10-diaza-10-methyl-pentadecan-15-yl-bis(3-methoxybenzyl)carbamate or 3,17-dioxo-1,19-bis(2-thienyl)-2,18-bis(3-methoxybenzyl)-4,6,8,12,14,16-hexaoxa-2,10,18-triaza-10-methyl-nonadecane, (g) 3-oxo-1-(3-methoxyphenyl)-2-(4-dimethylaminobenzyl)-4-oxa-2,6-diaza-6-methyl-heptan-7-yl-(3-methoxybenzyl)(4-dimethylaminobenzyl)carbamate or 3,9-dioxo-1,11-bis(3-methoxyphenyl)-2,10-bis(3-methoxybenzyl)-4,8-dioxa-2,6,10-triaza-6-methyl-undecane, (h) 3-oxo-1-(3-methoxyphenyl)-2-(4-dimethylaminobenzyl)-4,6,10-trioxa-2,8-diaza-8-methyl-undecan-11-yl-(3-methoxybenzyl)(4-dimethylaminobenzyl)carbamate or 3,13-dioxo-1,15-bis(3-methoxyphenyl)-2,14-bis(3-methoxybenzyl)-4,6,10,12-tetraoxa-2,8,14-triaza-8-methyl-pentadecane, (i) 3-oxo-1-(3-methoxyphenyl)-2-(4-dimethylaminobenzyl)-4,6,8,12,14-pentaoxa-2,10-diaza-10-methyl-pentadecan-15-yl-(3-methoxybenzyl)(4-dimethylaminobenzyl)carbamate or 3,17-dioxo-1,19-bis(2-thienyl)-2,18-bis(3-methoxybenzyl)-4,6,8,12,14,16-hexaoxa-2,10,18-triaza-10-methyl-nonadecane, (j) 3-oxo-1-(4-methoxyphenyl)-2-(4-methoxybenzyl)-4-oxa-2,6-diaza-6-methyl-heptan-7-yl-bis(4-methoxybenzyl)carbamate or 3,9-dioxo-1,11-bis(4-methoxyphenyl)-2,10-bis(4-methoxybenzyl)-4,8-dioxa-2,6,10-triaza-6-methyl-undecane, (k) 3-oxo-1-(4-methoxyphenyl)-2-(4-methoxybenzyl)-4,6,10-trioxa-2,8-diaza-8-methyl-undecan-11-yl-bis(4-methoxybenzyl)carbamate or 3,13-dioxo-1,15-bis(4-methoxyphenyl)-2,14-bis(4-methoxybenzyl)-4,6,10,12-tetraoxa-2,8,14-triaza-8-methyl-pentadecane, (l) 3-oxo-1-(4-methoxyphenyl)-2-(4-methoxybenzyl)-4,6,8,12,14-pentaoxa-2,10-diaza-10-methyl-pentadecan-15-yl-bis(4-methoxybenzyl)carbamate or 3,17-dioxo-1,19-bis(4-methoxyphenyl)-2,18-bis(4-methoxybenzyl)-4,6,8,12,14,16-hexaoxa-2,10,18-triaza-10-methyl-nonadecane, (m) 3-oxo-1-(4-methoxyphenyl)-2-(4-dimethylaminobenzyl)-4-oxa-2,6-diaza-6-methyl-heptan-7-yl-(4-methoxybenzyl)(4-dimethylaminobenzyl)carbamate or 3,9-dioxo-1,11-bis(4-methoxyphenyl)-2,10-bis(4-methoxybenzyl)-4,8-dioxa-2,6,10-triaza-6-methyl-undecane, (n) 3-oxo-1-(4-methoxyphenyl)-2-(4-dimethylaminobenzyl)-4,6,10-trioxa-2,8-diaza-8-methyl-undecan-11-yl-(4-methoxybenzyl)(4-dimethylaminobenzyl)carbamate or 3,13-dioxo-1,15-bis(4-methoxyphenyl)-2,14-bis(4-methoxybenzyl)-4,6,10,12-tetraoxa-2,8,14-triaza-8-methyl-pentadecane, (o) 3-oxo-1-(4-methoxyphenyl)-2-(4-dimethylaminobenzyl)-4,6,8,12,14-pentaoxa-2,10-diaza-10-methyl-pentadecan-15-yl-(4-methoxybenzyl)(4-dimethylaminobenzyl)carbamate or 3,17-dioxo-1,19-bis(2-thienyl)-2,18-bis(4-methoxybenzyl)-4,6,8,12,14,16-hexaoxa-2,10,18-triaza-10-methyl-nonadecane, (p) N-methylbis[(9-carbazolylcarbonyloxy)methyl]amine, (q) N-methylbis{[(9-carbazolylcarbonyloxy)methoxy]methyl}amine, (r) N-methylbis({[(9-carbazolylcarbonyloxy)methoxy]methoxy}methyl)amine, (s) N-methylbis[(3,6-dimethoxy-9-carbazolylcarbonyloxy)methyl]amine, (t) N-methylbis{[(3,6-dimethoxy-9-carbazolylcarbonyloxy)methoxy]methyl}amine, (u) N-methylbis({[(3,6-dimethoxy-9-carbazolylcarbonyloxy)methoxy]methoxy}methyl)amine, (v) higher analogs, or (w) mixtures and combinations thereof.

In other embodiments, the integrin activating compounds comprise one or more of the following integrin activating compound: (a) 3-oxo-1-(2-thienyl)-2-(2-thienylmethyl)-4-oxa-2,7-diaza-7-methyl-nonan-9-yl-bis(2-thienylmethyl) carbamate or 3,11-dioxo-1,13-bis(2-thienyl)-2,11-bis(2-thienylmethyl)-4,10-dioxa-2,6,12-triaza-7-methyl-tridecane, (b) 3-oxo-1-(2-thienyl)-2-(2-thienylmethyl)-4,7,13-trioxa-2,10-diaza-10-methyl-pentadecan-15-yl-bis(2-thienylmethyl) carbamate, (c) 3-oxo-1-(2-thienyl)-2-(2-thienylmethyl)-4,7,10,16,19-pentaoxa-2,13-diaza-13-methyl-heneicosan-21-yl-bis(2-thienylmethyl)carbamate, (d) 3-oxo-1-(3-methoxyphenyl)-2-(3-methoxybenzyl)-4-oxa-2,7-diaza-7-methyl-nonan-9-yl-bis(3-methoxybenzyl)carbamate, (e) 3-oxo-1-(3-methoxyphenyl)-2-(3-methoxybenzyl)-4,7,13-trioxa-2,10-diaza-10-methyl-pentadecan-15-yl-bis(3-methoxybenzyl)carbamate, (f) 3-oxo-1-(3-methoxyphenyl)-2-(3-methoxybenzyl)-4,7,10,16,19-pentaoxa-2,13-diaza-13-methyl-heneicosan-21-yl-bis(3-methoxybenzyl)carbamate, (g) 3-oxo-1-(3-methoxyphenyl)-2-(4-dimethylaminobenzyl)-4-oxa-2,7-diaza-7-methyl-nonan-9-yl-(3-methoxybenzyl)(4-dimethylaminobenzyl)carbamate, (h) 3-oxo-1-(3-methoxyphenyl)-2-(4-dimethylaminobenzyl)-4,7,13-trioxa-2,10-diaza-10-methyl-pentadecan-15-yl-(3-methoxybenzyl)(4-dimethylaminobenzyl)carbamate, (i) 3-oxo-1-(3-methoxyphenyl)-2-(4-dimethylaminobenzyl)-4,7,10,16,19-pentaoxa-2,13-diaza-13-methyl-heneicosan-21-yl-(3-methoxybenzyl)(4-dimethylaminobenzyl)carbamate, (j) 3-oxo-1-(4-methoxyphenyl)-2-(4-methoxybenzyl)-4-oxa-2,7-diaza-7-methyl-nonan-9-yl-bis(4-methoxybenzyl)carbamate, (k) 3-oxo-1-(4-methoxyphenyl)-2-(4-methoxybenzyl)-4,7,13-trioxa-2,10-diaza-10-methyl-pentadecan-15-yl-bis(4-methoxybenzyl)carbamate, (l) 3-oxo-1-(4-methoxyphenyl)-2-(4-methoxybenzyl)-4,7,10,16,19-pentaoxa-2,13-diaza-13-methyl-heneicosan-21-yl-bis(4-methoxybenzyl)carbamate, (m) 3-oxo-1-(4-methoxyphenyl)-2-(4-dimethylaminobenzyl)-4-oxa-2,7-diaza-7-methyl-nonan-9-yl-(4-methoxybenzyl)(4-dimethylaminobenzyl) carbamate, (n) 3-oxo-1-(4-methoxyphenyl)-2-(4-dimethylaminobenzyl)-4,7,13-trioxa-2,10-diaza-10-methyl-pentadecan-15-yl-(4-methoxybenzyl)(4-dimethylaminobenzyl)carbamate, (o) 3-oxo-1-(4-methoxyphenyl)-2-(4-dimethylaminobenzyl)-4,7,10,16,19-pentaoxa-2,13-diaza-13-methyl-heneicosan-21-yl-(4-methoxybenzyl)(4-dimethylaminobenzyl)carbamate, (p) 2-{[2-(9H-carbazol-9-ylcarbonyloxy)ethyl]-N-methylamino}ethyl 9H-carbazole-9-carboxylate, (q) 2-[2-({2-[2-(9H-carbazol-9-ylcarbonyloxy)ethoxy]ethyl}-N-methylamino)ethoxy] ethyl 9H-carbazole-9-carboxylate, (r) 2-(2-{2-[(2-{2-[2-(9-carbazolylcarbonyloxy)ethoxy]ethoxy}ethyl)-N-methylamino]ethoxy}ethoxy)ethyl 9-carbazolecarboxylate, (s) 2-{[2-(3,6-dimethoxy-9H-carbazol-9-ylcarbonyloxy)ethyl]-N-methylamino}ethyl 3,6-dimethoxy-9H-carbazole-9-carboxylate, (t) 2-[2-({2-[2-(3,6-dimethoxy-9H-carbazol-9-ylcarbonyloxy)ethoxy]ethyl}-N-methylamino)ethoxy]ethyl 3,6-dimethoxy-9H-carbazole-9-carboxylate, (u) 2-(2-{2-[(2-{2-[2-(3,6-dimethoxy-9-carbazolylcarbonyloxy)ethoxy]ethoxy}ethyl)-N-methylamino]ethoxy}ethoxy)ethyl 3,6-dimethoxy-9-carbazolecarboxylate, (v) higher analogs, or (w) mixtures and combinations thereof.

$R^a$ and $R^b$=$(OCH_2)_n$ or $(CH_3)(CH_2O)_n$ and Z=2,6-Dihydroxy Pyridine Class Agonists In certain embodiments, the integrin activating compounds comprise one or more compound of Formula (I), wherein the $R^a$ and $R^b$ group comprises $(OCH_2)_n$ or $(OCH_2CH_2)_n$, wherein n is an integer between 1 and 6 and Z is derived from 2,6-dihydroxypyridine. In other embodiments, the integrin activating compounds comprise one or more of the following integrin activating compound: (a) 2-[bis(thenyl)aminocarbonyloxy],6-[bis(thenyl)aminocarbonyloxy]pyridine, (b) 2-[bis(3-methoxybenzyl)aminocarbonyloxy],6-[bis(3-methoxybenzyl)aminocarbonyloxy]pyridine, (c) 2-[(3-methoxybenzyl)(4-dimethylaminobenzyl)

aminocarbonyloxy],6-[(3-methoxybenzyl)(4-dimethylaminobenzyl)aminocarbonyloxy]pyridine, (d) 2-[bis(4-methoxybenzyl)aminocarbonyloxy],6-[bis(4-methoxybenzyl)aminocarbonyloxy]pyridine, (e) 2-[(4-methoxybenzyl)(4-dimethylaminobenzyl)aminocarbonyloxy],6-[(4-methoxybenzyl)(4-dimethylaminobenzyl)aminocarbonyloxy]pyridine, (f) 6-(9H-carbazol-9-ylcarbonyloxy)-2-pyridyl 9H-carbazole-9-carboxylate, (g) 6-(3,6-dimethoxy-9H-carbazol-9-ylcarbonyloxy)-2-pyridyl 3,6-dimethoxy-9H-carbazole-9-carboxylate, or (h) mixtures and combinations thereof. In other embodiments, the integrin activating compounds comprise one or more of the following integrin activating compound: (a) 2-[bis(thenyl)aminocarbonyloxymethoxy],6-[bis(thenyl)amino carbonyloxymethoxy]pyridine, (b) 2-[bis(thenyl)aminocarbonyloxymethoxymethoxy], 6-[bis(thenyl)aminocarbonyloxymethoxymethoxy]pyridine, (c) 2-[bis(3-methoxybenzyl) aminocarbonyloxymethoxy],6-[bis(3-methoxybenzyl)aminocarbonyloxymethoxy]pyridine, (d) 2-[bis(3-methoxybenzyl)aminocarbonyloxymethoxymethoxy],6-[bis(3-methoxybenzyl)amino carbonyloxymethoxyemthyloxy] pyridine, (e) 2-[(3-methoxybenzyl)(4-dimethylaminobenzyl) aminocarbonyloxymethoxy],6-[(3-methoxybenzyl)(4-dimethylaminobenzyl)aminocarbonyloxy methoxy]pyridine, (f) 2-[(3-methoxybenzyl)(4-dimethylaminobenzyl) aminocarbonyloxymethoxy methoxy],6-[(3-methoxybenzyl)(4-dimethylaminobenzyl)aminocarbonyloxy methoxymethoxy] pyridine, (g) 2-[bis(4-methoxybenzyl)aminocarbonyloxymethoxy],6-[bis(4-methoxybenzyl)aminocarbonyloxymethoxy]pyridine, (h) 2-[bis(4-methoxybenzyl)aminocarbonyloxymethoxymethoxy],6-[bis(4-methoxybenzyl) aminocarbonyloxymethoxymethoxy] pyridine, (i) 2-[(4-methoxybenzyl)(4-dimethylaminobenzyl)aminocarbonyloxymethoxy], 6-[(4-methoxybenzyl)(4-dimethylaminobenzyl)aminocarbonyloxymethoxy]pyridine, (j) 2-[(4-methoxybenzyl)(4-dimethylaminobenzyl)aminocarbonyloxymethoxymethoxy], 6-[(4-methoxybenzyl)(4-dimethylaminobenzyl)aminocarbonyloxymethoxymethoxy]pyridine, (k) 2-{6-[2-(9H-carbazol-9-ylcarbonyloxy)methoxy]-2-pyridyloxy}methyl 9H-carbazole-9-carboxylate, (l) 2-[2-(6-{2-[2-(9-carbazolylcarbonyloxy)methoxy]methoxy}-2-pyridyloxy)methoxy]methyl 9-carbazolecarboxylate, (m) 2-{6-[2-(3,6-dimethoxy-9H-carbazol-9-ylcarbonyloxy)methoxy]-2-pyridyloxy}methyl 3,6-dimethoxy-9H-carbazole-9-carboxylate, (n) 2-[2-(6-{2-[2-(3,6-dimethoxy-9-carbazolylcarbonyloxy)methoxy]methoxy}-2-pyridyloxy)methoxy]methyl 3,6-dimethoxy-9-carbazolecarboxylate, (o) higher analogs, or (p) mixtures and combinations thereof. In other embodiments, the integrin activating compounds comprise one or more of the following integrin activating compound: (a) 2-[bis(thenyl)aminocarbonyloxyethoxy],6-[bis(thenyl) amino carbonyloxyethoxy]pyridine, (b) 2-[bis(thenyl)aminocarbonyloxyethoxyethoxy], 6-[bis(thenyl)aminocarbonyloxyethoxy ethoxy]pyridine, (c) 2-[bis(3-methoxybenzyl) aminocarbonyloxyethoxy],6-[bis(3-methoxybenzyl)aminocarbonyloxy ethoxy]pyridine, (d) 2-[bis(3-methoxybenzyl) aminocarbonyloxyethoxyethoxy],6-[bis(3-methoxybenzyl) aminocarbonyloxyethoxyethoxy] pyridine, (e) 2-[(3-methoxybenzyl)(4-dimethylaminobenzyl) aminocarbonyloxyethoxy],6-[(3-methoxybenzyl)(4-dimethylaminobenzyl) aminocarbonyloxyethoxy]pyridine, (f) 2-[(3-methoxybenzyl)(4-dimethylaminobenzyl) aminocarbonyloxyethoxyethoxy],6-[(3-methoxybenzyl)(4-dimethylaminobenzyl) aminocarbonyloxyethoxyethoxy]pyridine, (g) 2-[bis(4-methoxybenzyl) aminocarbonyloxyethoxy],6-[bis(4-methoxybenzyl)aminocarbonyloxyethoxy]pyridine, (h) 2-[bis(4-methoxybenzyl)aminocarbonyloxyethoxyethoxy], 6-[bis(4-methoxybenzyl)aminocarbonyloxyethoxyethoxy] pyridine, (i) 2-[(4-methoxybenzyl)(4-dimethyl aminobenzyl)aminocarbonyloxyethoxy],6-[(4-methoxybenzyl)(4-dimethylaminobenzyl)aminocarbonyloxyethoxy]pyridine, (j) 2-[(4-methoxybenzyl)(4-dimethylaminobenzyl)aminocarbonyloxyethoxyethoxy],6-[(4-methoxybenzyl)(4-dimethylaminobenzyl)aminocarbonyloxyethoxyethoxy]pyridine, (k) 2-{6-[2-(9H-carbazol-9-ylcarbonyloxy)ethoxy]-2-pyridyloxy}ethyl 9H-carbazole-9-carboxylate, (l) 2-[2-(6-{2-[2-(9-carbazolylcarbonyloxy) ethoxy]ethoxy}-2-pyridyloxy) ethoxy]ethyl 9-carbazolecarboxylate, (m) 2-{6-[2-(3,6-dimethoxy-9H-carbazol-9-ylcarbonyloxy)ethoxy]-2-pyridyloxy}ethyl 3,6-dimethoxy-9H-carbazole-9-carboxylate, (n) 2-[2-(6-{2-[2-(3,6-dimethoxy-9-carbazolylcarbonyloxy) ethoxy]ethoxy}-2-pyridyloxy)ethoxy]ethyl 3,6-dimethoxy-9-carbazolecarboxylate, (o) higher analogs, or (p) mixtures and combinations thereof.

$R^a$ and $R^b$=$(OCH_2)_n$ or $CH_3)(CH_2O)_n$ and Z=2,6-Dimethanol Pyridine Class Agonists In certain embodiments, the integrin activating compounds comprise one or more compound of Formula (I), wherein the $R^a$ and $R^b$ group comprises $(OCH_2)_n$ or $(OCH_2CH_2)_n$, wherein n is an integer between 1 and 6 and Z is derived from 2,6-dimethanolpyridine. In other embodiments, the integrin activating compounds comprise one or more of the following integrin activating compound: (a) 2-({bis[(2-thienyl)methyl]aminocarbonyloxy}methyl)-6-({bis[(2-thienyl)methyl]aminocarbonyloxy}methyl)pyridine, (b) 2-({bis(3-methoxybenzyl)aminocarbonyloxy}methyl)-6-({bis(3-methoxybenzyl)aminocarbonyloxy}methyl)pyridine, (c) 2-(3-methoxybenzyl,4-dimethylaminobenzyl)aminocarbonyloxy}methyl)-6-(3-methoxybenzyl,4-dimethylamino benzyl)aminocarbonyloxy}methyl) pyridine, (d) 2-({bis(4-methoxybenzyl)aminocarbonyloxy}methyl)-6-({bis(4-methoxybenzyl)aminocarbonyloxy}methyl)pyridine, (e) 2-(4-methoxybenzyl,4-dimethylaminobenzyl)aminocarbonyloxy}methyl)-6-(4-methoxybenzyl,4-dimethylaminobenzyl) aminocarbonyloxy}methyl) pyridine, (f) {6-[(9H-carbazol-9-ylcarbonyloxy)methyl]-2-pyridyl}methyl 9H-carbazole-9-carboxylate, (g) {6-[(3,6-dimethoxy-9H-carbazol-9-ylcarbonyloxy)methyl]-2-pyridyl}methyl 3,6-dimethoxy-9H-carbazole-9-carboxylate, or (h) mixtures and combinations thereof. In other embodiments, the integrin activating compounds comprise one or more of the following integrin activating compound: (a) 2-{bis[(2-thienyl)methyl]aminocarbonyloxy}methoxy)methyl]-6-{bis[(2-thienyl)methyl]aminocarbonyloxy}methoxy)methyl]pyridine, (b) 2-{bis[(2-thienyl)methyl]aminocarbonyloxy}methoxymethoxy)methyl]-6-{bis[(2-thienyl)methyl]aminocarbonyloxy}methoxymethoxy)methyl]pyridine, (c) 2-{bis(3-methoxy benzyl)aminocarbonyloxy}methoxy)methyl]-6-{bis(3-methoxybenzyl)aminocarbonyloxy}methoxy) methyl]pyridine, (d) 2-{bis(3-methoxybenzyl)amino- carbonyloxy}methoxymethoxy)methyl]-6-{bis(3-methoxybenzyl)aminocarbonyloxy}methoxymethoxy) methyl]pyridine, (e) 2-(3-methoxybenzyl,4-dimethylaminobenzyl)aminocarbonyloxy}methoxy) methyl]-6-(3-methoxybenzyl,4-dimethylaminobenzyl)aminocarbonyloxy}methoxy)methyl]pyridine, (f) 2-(3-methoxybenzyl,4-dimethylaminobenzyl) aminocarbonyloxy}methoxymethoxy)methyl]-6-(3-methoxybenzyl,4-dimethylaminobenzyl)aminocarbonyloxy}methoxyemthoxy)methyl]pyridine, (g) 2-{bis(4-methoxybenzyl)aminocarbonyloxy}methoxy)methyl]-6-{bis(4-methoxybenzyl) aminocarbonyloxy}methoxy)methyl]pyridine, (h) 2-{bis(4-methoxybenzyl) aminocarbonyloxy}methoxymethoxy)methyl]-6-{bis(4-methoxybenzyl) aminocarbonyloxy}methoxymethoxy)methyl]pyridine, (i)

2-(4-methoxybenzyl,4-dimethylaminobenzyl) aminocarbonyloxy}methoxy)methyl]-6-(4-methoxybenzyl,4-dimethylaminobenzyl)amino carbonyloxy}methoxy)methyl]pyridine, (j) 2-(4-methoxybenzyl,4-dimethylaminobenzyl) amino carbonyloxy}methoxyemthoxy)methyl]-6-(4-methoxybenzyl,4-dimethylaminobenzyl)amino carbonyloxy}methoxymethoxy)methyl]pyridine, (k) 2-[(6-{[2-(9H-carbazol-9-ylcarbonyloxy)methoxy]methyl}-2-pyridyl)methoxy]ethyl 9H-carbazole-9-carboxylate, (l) 2-(2-{[6-({2-[2-(9H-carbazolyl carbonyloxy)methoxy]methoxy}methyl)-2-pyridyl]methoxy}ethoxy)ethyl 9-carbazolecarboxylate, (m) 2-[(6-{[2-(3,6-dimethoxy-9H-carbazol-9-ylcarbonyloxy)methoxy]methyl}-2-pyridyl)methoxy]ethyl 3,6-dimethoxy-9H-carbazole-9-carboxylate, (n) 2-(2-{[6-({2-[2-(3,6-dimethoxy-9H-carbazolylcarbonyloxy)methoxy]methoxy}methyl)-2-pyridyl]methoxy}methoxy)ethyl 3,6-dimethoxy-9-carbazolecarboxylate, (o) higher analogs, or (p) mixtures and combinations thereof. In other embodiments, the integrin activating compounds comprise one or more of the following integrin activating compound: (a) 2-{bis[(2-thienyl)methyl]aminocarbonyloxy}ethoxy)methyl]-6-{bis[(2-thienyl)methyl]aminocarbonyloxy}ethoxy)methyl]pyridine, (b) 2-{bis[(2-thienyl)methyl]aminocarbonyloxy} ethoxyethoxy)methyl]-6-{bis[(2-thienyl)methyl]aminocarbonyloxy}ethoxyethoxy)methyl]pyridine, (c) 2-{bis(3-methoxybenzyl)aminocarbonyloxy}ethoxy)methyl]-6-{bis(3-methoxybenzyl)amino carbonyloxy}ethoxy)methyl]pyridine, (d) 2-{bis(3-methoxybenzyl)aminocarbonyloxy}ethoxyethoxy)methyl]-6-{bis(3-methoxybenzyl)aminocarbonyloxy}ethoxyethoxy)methyl]pyridine, (e) 2-(3-methoxybenzyl,4-dimethylaminobenzyl)aminocarbonyloxy}ethoxy)methyl]-6-(3-methoxybenzyl,4-dimethylaminobenzyl)aminocarbonyloxy}ethoxy)methyl]pyridine, (f) 2-(3-methoxybenzyl,4-dimethylaminobenzyl)aminocarbonyloxy}ethoxyethoxy)methyl]-6-(3-methoxybenzyl,4-dimethylaminobenzyl)aminocarbonyloxy}ethoxyethoxy)methyl]pyridine, (g) 2-{bis(4-methoxybenzyl)aminocarbonyloxy}ethoxy)methyl]-6-{bis(4-methoxybenzyl)aminocarbonyloxy}ethoxy)methyl]pyridine, (h) 2-{bis(4-methoxybenzyl)aminocarbonyloxy}ethoxyethoxy)methyl]-6-{bis(4-methoxybenzyl)aminocarbonyloxy}ethoxyethoxy)methyl]pyridine, (i) 2-(4-methoxybenzyl,4-dimethylaminobenzyl)aminocarbonyloxy}ethoxy)methyl]-6-(4-methoxybenzyl,4-dimethylaminobenzyl)aminocarbonyloxy}ethoxy)methyl]pyridine, (j) 2-(4-methoxybenzyl,4-dimethylaminobenzyl)aminocarbonyloxy}ethoxyethoxy)methyl]-6-(4-methoxybenzyl,4-dimethylaminobenzyl)aminocarbonyloxy}ethoxyethoxy)methyl]pyridine, (k) 2-[(6-{[2-(9H-carbazol-9-ylcarbonyloxy)ethoxy]methyl}-2-pyridyl)methoxy]ethyl 9H-carbazole-9-carboxylate, (l) 2-(2-{[6-({2-[2-(9H-carbazolylcarbonyloxy)ethoxy]ethoxy}methyl)-2-pyridyl]methoxy}ethoxy)ethyl 9-carbazolecarboxylate, (m) 2-[(6-{[2-(3,6-dimethoxy-9H-carbazol-9-ylcarbonyloxy)ethoxy]methyl}-2-pyridyl)methoxy]ethyl 3,6-dimethoxy-9H-carbazole-9-carboxylate, (n) 2-(2-{[6-({2-[2-(3,6-dimethoxy-9H-carbazolyl carbonyloxy)ethoxy]ethoxy}methyl)-2-pyridyl]methoxy}ethoxy)ethyl 3,6-dimethoxy-9-carbazolecarboxylate, (o) higher analogs, or (p) mixtures and combinations thereof.

$R^a$ and $R^b$=$(OCH_2)_n$ or $CH_3)(CH_2O)_n$ and Z=3,5-Dihydroxy Pyridine Class Agonists In certain embodiments, the integrin activating compounds comprise one or more compound of Formula (I), wherein the $R^a$ and $R^b$ group comprises $(OCH_2)_n$ or $(OCH_2CH_2)_n$, wherein n is an integer between 1 and 6 and Z is derived from 3,5-dihydroxypyridine. In other embodiments, the integrin activating compounds comprise one or more of the following integrin activating compound: (a) 3-[bis(thenyl)aminocarbonyloxy],5-[bis(thenyl)aminocarbonyloxy]pyridine, (b) 3-[bis(3-methoxybenzyl)aminocarbonyloxy],5-[bis(3-methoxybenzyl)aminocarbonyloxy]pyridine, (c) 3-[(3-methoxybenzyl)(4-dimethylaminobenzyl)aminocarbonyloxy],5-[(3-methoxybenzyl)(4-dimethylaminobenzyl)aminocarbonyloxy]pyridine, (d) 3-[bis(4-methoxybenzyl)aminocarbonyloxy],5-[bis(4-methoxybenzyl)aminocarbonyloxy]pyridine, (e) 3-[(4-methoxybenzyl)(4-dimethylaminobenzyl)aminocarbonyloxy],5-[(4-methoxybenzyl)(4-dimethylaminobenzyl)aminocarbonyloxy]pyridine, (f) 5-(9H-carbazol-9-ylcarbonyloxy)-3-pyridyl 9H-carbazole-9-carboxylate, (g) 5-(3,6-dimethoxy-9H-carbazol-9-ylcarbonyloxy)-3-pyridyl 3,6-dimethoxy-9H-carbazole-9-carboxylate, or (h) mixtures and combinations thereof. In other embodiments, the integrin activating compounds comprise one or more of the following integrin activating compound: (a) 3-[bis(thenyl)aminocarbonyloxymethoxy],5-[bis(thenyl)amino carbonyloxymethoxy]pyridine, (b) 3-[bis(thenyl)aminocarbonyloxymethyoxymethoxy], 5-[bis(thenyl)aminocarbonyloxymethoxymethoxy]pyridine, (c) 3-[bis(3-methoxybenzyl)aminocarbonyloxymethoxy],5-[bis(3-methoxybenzyl)aminocarbonyloxy methoxy]pyridine, (d) 3-[bis(3-methoxybenzyl)aminocarbonyloxymethoxymethoxy],5-[bis(3-methoxybenzyl)aminocarbonyloxymethoxymethoxy]pyridine, (e) 3-[(3-methoxybenzyl)(4-dimethylaminobenzyl)aminocarbonyloxymethoxy],5-[(3-methoxybenzyl)(4-dimethylaminobenzyl)aminocarbonyloxymethoxy]pyridine, (f) 3-[(4-methoxybenzyl)(4-dimethylaminobenzyl)aminocarbonyloxymethoxymethoxy],5-[(4-methoxybenzyl)(4-dimethylaminobenzyl)aminocarbonyloxymethoxymethoxy]pyridine, (g) 3-[bis(4-methoxybenzyl)aminocarbonyloxymethoxy],5-[bis(4-methoxybenzyl)aminocarbonyloxy methoxy]pyridine, (h) 3-[bis(3-methoxybenzyl)aminocarbonyloxymethoxymethoxy],5-[bis(3-methoxybenzyl)aminocarbonyloxymethoxymethoxy]pyridine, (i) 3-[(4-methoxybenzyl)(4-dimethylaminobenzyl)aminocarbonyloxymethoxy],5-[(4-methoxybenzyl)(4-dimethylaminobenzyl)aminocarbonyloxymethoxy]pyridine, (j) 3-[(4-methoxybenzyl)(4-dimethylaminobenzyl)aminocarbonyloxymethoxymethoxy], 5-[(4-methoxybenzyl)(4-dimethylaminobenzyl)aminocarbonyloxymethoxymethoxy]pyridine, (k) 2-{5-[2-(9H-carbazol-9-ylcarbonyloxy)methoxy]-3-pyridyloxy}ethyl 9H-carbazole-9-carboxylate, (l) 2-[2-(5-{2-[2-(9-carbazolylcarbonyloxy)methoxy]methoxy}-3-pyridyloxy)ethoxy]ethyl 9-carbazolecarboxylate, (m) 2-{5-[2-(3,6-dimethoxy-9H-carbazol-9-ylcarbonyloxy)methoxy]-3-pyridyloxy}ethyl 3,6-dimethoxy-9H-carbazole-9-carboxylate, (n) 2-[2-(5-{2-[2-(3,6-dimethoxy-9H-carbazolylcarbonyloxy)methoxy]methoxy}-3-pyridyloxy)ethoxy]ethyl 3,6-dimethoxy-9-carbazolecarboxylate, (o) higher analogs, or (p) mixtures and combinations thereof. In other embodiments, the integrin activating compounds comprise one or more of the following integrin activating compound: (a) 3-[bis(thenyl)aminocarbonyloxyethoxy],5-[bis(thenyl)aminocarbonyloxy ethoxy]pyridine, (b) 3-[bis(thenyl)aminocarbonyloxyethyoxyethoxy],5-[bis(thenyl) aminocarbonyloxyethyoxyethoxy]pyridine, (c) 3-[bis(3-methoxybenzyl)amino carbonyloxyethoxy],5-[bis(3-methoxybenzyl)aminocarbonyloxyethoxy]pyridine, (d) 3-[bis(3-methoxybenzyl)aminocarbonyloxyethoxyethoxy],5-[bis(3-methoxybenzyl)aminocarbonyloxy ethoxyethoxy]pyridine, (e) 3-[(3-methoxybenzyl)(4-dimethylaminobenzyl)aminocarbonyloxy],5-[(3-methoxybenzyl)(4-dimethylaminobenzyl)aminocarbonyloxy]pyridine, (f) 3-[(3-methoxybenzyl)(4-dimethylaminobenzyl)aminocarbonyloxyethoxy],5-[(3-methoxybenzyl)

(4-dimethylaminobenzyl)aminocarbonyloxyethoxy]pyridine, (g) 3-[(4-methoxybenzyl)(4-dimethylaminobenzyl)aminocarbonyloxyethoxyethoxy],5-[(4-methoxybenzyl)(4-dimethylaminobenzyl)aminocarbonyloxyethoxyethoxy]pyridine, (h) 3-[bis(4-methoxybenzyl)aminocarbonyloxyethoxy],5-[bis(4-methoxybenzyl)amino carbonyloxyethoxy]pyridine, (i) 3-[bis(3-methoxybenzyl)aminocarbonyloxy ethoxyethoxy],5-[bis(3-methoxybenzyl)aminocarbonyloxyethoxyethoxy]pyridine, (j) 3-[(4-methoxybenzyl)(4-dimethylaminobenzyl)aminocarbonyloxyethoxy],5-[(4-methoxybenzyl)(4-dimethylaminobenzyl)aminocarbonyloxyethoxy]pyridine, (k) 3-[(4-methoxybenzyl)(4-dimethylaminobenzyl)aminocarbonyloxyethoxyethoxy],5-[(4-methoxybenzyl)(4-dimethylaminobenzyl)aminocarbonyloxyethoxyethoxy]pyridine, (l) 2-{5-[2-(9H-carbazol-9-ylcarbonyloxy)ethoxy]-3-pyridyloxy}ethyl 9H-carbazole-9-carboxylate, (m) 2-[2-(5-{2-[2-(9-carbazolylcarbonyloxy)ethoxy]ethoxy}-3-pyridyloxy)ethoxy]ethyl 9-carbazolecarboxylate, (n) 2-{5-[2-(3,6-dimethoxy-9H-carbazol-9-ylcarbonyloxy)ethoxy]-3-pyridyloxy}ethyl 3,6-dimethoxy-9H-carbazole-9-carboxylate, (o) 2-[2-(5-{2-[2-(3,6-dimethoxy-9H-carbazolylcarbonyloxy)ethoxy]ethoxy}-3-pyridyloxy)ethoxy]ethyl 3,6-dimethoxy-9-carbazolecarboxylate, (p) higher analogs, or (q) mixtures and combinations thereof.

$R^a$ and $R^b$=(OCH$_2$)$_n$ or CH$_3$)(CH$_2$O)$_n$ and Z=3,5-Dimethanol Pyridine Class Agonists In certain embodiments, the integrin activating compounds comprise one or more compound of Formula (I), wherein the $R^a$ and $R^b$ group comprises (OCH$_2$)$_n$ or (OCH$_2$CH$_2$)$_n$, wherein n is an integer between 1 and 6 and Z is derived from 3,5-dimethanolpyridine. In other embodiments, the integrin activating compounds comprise one or more of the following integrin activating compound: (a) 3-({bis[(2-thienyl)methyl]aminocarbonyloxy}methyl)-5-({bis[(2-thienyl)methyl]amino carbonyloxy}methyl)pyridine, (b) 3-({bis(3-methoxybenzyl)aminocarbony- loxy}methyl)-5-({bis(3-methoxybenzyl)aminocarbo- nyloxy}methyl)pyridine, (c) 3-(3-methoxybenzyl,4-dimethyl aminobenzyl)aminocarbonyloxy}methyl)-5-(3-methoxybenzyl,4-dimethylaminobenzyl) aminocarbonyloxy}methyl)pyridine, (d) 3-({bis(4-methoxybenzyl)aminocarbonyloxy}methyl)-5-({bis(4-methoxybenzyl)aminocarbonyloxy}methyl)pyridine, (e) 3-(4-methoxybenzyl,4-dimethylaminobenzyl)aminocarbonyloxy}methyl)-5-(4-methoxybenzyl,4-dimethylaminobenzyl) aminocarbonyloxy}methyl)pyridine, (f) {5-[(9H-carbazol-9-ylcarbonyloxy)methyl]-3-pyridyl}methyl 9H-carbazole-9-carboxylate, (g) {5-[(3,6-dimethoxy-9H-carbazol-9-ylcarbonyloxy)methyl]-3-pyridyl}methyl 3,6-dimethoxy-9H-carbazole-9-carboxylate, or (h) mixtures and combinations thereof. In other embodiments, the integrin activating compounds comprise one or more of the following integrin activating compound: (a) 3-{bis[(2-thienyl)methyl]aminocarbonyloxy}methoxy)methyl]-5-{bis[(2-thienyl)methyl]aminocarbonyloxy}methoxy)methyl]pyridine, (b) 3-{bis[(2-thienyl)methyl]aminocarbonyloxy}methoxymethoxy)methyl]-5-{bis[(2-thienyl)methyl]aminocarbonyloxy}methoxymethoxy)methyl]pyridine, (c) 3-{bis(3-methoxybenzyl)amino carbonyloxy}methoxy)methyl]-5-{bis(3-methoxybenzyl)aminocarbonyloxy}methoxy) methyl]pyridine, (d) 3-{bis(3-methoxybenzyl)aminocarbonyloxy}methoxymethoxy)methyl]-5-{bis(3-methoxybenzyl)aminocarbonyloxy}methoxymethoxy)methyl]pyridine, (e) 3-(3-methoxybenzyl,4-dimethylaminobenzyl)aminocarbonyloxy}methoxy)methyl]-5-(3-methoxybenzyl,4-dimethylaminobenzyl)aminocarbonyloxy}methoxy)methyl]pyridine, (f) 3-(3-methoxybenzyl,4-dimethylaminobenzyl)aminocarbonyloxy}methoxymethoxy)methyl]-5-(3-methoxybenzyl,4-dimethylaminobenzyl)aminocarbonyloxy}methoxymethoxy)methyl]pyridine, (g) 3-{bis(4-methoxybenzyl)aminocarbonyloxy}methoxy)methyl]-5-{bis(4-methoxybenzyl) aminocarbonyloxy}methoxy)methyl]pyridine, (h) 3-{bis(4-methoxybenzyl)aminocarbonyloxy}methoxyethoxy)methyl]-5-{bis(4-methoxybenzyl)aminocarbonyloxy}methoxymethoxy) methyl]pyridine, (l) 3-(4-methoxybenzyl,4-dimethylaminobenzyl)aminocarbonyloxy}methoxy)methyl]-5-(4-methoxybenzyl,4-dimethylaminobenzyl)aminocarbonyloxy}methoxy) methyl]pyridine, (j) 3-(4-methoxybenzyl,4-dimethylaminobenzyl)aminocarbonyloxy}methoxymethoxy)methyl]-5-(4-methoxybenzyl,4-dimethylaminobenzyl)aminocarbonyloxy}methoxymethoxy)methyl]pyridine, (k) 2-[(5-{[2-(9H-carbazol-9-ylcarbonyloxy)methoxy]methyl}-3-pyridyl)methoxy]ethyl 9H-carbazole-9-carboxylate, (l) 2-(2-{[5-({2-[2-(9-carbazolylcarbonyloxy) methoxy]methoxy}methyl)-3-pyridyl] methoxy}ethoxy)ethyl 9-carbazolecarboxylate, (m) 2-[(5-{[2-(3,6-dimethoxy-9H-carbazol-9-ylcarbonyloxy)methoxy]methyl}-3-pyridyl)methoxy]ethyl 3,6-dimethoxy-9H-carbazole-9-carboxylate, (n) 2-(2-{[5-({2-[2-(3,6-dimethoxy-9-carbazolylcarbonyloxy)methoxy]methoxy}methyl)-3-pyridyl]methoxy}ethoxy)ethyl 3,6-dimethoxy-9-carbazolecarboxylate, (o) higher analogs, or (p) mixtures and combinations thereof. In other embodiments, the integrin activating compounds comprise one or more of the following integrin activating compound: (a) 3-{bis[(2-thienyl)methyl]aminocarbonyloxy}ethoxy)methyl]-5-{bis[(2-thienyl)methyl]aminocarbonyloxy}ethoxy)methyl]pyridine, (b) 3-{bis[(2-thienyl) methyl]aminocarbonyloxy}ethoxymethoxy)methyl]-5-{bis[(2-thienyl)methyl]aminocarbonyloxy}ethoxyethoxy)methyl]pyridine, (c) 3-{bis(3-methoxybenzyl)aminocarbonyloxy}ethoxy)methyl]-5-{bis(3-methoxybenzyl)aminocarbonyloxy}ethoxy)methyl]pyridine, (d) 3-{bis(3-methoxybenzyl) aminocarbonyloxy}ethoxyethoxy)methyl]-5-{bis(3-methoxybenzyl)aminocarbo- nyloxy}ethoxyethoxy)methyl]pyridine, (e) 3-(3-methoxybenzyl,4-dimethylaminobenzyl) aminocarbonyloxy}eth- oxy)methyl]-5-(3-methoxybenzyl,4-dimethylaminobenzyl)aminocarbonyloxy}ethoxy)methyl]pyridine, (f) 3-(3-met- hoxybenzyl,4-dimethylaminobenzyl)aminocarbon- yloxy}ethoxymethoxy)methyl]-5-(3-methoxybenzyl,4-dimethylaminobenzyl)aminocarbonyloxy}ethoxyethoxy)methyl]pyridine, (g) 3-{bis(4-methoxybenzyl)aminocarbonyloxy} ethoxy)methyl]-5-{bis(4-methoxybenzyl)aminocarbonyloxy} ethoxy)methyl]pyridine, (h) 3-{bis(4-methoxybenzyl) aminocarbonyloxy}ethoxyethoxy)methyl]-5-{bis(4-methoxybenzyl)aminocarbonyloxy}ethoxyethoxy)methyl]pyridine, (i) 3-(4-methoxybenzyl,4-dimethylaminobenzyl) aminocarbonyloxy}ethoxy)methyl]-5-(4-methoxybenzyl,4-dimethylaminobenzyl)aminocarbonyloxy}ethoxy)methyl]pyridine, (j) 3-(4-methoxybenzyl,4-dimethylaminobenzyl)aminocarbonyloxy}ethoxyethoxy)methyl]-5-(4-methoxybenzyl,4-dimethylaminobenzyl)aminocarbonyloxy}ethoxyethoxy)methyl]pyridine, (k) 2-[(5-{[2-(9H-carbazol-9-ylcarbonyloxy)ethoxy]methyl}-3-pyridyl)methoxy]ethyl 9H-carbazole-9-carboxylate, (l) 2-(2-{[5-({2-[2-(9-carbazolylcarbonyloxy)ethoxy]ethoxy}methyl)-3-pyridyl]methoxy} ethoxy)ethyl 9-carbazolecarboxylate, (m) 2-[(5-{[2-(3,6-dimethoxy-9H-carbazol-9-ylcarbonyloxy)ethoxy]methyl}-3-pyridyl)methoxy]ethyl 3,6-dimethoxy-9H-carbazole-9-carboxylate, (n) 2-(2-{[5-({2-[2-(3,6-dimethoxy-9-carbazolylcarbonyloxy)ethoxy]ethoxy}methyl)-3-pyridyl]methoxy}ethoxy)ethyl 3,6-dimethoxy-9-carbazolecarboxylate, (o) higher analogs, or (p) mixtures and combinations thereof.

$R^a$ and $R^b$=$(OCH_2)_n$ or $CH_3)(CH_2O)_n$ and Z=3,5-Dihydroxy-Dimethyl Aniline Class Agonists In certain embodiments, the integrin activating compounds comprise one or more compound of Formula (I), wherein the $R^a$ and $R^b$ group comprises $(OCH_2)_n$ or $(OCH_2CH_2)_n$, wherein n is an integer between 1 and 6 and Z is derived from 3,5-dihydroxy-dimethylaniline. In other embodiments, the integrin activating compounds comprise one or more of the following integrin activating compound: (a) 3-[bis(thenyl)aminocarbonyloxy],5-[bis(thenyl)aminocarbonyloxy]dimethylamino benzene, (b) 3-[bis(3-methoxybenzyl)aminocarbonyloxy],5-[bis(3-methoxybenzyl)aminocarbonyloxy]dimethylaminobenzene, (c) 3-[(3-methoxybenzyl)(4-dimethylaminobenzyl)aminocarbonyloxy],5-[(3-methoxybenzyl)(4-dimethylaminobenzyl)aminocarbonyloxy]dimethylamino benzene, (d) 3-[bis(4-methoxybenzyl)aminocarbonyloxy],5-[bis(4-methoxybenzyl)aminocarbonyloxy]dimethylamino benzene, (e) 3-[(4-methoxybenzyl)(4-dimethylaminobenzyl)aminocarbonyloxy],5-[(4-methoxybenzyl)(4-dimethylaminobenzyl)aminocarbonyloxy]dimethylamino benzene, (f) 3-(9H-carbazol-9-ylcarbonyloxy)-5-(dimethylamino)phenyl 9H-carbazole-9-carboxylate, (g) 3-(3,6-dimethoxy-9H-carbazol-9-ylcarbonyloxy)-5-(dimethylamino)phenyl 3,6-dimethoxy-9H-carbazole-9-carboxylate, or (h) mixtures and combinations thereof. In other embodiments, the integrin activating compounds comprise one or more of the following integrin activating compound: (a) 3-[bis(thenyl)aminocarbonyloxymethoxy],5-[bis(thenyl)aminocarbonyloxymethoxy]dimethylamino benzene, (b) 3-[bis(thenyl)aminocarbonyloxymethoxymethoxy], 5-[bis(thenyl)aminocarbonyloxymethoxymethoxy]dimethylaminobenzene, (c) 3-[bis(3-methoxybenzyl)aminocarbonyloxymethoxy],5-[bis(3-methoxybenzyl)aminocarbonyloxy methoxy]dimethylaminobenzene, (d) 3-[bis(3-methoxybenzyl)aminocarbonyloxy methoxymethoxy],5-[bis(3-methoxybenzyl)aminocarbonyloxymethoxymethoxy]dimethylaminobenzene, (e) 3-[(3-methoxybenzyl)(4-dimethylaminobenzyl)amino carbonyloxymethoxy],5-[(3-methoxybenzyl)(4-dimethylaminobenzyl)aminocarbonyloxy methoxy]dimethylaminobenzene, (f) 3-[(3-methoxybenzyl)(4-dimethylaminobenzyl) aminocarbonyloxymethoxymethoxy],5-[(3-methoxybenzyl)(4-dimethylaminobenzyl)amino carbonyloxymethoxymethoxy]dimethylaminobenzene, (g) 3-[bis(4-methoxybenzyl)aminocarbonyloxymethoxy],5-[bis(4-methoxybenzyl)amino carbonyloxymethoxy]dimethylaminobenzene, (h) 3-[bis(4-methoxybenzyl)aminocarbonyloxy methoxymethoxy], 5-[bis(4-methoxybenzyl)aminocarbonyloxymethoxymethoxy]dimethylaminobenzene, (i) 3-[(4-methoxybenzyl)(4-dimethylaminobenzyl)aminocarbonyloxy methoxy],5-[(4-methoxybenzyl)(4-dimethylaminobenzyl)aminocarbonyloxymethoxy]dimethylaminobenzene, (j) 3-[(4-methoxybenzyl)(4-dimethylaminobenzyl)amino carbonyloxymethoxymethoxy],5-[(4-methoxybenzyl)(4-dimethylaminobenzyl)aminocarbonyloxy methoxymethoxy]dimethylaminobenzene, (k) 2-{3-[2-(9H-carbazol-9-ylcarbonyloxy)methoxy]-5-(dimethylamino)phenoxy}methyl 9H-carbazole-9-carboxylate, (l) 2-[2-(3-{2-[2-(9-carbazolylcarbonyloxy)methoxy]methoxy}-5-(dimethylamino)phenoxy)methoxy]ethyl 9-carbazolecarboxylate, (m) 2-{3-[2-(3,6-dimethoxy-9H-carbazol-9-ylcarbonyloxy)methoxy]-5-(dimethylamino)phenoxy}ethyl 3,6-dimethoxy-9H-carbazole-9-carboxylate, (n) 2-[2-(3-{2-[2-(3,6-dimethoxy-9-carbazolylcarbonyloxy)methoxy]methoxy}-5-(dimethylamino)phenoxy)methoxy] methyl 3,6-dimethoxy-9-carbazolecarboxylate, (o) higher analogs, or (p) mixtures and combinations thereof. In other embodiments, the integrin activating compounds comprise one or more of the following integrin activating compound: (a) 3-[bis(thenyl)aminocarbonyloxyethoxy],5-[bis(thenyl)aminocarbonyloxyethoxy]dimethylaminobenzene, (b) 3-[bis(thenyl)aminocarbonyloxyethoxyethoxy],5-[bis(thenyl)amino carbonyloxyethoxyethoxy]dimethylaminobenzene, (c) 3-[bis(3-methoxybenzyl) aminocarbonyloxyethoxy], 5-[bis(3-methoxybenzyl)aminocarbonyloxyethoxy]dimethylaminobenzene, (d) 3-[bis(3-methoxybenzyl) aminocarbonyloxyethoxyethoxy],5-[bis(3-methoxybenzyl)aminocarbonyloxyethoxyethoxy]dimethylaminobenzene, (e) 3-[(3-methoxybenzyl)(4-dimethylaminobenzyl)aminocarbonyloxyethoxy],5-[(3-methoxybenzyl)(4-dimethylaminobenzyl)aminocarbonyloxyethoxy] dimethylaminobenzene, (f) 3-[(3-methoxybenzyl)(4-dimethylaminobenzyl)aminocarbonyloxyethoxyethoxy],5-[(3-methoxybenzyl)(4-dimethylaminobenzyl)aminocarbonyloxyethoxyethoxy] dimethylaminobenzene, (g) 3-[bis(4-methoxybenzyl)aminocarbonyloxyethoxy],5-[bis(4-methoxybenzyl)aminocarbonyloxyethoxy]dimethylaminobenzene, (h) 3-[bis(4-methoxybenzyl)aminocarbonyloxyethoxyethoxy],5-[bis(4-methoxybenzyl)aminocarbonyloxy ethoxyethoxy]dimethylaminobenzene, (i) 3-[(4-methoxybenzyl)(4-dimethylaminobenzyl)aminocarbonyloxyethoxy], 5-[(4-methoxybenzyl)(4-dimethylaminobenzyl)aminocarbonyloxyethoxy]dimethylaminobenzene, (j) 3-[(4-methoxybenzyl)(4-dimethylaminobenzyl)aminocarbonyloxyethoxyethoxy],5-[(4-methoxybenzyl)(4-dimethylaminobenzyl)aminocarbonyloxyethoxyethoxy] dimethylaminobenzene, (k) 2-{3-[2-(9H-carbazol-9-ylcarbonyloxy)ethoxy]-5-(dimethylamino)phenoxy}ethyl 9H-carbazole-9-carboxylate, (l) 2-[2-(3-{2-[2-(9-carbazolylcarbonyloxy)ethoxy]ethoxy}-5-(dimethylamino)phenoxy)ethoxy] ethyl 9-carbazolecarboxylate, (m) 2-{3-[2-(3,6-dimethoxy-9H-carbazol-9-ylcarbonyloxy)ethoxy]-5-(dimethylamino)phenoxy}ethyl 3,6-dimethoxy-9H-carbazole-9-carboxylate, (n) 2-[2-(3-{2-[2-(3,6-dimethoxy-9-carbazolylcarbonyloxy)ethoxy]ethoxy}-5-(dimethylamino)phenoxy)ethoxy]ethyl 3,6-dimethoxy-9-carbazolecarboxylate, (o) higher analogs, or (p) mixtures and combinations thereof.

$R^a$ and $R^b$=$(OCH_2)_n$ or $CH_3)(CH_2O)_n$ and Z=3,5-Dihydroxy-Dimethyl Benzyl Amine Class Agonists In certain embodiments, the integrin activating compounds comprise one or more compound of Formula (I), wherein the $R^a$ and $R^b$ group comprises $(OCH_2)_n$ or $(OCH_2CH_2)_n$, wherein n is an integer between 1 and 6 and Z is derived from 3,5-dihydroxy-Dimethyl-BenzylAmine. In other embodiments, the integrin activating compounds comprise one or more of the following integrin activating compound: (a) 3-[bis(thenyl)aminocarbonyloxy],5-[bis(thenyl)aminocarbonyloxy]dimethylamino benzylamine, (b) 3-[bis(3-methoxybenzyl)aminocarbonyloxy],5-[bis(3-methoxybenzyl)aminocarbonyloxy]dimethylamino benzylamine, (c) 3-[(3-methoxybenzyl)(4-dimethylaminobenzyl)aminocarbonyloxy],5-[(3-methoxybenzyl)(4-dimethylaminobenzyl)amino carbonyloxy]dimethylamino benzylamine, (d) 3-[bis(4-methoxybenzyl)aminocarbonyloxy],5-[bis(4-methoxybenzyl)aminocarbonyloxy]dimethylaminobenzylamine, (e) 3-[(4-methoxybenzyl)(4-dimethylaminobenzyl) aminocarbonyloxy],5-[(4-methoxybenzyl)(4-dimethylaminobenzyl)aminocarbonyloxy] dimethylaminobenzylamine, (f) 3-(9H-carbazol-9-ylcarbonyloxy)-5-[(methylamino)methyl]phenyl 9H-carbazole-9-carboxylate, (g) 3-(3,6-dimethoxy-9H-carbazol-9-ylcarbonyloxy)-5-[(dimethylamino)methyl]phenyl 3,6-dimethoxy-9H-carbazole-9-carboxylate, or (h) mixtures and combinations thereof. In other embodiments, the integrin activating compounds comprise one or more of the following integrin activating compound: (a) 3-[bis(thenyl)aminocarbonyloxymethoxy], 5-[bis(thenyl)aminocarbonyloxymethoxy]dimethylaminobenzylamine, (b) 3-[bis(thenyl)aminocarbonyloxymethoxymethoxy], 5-[bis(thenyl)aminocarbonyloxymethoxymethoxy]dimethylaminobenzylamine, (c) 3-[bis(3-methoxybenzyl)aminocarbonyloxymethoxy],5-[bis(3-methoxybenzyl)aminocarbonyloxy methoxy]dimethylaminobenzylamine, (d) 3-[bis(3-methoxybenzyl)amino carbonyloxymethoxymethoxy],5-[bis(3-methoxybenzyl)aminocarbonyloxymethoxymethoxy] dimethylaminobenzylamine, (e) 3-[(3-methoxybenzyl)(4-dimethylaminobenzyl)aminocarbonyloxy methoxy],5-[(3-methoxybenzyl)(4-dimethylaminobenzyl)aminocarbonyloxymethoxy]dimethylaminobenzylamine, (f) 3-[(3-methoxybenzyl)(4-dimethylaminobenzyl)aminocarbonyloxy methoxymethoxy],5-[(3-methoxybenzyl)(4-dimethylaminobenzyl)aminocarbonyloxy methoxymethoxy], dimethylaminobenzylamine, (g) 3-[bis(4-methoxybenzyl)aminocarbonyloxymethoxy],5-[bis(4-methoxybenzyl)aminocarbonyloxymethoxy]dimethylaminobenzylamine, (h) 3-[bis(4-methoxybenzyl)aminocarbonyloxymethoxymethoxy],5-[bis(4-methoxybenzyl)aminocarbonyloxy ethoxymethoxy]dimethylaminobenzylamine, (i) 3-[(4-methoxybenzyl)(4-dimethylaminobenzyl)aminocarbonyloxymethoxy],5-[(4-methoxybenzyl)(4-dimethylaminobenzyl)aminocarbonyloxymethoxy]dimethylaminobenzylamine, (j) 3-[(4-methoxybenzyl)(4-dimethylaminobenzyl)aminocarbonyloxymethoxymethoxy],5-[(4-methoxybenzyl)(4-dimethylaminobenzyl)aminocarbonyloxymethoxymethoxy]dimethylaminobenzylamine, (k) 2-{3-[2-(9H-carbazol-9-ylcarbonyloxy)methoxy]-5-[(dimethylamino)methyl]phenoxy}methyl 9H-carbazole-9-carboxylate, (l) 2-[2-(3-{2-[2-(9-carbazolylcarbonyloxy)methoxy]methoxy}-5-[(dimethylamino)methyl]phenoxy)methoxy]methyl 9-carbazolecarboxylate, (m) 2-{3-[2-(3,6-dimethoxy-9H-carbazol-9-ylcarbonyloxy)ethoxy]-5-[(dimethylamino)methyl]phenoxy}methyl 3,6-dimethoxy-9H-carbazole-9-carboxylate, (n) 2-[2-(3-{2-[2-(3,6-dimethoxy-9-carbazolylcarbonyloxy)methoxy]methoxy}-5-[(dimethylamino)methyl]phenoxy)methoxy]methyl 3,6-dimethoxy-9-carbazolecarboxylate, (o) higher analogs, or (p) mixtures and combinations thereof. In other embodiments, the integrin activating compounds comprise one or more of the following integrin activating compound: (a) 3-[bis(thenyl)aminocarbonyloxyethoxy],5-[bis(thenyl)aminocarbonyloxyethoxy]dimethylaminobenzylamine, (b) 3-[bis(thenyl)aminocarbonyloxyethoxyethoxy], 5-[bis(thenyl)aminocarbonyloxyethoxyethoxy]dimethylaminobenzylamine, (c) 3-[bis(3-methoxybenzyl)aminocarbonyloxyethoxy],5-[bis(3-methoxybenzyl)aminocarbonyloxyethoxy]dimethylaminobenzylamine, (d) 3-[bis(3-methoxybenzyl)aminocarbonyloxyethoxy ethoxy],5-[bis(3-methoxybenzyl)aminocarbonyloxyethoxyethoxy]dimethylaminobenzylamine, (e) 3-[(3-methoxybenzyl)(4-dimethylaminobenzyl)aminocarbonyloxyethoxy], 5-[(3-methoxybenzyl)(4-dimethylaminobenzyl)aminocarbonyloxyethoxy]dimethylaminobenzylamine, (f) 3-[(3-methoxybenzyl)(4-dimethylaminobenzyl)aminocarbonyloxyethoxyethoxy],5-[(3-methoxybenzyl)(4-dimethylaminobenzyl)aminocarbonyloxyethoxyethoxy], dimethylaminobenzylamine, (g) 3-[bis(4-methoxybenzyl)aminocarbonyloxyethoxy],5-[bis(4-methoxybenzyl)aminocarbonyloxyethoxy]dimethylaminobenzylamine, (h) 3-[bis(4-methoxybenzyl)aminocarbonyloxyethoxyethoxy],5-[bis(4-methoxybenzyl)aminocarbonyloxy ethoxyethoxy]dimethylaminobenzylamine, (i) 3-[(4-methoxybenzyl)(4-dimethylaminobenzyl)aminocarbonyloxyethoxy],5-[(4-methoxybenzyl)(4-dimethylaminobenzyl)aminocarbonyloxyethoxy]dimethylaminobenzylamine, (j) 3-[(4-methoxybenzyl)(4-dimethylaminobenzyl)aminocarbonyloxyethoxyethoxy],5-[(4-methoxybenzyl)(4-dimethylaminobenzyl)aminocarbonyloxyethoxyethoxy] dimethylaminobenzylamine, (k) 2-{3-[2-(9H-carbazol-9-ylcarbonyloxy)ethoxy]-5-[(dimethylamino)methyl]phenoxy}ethyl 9H-carbazole-9-carboxylate, (l) 2-[2-(3-{2-[2-(9-carbazolylcarbonyloxy)ethoxy]ethoxy}-5-[(dimethylamino)methyl]phenoxy)ethoxy]ethyl 9-carbazolecarboxylate, (m) 2-{3-[2-(3,6-dimethoxy-9H-carbazol-9-ylcarbonyloxy)ethoxy]-5-[(dimethylamino)methyl]phenoxy}ethyl 3,6-dimethoxy-9H-carbazole-9-carboxylate, (n) 2-[2-(3-{2-[2-(3,6-dimethoxy-9-carbazolylcarbonyloxy)ethoxy]ethoxy}-5-[(dimethylamino)methyl]phenoxy)ethoxy]ethyl 3,6-dimethoxy-9-carbazolecarboxylate, (o) higher analogs, or (p) mixtures and combinations thereof.

$R^a$ and $R^b$=(OCH$_2$)$_n$ or (CH$_3$)(CH$_2$O)$_n$ and Z=2,6-Pyridine Dicarboxylic Acid Chloride Class Agonists In certain embodiments, the integrin activating compounds comprise one or more compound of Formula (I), wherein the $R^a$ and $R^b$ group comprises (OCH$_2$)$_n$ or (OCH$_2$CH$_2$)$_n$, wherein n is an integer between 1 and 6 and Z is derived from 2,6-pyridine dicarboxylic acid chloride. In other embodiments, the integrin activating compounds comprise one or more of the following integrin activating compound: (a) N,N,N,N-tetra(2-thienylmethyl)-2,6-pyridinedicarboxamide, (b) N,N,N,N-tetra(3-methoxybenzyl)-2,6-pyridinedicarboxamide, (c) N,N-bis(3-methoxybenzyl)-N,N-bis(4-dimethylaminobenzyl)-2,6-pyridinedicarboxamide, (d) N,N,N,N-tetra(4-methoxybenzyl)-2,6-pyridinedicarboxamide, (e) N,N-bis(4-methoxybenzyl)-N,N-bis(4-dimethylaminobenzyl)-2,6-pyridinedicarboxamide, (f) or mixtures and combinations thereof. In other embodiments, the integrin activating compounds comprise one or more of the following integrin activating compound: (a) bis(2-{bis(2-thienylmethyl)aminocarbonyloxy}methyl)2,6-pyridinedicarboxylate, (b) bis(2-{bis(2-thienylmethyl)aminocarbonyloxymethoxy}methyl)2,6-pyridinedicarboxylate, (c) bis(2-{bis[3-methoxybenzyl]aminocarbonyloxy}methyl)2,6-pyridinedicarboxylate, (d) bis(2-{bis[3-methoxybenzyl]aminocarbonyloxymethoxy}methyl)2,6-pyridinedicarboxylate, (e) bis(2-{(3-methoxybenzyl)(4-dimethylaminobenzyl)aminocarbonyloxy}methyl) 2,6-pyridinedicarboxylate, (f) bis(2-{(4-methoxybenzyl)(4-dimethylaminobenzyl)aminocarbonyloxy methoxy}methyl)2,6-pyridinedicarboxylate, (g) bis(2-{bis[4-methoxybenzyl]aminocarbonyloxy}methyl)2,6-pyridinedicarboxylate, (h) bis(2-{bis[4-methoxybenzyl]aminocarbonyloxymethoxy}methyl)2,6-pyridinedicarboxylate, (i) bis(2-{(4-methoxybenzyl)(4-dimethylaminobenzyl) aminocarbonyloxy}methyl)2,6-pyridinedicarboxylate, (j) bis(2-{(4-methoxybenzyl)(4-dimethylaminobenzyl)aminocarbonyloxymethoxy}methyl)2,6-pyridinedicarboxylate, (k) higher analogs, or (l) mixtures and combinations thereof. In other embodiments, the integrin activating compounds comprise one or more of the following integrin activating compound: (a) bis(2-{bis(2-thienylmethyl)aminocarbonyloxy}ethyl)2,6-pyridinedicarboxylate, (b) bis(2-{bis(2-thienylmethyl)aminocarbonyloxyethoxy}ethyl)2,6-pyridinedicarboxylate, (c) bis(2-{bis

[3-methoxybenzyl]aminocarbonyloxy}ethyl)2,6-pyridinedicarboxylate, (d) bis(2-{bis[3-methoxybenzyl]aminocarbonyloxyethoxy}ethyl)2,6-pyridinedicarboxylate, (e) bis(2-{(3-methoxybenzyl)(4-dimethylaminobenzyl)aminocarbonyloxy}ethyl) 2,6-pyridinedicarboxylate, (f) bis(2-{(4-methoxybenzyl)(4-dimethylaminobenzyl)amino carbonyloxyethoxy}ethyl)2,6-pyridinedicarboxylate, (g) bis(2-{bis[4-methoxybenzyl]amino carbonyloxy}ethyl)2,6-pyridinedicarboxylate, (h) bis(2-{bis[4-methoxybenzyl]aminocarbonyloxy ethoxy}ethyl)2,6-pyridinedicarboxylate, (i) bis(2-{(4-methoxybenzyl)(4-dimethylaminobenzyl)aminocarbonyloxy}ethyl)2,6-pyridinedicarboxylate, (j) bis(2-{(4-methoxybenzyl)(4-dimethylaminobenzyl)aminocarbonyloxyethoxy}ethyl) 2,6-pyridinedicarboxylate, (k) higher analogs, or (l) mixtures and combinations thereof.

$R^a$ and $R^b$=(OCH$_2$)$_n$ or CH$_3$)(CH$_2$O)$_n$ and Z=3.5-Pyridine Dicarboxylic Acid Chloride Class Agonists In certain embodiments, the integrin activating compounds comprise one or more compound of Formula (I), wherein the $R^a$ and $R^b$ group comprises (OCH$_2$)$_n$ or (OCH$_2$CH$_2$)$_n$, wherein n is an integer between 1 and 6 and Z is derived from 3,5-pyridine diecarboxylic acid chloride. In other embodiments, the integrin activating compounds comprise one or more of the following integrin activating compound: (a) N,N,N,N-tetra(2-thienylmethyl)-3,5-pyridinedicarboxamide, (b) N,N,N,N-tetra(4-methoxybenzyl)-3,5-pyridinedicarboxamide, (c) N,N-bis(3-methoxybenzyl)-N,N-bis(4-dimethylaminobenzyl)-3,5-pyridinedicarboxamide, (d) N,N,N,N-tetra(4-methoxybenzyl)-3,5-pyridinedicarboxamide, (e) N,N-bis(4-methoxybenzyl)-N,N-bis(4-dimethylaminobenzyl)-3,5-pyridinedicarboxamide, or (f) mixture and combinations thereof. In other embodiments, the integrin activating compounds comprise one or more of the following integrin activating compound: (a) bis(2-{bis(2-thienylmethyl]aminocarbonyloxy}methyl)3,5-pyridinedicarboxylate, (b) bis(2-{bis(2-thienylmethyl]aminocarbonyloxymethoxy}methyl)3,5-pyridinedicarboxylate, (c) bis(2-{bis(3-methoxybenzyl)aminocarbonyloxy}methyl)3,5-pyridinedicarboxylate, (d) bis(2-{bis[3-methoxybenzyl]aminocarbonyloxymethoxy}methyl)3,5-pyridinedicarboxylate, (e) bis(2-{(3-methoxybenzyl)(4-methyl aminobenzyl)aminocarbonyloxy}methyl) 3,5-pyridinedicarboxylate, (f) bis(2-{(3-methoxybenzyl)(4-dimethylaminobenzyl)aminocarbonyloxy methoxy}methyl)3,5-pyridinedicarboxylate (g) bis(2-{bis(4-methoxybenzyl)aminocarbonyloxy}methyl)3,5-pyridinedicarboxylate (h) bis(2-{bis[4-methoxybenzyl]aminocarbonyloxymethoxy}methyl)3,5-pyridinedicarboxylate (i) bis(2-{bis(4-methoxybenzyl)(4-methylaminobenzyl)amino carbonyloxy}methyl)3,5-pyridinedicarboxylate (j) bis(2-{(4-methoxybenzyl)(4-dimethylaminobenzyl)aminocarbonyloxymethoxy}methyl)3,5-pyridinedicarboxylate, (k) higher analogs, or (l) mixtures and combinations thereof. In other embodiments, the integrin activating compounds comprise one or more of the following integrin activating compound: (a) bis(2-{bis(2-thienylmethyl]aminocarbonyloxy}ethyl)3,5-pyridinedicarboxylate, (b) bis(2-{bis(2-thienylmethyl]aminocarbonyloxyethoxy}ethyl)3,5-pyridinedicarboxylate, (c) bis(2-{bis(3-methoxybenzyl)aminocarbonyloxy}ethyl)3,5-pyridinedicarboxylate, (d) bis(2-{bis[3-methoxybenzyl]aminocarbonyloxyethoxy}ethyl)2,6-pyridinedicarboxylate, (e) bis(2-{(3-methoxybenzyl)(4-methylaminobenzyl)aminocarbonyloxy}ethyl) 3,5-pyridinedicarboxylate, (f) bis(2-{(3-methoxybenzyl)(4-dimethylaminobenzyl)aminocarbonyloxy ethoxy}ethyl)2,6-pyridinedicarboxylate, (g) bis(2-{bis(4-methoxybenzyl)aminocarbonyloxy}ethyl)3,5-pyridinedicarboxylate (h) bis(2-{bis[4-methoxybenzyl]aminocarbonyloxyethoxy}ethyl) 3,5-pyridinedicarboxylate (i) bis(2-{bis(4-methoxybenzyl)(4-methylaminobenzyl)aminocarbonyloxy}ethyl)3,5-pyridinedicarboxylate, (j) bis(2-{(4-methoxybenzyl)(4-dimethylaminobenzyl)amino carbonyloxyethoxy}ethyl)2,6-pyridinedicarboxylate, (k) higher analogs, or (l) mixtures and combinations thereof.

$R^a$ and $R^b$=(OCH$_2$)$_n$ or CH$_3$)(CH$_2$O)$_n$ and Z=3-Dimethylamino-1,5-Pentane Diol Class Agonists In certain embodiments, the integrin activating compounds comprise one or more compound of Formula (I), wherein the $R^a$ and $R^b$ group comprises (OCH$_2$)$_n$ or (OCH$_2$CH$_2$)$_n$, wherein n is an integer between 1 and 6 and Z is derived from 3-dimethylamino-1,5-pentane diol. In other embodiments, the integrin activating compounds comprise one or more of the following integrin activating compound: (a) 1-[bis(2-thienylmethyl)aminocarbonyloxy]-5-[bis(2-thienylmethyl)aminocarbonyloxy]-3-(dimethylamino)pentane, (b) 1-[bis(3-methoxybenzyl)aminocarbonyloxy]-5-[bis(3-methoxybenzyl)aminocarbonyloxy]-3-(dimethylamino)pentane, (c) 1-[(3-methoxybenzyl),(4-dimethylaminobenzyl) aminocarbonyloxy]-5-[bis(3-methoxybenzyl),(4-dimethylaminobenzyl) aminocarbonyloxy]-3-(dimethylamino)pentane, (d) 1-[bis(4-methoxybenzyl)aminocarbonyloxy]-5-[bis(4-methoxybenzyl)aminocarbonyloxy]-3-(dimethylamino)pentane, (e) 1-[(4-methoxybenzyl),(4-dimethylaminobenzyl) aminocarbonyloxy]-5-[bis(4-methoxybenzyl),(4-dimethylaminobenzyl) aminocarbonyloxy]-3-(dimethylamino)pentane, or (f) mixtures and combinations thereof. In other embodiments, the integrin activating compounds comprise one or more of the following integrin activating compound: (a) 1-[bis(2-thienylmethyl)aminocarbonyloxymethoxy]-5-[bis(2-thienylmethyl) aminocarbonyloxymethoxy]-3-(dimethylamino)pentane, (b) 1-[bis(2-thienylmethyl)aminocarbonyloxymethoxy]-5-[bis(2-thienylmethyl)aminocarbonyloxymethoxy]-3-(dimethylamino)pentane, or (c) 1-[bis(3-methoxybenzyl)aminocarbonyloxymethoxy]-5-[bis(3-methoxybenzyl)aminocarbonyloxymethoxy]-3-(dimethylamino)pentane, (d) 1-[bis(3-methoxybenzyl)aminocarbonyloxymethoxymethoxy]-5-[bis(3-methoxybenzyl)aminocarbonyloxymethoxymethoxy]-3-(dimethylamino)pentane, (e) 1-{[(3-methoxybenzyl)(4-dimethylaminobenzyl) amino]carbonyloxymethoxy}-5-{[(3-methoxybenzyl)(4-dimethylaminobenzyl) amino]carbonyloxymethoxy}-3-(dimethylamino)pentane, (f) 1-{[(3-methoxybenzyl)(4-dimethylaminobenzyl) amino]carbonyloxymethoxymethoxy}-5-{[(3-methoxybenzyl)(4-dimethylaminobenzyl) amino]carbonyloxymethoxymethoxy}-3-(dimethylamino)pentane, (g) 1-[bis(4-methoxybenzyl)aminocarbonyloxymethoxy]-5-[bis(4-methoxybenzyl)aminocarbonyloxymethoxy]-3-(dimethylamino)pentane, (h) 1-[bis(4-methoxybenzyl)aminocarbonyloxymethoxymethoxy]-5-[bis(4-methoxybenzyl)aminocarbonyloxy methoxymethoxy]-3-(dimethylamino)pentane, (i) 1-{[(4-methoxybenzyl)(4-dimethylaminobenzyl) amino]carbonyloxymethoxy}-5-{[(4-methoxybenzyl)(4-dimethylaminobenzyl) amino]carbonyloxymethoxy}-3-(dimethylamino)pentane, (j) 1-{[(4-methoxybenzyl)(4-dimethylaminobenzyl) amino]carbonyloxymethoxymethoxy}-5-{[(4-methoxybenzyl)(4-dimethylaminobenzyl) amino]carbonyloxymethoxymethoxy}-3-(dimethylamino)pentane, (k) higher analogs, or (l) mixtures and combinations thereof. In other embodiments, the integrin activating compounds comprise one or more of the following integrin activating compound: (a) 1-[bis(2-thienylmethyl)aminocarbonyloxyethoxy]-5-[bis(2-thienylmethyl)aminocarbonyloxyethoxy]-3-(dimethylamino)pentane, (b) 1-[bis(2-thienylmethyl)aminocarbonyloxyethoxyethoxy]-5-[bis(2-thienylmethyl)

aminocarbonyloxyethoxyethoxy]-3-(dimethylamino)pentane, or (c) 1-[bis(3-methoxybenzyl)aminocarbonyloxyethoxy]-5-[bis(3-methoxybenzyl)aminocarbonyloxyethoxy]-3-(dimethylamino)pentane, (d) 1-[bis(3-methoxybenzyl)aminocarbonyloxyethoxy]-5-[bis(3-methoxybenzyl)aminocarbonyloxyethoxyethoxy]-3-(dimethylamino)pentane, (e) 1-{[(3-methoxybenzyl)(4-dimethylaminobenzyl) amino]carbonyloxyethoxy}-5-{[(3-methoxybenzyl)(4-dimethylaminobenzyl) amino]carbonyloxyethoxy}-3-(dimethylamino)pentane, (f) 1-{[(3-methoxybenzyl)(4-dimethylaminobenzyl) amino]carbonyloxyethoxyethoxy}-5-{[(3-methoxybenzyl)(4-dimethylaminobenzyl) amino]carbonyloxyethoxyethoxy}-3-(dimethylamino)pentane, (g) 1-[bis(4-methoxybenzyl)aminocarbonyloxyethoxy]-5-[bis(4-methoxybenzyl)aminocarbonyloxyethoxy]-3-(dimethylamino)pentane, (h) 1-[bis(4-methoxybenzyl)aminocarbonyloxyethoxyethoxy]-5-[bis(4-methoxybenzyl)aminocarbonyloxy ethoxyethoxy]-3-(dimethylamino)pentane, (i) 1-{[(4-methoxybenzyl)(4-dimethylaminobenzyl) amino]carbonyloxyethoxy}-5-{[(4-methoxybenzyl)(4-dimethylaminobenzyl) amino]carbonyloxyethoxy}-3-(dimethylamino)pentane, (j) 1-{[(4-methoxybenzyl)(4-dimethylaminobenzyl) amino]carbonyloxyethoxyethoxy}-5-{[(4-methoxybenzyl)(4-dimethylaminobenzyl) amino]carbonyloxyethoxyethoxy}-3-(dimethylamino)pentane, (k) higher analogs, or (l) mixtures and combinations thereof.

$R^a$=$(OCH_2)_n$ or $CH_3(CH_2O)_n$ and Z=3-DimethylAmine Class Agonists

In certain embodiments, the integrin activating compounds comprise one or more compound of Formula (I), wherein the $R^a$ group comprises $(OCH_2)_n$ or $(OCH_2CH_2)_n$, wherein n is an integer between 1 and 6 and Z is dimethylamine. In other embodiments, the integrin activating compounds comprise one or more of the following integrin activating compound: (a) 5-oxo-7-(2-thienyl)-6-(2-thienylmethyl)-2,4-dioxa-6-aza-heptanyl-N,N-dimethylamine, (b) 5-oxo-7-(3-methoxyphenyl)-6-(3-methoxybenzyl)-2,4-dioxa-6-aza-heptanyl-N,N-dimethylamine, (c) 5-oxo-7-(3-methoxyphenyl)-6-(4-dimethylaminobenzyl)-2,4-dioxa-6-aza-heptanyl-N,N-dimethylamine, (d) 5-oxo-7-(4-methoxyphenyl)-6-(4-methoxybenzyl)-2,4-dioxa-6-aza-heptanyl-N,N-dimethylamine, (e) 5-oxo-7-(4-methoxyphenyl)-6-(4-dimethylaminobenzyl)-2,4-dioxa-6-aza-heptanyl-N,N-dimethylamine, (f) 7-oxo-9-(2-thienyl)-8-(2-thienylmethyl)-2,4,6-trioxa-8-aza-nonayl-N,N-dimethylamine, (g) 7-oxo-9-(3-methoxyphenyl)-8-(3-methoxybenzyl)-2,4,6-trioxa-8-aza-undecyl-N,N-dimethylamine, (h) 7-oxo-9-(3-methoxyphenyl)-8-(4-dimethylaminobenzyl)-2,4,6-trioxa-8-aza-dodecyl-N,N-dimethylamine, (i) 7-oxo-9-(3-methoxyphenyl)-8-(3-methoxybenzyl)-2,4,6-trioxa-8-aza-dodecyl-N,N-dimethylamine, (j) 7-oxo-9-(3-methoxyphenyl)-8-(4-dimethylaminobenzyl)-2,4,6-trioxa-8-aza-dodecyl-N,N-dimethylamine, (k) 9-oxo-11-(2-thienyl)-10-(2-thienylmethyl)-2,4,6,8-tetraoxa-10-aza-undecyl-N,N-dimethylamine, (l) 9-oxo-11-(3-methoxyphenyl)-10-(3-methoxybenzyl)-2,4,6,8-tetraoxa-10-aza-pentadecyl-N,N-dimethylamine, (m) 9-oxo-11-(3-methoxyphenyl)-10-(4-dimethylaminobenzyl)-2,4,6,8-tetraoxa-10-aza-pentadecyl-N,N-dimethylamine, (n) 9-oxo-11-(4-methoxyphenyl)-10-(4-methoxybenzyl)-2,4,6,8-tetraoxa-10-aza-pentadecyl-N,N-dimethylamine, (o) 9-oxo-11-(3-methoxyphenyl)-10-(4-dimethylaminobenzyl)-2,4,6,8-tetraoxa-10-aza-pentadecyl-N,N-dimethylamine, (p) higher analogs, or (q) mixtures and combinations thereof. In other embodiments, the integrin activating compounds comprise one or more of the following integrin activating compound: (a) 7-oxo-9-(2-thienyl)-8-(2-thienylmethyl)-3,6-dioxa-8-aza-nonanyl-N,N-dimethylamine, (b) 7-oxo-9-(3-methoxyphenyl)-8-(3-methoxybenzyl)-3,6-dioxa-8-aza-nonanyl-N,N-dimethylamine, (c) 7-oxo-9-(3-methoxyphenyl)-8-(4-dimethylaminobenzyl)-3,6-dioxa-8-aza-nonanyl-N,N-dimethylamine, (d) 7-oxo-9-(4-methoxyphenyl)-8-(4-methoxybenzyl)-3,6-dioxa-8-aza-nonanyl-N,N-dimethylamine, (e) 7-oxo-9-(4-methoxyphenyl)-8-(4-dimethylaminobenzyl)-3,6-dioxa-8-aza-nonanyl-N,N-dimethylamine, or (f) mixtures and combinations thereof. (g) 10-oxo-12-(2-thienyl)-11-(2-thienylmethyl)-3,6,9-trioxa-11-aza-dodecyl-N,N-dimethylamine, (h) 10-oxo-12-(3-methoxyphenyl)-11-(3-methoxybenzyl)-3,6,9-trioxa-11-aza-dodecyl-N,N-dimethylamine, (i) 10-oxo-12-(3-methoxyphenyl)-11-(4-dimethylaminobenzyl)-3,6,9-trioxa-11-aza-dodecyl-N,N-dimethylamine, (j) 10-oxo-12-(3-methoxyphenyl)-11-(3-methoxybenzyl)-3,6,9-trioxa-11-aza-dodecyl-N,N-dimethylamine, (k) 10-oxo-12-(3-methoxyphenyl)-11-(4-dimethylaminobenzyl)-3,6,9-trioxa-11-aza-dodecyl-N,N-dimethylamine, (l) 13-oxo-15-(2-thienyl)-14-(2-thienylmethyl)-3,6,9,12-tetraoxa-14-aza-pentadecyl-N,N-dimethylamine, (m) 13-oxo-15-(3-methoxyphenyl)-14-(3-methoxybenzyl)-3,6,9,12-tetraoxa-14-aza-pentadecyl-N,N-dimethylamine, (n) 13-oxo-15-(3-methoxyphenyl)-14-(4-dimethylaminobenzyl)-3,6,9,12-tetraoxa-14-aza-pentadecyl-N,N-dimethylamine, (o) 13-oxo-15-(4-methoxyphenyl)-14-(4-methoxybenzyl)-3,6,9,12-tetraoxa-14-aza-pentadecyl-N,N-dimethylamine, (p) 13-oxo-15-(3-methoxyphenyl)-14-(4-dimethylaminobenzyl)-3,6,9,12-tetraoxa-14-aza-pentadecyl-N,N-dimethylamine, (q) higher analogs, or (r) mixtures and combinations thereof.

In certain embodiments, the effective amount of the activators or agonists of the disclosure is between about 1 fM and about 300 µM or any subrange such as between about 1 fM and about 200 µM, between about 1 fM and about 100 µM, between about 1 fM and about 50 µM, between about 1 fM and about 25 µM, between about 1 fM and about 20 µM, between about 1 fM and about 15 µM, between about 1 fM and about 5 µM, between about 1 fM and about 1 µM, between about 1 fM and about 100 nM, between about 1 fM and about 75 nM, between about 1 fM and about 50 nM, between about 1 fM and about 25 nM, or any other subrange.

Generally, plasma concentrations are represented in ng/mL. In certain embodiments, the plasma concentration of the agonist(s) is(are) between about 1 nanogram/milliliter (ng/mL) and about 25 ng/mL or any subrange such as between about 1 ng/mL and about 20 ng/mL, between about 1 ng/mL and about 15 ng/mL, between about 1 ng/mL and about 5 ng/mL, between about 1 ng/mL and about 1 ng/mL, between about 1 ng/mL and about 100 ng/mL, between about 1 ng/mL and about 75 ng/mL, between about 1 ng/mL and about 50 ng/mL, between about 1 ng/kg and about 25 ng/mL, or any other subrange.

In certain embodiments, the therapeutic effective amount of cells are between about $1 \times 10^4$ cells per kg and about $1 \times 10^9$ cells per kg of the animal, mammal, or human receiving the cells or any subrange such as between about $1 \times 10^4$ cells per kg and about $1 \times 10^8$ cells per kg, between about $1 \times 10^4$ cells per kg and about $1 \times 10^7$ cells per kg, or between about $1 \times 10^4$ cells per kg, about $1 \times 10^6$ cells per kg, between about $1 \times 10^4$ cells per kg and about $1 \times 10^5$ cells per kg, or any other subrange.

Agonist Pretreated or Treated Integrin Expressing Cells

Embodiments of this disclosure broadly relate to treating or pre-treating cells with an effective amount of one or more agonists of the Formula (I), wherein the integrins located on an outer surface of the cells, the integrins are activated by the one or more agonists, and the activated integrins are involved in certain intercellular interactions. The cells may be any cell for which activated integrins enhance a desired cellular activity such as homing, migrating, infiltrating, and/or grafting. The treated or pre-treated cells may be used to promote stem cell based therapies such as reestablishing bone marrow, etc., effector cell based therapies, anti-body therapies, anti-body/cell based therapies, check point inhibitor therapies, check point inhibitor/cell based therapies, etc. In certain embodiments, the cells may be treated or pre-treated with one or more agonists of Formula (I) as a solution including an effective amount of one or more agonists of Formula (I) in an acceptable pharmaceutically diluent or carrier such as cell culture media so that the cells are suspended in and mixed with the carrier. In this disclosure, treated cells mean that the cells and the one or more agonists of Formula (I) are co-administered. In this disclosure, pre-treated cells mean that the cells are treated with an effective amount of the one or more agonists of Formula (I) prior to being administered. The resulting agonist-treated cells or pre-treated cells are administered to a subject either systemically or via injection into a target tissue. In certain embodiments, an integrin binding protein or ligand is the vascular cell adhesion molecule-1 (VCAM 1), fibronectin, mucosal addressin cellular adhesion molecule-1 (MAdCAM-1), intercellular adhesion molecule-1 (ICAM-1), intercellular adhesion molecule-2 (ICAM-2) or vitronectin. As a result of the agonist treatment or pre-treatment, the binding of the agonist-treated cells to the ligand is enhanced or increased compared to binding of integrin-expressing cells in the absence of agonist pre-treatment or treatment. In other embodiments, at least 3 fold more agonist-treated cells are bound to a ligand-coated surface than untreated integrin-expressing cells. In some cases, up to 3 fold more agonist-treated cells than untreated cells are bound to an integrin binding protein. In other embodiments, the cells express one or more of the integrins selected from the group consisting of α4β1, α5β1, α4β7, αvβ and αLβ2. The pre-treatment or treatment of the cells generally involves contacting the integrin-expressing cells in vitro or ex vivo with one or more integrin agonists of Formula (I). After exposure to the agonist, the resulting agonist-treated cells have an enhanced ability to bind to a cognate ligand. The integrins that are targeted by the integrin agonists of Formula (I) are expressed on the surface of the cells, and may be either naturally occurring or transgenically expressed by a cell that has been transformed to express an exogenous integrin gene. The proteins or other cognate ligands to which the integrins bind are expressed either on a cell surface or as part of the extracellular matrix.

In other embodiments, regardless of the cell type, mechanism of action, or how they are delivered, cell homing and retention are key features in relevant therapies. Low levels of cell retention observed in animal models and clinical trials are considered one of the major impediments to the progress of cell-based therapies. Even when cells are injected locally, less than 10% of injected cells are typically retained after one hour and this number decreases over time in conventional cell-based therapies. The retention rates are even lower when the cells are delivered systemically. By comparison, many embodiments of the presently disclosed methods increase both cell homing and cell retention of exogenously delivered cells and will potentially greatly further efforts in regenerative medicine.

Embodiments of this disclosure broadly relate to methods for enhancing retention of exogenously-introduced cells at an in vivo target site in an animal, mammal or human, wherein the methods generally include the steps of (a) treating integrin-expressing cells in vitro or ex vivo with an effective amount of one or more small molecular integrin agonists; (b) administering a therapeutically effective amount of the agonist-treated cells to in vivo systemically or directly to a target tissue site in an animal, mammal or human; and (c) causing a greater number of the introduced agonist-treated cells to remain at the target tissue site relative to the number of untreated integrin-expressing cells. The target tissue site includes generally includes an integrin binding protein such as vascular cell adhesion molecule-1 (VCAM 1), fibronectin, mucosal addressin cellular adhesion molecule-1 (MAdCAM-1), inter-cellular adhesion molecule-1 (ICAM-1), inter-cellular adhesion molecule-2 (ICAM-2) or vitronectin, for example. In certain embodiments, the agonists are compounds having the general Formula (I), as described herein; however, any small molecular agonists that activates cell surface integrins may be used as well. Alternatively, the methods may include (a) administering integrin expressing cells and one or more small molecular agonists in vivo systemically or directly to a target tissue site in an animal, mammal or human; and (b) causing a greater number of the introduced agonist-treated cells to remain at the target tissue site relative to the number of untreated integrin-expressing cells.

In other embodiments, the agonist-treated cells prepared as described above are administered to a damaged or diseased vascular site in a vessel of an animal, mammal or human. The cells are injected directly into, or around a site of damaged or diseased vascular tissue, as often occurs in tissue due to ischemia following a heart attack or in peripheral arterial disease. Alternatively, in some cases the agonist-treated cells are injected intravenously for homing to a damaged or diseased site where treatment is desired. The damaged or diseased tissue contains cells (e.g., endothelial cells) that express VCAM-1, and in which VCAM-1 exists on the cell surface. Expression of VCAM-1 is induced in many cases by inflammatory cytokines such as tumor necrosis factor-α, interleukin-4 and interleukin-1p. In some instances, cells or extracellular matrix at or adjacent to a treatment site express and bear on their surface one or more other integrin-binding protein such as fibronectin, mucosal addressin cellular adhesion molecule-1 (MAdCAM-1), intercellular adhesion molecule-1 (ICAM-1), intercellular adhesion molecule-2 (ICAM-2) or vitronectin. In those instances, the injected agonist-treated cells adhere to the cognate ligands at the damaged or diseased tissue site, causing a greater number of the administered agonist-treated cells to remain at the treatment site compared to the number of untreated integrin-expressing cells that would be retained if administered instead. The agonist-treated cells retained at the treatment site are allowed to grow and/or release paracrine factors, to regenerate vascular tissue at the damaged or diseased site, e.g., damage due to ischemia, autoimmune reactions, or mechanical injury. Paracrine factors are substances released from a cell that have effects on a neighboring cell, such as growth factors or cytokines.

In other embodiments, the methods of this disclosure contemplate using the agonist-pretreated cells or the agonist-treated cells to treat any number of diseases or conditions that are amenable to a cell-based therapy. For example, the agonist-pretreated cells or the agonist-treated cells may be used to treat myocardial infarction, peripheral artery disease, diabetes, diabetes wound healing, renal failure, systemic lupus erythematosus, multiple sclerosis, pulmonary fibrosis, pulmonary hypertension, acute respiratory distress syndrome, Alzheimer's disease, Huntington's disease, Parkinson's disease, spinal cord injury, infertility and bone marrow transplant in some embodiments by injecting an above-described cell suspension intravenously, intraarterially, or directly in or around the injured area. New tissue is generated either by proliferation and differentiation of the injected cells and/or release of paracrine factors by the injected cells which induce proliferation and differentiation of neighboring host cells.

Media Compositions

The agonists or activator compounds of this disclosure used in the ex vivo media production of treated or pre-treated integrin expressing cells described herein may be used in the form of pharmaceutically acceptable salts of the agonists or activator compounds derived from inorganic or organic acids. The phrase "pharmaceutically acceptable salt" means those salts which are, within the scope of sound medical judgment, suitable for use in contact with the tissues of humans, mammals, or animals without undue toxicity, irritation, allergic response and the like and are commensurate with a reasonable benefit/risk ratio. Pharmaceutically acceptable salts are well-known in the art. For example, S. M. Berge et al. describe pharmaceutically acceptable salts in detail in J. Pharmaceutical Sciences, 1977, 66: 1 et seq. The salts may be prepared in situ during the final isolation and purification of the compounds or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphor sulfonate, digluconate, glycerophosphate, hemisulfate, heptanoate, hexanoate, fumarate, hydrochloride, hydrobromide, hydroiodide, 2-hydroxyethansulfonate (isothionate), lactate, maleate, methane sulfonate, nicotinate, 2-naphthalene sulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

In certain embodiments, basic addition salts are prepared in situ during the final isolation and purification of a disclosed compound by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylammonium, dimethylammonium, trimethylammonium, triethylammonium, diethylammonium, and ethylammonium among others. Other representative organic amines useful for the formation of base addition salts include ethylenediamine, ethanolamine, diethanolamine, piperidine, piperazine and the like.

Actual concentration of ingredients in the media compositions may be varied so as to obtain an amount of the compound(s) which is effective to achieve the desired therapeutic response mediated by the cell therapeutic treated with media for a particular patient, compositions and mode of administration. The selected concentration level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used for the production of cells for various therapeutic treatments, a therapeutically effective amount of one or more of the disclosed compounds be employed in pure form or, where such forms exist, in pharmaceutically acceptable salt, ester, or pro-drug form (drug precursor—breaks down in the body to form the active drug). In some cases, the compound is administered as a pharmaceutical composition containing the compound of interest in combination with one or more other pharmaceutically acceptable inactive ingredients or excipients. The phrase "therapeutically effective amount" of a disclosed compound means a sufficient amount of the compound to generate a cell therapeutic composition to treat disorders, at a reasonable benefit/risk ratio applicable to any medical treatment. The specific therapeutically effective concentration of the compound and cell dose for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start cell doses of the compound at levels lower than required to achieve the desired therapeutic effect and to gradually increase the dosage until the desired effect is achieved.

The concentration of the disclosed compounds in the ex vivo treatment media alone or in combination with therapeutic cells in a suitable media to infuse a human or lower animal may be between about 1 fM (1 femto molar or $1 \times 10^{-15}$ M) and about 300 µM, between about 1 nM and than about 200 µM, between about 10 nm and 100 µM, between about 10 nm and 50 µM, between about 25 nm and 10 µM, between about 25 nm and 10 µM, and any other range in between about 1 fM and about 300 µM. If desired, the effective concentration can be divided into multiple doses for purposes of administration; consequently, single dose compositions may contain such amounts or submultiples thereof to make up the daily dose of cell or compound.

The total daily concentrations of the disclosed compounds administered in combination with therapeutic cells in a suitable media to a human or lower animal may be between about 1 fM (1 femto molar or $1 \times 10^{-15}$ M) and about 300 µM. If desired, the effective daily dose can be divided into multiple doses for purposes of administration; consequently, single dose compositions may contain such amounts or submultiples thereof to make up the daily dose of cell or exposure of the compound.

Compositions suitable for parenteral injection may comprise physiologically acceptable, sterile aqueous or non-aqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), vegetable oils (such as olive oil), injectable organic esters such as ethyl oleate, and suitable mixtures thereof. These compositions can also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monostearate and gelatin.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like. Proper fluidity can be maintained, for example, by the use of coating materials such as lecithin, by the maintenance of the required particle size in the case of dispersions and by the use of surfactants.

In some cases, for compounds with minimal solubility, solubility enhancers without limitation include surfactants such as zwitterionic phospholipids, non-esterified fatty acids, mono-, di- or triglycerides alone or in combinations secondary surfactants may be used.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

In other embodiments, compositions for media to carry integrin expressing cells comprises one or more small molecule integrin agonists in an electrolyte solution. Representative media or cell carriers may include, without limitation, (1) multiple electrolytes injection, Type 1, USP with nominal pH ranges of 5.5 to 8.0, wherein the media may be sterile, nonpyrogenic isotonic solution, (2) tissue culture media (e.g., RPMI-1640 [RPMI]) without phenol red), (3) minimal media comprising of a saline solution (0.9% NaCl) containing 5% human serum albumin (Baxter or Talecris) and 8% Dextran 40 (Hospira) (LMD/HSA), 4) culture and expansion medium such as StemSpan-SFEM (Stem Cell Technologies), and 5) any isotonic solution comprising $MnCl_2$. The representative media may contain osmotic stabilizer of cells or cell membranes comprising, without limitation, protein derived from serum or plasma (present in amounts from 0.5 wt. % to 50 wt. %).

Homing, Migrating, Infiltrating, and Grafting of Hematopoietic Stem Cells (HSCs)

Embodiments of this disclosure also broadly relate to compositions and methods for hematopoietic stem cells (HSCs) therapies. The compositions including one or more small molecule integrin activator of Formula (I) and treated or untreated HSCs, wherein the integrin activators of Formula (I) enhance the integrin-mediated binding of the HSCs cells to their respective ligands. The integrin activators target at least the integrins $\alpha 4\beta 1$, $\alpha 4\beta 7$, $\alpha 5\beta 1$, $\alpha L\beta 2$ and/or $\alpha V\beta 3$, which enhance the interaction of these integrins with at least the ligands VCAM-1, fibronectin, MAdCAM-1, ICAM-1, ICAM-2 and/or vitronectin. Again, the mode of action is believed to be due to the ability for the integrin activators to affect a conformational change in exterior surface integrins from a low active or inactive state to an active or highly active state.

In certain embodiments, the integrin activators are administered before, during, and/or after the administration of the HSCs, whether the HSCs are treated or untreated. Again, treated HSCs are cells that have been pre-treated with one or more of the integrin activators in vitro or ex vivo, wherein the treatment of HSCs generally occurs in an acceptable media for cell treatment, expansion, and proliferation. The integrin activators may be administered systemically via oral administration or a composition including treated or untreated HSCs may be administered parenterally or injected directly into the bone, wherein the integrin activators enhance the adhesion of HSCs in bone marrow and stimulate the reestablishment of healthy bone marrow tissue.

In certain embodiments, the HSCs are derived from bone marrow, umbilical cord blood, and/or peripheral blood. In other embodiments, the HSCs consist essentially of $CD34^+$ HSCs.

In other embodiments, the compositions including an effective amount of one or more integrin activators of Formula (I) and an therapeutically effective amount of treated and/or untreated HSCs are used to treat various cancers and/or genetic disorders selected from the group consisting of acute myelogenous leukemia (AML), acute lymphoblastic leukemia (ALL), chronic myelogenous leukemia (CML), chronic lymphocytic leukemia (CLL), juvenile myelomonocytic leukemia, Hodgkin's lymphoma, non-Hodgkin's lymphoma, multiple myeloma, severe aplastic anemia, Fanconi's anemia, paroxysmal nocturnal hemoglobinuria (PNH), pure red cell aplasia, amegakaryocytosis/congenital thrombocytopenia, severe combined immunodeficiency syndrome (SCID), Wiskott-Aldrich syndrome, beta-thalassemia major, sickle cell disease, Hurler's syndrome, adrenoleukodystrophy, metachromatic leukodystrophy, myelodysplasia, refractory anemia, chronic myelomonocytic leukemia, agnogenic myeloid metaplasia, familial erythrophagocytic lymphohistiocytosis, solid tumors, chronic granulomatous disease, mucopolysaccharidoses, and Diamond Blackfan syndrome.

Adaptive or Adoptive Cell Therapies

Embodiments of this disclosure broadly relate to adaptive or adoptive cell therapy compositions including an effective amount of one or more integrin agonists of Formula (I) and a therapeutically effective amount of untreated and/or untreated effector cells, wherein the integrin activators or agonists of Formula (I) enhance the integrin-mediated binding of the effector cells to their respective ligands. The integrin agonists target at least the integrins $\alpha 4\beta 1$-VCAM-1, $\alpha 4\beta 7$/MAdCAM-1, and/or $\alpha L\beta 2$-ICAM-1, which enhance the interaction of these integrins with at least the ligands VCAM-1, fibronectin, MAdCAM-1, ICAM-1, ICAM-2 and/or vitronectin. Again, the mode of action is believed to be due to the ability for the integrin activators to affect a conformational change in exterior surface integrins from a low active or inactive state to an active or highly active state. The one or more small molecule integrin agonists of Formula (I) may be administered before, during, and/or after the administration of the one or more untreated and/or untreated effector cells.

Embodiments of this disclosure broadly relate to methods including administering: (a) therapeutically effective amount of untreated and/or untreated effector cells in an acceptable carrier to a host (e.g., animal, mammal, or human), wherein the therapeutically effective amount is sufficient to elicit a desired therapeutic response in the host; and (b) one or more small molecule integrin agonists of Formula (I) before, during, and/or after the antigen administration to the host, wherein the one or more small molecule integrin agonists of Formula (I) enhance the efficacy of the treated and/or untreated effector cells.

Methods for Antitumor Activity

Embodiments of this disclosure broadly relate to methods including administering one or more small molecule integrin agonists of Formula (I), wherein the one or more small molecule integrin agonists of Formula (I) reduce tumor growth, reduce tumor size, reduce the symptoms of solid tumor cancers, enhance host survival, and/or eliminate or substantially eliminate cancerous tumors.

Antibody Therapies and Antibody Dependent Cellular Cytotoxicity (ADCC)

Embodiments of this disclosure broadly relate to adaptive or adoptive cell therapy compositions including an effective amount of one or more integrin agonists of Formula (I) and a therapeutically effective amount of untreated and/or untreated effector cells, wherein the integrin activators or agonists of Formula (I) enhance the integrin-mediated binding of the effector cells to their respective ligands. The integrin agonists target at least the integrins α4β1-VCAM-1, α4β7/MAdCAM-1, and/or αLβ2-ICAM-1, which enhance the interaction of these integrins with at least the ligands VCAM-1, fibronectin, MAdCAM-1, ICAM-1, ICAM-2 and/or vitronectin. Again, the mode of action is believed to be due to the ability for the integrin activators to affect a conformational change in exterior surface integrins from a low active or inactive state to an active or highly active state. The one or more small molecule integrin agonists of Formula (I) may be administered before, during, and/or after the administration of the one or more untreated and/or untreated effector cells.

Embodiments of this disclosure broadly relate to methods including administering: (a) an effector cell effective amount of untreated or untreated effector cells in an acceptable carrier to a host (e.g., animal, mammal, or human), wherein the effector cell effective amount is sufficient to elicit a desired effector cell response in the host; and (b) one or more small molecule integrin agonists of Formula (I) before, during, and/or after the antigen administration to the host, wherein the integrin activators or agonists of Formula (I) enhance the integrin-mediated binding of the effector cells to their respective ligands. The integrin agonists target at least the integrins α4β1-VCAM-1, α4β7/MAdCAM-1, and/or αLβ2-ICAM-1, which enhance the interaction of these integrins with at least the ligands VCAM-1, fibronectin, MAdCAM-1, ICAM-1, ICAM-2 and/or vitronectin. Again, the mode of action is believed to be due to the ability for the integrin activators to affect a conformational change in exterior surface integrins from a low active or inactive state to an active or highly active state.

Checkpoint Inhibitor and Immune Checkpoint Inhibitor Therapies

Embodiments of this disclosure broadly relate to adaptive or adoptive cell therapy compositions including an effective amount of one or more integrin agonists of Formula (I) and a therapeutically effective amount of one or more checkpoint inhibitors and/or immune checkpoint inhibitors, wherein the integrin activators or agonists of Formula (I) enhance the integrin-mediated interactions. The integrin agonists target at least the integrins α4β1, α4β7, 5β1, αLβ2, αVβ3, 4β1-VCAM-1, α4β7/MAdCAM-1, and/or αLβ2-ICAM-1, which enhance the interaction of these integrins with at least the ligands VCAM-1, fibronectin, MAdCAM-1, ICAM-1, ICAM-2 and/or vitronectin. Again, the mode of action is believed to be due to the ability for the integrin activators to affect a conformational change in exterior surface integrins from a low active or inactive state to an active or highly active state. The one or more small molecule integrin agonists of Formula (I) may be administered before, during, and/or after the administration of the one or more untreated and/or untreated effector cells.

Embodiments of this disclosure broadly relate to methods for immunizing a host, wherein the methods include administering: (a) an antigen effective amount of one or more antigens in an acceptable vaccine carrier to a host (e.g., animal, mammal, or human), wherein the antigen effective amount is sufficient to elicit a desired immune response in the host; and (b) administering one or more small molecule integrin agonists of Formula (I) before, during, and/or after the antigen administration to the host, wherein the integrin activators or agonists of Formula (I) enhance the integrin-mediated interactions. The integrin agonists target at least the integrins α4β1, α4β7, α5β1, αLβ2, αVβ3, 4β1-VCAM-1, α4β7/MAdCAM-1, and/or αLβ2-ICAM-1, which enhance the interaction of these integrins with at least the ligands VCAM-1, fibronectin, MAdCAM-1, ICAM-1, ICAM-2 and/or vitronectin. Again, the mode of action is believed to be due to the ability for the integrin activators to affect a conformational change in exterior surface integrins from a low active or inactive state to an active or highly active state. The one or more small molecule integrin agonists of Formula (I) may be administered before, during, and/or after the administration of the one or more untreated and/or untreated effector cells.

Immunotherapies

Embodiments of this disclosure broadly relate to adaptive or adoptive cell therapy compositions including an effective amount of one or more integrin agonists of Formula (I) and a therapeutically effective amount of one or more immunotherapeutic agents, wherein the integrin activators or agonists of Formula (I) enhance the integrin-mediated cell binding. The integrin agonists target at least the integrins α4β1, α4β7, 5β1, αLβ2, αVβ3, 4β1-VCAM-1, α4β7/MAdCAM-1, and/or αLβ2-ICAM-1, which enhance the interaction of these integrins with at least the ligands VCAM-1, fibronectin, MAdCAM-1, ICAM-1, ICAM-2 and/or vitronectin. Again, the mode of action is believed to be due to the ability for the integrin activators to affect a conformational change in exterior surface integrins from a low active or inactive state to an active or highly active state. The one or more small molecule integrin agonists of Formula (I) may be administered before, during, and/or after the administration of the one or more untreated and/or untreated effector cells.

Embodiments of this disclosure broadly relate to methods for immunizing a host, wherein the methods include administering: (a) an antigen effective amount of one or more antigens in an acceptable vaccine carrier to a host (e.g., animal, mammal, or human), wherein the antigen effective amount is sufficient to elicit a desired immune response in the host; and (b) administering one or more small molecule integrin agonists of Formula (I) before, during, and/or after the antigen administration to the host, wherein the integrin activators or agonists of Formula (I) enhance the integrin-mediated cell binding. The integrin agonists target at least the integrins α4β1, α4β7, α5β1, αLβ2, αVβ3, 4β1-VCAM-1, α4β7/MAdCAM-1, and/or αLβ2-ICAM-1, which enhance the interaction of these integrins with at least the ligands VCAM-1, fibronectin, MAdCAM-1, ICAM-1, ICAM-2 and/or vitronectin. Again, the mode of action is believed to be due to the ability for the integrin activators to affect a conformational change in exterior surface integrins from a low active or inactive state to an active or highly active state. The one or more small molecule integrin agonists of Formula (I) may be administered before, during, and/or after the administration of the one or more untreated and/or untreated effector cells.

Vaccines
Background

During the priming and effector phases of the immune response, one or more antigens are taken up by cells termed antigen presenting cells (APCs). APCs then present the one or more antigens in the context of major histocompatibility complex (MHC) molecules on their cell surface, to stimulate lymphocyte activation, proliferation, and differentiation into effector cells that may eventually protect the host from the one or more antigens or affect an immunity of the host to the one or more antigens. CD4+ T-helper 1 cells (Th1 cells) directly interact with APCs and produce cytokines, which drive lymphocyte proliferation and the eventual development of memory T cells, and effector cytotoxic T Lymphocytes (CTLs). CD4+ T-helper 2 cells (Th2 cells) directly interact with antigen presenting cells and drive B-cell activation and proliferation, eventually resulting in the production of a humoral, antibody-dependent immune response.

Integrins are also essential in the priming phase of the immune response, as this phase requires the direct interaction between lymphocytes and APCs. The integrins α4β1 and αLβ2 both have been shown to be important in lymphocyte conjugation with APCs and have been shown to be able to provide costimulatory signals that result in lymphocyte activation, proliferation, differentiation and even positive selection. Fibronectin promotes proliferation of naive and memory T cells by signaling through both the VLA-4 and VLA-5 integrins. Activating these integrins to promote efficient conjugation between lymphocytes and APCs has been shown to augment the immune response by enhancing integrin costimulatory effects. For a number of diseases, current vaccination strategies are inadequate to generate long term protective immunity, especially true in the case of vaccines directed towards tumor-associated antigens in cancer. We have found that the small molecule integrin agonists of Formula (I) effectively function as: (1) targeted adjuvant to safely increase the priming responses with current vaccination approaches, and (2) increase effector functions of both humoral and innate immune responses. The small molecule integrin agonists of Formula (I) may be used to enhance multiple aspects of the immune response as described below.

Vaccines Embodiments

Embodiments of this disclosure broadly relate to vaccine compositions comprising one or more antigens and an effective amount of one or more small molecule integrin agonists of Formula (I), wherein the agonists are capable of enhancing integrin-mediated binding of surface integrins of a cell to their respective ligand on another cell. The one or more small molecule integrin agonists of Formula (I) may be administered before, during, and/or after the administration of the one or more antigens.

Embodiments of this disclosure broadly relate to anticancer vaccine compositions comprising one or more anticancer antigens and an effective amount of one or more small molecule integrin agonists of Formula (I), wherein the agonists are capable of enhancing integrin-mediated binding of surface integrins of a cell to their respective ligand on another cell. The one or more small molecule integrin agonists of Formula (I) may be administered before, during, and/or after the administration of the one or more anticancer antigens.

In certain embodiments, the vaccine compositions may include one or more adjuvants, wherein the adjuvant is non-specific or specific substance capable of eliciting an immune response in response to an antigen. Examples of non-specific adjuvants include BCG, complete Freunds adjuvant, alum, or noscapine. Specific adjuvants include without limitations G-CSF, FGF, Toll-like receptor agonists, and/or immune checkpoint inhibitors (CTLA-4, PD-1, PD-L1, IDO-1, etc.). In fact, the small molecule integrin agonists of Formula (I) may be considered specific vaccine adjuvants.

Embodiments of this disclosure broadly relate to methods for immunizing a host, wherein the methods include administering: (a) an antigen effective amount of one or more antigens in an acceptable vaccine carrier to a host (e.g., animal, mammal, or human), wherein the antigen effective amount is sufficient to elicit a desired immune response in the host; and (b) administering one or more small molecule integrin agonists of Formula (I) before, during, and/or after the antigen administration to the host, wherein the one or more small molecule integrin agonists of Formula (I) promote antigen presentation, stimulate APC activation, proliferation, and differentiation, stimulate B-cell activation, proliferation, and differentiation, and/or stimulate lymphocyte activation, proliferation, and differentiation. In certain embodiments, the antigen effective amount is a therapeutically ineffective amount, wherein the one or more small molecule integrin agonists of Formula (I) enhances the immune response raising the immune response to an effective immune response. In certain embodiments, the antigen and/or agonist compositions may be included immune checkpoint inhibitors, therapeutic antibodies, cytotoxic chemotherapeutic agents, and/or any other co-therapy. In certain embodiments, the integrins include α4β1, α4β7, α5β1, and/or αLβ2 and the ligands include VCAM-1, fibronectin, MAdCAM-1, ICAM-1, and/or ICAM-2. In certain cancer embodiments, cancers include, without limitation, lung cancer, prostate cancer, breast cancers, colon cancers, skin cancers, brain cancers, and/or pancreas cancers. The modes of administration may include systemic administration (oral, nasal, eye, etc.), enteral administration, and/or parenteral administration.

SYNTHETIC EXPERIMENTS OF THE DISCLOSURE

The compounds and processes described herein will be better understood in connection with the following synthetic schemes which illustrate the methods by which the disclosed compounds may be prepared. A detailed description of the preparation of representative agonist compounds is set forth in the Examples. It should be understood that the same or similar synthetic methods may also be used to synthesize other agonist compounds disclosed herein. These Examples are presented to describe preferred embodiments and uses of the compounds and agonist-treated cells, and are not meant to limit the disclosure unless otherwise stated in the claims appended hereto.

All Log P data presented in the tables below are calculated using Chem Doodles algorithms for NC+NHET$^a$, A log P98[b], and Y log Pv2.0[c] and Log P calculated using ACD Chem-Sketch algorithm[d]. The values are to be compared to the values for (ethane-1,2-diylbis(oxy))bis(ethane-2,1-diyl)-bis(bis(thiophene-2-yl-methyl)carbamate), which has the following Log P values 3.44[a], 6.71[b], 4.76[c], and 6.22[d]. Please note that while a comparison of Log P values is an indication of relative hydrophobicity, the integrin activating compounds or agonists of this disclosure were designed to be able to be protonated so that salts of the integrin activating compounds or agonists, which would be water soluble.

$Q^1$ and $Q^2$ Syntheses

Example 1

This example illustrates the synthesis of N,N-bis(thiophen-2-ylmethyl)imidazol-1-yl carboxamide (2-3a), wherein $R^1$ and $R^2$ are both 2-thienylmethyl.

Figure 1:
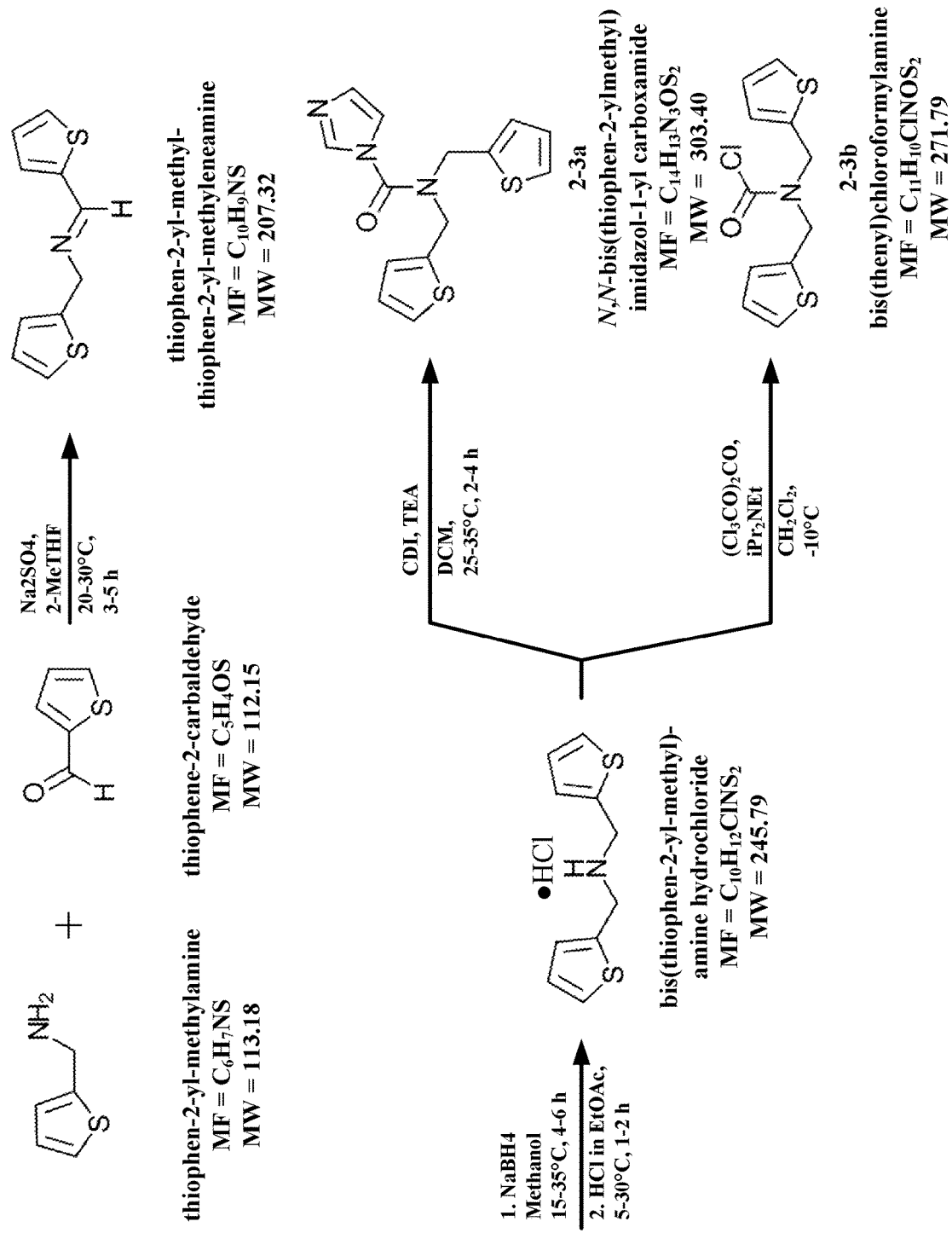
FIG. 1 depicts syntheses of the di-2-thienylmethyl end group intermediates 2-3a&b.

Referring now to FIG. 1, the synthetic scheme for preparing N,N-bis(thiophen-2-ylmethyl)imidazol-1-ylcarboxamide (2-3a) is shown to include two stages, Stage 1 and Stage 2. Stag 1 involves the synthesis of a Stage 1 imine intermediate (2-1) and amine hydrochloride intermediate (2-2), while Stage 2 involves the synthesis of a Stage 2 carboxamide intermediate (2-3a). The Stage 1 synthesis procedure follows:
1. Thiophen-2-yl-methylamine (1-1)(8.8 millimoles) and thiophene-2-carbaldehyde (1-2) (8.8 millimoles) are mixed in 5 mL of 2-methyl tetrahydrofuran.
2. Anhydrous sodium sulphate (0.3 g) is added to the mixture.
3. The reaction mixture is stirred at 20-30° C. for 3 h [Note: Reaction is exothermic and control of the temperature is maintained by external cooling].
4. The reaction mixture is sampled for GC analysis to check for remaining thiophen-2-yl-methylamine. [Content of thiophen-2-yl-methylamine (1-1) should be less than 0.9% (a/a)].
5. If the content of thiophen-2-yl-methylamine (1-1) is more than 0.9%, stir the reaction mixture at 25-35° C. until the in-process limit is achieved.
6. Filter the reaction mixture to separate sodium sulphate and wash the solid with 2-methyl tetrahydrofuran (1 mL).
7. Concentrate the filtrate completely and add n-heptane (3 mL) to the residue and stir the mixture at 10-15° C. for 1 h.
8. Filter the slurry and wash the solid with n-heptane (1 mL).
9. Dry the solid at 40-45° C. for 1 h. This isolated compound is the Stage-1 imine intermediate (2-1). Analyze for content of thiophen-2-yl-methylamine and if the remaining content of thiophen-2-yl-methylamine (1-1) is more than 0.09%, repeat operations 7-8.
10. Dissolve Stage-1 imine intermediate (2-1) in methanol (5 mL) and stir the mixture at 20-30° C. for 5 minutes. Cool the solution to 15-20° C.
11. Add sodium borohydride (0.233 g) in small lots over a period of 45 minutes at 15-30° C. to form the Stage 1 amine hydrochloride intermediate (2-2).
12. Stir the reaction mixture at 25-35° C. for 4 h.
13. The reaction mixture is checked for completion by GC analysis [Content of Stage-1 imine intermediate (2-1) should be less than 0.9%].
14. If the content of Stage-1 imine intermediate (2-1) is more than 0.9%, add sodium borohydride (0.033 g) and stir the reaction mixture at 20-30° C. for 2 h. Check the reaction mixture for reaction completion.
15. If the content of Stage-1 imine intermediate (2-1) is more than 0.9% repeat operation 11 until the in-process limit is achieved. Do not perform this reduction step more than 6 times.
16. Concentrate the reaction mixture at 40-45° C. and degas for 30 mins. Add ethyl acetate (10 mL) to the reaction mixture and stir for 5 mins to obtain a clear solution.
17. Add 10% aqueous potassium carbonate solution (5 mL) and stir the mixture.
18. Separate the aqueous layer and add 10% aqueous potassium carbonate solution (5 mL) to the organic layer.
19. Stir the mixture and separate the aqueous layer. Add water (5 mL) to the organic layer.
20. Stir the mixture and separate the aqueous layer. Dry the organic layer over anhydrous sodium sulphate (1 g).
21. Filter the dried organic layer and add HCl in ethyl acetate (10-150% solution) (3.5 mL) slowly at 5-10° C. over a period of 30 minutes. Stir the slurry at 25-30° C. for 1 h.
22. Filter the slurry to separate the solid and wash the solid with ethyl acetate (2 mL).
23. Dry the solid in vacuum oven at 40-45° C. for 4 h. This solid is Stage 1 amine hydrochloride intermediate (2-2).
24. The Stage 1 amine hydrochloride intermediate (2-2) is tested for residual water (content should be less than 0.9%). If water content is greater than 0.9% the solid is further dried at 40-45° C. under vacuum till the in-process limit is achieved.

The synthesis yielded 1.90-1.95 g of the Stage 1 amine hydrochloride intermediate (2-2) at a yield of 87-90%; (1.9-1.95 w/w).

The Stage 2 carboxamide intermediate (2-3a) synthesis procedure follows:
1. Mix Stage 1 amine hydrochloride intermediate (2-2) (1 g) dichloromethane (10 mL). Add triethylamine (1.125 mL) into the reaction mixture at 15-25° C. over a period of 15 min.
2. Stir the reaction mixture at 25-35° C. for 30 min. Maintain nitrogen atmosphere.
3. Add 1,1'-carbonyldiimidazole (CDI) (0.7916 g) in small lots over a period of 1 h at 20-30° C. Stir the reaction mixture at 25-35° C. for 2 h.
4. Test the reaction mixture for reaction completion by HPLC analysis. [IPC limit: Content of Stage 1 amine hydrochloride intermediate (2-2) should be less than 0.9% (a/a)].
5. If the content of Stage 1 amine hydrochloride intermediate (2-2) is more than 0.9%, add 1,1'-carbonyldiimidazole (CDI) (0.198 g) to the reaction mixture in small portions over a period of 30 min at 25-35° C. Stir the reaction mixture at 25-35° C. for 2 h. If the content of Stage 1 amine hydrochloride intermediate (2-2) is more than 0.9%, repeat additional reaction with CDI for no more than 6 times.
6. After reaction completion is confirmed, add water (5 mL) into the reaction mixture and stir the mixture for 10 min.
7. Separate the aqueous layer and add water (5 mL) to the organic layer. Stir the mixture and allow the layers to separate.
8. Dry the organic layer over anhydrous sodium sulphate (1 g) and concentrate the organic layer at 40-45° C. to obtain crude Stage-2 intermediate.

9. Dissolve the crude intermediate compound in ethyl acetate (1.25 mL) by heating the mixture at 40-45° C. under gentle stirring to obtain a clear solution.
10. Add n-heptane (1.75 mL) slowly to the solution. Stir the slurry at 25-35° C. for 1 h.
11. Filter the slurry to separate solid. Wash the solid with 40% ethyl acetate in n-heptane (1 mL). Dry the solid in vacuum oven at 40-45° C. for 4 h.
12. Charge ethyl acetate lot-2 (1.50 mL) into a clean reactor.
13. Dissolve the solid (~1 g) obtained in operation 11 in ethyl acetate (~1.5 mL) [Note: Quantity of ethyl acetate should be 1.5 times the weight of solid obtained in operation 11]. Heat the mixture to 40-45° C. until a clear solution is achieved.
14. Cool the mixture gradually and filter the slurry to separate out the solid. Wash the solid with chilled (0-5° C.) ethyl acetate (50 mL). Dry the solid in vacuum oven at 40-45° C. for 4 h.
15. Sample the dried carboxamide intermediate (2-3) and analyze by HPLC. [IPC limits: Regio-isomer of carboxamide intermediate (2-3) NMT1 0.18%; 1-impurity NMT 0.09%; Stage-1 NMT 0.09%.]
16. If the IPC limits do not comply, repeat operations 13-14.
17. If the IPC limits are met, dry the material in vacuum oven at 40-45° C. for 3 h. Sample and check for water content [IPC limit for water content: NMT 0.45%].
18. Continue drying if the IPC limit for water content are not met.
19. If the IPC limit for water content is met, check content of residual solvents by GC. [IPC limit for content of residual solvents: Methanol NMT 10 ppm; ethanol NMT 10 ppm; 1-propanol NMT 1000 ppm; 2-propanol NMT 10 ppm; ethyl acetate NMT 10 ppm.]
20. Continue drying if the IPC limits for residual solvent are not met.

The synthesis yielded 0.65-0.80 g of the carboxamide intermediate (2-3a) at a yield pf 53-65% (0.65%-0.80 w/w) and a purity by HPLC: >99% (a/a by HPLC).

Alternatively, the $Q^1$ and $Q^2$ may be synthesized to from N,N-bis(thiophen-2-ylmethyl)chloroformylamine (2-3b) via the synthetic scheme set forth in FIG. 1.

Example 2

This example illustrates the synthesis of N,N-di(3-methoxybenyl)-1-imidazolecarboxamide (2-6a), wherein $R^1$ and $R^2$ are both 3-methoxybenzyl.

Figure 2:
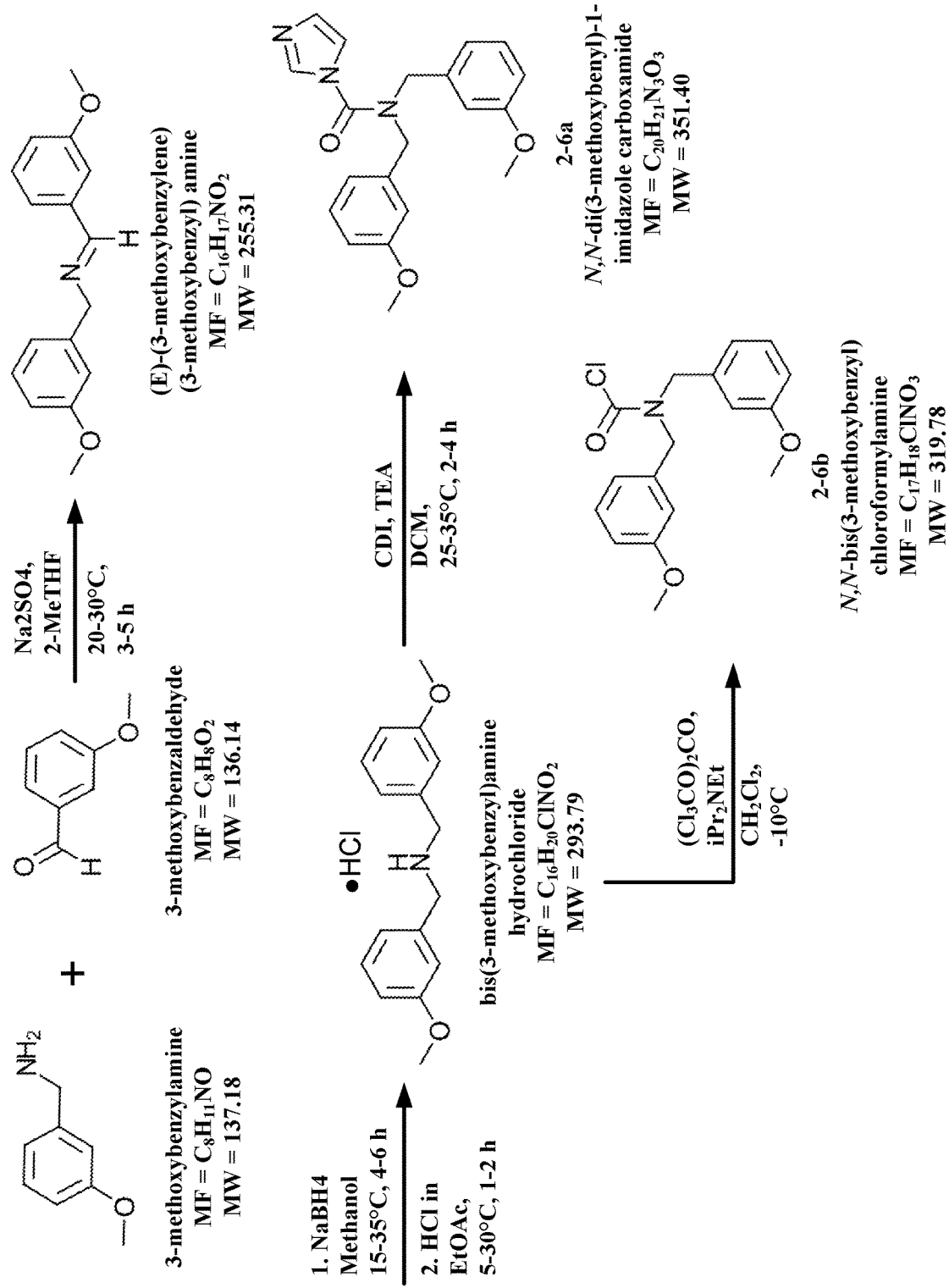
FIG. 2 depicts syntheses of the di-3-methoxybenzyl end group intermediates 2-6a&b.

Referring now to FIG. 2, the synthetic scheme for preparing N,N-di(3-methoxybenyl)-1-imidazolecarboxamide (2-6a) is shown to include two stages, Stage 1 and Stage 2. Stag 1 includes the synthesis of Stage 1 imine intermediate (2-4) and State 1 amine hydrochloride intermediate (2-5), while Stage 2 includes the synthesis of a Stage 2 carboxamide intermediate (2-6a). The synthetic procedure was as set forth in Example 15, except that the starting materials were 3-methoxybenzylamine (1-3) and 3-methoxybenzaldehyde (1-4).

Alternatively, the $Q^1$ and $Q^2$ may be synthesized to from N,N-bis(3-methoxybenzyl)chloroformylamine (2-6b) via the synthetic scheme set forth in FIG. 2.

Example 3

This example illustrates the synthesis of N-(4-dimethylaminobenzyl)-N-(3-methoxybenzyl)-1-imidazole carboxamide (2-9a), wherein $R^1$ is 4-dimethylaminobenzyl and $R^2$ is 3-methoxybenzyl.

Figure 3:
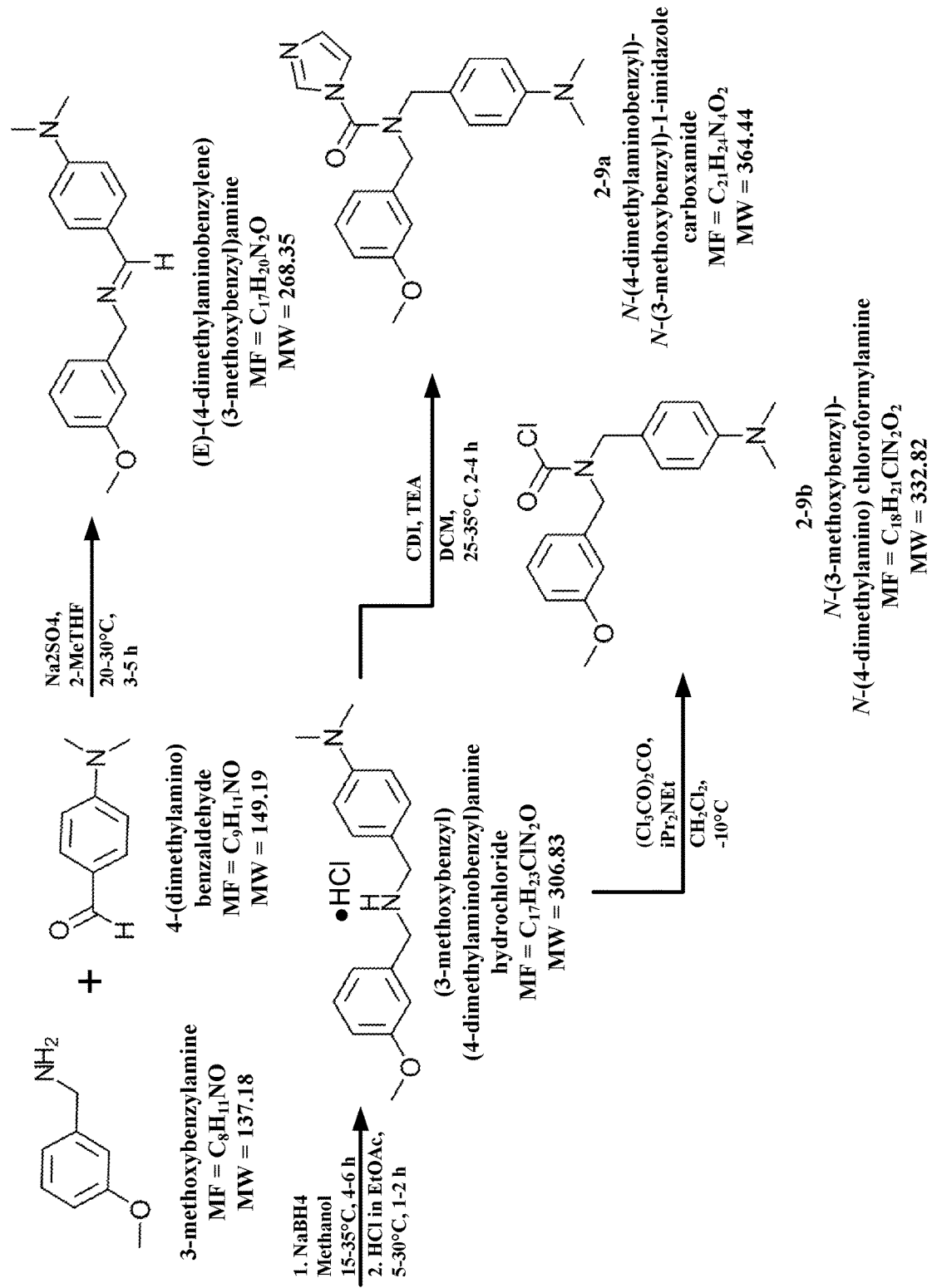
FIG. 3 depicts syntheses of the 3-methoxybenzyl,4-dimethylamino end group intermediates 2-9a&b.

Referring now to FIG. 3, the synthetic scheme for preparing N-(4-dimethylaminobenzyl)-N-(3-methoxybenzyl)-1-imidazole carboxamide (2-9a) is shown to include two stages, Stage 1 and Stage 2. Stage 1 imine intermediate (2-7) and State 1 amine hydrochloride intermediate (2-8), while Stage 2 includes the synthesis of a Stage 2 carboxamide intermediate (2-9a). The synthetic procedure was as set forth in Example 15, except that the starting materials were 3-methoxybenzylamine (1-3) and 4-(dimethylamino)benzaldehyde (1-5).

Alternatively, the $Q^1$ and $Q^2$ may be synthesized to from N-(3-methoxybenzyl)-N-(4-dimethylamino) chloroformylamine (2-9b) via the synthetic scheme set forth in FIG. 3.

Example 4

This example illustrates the synthesis of N,N-di(3-methoxybenyl)-1-imidazolecarboxamide (2-12a), wherein $R^1$ and $R^2$ are both 4-methoxybenzyl.

Figure 4:
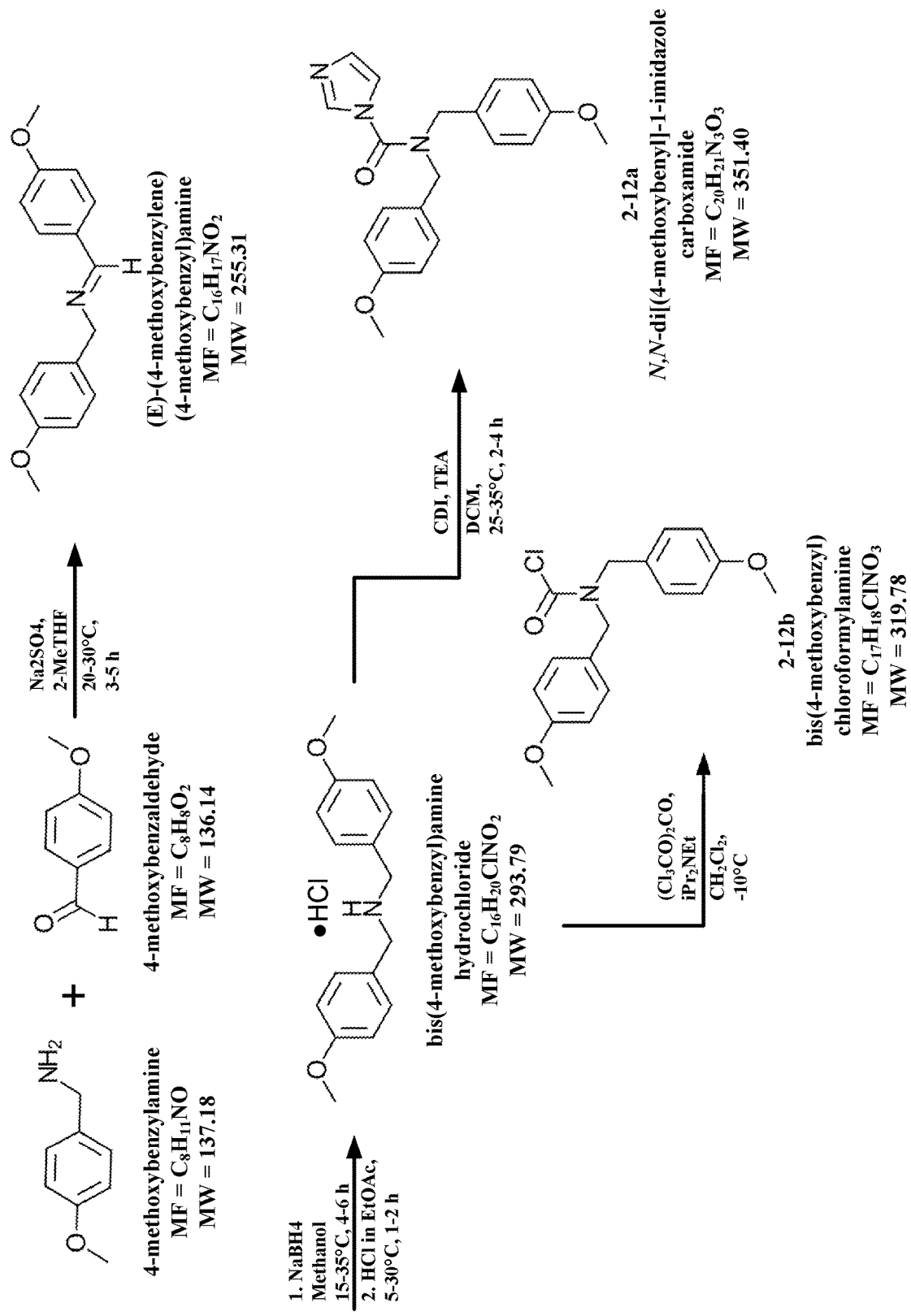
FIG. 4 depicts syntheses of the di-3-methoxybenzyl end group intermediates 2-12a&b.

Referring now to FIG. 4, the synthetic scheme for preparing N,N-di(3-methoxybenyl)-1-imidazolecarboxamide (2-12a) is shown to include two stages, Stage 1 and Stage 2. Stag 1 includes the synthesis of Stage 1 imine intermediate (2-10) and State 1 amine hydrochloride intermediate (2-11), while Stage 2 includes the synthesis of a Stage 2 carboxamide intermediate (2-12a). The synthetic procedure was as set forth in Example 15, except that the starting materials were 4-methoxybenzylamine (1-6) and 4-methoxybenzaldehyde (1-7).

Alternatively, the $Q^1$ and $Q^2$ may be synthesized to from bis(4-methoxybenzyl)chloroformylamine (2-12b) via the synthetic scheme set forth in FIG. 4.

Example 5

This example illustrates the synthesis of N-(4-dimethylaminobenzyl)-N-(4-methoxybenzyl)-1-imidazole carboxamide (2-15a), wherein $R^1$ is 4-dimethylaminobenzyl and $R^2$ is 3-methoxybenzyl.

Figure 5:
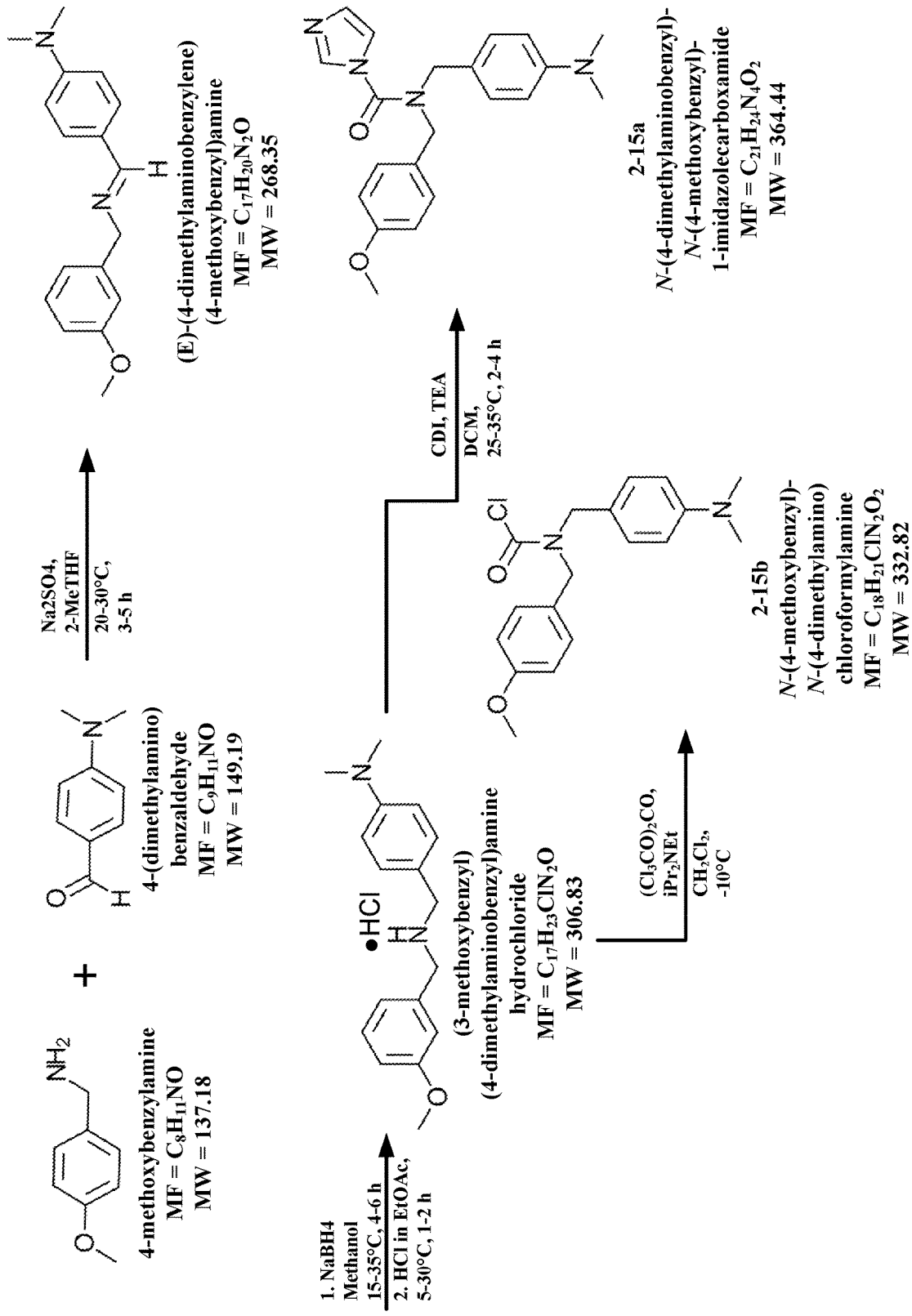
FIG. 5 depicts syntheses of the 3-methoxybenzyl,4-dimethylamino end group intermediates 2-15a&b.

Referring now to FIG. 5, the synthetic scheme for preparing N-(4-dimethylaminobenzyl)-N-(4-methoxybenzyl)-1-imidazole carboxamide (2-15a) is shown to include two stages, Stage 1 and Stage 2. Stage 1 imine intermediate (2-13) and State 1 amine hydrochloride intermediate (2-14), while Stage 2 includes the synthesis of a Stage 2 carboxamide intermediate (2-15a). The synthetic procedure was as set forth in Example 15, except that the starting materials were 4-methoxybenzylamine (1-6) and 4-(dimethylamino) benzaldehyde (1-5).

Alternatively, the $Q^1$ and $Q^2$ may be synthesized to from N-(4-methoxybenzyl)-N-(4-dimethylamino) chloroformylamine (2-15b) via the synthetic scheme set forth in FIG. 5.

Example 6

This example illustrates the synthesis of $R^1$ and $R^2$ form carbazole (1-8).

Figure 6:
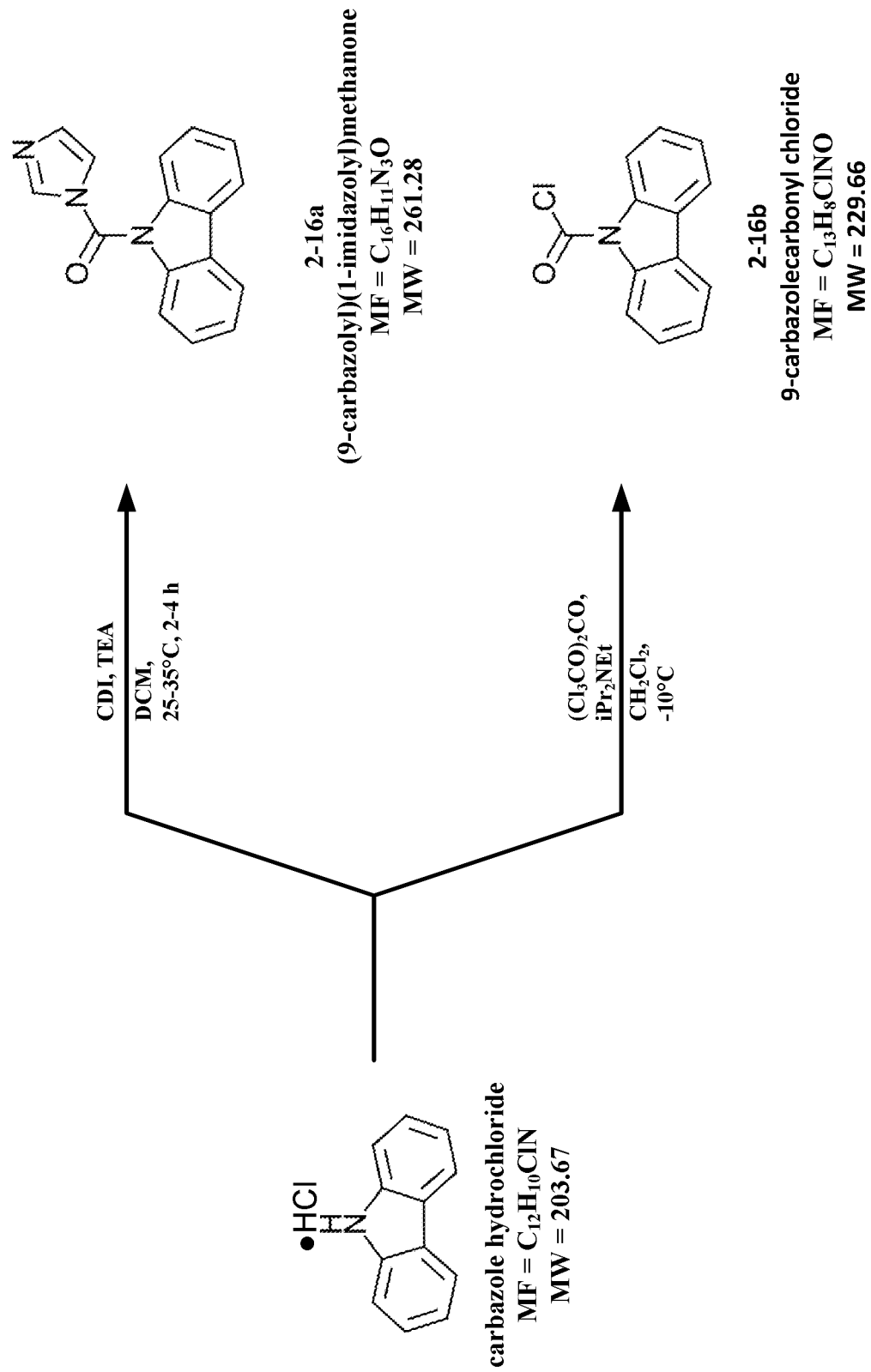
FIG. 6 depicts syntheses of the di-carbazoleyl end group intermediates 2-16a&b.

Referring now to FIG. 6, the synthetic scheme for preparing is shown to include only Stage 2. Stage 2 includes the synthesis of a Stage 2 carboxamide intermediate (2-16). The synthetic procedure was as set forth in Example 15, except that the starting materials was carbazole (1-8) hydrochloride.

Alternatively, the $Q^1$ and $Q^2$ may be synthesized to from 9-Carbazolecarbonyl chloride (Molecular Formula=$C_{13}H_8ClNO$; Molecular Mass=229.66) via the synthetic scheme set forth in FIG. 6.

Example 7

This example illustrates the synthesis of $R^1$ and $R^2$ form 3,6-dimethoxycarbazole (1-9).

Figure 7:
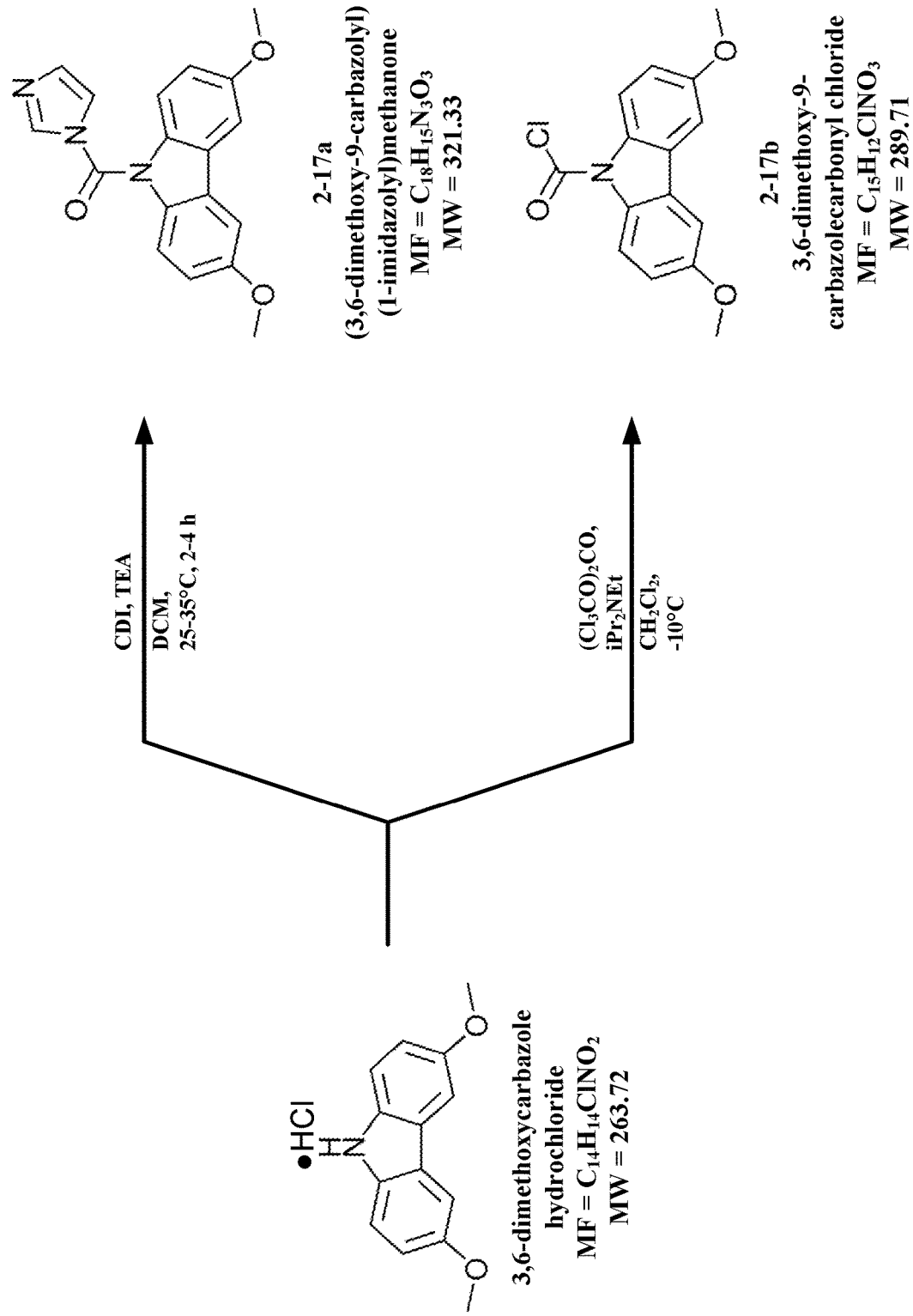
FIG. 7 depicts syntheses of the di-3,6-dimethoxycarbazoleyl end group intermediates 2-17a&b.

Referring now to FIG. 7, the synthetic scheme for preparing is shown to include only Stage 2. Stage 2 includes the synthesis of a Stage 2 carboxamide intermediate (2-17). The synthetic procedure was as set forth in Example 15, except that the starting materials was 3,6-dimethoxycarbazole (1-9) hydrochloride.

Alternatively, the $Q^1$ and $Q^2$ may be synthesized to from 3,6-dimethoxy-9-carbazolecarbonyl chloride (Molecular Formula=$C_{15}H_{12}ClNO_3$; Molecular Mass=289.71) via the synthetic scheme set forth in FIG. 7.

Ethoxylated Products

The ethoxylated intermediates 2-18 through 2-35 may be prepared by standard synthetic means. For example, the formation of 2-8 may be carried out as follows:

90 millimoles of starting diols (1-13) was placed in a dry, stirred pressure vessel fitted with a nitrogen inlet. A catalytic amount (26 milligrams) of KOH was added as a 40% aqueous solution. The vessel was purged with nitrogen and heated to 110° C. Vacuum was applied for 1 hour to remove the water vapors from the headspace of the vessel, and the mixture was further heated to 130° C. After 180 millimoles of ethylene oxide were added, the reaction mixture was stirred for additional 3 hours to complete the reaction. The progress of the reaction was monitored by the uptake of the reagent and the measurement of the pressure in the vessel. The reaction mixture was cooled to 110° C., and a vacuum was applied for approximately 1 hour. To neutralize KOH in the reaction mixture, 29 milligrams of 25% sulfuric acid was added. The mixture was stirred for 10 minutes, and the pH was adjusted to 5.7 giving a crude (2-8), which may purified by column chromatography. The synthesis of high ethoxylated intermediates may be affected by reacting the 90 millimoles of intermediate (2-8) with 180 millimoles of ethylene oxide to form crude intermediate (2-20), which may purified by column chromatography.

List of Starting Materials and Intermediates

The following Table I includes a list of all the starting materials and intermediated used in the preparation of the integrin activators specifically described in the examples that follow.

TABLE I

List of Starting Materials and Intermediates

Starting Material

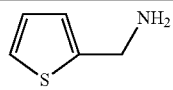

1-1
thiophen-2-yl-methylamine
Molecular Formula = $C_5H_7NS$
Molecular Mass = 113.18

TABLE I-continued

List of Starting Materials and Intermediates

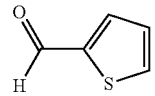

1-2
thiophene-2-carbaldehyde
Molecular Formula = $C_5H_4OS$
Molecular Mass = 112.15

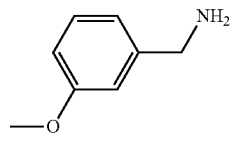

1-3
3-methoxybenzylamine
Molecular Formula = $C_8H_{11}NO$
Molecular Mass = 137.18

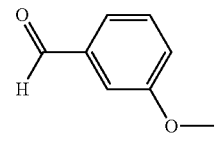

1-4
3-methoxybenzaldehyde
Molecular Formula = $C_8H_8O_2$
Molecular Mass = 136.14

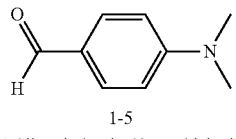

1-5
4-(dimethylamino)benzaldehyde
Molecular Formula = $C_9H_{11}NO$
Molecular Mass = 149.19

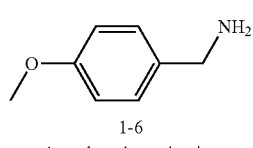

1-6
4-methoxybenzylamine
Molecular Formula = $C_8H_{11}NO$
Molecular Mass = 137.18

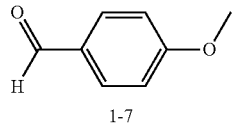

1-7
4-methoxybenzaldehyde
Molecular Formula = $C_8H_8O_2$
Molecular Mass = 136.14

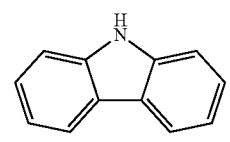

1-8
carbazole
Molecular Formula = $C_{12}H_9N$
Molecular Mass = 167.21

TABLE I-continued

List of Starting Materials and Intermediates

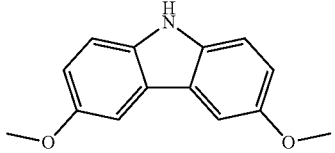

1-9
3,6-dimethoxycarbazole
Molecular Formula = $C_{14}H_{13}NO_2$
Molecular Mass = 227.26

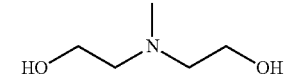

1-10
N-methyldiethanolamine
2-[(2-hydroxyethyl)-N-methylamino]ethanol
Molecular Formula = $C_5H_{13}NO_2$
Molecular Mass = 119.16

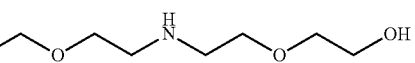

1-11a
di-[2-(2-hydroxyethoxy)ethyl]amine
2-{2-[2-(2-hydroxyethoxy)ethylamino]
ethoxy}ethanol
Molecular Formula = $C_8H_{19}NO_4$
Molecular Mass = 193.24

1-11b
N-methyl-di-[2-(2-hydroxyethoxy)ethyl]amine
2-(2-{[2-(2-hydroxyethoxy)ethyl]-
N-methylamino}ethoxy)ethanol
Molecular Formula = $C_9H_{21}NO_4$
Molecular Mass = 207.27

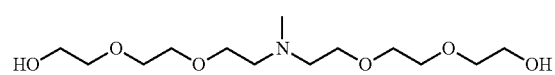

1-12
N-methyl-di-{2-[2-(2-hydroxyethoxy)ethoxy]
ethyl}amine
2- {2-[2-({2-[2-(2-hydroxyethoxy)ethoxy]
ethyl}-N-methylamino)ethoxy]ethoxy}ethanol
Molecular Formula = $C_{13}H_{29}NO_6$
Molecular Mass = 295.37

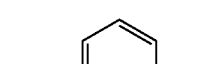

1-13
2,6-pyridinediol or 2,6-dihydroxypyridine
Molecular Formula = $C_5H_5NO_2$
Molecular Mass = 111.10

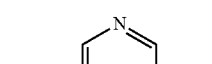

1-14
3,5-pyridinediol or 3,5-dihydroxypyridine
Molecular Formula = $C_5H_5NO_2$
Molecular Mass = 111.10

TABLE I-continued

List of Starting Materials and Intermediates

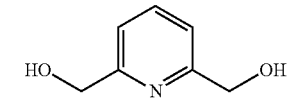

1-15
2,6-dimethanolpyridine
[6-(hydroxymethyl)-2-pyridyl]methanol
Molecular Formula = $C_7H_9NO_2$
Molecular Mass = 139.15

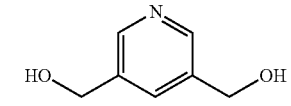

1-16
3,5-dimethanolpyridine
[5-(hydroxymethyl)-3-pyridyl]methanol
Molecular Formula = $C_7H_9NO_2$
Molecular Mass = 139.15

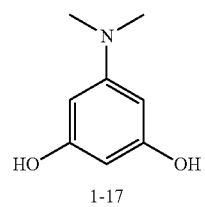

1-17
5-(dimethylamino)resorcinol
1,3-dihydroxy-5-dimethylaminobenzene
Molecular Formula = $C_8H_{11}NO_2$
Molecular Mass = 153.18

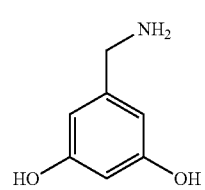

1-18a
5-(aminomethyl)resorcinol
1,3-dihydroxy-5-dimethylaminobenzene
Molecular Formula = $C_7H_9NO_2$
Molecular Mass = 139.15

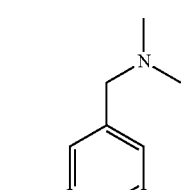

1-18b
5-[(dimethylamino)methyl]resorcinol
1,3-dihydroxy-5-dimethylaminomethylbenzene
Molecular Formula = $C_9H_{13}NO_2$
Molecular Mass = 137.21

TABLE I-continued

List of Starting Materials and Intermediates

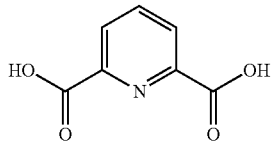

1-19
2,6-pyridinedicarboxylic acid
Molecular Formula = $C_7H_5NO_4$
Molecular Mass = 167.12

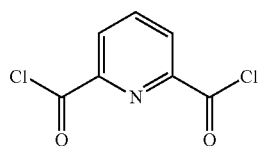

1-20
2,6-pyridinedicarbonyl dichloride
Molecular Formula = $C_7H_3Cl_2NO_4$
Molecular Mass = 201.01

1-21
3,5-pyridinedicarboxylic acid
Molecular Formula = $C_7H_5NO_4$
Molecular Mass = 167.12

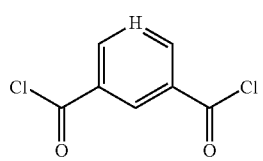

1-22
3,5-pyridinedicarbonyl dichloride
Molecular Formula = $C_7H_3Cl_2NO_4$
Molecular Mass = 201.01

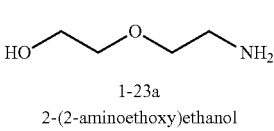

1-23a
2-(2-aminoethoxy)ethanol
Molecular Formula = $C_4H_{11}NO_2$
Molecular Mass = 105.14

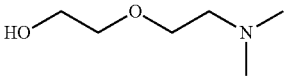

1-23b
2-[2-(dimethylamino)ethoxy]ethanol
Molecular Formula = $C_6H_{15}NO_2$
Molecular Mass = 133.19

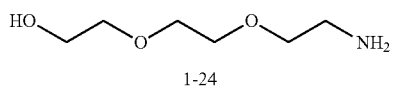

1-24
2-[2-(2-aminoethoxy)ethoxy]ethanol
Molecular Formula = $C_6H_{15}NO_3$
Molecular Mass = 149.19

TABLE I-continued

List of Starting Materials and Intermediates

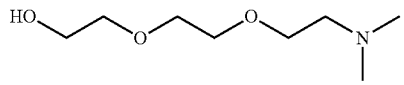

1-24b
2-{2-[2-(dimethylamino)ethoxy]ethoxy}ethanol
Molecular Formula = $C_8H_{19}NO_3$
Molecular Mass = 177.24

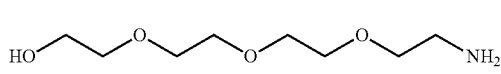

1-25a
2-{2-[2-(2-aminoethoxy)ethoxy]ethoxy}ethanol
Molecular Formula = $C_8H_{19}NO_4$
Molecular Mass = 193.24

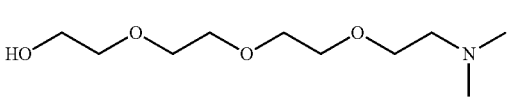

1-25b
2-(2-{2-[2-(dimethylamino)ethoxy]ethoxy}ethoxy)ethanol
Molecular Formula = $C_{10}H_{23}NO_4$
Molecular Mass = 221.29

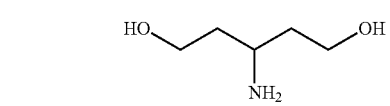

1-26
3-amino-1,5-pentanediol
Molecular Formula = $C_5H_{13}NO_2$
Molecular Mass = 119.16

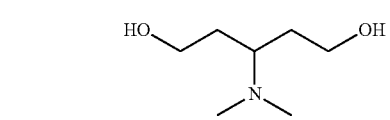

1-27
3-(dimethylamino)-1,5-pentanediol
Molecular Formula = $C_7H_{17}NO_2$
Molecular Mass = 147.21

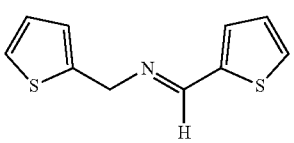

1-28
oxirane
Molecular Formula = $C_2H_4O$
Molecular Mass = 44.05

Intermediates

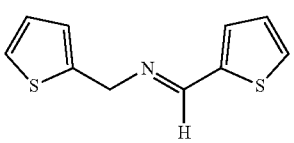

2-1
(E)-(thiophen-2-ylmethyl)
thiophen-2-ylmethylene)amine
Molecular Formula = $C_{10}H_9NS_2$
Molecular Mass = 207.32

TABLE I-continued

List of Starting Materials and Intermediates

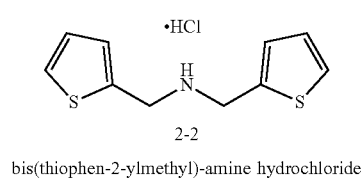

2-2 bis(thiophen-2-ylmethyl)-amine hydrochloride
Molecular Formula = $C_{10}H_{12}ClNS_2$
Molecular Mass = 245.79

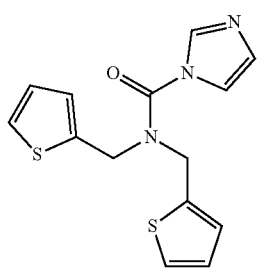

2-3a

N,N-bis(thiophen-2-ylmethyl)imidazol-1-yl
carboxamide
Molecular Formula = $C_{14}H_{13}N_3OS_2$
Molecular Mass = 303.40

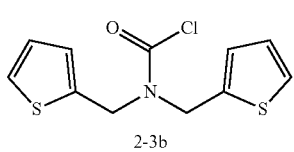 [SMILES: O=C(Cl)N(Cc1cccs1)Cc1cccs1]

2-3b

N,N-bis(thiophen-2-ylmethyl)chloroformyl
amine
Molecular Formula = $C_{11}H_{10}ClNOS_2$
Molecular Mass = 271.79

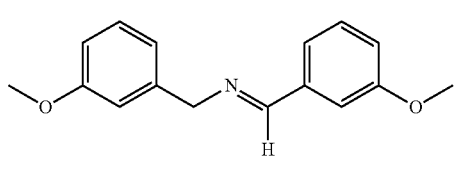

2-4

(E)-(3-methoxybenzylene)(3-methoxybenzyl)
amine
Molecular Formula = $C_{16}H_{17}NO_2$
Molecular Mass = 255.31

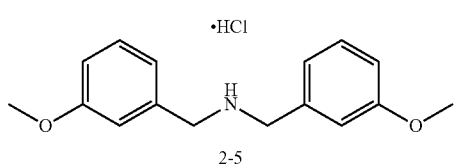

2-5 bis(3-methoxybenzyl)amine hydrochloride
Molecular Formula = $C_{16}H_{20}ClNO_2$
Molecular Mass = 293.79

TABLE I-continued

List of Starting Materials and Intermediates

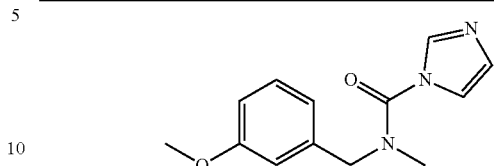

2-6a

N,N-di(3-methoxybenyl)-1-imidazole
carboxamide
Molecular Formula = $C_{20}H_{21}N_3O_3$
Molecular Mass = 351.40

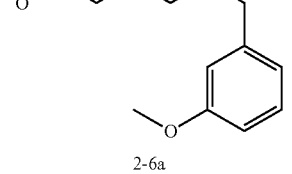

2-6b

N,N-bis(3-methoxybenzyl)chloroformylamine
Molecular Formula = $C_{17}H_{18}ClNO_3$
Molecular Mass = 319.78

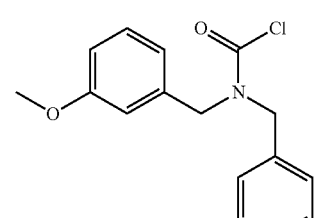

2-7

(E)-(4-dimethylaminobenzylene)
(3-methoxybenzyl)amine
Molecular Formula = $C_{17}H_{20}N_2O$
Molecular Mass = 268.35

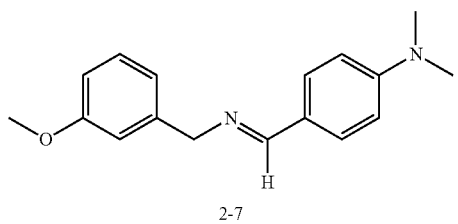

2-8

(3-methoxybenzyl)(4-dimethylaminobenzyl)
amine hydrochloride
Molecular Formula = $C_{17}H_{23}ClN_2O$
Molecular Mass = 306.83

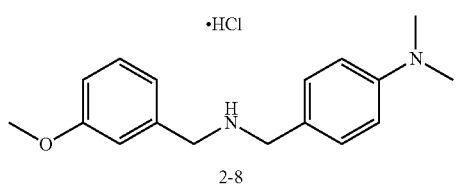

TABLE I-continued

List of Starting Materials and Intermediates

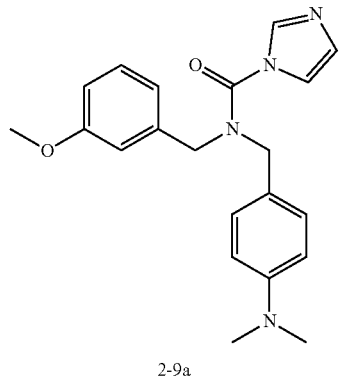 [SMILES: COc1cccc(CN(Cc2ccc(N(C)C)cc2)C(=O)n2ccnc2)c1]

2-9a
N-(4-dimethylaminobenzyl)-
N-(3-methoxybenzyl)-1-imidazole
carboxamide
Molecular Formula = $C_{21}H_{24}N_4O_2$
Molecular Mass = 364.44

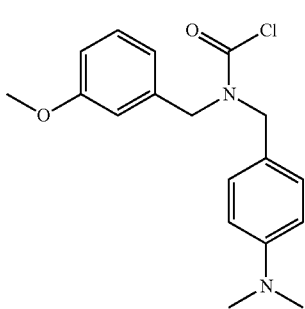

2-9b
N-(3-methoxybenzyl)-N-(4-dimethylamino)
chloroformylamine
Molecular Formula = $C_{18}H_{21}ClN_2O_2$
Molecular Mass = 332.82

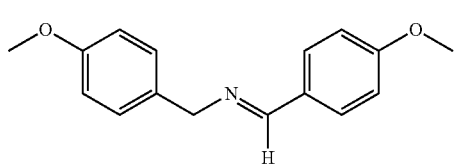

2-10
(E)-(4-methoxybenzylene)(4-methoxybenzyl)
amine
Molecular Formula = $C_{16}H_{17}NO_2$
Molecular Mass = 255.31

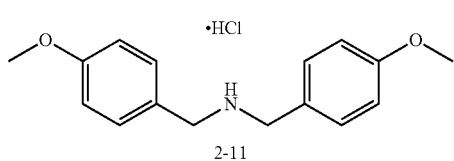

2-11
bis(4-methoxybenzyl)amine hydrochloride
Molecular Formula = $C_{16}H_{20}ClNO_2$
Molecular Mass = 293.79

TABLE I-continued

List of Starting Materials and Intermediates

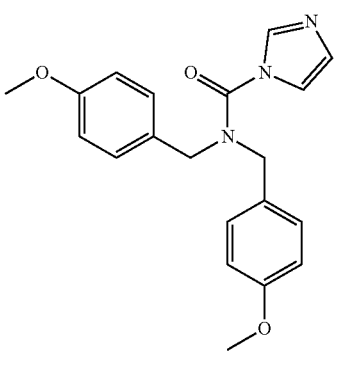

2-12a
N,N-di[(4-methoxybenyl]-1-imidazole
carboxamide
Molecular Formula = $C_{20}H_{21}N_3O_3$
Molecular Mass = 351.40

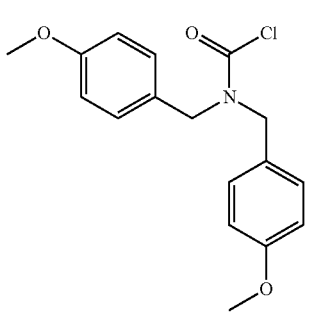

2-12b
bis(4-methoxybenzyl)chloroformylamine
Molecular Formula = $C_{17}H_{18}ClNO_3$
Molecular Mass = 319.78

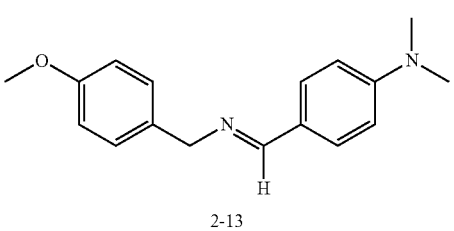

2-13
(E)-(4-dimethylaminobenzylene)
(4-methoxybenzyl)amine
Molecular Formula = $C_{17}H_{20}N_2O$
Molecular Mass = 268.35

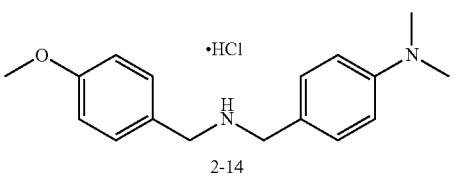

2-14
(3-methoxybenzyl)(4-dimethylaminobenzyl)
amine hydrochloride
Molecular Formula = $C_{17}H_{23}ClN_2O$
Molecular Mass = 306.83

TABLE I-continued

List of Starting Materials and Intermediates

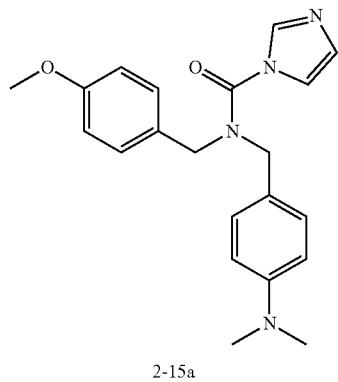 [SMILES: COc1ccc(CN(Cc2ccc(N(C)C)cc2)C(=O)n2ccnc2)cc1]

2-15a
N-(4-dimethylaminobenzyl)-
N-(4-methoxybenzyl)-1-imidazole
carboxamide
Molecular Formula = $C_{21}H_{24}N_4O_2$
Molecular Mass = 364.44

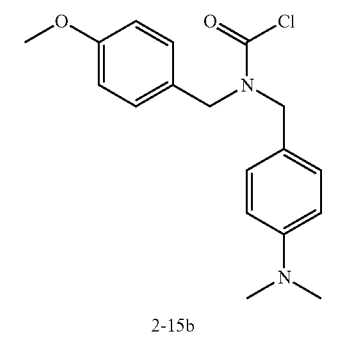

2-15b
N-(4-methoxybenzyl)-N-(4-dimethylamino)
chloroformylamine
Molecular Formula = $C_{18}H_{21}ClN_2O_2$
Molecular Mass = 332.82

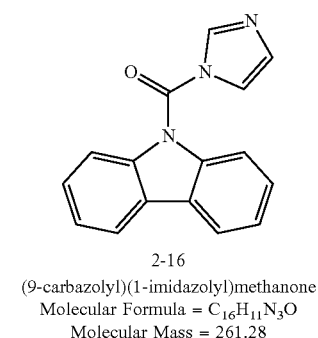

2-16
(9-carbazolyl)(1-imidazolyl)methanone
Molecular Formula = $C_{16}H_{11}N_3O$
Molecular Mass = 261.28

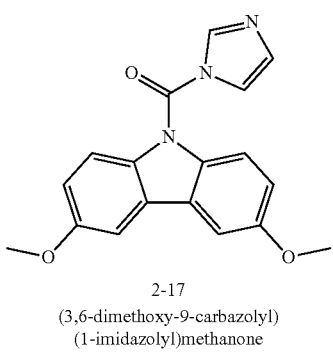

2-17
(3,6-dimethoxy-9-carbazolyl)
(1-imidazolyl)methanone
Molecular Formula = $C_{18}H_{15}N_3O_3$
Molecular Mass = 321.33

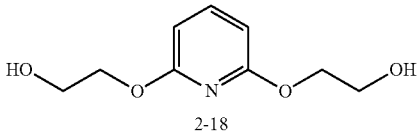 [SMILES: OCCOc1cccc(OCCO)n1]

2-18
2-(2-hydroxyethoxy)-
6-(2-hydroxyethoxy) pyridine
Molecular Formula = $C_9H_{13}NO_4$
Molecular Mass = 199.20

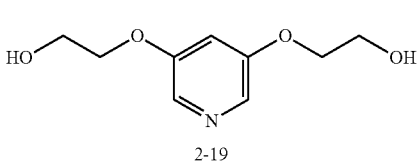 [SMILES: OCCOc1cncc(OCCO)c1]

2-19
3-(2-hydroxyethoxy)-
5-(2-hydroxyethoxy) pyridine
Molecular Formula = $C_9H_{13}NO_4$
Molecular Mass = 199.20

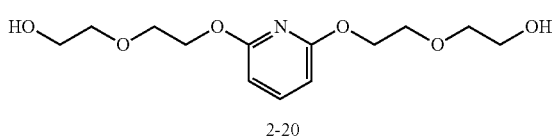 [SMILES: OCCOCCOc1cccc(OCCOCCO)n1]

2-20
2-[2-(2-hydroxyethoxy)ethoxy]-
6-[2-(2-hydroxyethoxy)ethoxy]pyridine
Molecular Formula = $C_{13}H_{21}NO_6$
Molecular Mass = 287.31

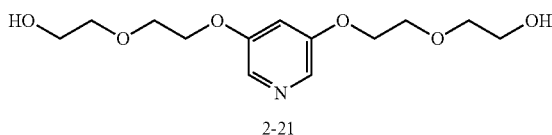 [SMILES: OCCOCCOc1cncc(OCCOCCO)c1]

2-21
3-[2-(2-hydroxyethoxy)ethoxy]-
5-[2-(2-hydroxyethoxy)ethoxy]pyridine
Molecular Formula = $C_{s13}H_{21}NO_6$
Molecular Mass = 287.31

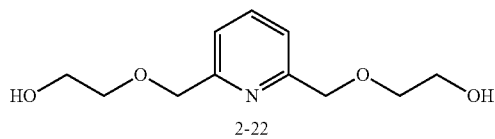 [SMILES: OCCOCc1cccc(COCCO)n1]

2-22
2-[(2-hydroxyethoxy)methyl]-
6-[(2-hydroxyethoxy)methyl]pyridine
Molecular Formula = $C_{11}H_{17}NO_4$
Molecular Mass = 224.26

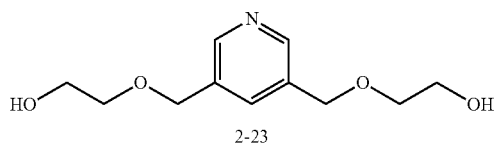 [SMILES: OCCOCc1cncc(COCCO)c1]

2-23
3-[(2-hydroxyethoxy)methyl]-
5-[(2-hydroxyethoxy)methyl]pyridine
Molecular Formula = $C_{11}H_{17}NO_4$
Molecular Mass = 224.26

TABLE I-continued

List of Starting Materials and Intermediates

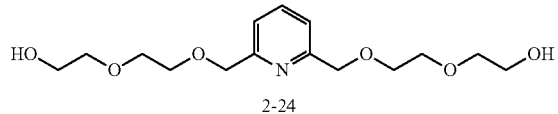 [SMILES: OCCOCCOCc1cccc(COCCOCCO)n1]

2-24
2-{[2-(2-hydroxyethoxy)ethoxy]methyl}-
6-{[2-(2-hydroxyethoxy)ethoxy]methyl}
pyridine
Molecular Formula = $C_{15}H_{25}NO_6$
Molecular Mass = 315.36

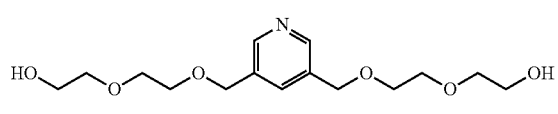

2-25
3-{[2-(2-hydroxyelhoxy)ethoxy]methyl}-
5-{[2-(2-hydroxyethoxy)ethoxy]methyl}
pyridine
Molecular Formula = $C_{15}H_{25}NO_6$
Molecular Mass = 315.36

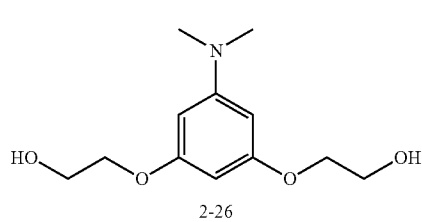 [SMILES: CN(C)c1cc(OCCO)cc(OCCO)c1]

2-26
1,3-di(hydroxyethoxy)-
5-dimethylamino benzene
Molecular Formula = $C_{12}H_{19}NO_4$
Molecular Mass = 241.28

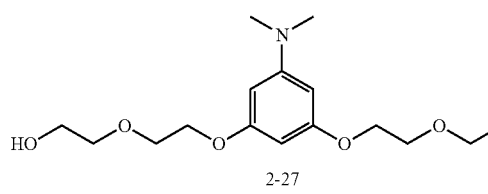

2-27
1,3-di(hydroxyethoxyethyoxy)-
5-dimethylamino benzene
Molecular Formula = $C_{16}H_{27}NO_6$
Molecular Mass = 329.39

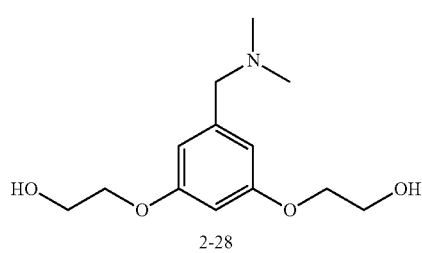 [SMILES: CN(C)Cc1cc(OCCO)cc(OCCO)c1]

2-28
1,3-di(hydroxyethoxy)-
5-dimethylaminomethyl benzene
Molecular Formula = $C_{13}H_{21}NO_4$
Molecular Mass = 255.31

TABLE I-continued

List of Starting Materials and Intermediates

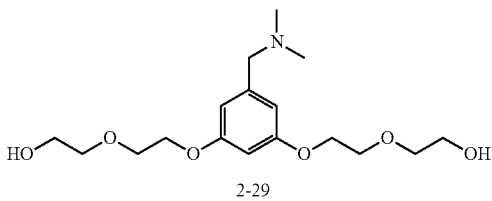 [SMILES: CN(C)Cc1cc(OCCOCCO)cc(OCCOCCO)c1]

2-29
1,3-di(hydroxyethoxyethoxy)-
5-dimethylaminomethyl benzene
Molecular Formula = $C_{17}H_{29}NO_6$
Molecular Mass = 343.42

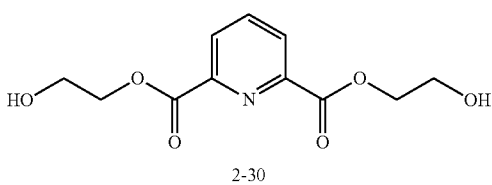 [SMILES: O=C(OCCO)c1cccc(C(=O)OCCO)n1]

2-30
di-(2-hydroxyethyl)-
2,6-pyridinedicarboxylate
Molecular Formula = $C_{11}H_{13}NO_6$
Molecular Mass = 255.22

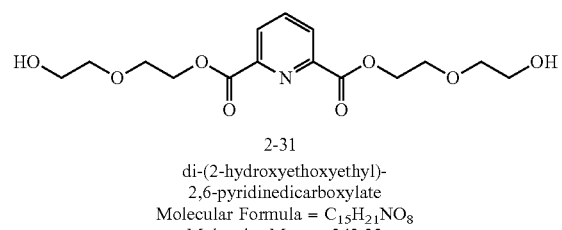

2-31
di-(2-hydroxyethoxyethyl)-
2,6-pyridinedicarboxylate
Molecular Formula = $C_{15}H_{21}NO_8$
Molecular Mass = 343.33

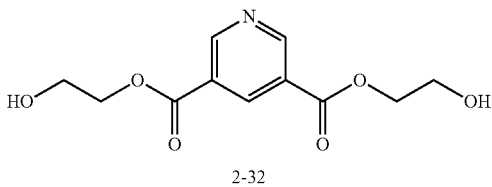 [SMILES: O=C(OCCO)c1cncc(C(=O)OCCO)c1]

2-32
di-(2-hydroxyethyl)-
3,5-pyridinedicarboxylate
Molecular Formula = $C_{11}H_{13}NO_6$
Molecular Mass = 255.22

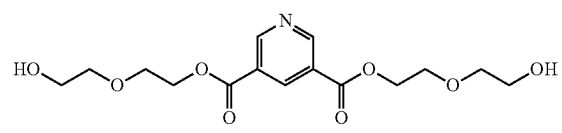

2-33
di-(2-hydroxyethoxyethyl)-
3,5-pyridinedicarboxylate
Molecular Formula = $C_{15}H_{21}NO_8$
Molecular Mass = 343.33

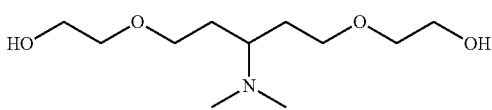

2-34
1,5-di(2-hydroxyethoxy)-3-(dimethylamino)-
pentane
Molecular Formula = $C_{11}H_{25}NO_4$
Molecular Mass = 235.32

TABLE I-continued

List of Starting Materials and Intermediates

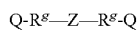

2-35
1,5-di(2-hydroxyethoxyethoxy)-
3-(dimethylamino)-pentane
Molecular Formula = $C_{15}H_{33}NO_6$
Molecular Mass = 323.43

Example 8—Synthesis of Integrin Agonists of Formula (IIa&b)

The following generalized synthetic schemes were used to prepare integrin agonists of the general Formula (IIa):

$$Q-R^g-Z-R^g-Q \qquad (IIa)$$

wherein:
the Q group comprise $R^1R^2NC(=O)-$;
the $R^1$ and $R^2$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof;
the $R^fZR^f$ group comprises $(OCH_2CH_2)_nN(Me)(CH_2CH_2O)_n$; and
n is an integer having a value between 1 and 6, or

the Q groups comprise $R^1R^2NC(=O)-$;
the $R^1$ and $R^2$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof; and
n is an integer having a value between 1 and 6.

The synthetic scheme for preparing the integrin activating compounds or agonists of Formula (II) is outlined below:
20. Prepare a slurry of sodium hydride (0.144 g) tetrahydrofuran (3 mL) under nitrogen atmosphere. Stir the contents gently and cool the slurry formed to 0-5° C.
21. Add Z group precursors=$H(OCH_2CH_2)_{n1}N(Me)(CH_2CH_2O)_{n2}H$ groups, wherein n1 and n2 are independently integers having a value between 1 and 6 precursor (1.5 millimoles) drop-wise while maintaining the temperature at 0-10° C. over a period of 20-30 min. [Note: Addition is exothermic and hydrogen gas liberates during the addition. Maintain gentle flow of dry nitrogen gas.]
22. Dissolve Stage-2 of carboxamide intermediate (3.3 millimoles) in tetrahydrofuran (3 mL) and add the solution into the Z group precursors/sodium hydride reaction mixture drop-wise while maintaining the temperature at 0-10° C. over a period of ~1 h. Check for reaction completion by HPLC analysis. The content of mono-substituted by-product should be less than 0.05% (a/a by HPLC). If the content of mono-substituted by-product is more than 0.05%, continue stirring the reaction mixture at 0-10° C. for 4 h.
23. If the content of mono-substituted by-product is more than 0.05%, add sodium hydride (55-60%) (0.013 g) followed by Stage-2 carboxamide intermediate (0.15 millimoles).
24. Stir the reaction mixture at 0-10° C. for 2 h. Check for reaction completion by HPLC analysis. The content of mono-substituted by-product should be less than 0.05% (a/a by HPLC). If the content of mono-substituted by-product is more than 0.05%, continue adding sodium hydride (55-60%) (1.3 g) and the desired Stage-2 carboxamide intermediate (0.15 millimoles) into the reaction mixture at 0-10° C. till the IPC limit is achieved.
25. If the content of mono-substituted by-product is less than 0.05% (a/a), add water (3 mL) to the reaction mixture drop-wise while maintaining the temperature at 0-10° C. Stir the reaction mixture at 0-10° C. for 5-10 min.
26. Separate the organic layer (OL-1). Add ethyl acetate (5 mL) to the aqueous layer. Stir the mixture for 5-10 minutes at 25-30° C.
27. Separate the organic layer (OL-2). Add ethyl acetate (5 mL) to the aqueous layer. Stir the mixture for 5-10 minutes at 25-30° C.
28. Separate the organic layer (OL-3). Combine the organic layers (OL-1+OL-2+OL-3). Add water (3 mL) to the combined organic fractions. Stir the mixture for 5-10 minutes at 25-30° C.
29. Separate the aqueous layer and cool the organic layer to 15-20° C. Add aqueous hydrochloric acid (4.0 N) (300 mL) to the organic layer. Stir the mixture at 25-30° C. for about 3 min.
30. Separate the aqueous layer and add aqueous hydrochloric acid (4.0 N) (3 mL) to the organic layer. Stir the mixture at 25-30° C. for about 3 min.
31. Separate the aqueous layer and add aqueous hydrochloric acid (4.0 N) (3 mL) to the organic layer. Stir the mixture at 25-30° C. for about 3 min.
32. Test a sample of the integrin activator for content of the desired Stage-2 of carboxamide intermediate. [IPC limit: less than 0.08% (a/a by HPLC).]
33. If content of the desired Stage 2 carboxamide intermediate is more than 0.08% continue washing the organic layer with aqueous hydrochloric acid (4.0 N) until IPC limit is achieved.
34. If content of the desired Stage 2 carboxamide intermediate is less than 0.08%, add brine solution (5%, 300 mL) to the organic layer. Stir the mixture at 25-30° C. for about 5 min.
35. Add 5% sodium bicarbonate solution (3 mL) to the organic layer. Stir the mixture at 20-25° C. for about 5 min. Separate aqueous layer. Repeat sodium bicarbonate washing.
36. Add brine solution (5%, 300 mL) to the organic layer. Stir the mixture at 25-30° C. for about 5 min. Separate aqueous layer. Repeat brine washing.
37. Dry the organic layer over anhydrous sodium sulphate (0.5 g). Add activated charcoal (0.10 g) to the organic layer at 25-30° C. Filter the mixture through celite to remove charcoal. Wash the celite bed with ethyl acetate (1 mL). Concentrate the filtrate under vacuum at 45-50° C. to obtain an oil or solid integrin agonist of Formula (II).
38. Add n-heptane (3 mL) to the residue. Stir the mixture at 25-30° C. for 30 min. Remove the n-heptane. Repeat n-heptane washing 2 more times.

39. Perform IPC analysis by HPLC to check the content of impurities. If the impurity limit is not achieved, continue washing the oily compound with n-heptane till the impurity limit is achieved. Use 300 mL of n-heptane and stir the mixture for 30 min during each wash.
40. If the impurity limit for the impurities is achieved, degas the oil at 45-50° C. for 4 h. Test residue on ignition (ROI) and Z group precursors (w/w) content. [IPC limit: ROI and Z group precursor content less than 0.09%]. If the in-process limit for ROI or triethylene glycol content is not achieved, dissolve the oily compound in ethyl acetate (5 mL). Add brine solution (5%, 3 mL) to the ethyl acetate solution. Stir the mixture at 25-30° C. for about 5 min. Separate aqueous layer and dry the organic layer over anhydrous sodium sulphate (0.5 g).
41. Concentrate the organic layer under vacuum at 45-50° C. and degas for 2-3 h. Test residue for residue on ignition (ROI) and Z group precursor (w/w) content. [impurity limit: ROI and Z group precursor content less than 0.09%]. If the in-process limit for ROI or Z group precursor is not achieved repeat operation 21-22 until the impurity limits are achieved.
42. If the in-process limits for ROI and Z group precursor are achieved, test for water content. [impurity limit for water content NMT 0.90%.]. If water content is more than 0.90%, continue degassing the oil at 45-50° C. till the IPC limit is achieved.
43. If water content is less than 0.90%, test for residual solvents by GC. [impurity limit: Ethyl acetate 45 ppm; 2-methyl tetrahydrofuran 450 ppm; methanol 27 ppm; n-heptane: 45 ppm; dichloromethane: 5.40 ppm; tetrahydrofuran: 6.50 ppm; acetic acid 45 ppm; triethylamine 45 ppm.]. If the impurity limit for residual solvents is not achieved, continue degassing the oil at 45-50° C. till the impurity limit is achieved.
44. The isolated integrin activator may be an oil, a waxy solid or a solid.
45. Package isolated integrin activator, under nitrogen, in amber colored glass bottle closed with HDPE screw cap. Store at 2-8° C.

The synthesis yields between 0.80-0.87 g of the desired integrin activating compounds of Formula (II) at a yield of between 86-93.5% (3.55-3.87 w/w).

Referring now to FIG. 8A through FIG. 13C, the above synthetic procedure is used to prepare the integrin activating compounds or agonists of Formula (IIa&b), 10001-10021, by reaction head group intermediates 2-3a, 2-6a, 2-9a, 2-12a, 2-15a, 2-16, or 2-17 with the starting materials 1-10, 1-11b, or 1-12. Alternatively, the agonists 10001-10021 may be synthesized by reacting 2-3b, 2-6b, 2-9b, 2-12b, 2-15b, and the acid chloride of carbazole and 3,6-dimethoxycarbazole with the starting materials 1-10, 1-11b, or 1-12.

Table II includes a list of integrin activating compounds or agonists of Formula (IIa&b), wherein n=1, 2, or 3, for brevity, the same synthetic procedure may be used for preparing integrin activating compounds or agonists of Formula (IIa&b), wherein n=4, 5, or 6.

TABLE II

R$^a$ZR$^b$ IS Derived from N-Methyl DiAlkenol Amines

| Code | Structures | M.W. | Formula | LogP |
|---|---|---|---|---|
| 10001 | 3-oxo-1-(2-thienyl)-2-(2-thienylmethyl)-4-oxa-2,7-diaza-7-methyl-nonan-9-yl-bis(2-thienylmethyl)carbamate | 589.82 | C$_{27}$H$_{31}$N$_3$O$_4$S$_4$ | 3.22$^a$<br>6.24$^b$<br>3.76$^c$<br>6.72$^d$ |
| 10002 | 3-oxo-1-(3-methoxyphenyl)-2-(3-methoxybenzyl)-4-oxa-2,7-diaza-7-methyl-nonan-9-yl-bis(3-methoxybenzyl)carbamate | 685.80 | C$_{39}$H$_{47}$N$_3$O$_8$ | 4.54$^a$<br>6.02$^b$<br>8.65$^c$<br>7.67$^d$ |

TABLE II-continued

R$^a$ZR$^b$ IS Derived from N-Methyl DiAlkenol Amines

| Code | Structures | M.W. | Formula | LogP |
|---|---|---|---|---|
| 10003 | 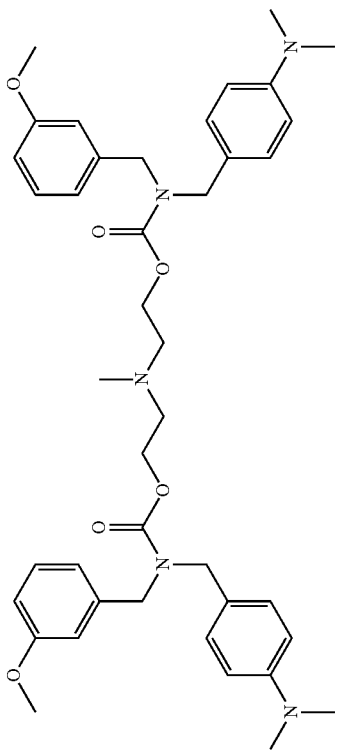 3-oxo-1-(3-methoxyphenyl)-2-(4-dimethylaminobenzyl)-4-oxa-2,7-diaza-7-methyl-nonan-9-yl-(3-methoxybenzyl)(4-dimethylaminobenzyl)carbamate | 711.89 | C$_{41}$H$_{53}$N$_5$O$_6$ | 4.76$^a$<br>6.14$^b$<br>10.08$^c$<br>8.06$^d$ |
| 10004 | 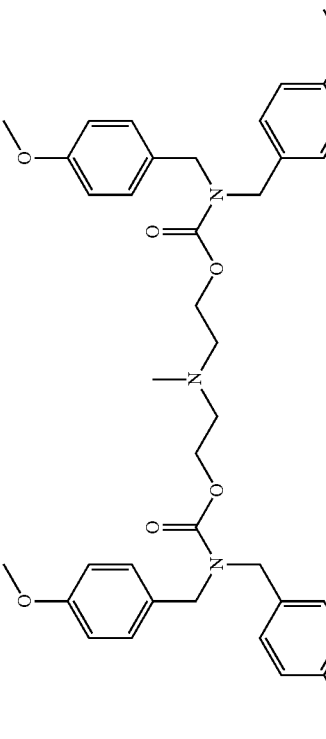 3-oxo-1-(4-methoxyphenyl)-2-(4-methoxybenzyl)-4-oxa-2,7-diaza-7-methyl-nonan-9-yl-bis(4-methoxybenzyl)carbamate | 685.80 | C$_{39}$H$_{47}$N$_3$O$_8$ | 4.54$^a$<br>6.02$^b$<br>10.34$^c$<br>7.67$^d$ |

TABLE II-continued

R$^a$ZR$^b$ IS Derived from N-Methyl DiAlkenol Amines

| Code | Structures | M.W. | Formula | LogP |
|---|---|---|---|---|
| 10005 | 3-oxo-1-(4-methoxyphenyl)-2-(4-dimethylaminobenzyl)-4-oxa-2,7-diaza-7-methyl-nonan-9-yl-(4-methoxybenzyl)(4-dimethylaminobenzyl) carbamate | 711.89 | C$_{41}$H$_{53}$N$_5$O$_6$ | 4.76$^a$ 6.14$^b$ 10.93$^c$ 8.06$^d$ |
| 10006 | 3-oxo-1-(2-thienyl)-2-(2-thienylmethyl)-4,7,13-trioxa-2,10-diaza-10-methyl-pentadecan 15-yl-bis(2-thienylmethyl)carbamate | 677.93 | C$_{31}$H$_{39}$N$_3$O$_6$S$_4$ | 3.44$^a$ 6.27$^b$ 4.48$^c$ 5.07$^d$ |

TABLE II-continued

R$^a$ZR$^b$ IS Derived from N-Methyl DiAlkenol Amines

| Code | Structures | M.W. | Formula | LogP |
|---|---|---|---|---|
| 10007 | 3-oxo-1-(3-methoxyphenyl)-2-(3-methoxybenzyl)-4,7,13-trioxa-2,10-diaza-10-methyl-pentadecan-15-yl-bis(3-methoxybenzyl)carbamate | 773.91 | C$_{45}$H$_{55}$N$_3$O$_{10}$ | 4.76$^a$<br>6.06$^b$<br>9.37$^c$<br>6.02$^d$ |
| 10008 | 3-oxo-1-(3-methoxyphenyl)-2-(4-dimethylaminobenzyl)-4,7,13-trioxa-2,10-diaza-10-methyl-pentadecan-15-yl-(3-methoxybenzyl)(4-dimethylaminobenzyl)carbamate | 799.99 | C$_{45}$H$_{61}$N$_5$O$_8$ | 4.98$^a$<br>6.17$^b$<br>10.80$^c$<br>6.41$^d$ |

TABLE II-continued

R$^a$ZR$^b$ IS Derived from N-Methyl DiAlkenol Amines

| Code | Structures | M.W. | Formula | LogP |
|---|---|---|---|---|
| 10009 | 3-oxo-1-(4-methoxyphenyl)-2-(4-methoxybenzyl)-4,7,13-trioxa-2,10-diaza-10-methyl-pentadecan-15-yl-bis(4-methoxybenzyl)carbamate | 773.91 | C$_{45}$H$_{55}$N$_3$O$_{10}$ | 4.76$^a$ 6.06$^b$ 11.06$^c$ 6.02$^d$ |
| 10010 | 3-oxo-1-(4-methoxyphenyl)-2-(4-dimethylaminobenzyl)-4,7,13-trioxa-2,10-diaza-10-methyl-pentadecan-15-yl-(4-methoxybenzyl)(4-dimethylaminobenzyl)carbamate | 799.99 | C$_{45}$H$_{61}$N$_5$O$_8$ | 4.98$^a$ 6.17$^b$ 11.64$^c$ 6.41$^d$ |

TABLE II-continued

R$^a$ZR$^b$ IS Derived from N-Methyl DiAlkenol Amines

| Code | Structures | M.W. | Formula | LogP |
|---|---|---|---|---|
| 10011 | 3-oxo-1-(2-thienyl)-2-(2-thienylmethyl)-4,7,10,16,19-pentaoxa-2,13-diaza-13-methyl-heneicosan-21-yl-bis(2-thienylmethyl)carbamate | 766.03 | C$_{35}$H$_{47}$N$_3$O$_8$S$_4$ | 3.66$^a$<br>6.30$^b$<br>5.20$^c$ |
| 10012 | 3-oxo-1-(3-methoxyphenyl)-2-(3-methoxybenzyl)-4,7,10,16,19-pentaoxa-2,13-diaza-13-methyl-heneicosan-21-yl-bis(3-methoxybenzyl)carbamate | 862.02 | C$_{47}$H$_{63}$N$_3$O$_{12}$ | 4.98$^a$<br>6.09$^b$<br>10.83$^c$ |

TABLE II-continued $R^aZR^b$ IS Derived from N-Methyl DiAlkenol Amines

| Code | Structures | M.W. | Formula | LogP |
|---|---|---|---|---|
| 10013 | 3-oxo-1-(3-methoxyphenyl)-2-(4-dimethylaminobenzyl)-4,7,10,16,19-pentaoxa-2,13-diaza-13-methyl-heneicosan-21-yl-(3-methoxybenzyl)(4-dimethylaminobenzyl)carbamate | 888.10 | $C_{49}H_{69}N_5O_{10}$ | $5.20^a$ $6.02^b$ $11.52^c$ |
| 10014 | 3-oxo-1-(4-methoxyphenyl)-2-(4-methoxybenzyl)-4,7,10,16,19-pentaoxa-2,13-diaza-13-methyl-heneicosan-21-yl-bis(4-methoxybenzyl)carbamate | 862.02 | $C_{47}H_{63}N_3O_{12}$ | $4.98^a$ $6.10^b$ $11.77^c$ |

TABLE II-continued

R$^a$ZR$^b$ IS Derived from N-Methyl DiAlkenol Amines

| Code | Structures | M.W. | Formula | LogP |
|---|---|---|---|---|
| 10015 | 3-oxo-1-(4-methoxyphenyl)-2-(4-dimethylaminobenzyl)-4,7,10,16,19-pentaoxa-2,13-diaza-13-methyl-heneicosan-21-yl-(4-methoxybenzyl)(4-dimethylaminobenzyl) carbamate | 888.10 | C$_{49}$H$_{69}$N$_5$O$_{10}$ | 5.20$^a$<br>6.02$^b$<br>12.40$^c$ |
| 10016 | 2-{[2-(9H-carbazol-9-ylcarbonyloxy)ethyl]-N-methylamino}ethyl 9H-carbazole-9-carboxylate | 505.56 | C$_{31}$H$_{27}$N$_3$O$_4$ | 4.10$^a$<br>6.50$^b$<br>5.74$^c$<br>8.40$^d$ |

TABLE II-continued

R$^a$ZR$^b$ IS Derived from N-Methyl DiAlkenol Amines

| Code | Structures | M.W. | Formula | LogP |
|---|---|---|---|---|
| 10017 | 2-{[2-(3,6-dimethoxy-9H-carbazol-9-yl)carbonyloxy)ethyl]-N-methylamino]ethyl 3,6-dimethoxy-9H-carbazole-9-carboxylate | 625.67 | C$_{35}$H$_{35}$N$_3$O$_8$ | 4.10$^a$<br>6.54$^b$<br>5.40$^c$<br>8.06$^d$ |
| 10018 | 2-[2-({2-[2-(9H-carbazol-9-yl)carbonyloxy)ethoxy]ethyl}-N-methylamino)ethoxy]ethyl 9H-carbazole-9-carboxylate | 593.67 | C$_{35}$H$_{35}$N$_3$O$_6$ | 4.32$^a$<br>6.54$^b$<br>6.46$^c$<br>6.75$^d$ |
| 10019 | 2-[2-({2-[2-(3,6-dimethoxy-9H-carbazol-9-yl)carbonyloxy)ethoxy]ethyl}-N-methylamino)ethoxy]ethyl 3,6-dimethoxy-9H-carbazole-9-carboxylate | 713.77 | C$_{39}$H$_{43}$N$_3$O$_{10}$ | 4.32$^a$<br>6.57$^b$<br>6.12$^c$<br>6.41$^d$ |

TABLE II-continued

R$^a$ZR$^b$ IS Derived from N-Methyl DiAlkenol Amines

| Code | Structures | M.W. | Formula | LogP |
|---|---|---|---|---|
| 10020 | 2-(2-{2-[(2-{2-[2-(9-carbazolylcarbonyloxy)ethoxy]ethoxy}ethyl)-N-methylamino]ethoxy}ethoxy)ethyl 9-carbazolecarboxylate | 681.77 | C$_{39}$H$_{43}$N$_3$O$_8$ | 4.54$^a$<br>6.57$^b$<br>7.18$^c$ |
| 10021 | 2-(2-{2-[(2-{2-[2-(3,6-dimethoxy-9-carbazolylcarbonyloxy)ethoxy]ethoxy}ethyl)-N-methylamino]ethoxy}ethoxy)ethyl 3,6-dimethoxy-9-carbazolecarboxylate | 801.88 | C$_{45}$H$_{51}$N$_3$O$_{12}$ | 4.54$^a$<br>6.61$^b$<br>6.84$^c$ |

Example 9—Synthesis of Integrin Agonists of Formula (IIIa&b)

The following generalized synthetic schemes were used to prepare integrin agonists of the general Formula (IIa):

$$Q\text{-}R^a\text{—}Z\text{—}R^a\text{-}Q \qquad (IIa)$$

wherein:
the Q group comprise $R^1R^2NC(=O)$—;
the $R^1$ and $R^2$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof;
the Z group is derived from 2,6-dihydroxypyridine;
the $R^a$ groups comprise $(OCH_2CH_2)_n$; and
n is an integers having a value between 0 and 6, or (IIIb)

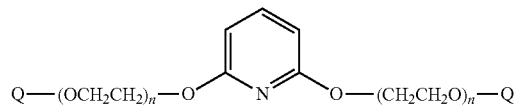

the Q groups comprise $R^2R^3NC(=O)$—,
the $R^2$ and $R^3$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof; and
n is an integer having a value between 0 and 6.

The synthetic procedure of Example 8 is used to prepare the integrin activating compounds or agonists of Formula (IIIa&b), 10022-10042, by reacting the head group intermediates 2-3a, 2-6a, 2-9a, 2-12a, 2-15a, 2-16, or 2-17 with starting materials or intermediates 1-13, 2-18, or 2-20. Alternatively, the agonists 10022-10042 may be synthesized by reacting 2-3b, 2-6b, 2-9b, 2-12b, 2-15b, and the acid chloride of carbazole and 3,6-dimethoxycarbazole with starting materials or intermediates 1-13, 2-18, or 2-20.

Table III includes a list of integrin activating compounds or agonists of Formula (IIIa&b), wherein n=0, 1, or 2, for brevity, the same synthetic procedure may be used for preparing integrin activating compounds or agonists of Formula (IIIa&b), wherein n=3, 4, 5, or 6.

TABLE III

| | Z Is Derived from 2,6-Dihydroxypyridine | | | | |
|---|---|---|---|---|---|
| Code | Structures | | M.W. | Formula | LogP |
| 10022 |  2-[bis(thenyl)aminocarbonyloxy], 6-[bis(thenyl)aminocarbonyloxy] pyridine | | 581.76 | $C_{27}H_{23}N_3O_4S_4$ | $3.22^a$ $7.12^b$ $4.34^c$ $6.12^d$ |
| 10023 | 2-[bis(3-methoxybenzyl)aminocarbonyloxy], 6-[bis(3-methoxybenzyl)aminocarbonyloxy] pyridine | | 677.74 | $C_{39}H_{39}N_3O_8$ | $4.54^a$ $6.91^b$ $9.23^c$ $7.07^d$ |

TABLE III-continued

| Z Is Derived from 2,6-Dihydroxypyridine ||||||
| Code | Structures | M.W. | Formula | LogP |
| --- | --- | --- | --- | --- |
| 10024 | 2-[(3-methoxybenzyl)(4-dimethylaminobenzyl)aminocarbonyloxy], 6-[(3-methoxybenzyl)(4-dimethylaminobenzyl)aminocarbonyloxy] pyridine | 703.82 | $C_{41}H_{45}N_5O_6$ | $4.76^a$ $7.03^b$ $10.66^c$ $7.46^d$ |
| 10025 | 2-[bis(4-methoxybenzyl)aminocarbonyloxy], 6-[bis(4-methoxybenzyl)aminocarbonyloxy] pyridine | 677.74 | $C_{39}H_{39}N_3O_8$ | $4.54^a$ $6.91^b$ $10.91^c$ $7.07^d$ |
| 10026 | 2-[(4-methoxybenzyl)(4-dimethylaminobenzyl)aminocarbonyloxy], 6-[(4-methoxybenzyl)(4-dimethylaminobenzyl)aminocarbonyloxy] pyridine | 703.82 | $C_{41}H_{45}N_5O_6$ | $4.76^a$ $7.03^b$ $11.50^c$ $7.46^d$ |

TABLE III-continued

Z Is Derived from 2,6-Dihydroxypyridine

| Code | Structures | M.W. | Formula | LogP |
|---|---|---|---|---|
| 10027 | 2-[bis(thenyl)aminocarbonyloxyethoxy], 6-[bis(thenyl)aminocarbonyloxyethoxy] pyridine | 669.87 | $C_{31}H_{31}N_3O_6S_4$ | $3.44^a$ $7.16^b$ $5.76^c$ $7.33^d$ |
| 10028 | 2-[bis(3-methoxybenzyl)aminocarbonyloxyethoxy], 6-[bis(3-methoxybenzyl)aminocarbonyloxyethoxy] pyridine | 765.85 | $C_{43}H_{47}N_3O_{10}$ | $4.76^a$ $6.94^b$ $10.64^c$ $8.79^d$ |
| 10029 | 2-[(3-methoxybenzyl)(4-dimethylaminobenzyl) amino carbonyloxyethoxy], 6-[(3-methoxybenzyl)(4-dimethylaminobenzyl)amino carbonyloxyethoxy] pyridine | 791.93 | $C_{45}H_{53}N_5O_8$ | $4.98^a$ $7.06^b$ $12.08^c$ $9.18^d$ |
| 10030 | 2-[bis(4-methoxybenzyl)aminocarbonyloxyethoxy], 6-[bis(4-methoxybenzyl)aminocarbonyloxyethoxy] pyridine | 765.85 | $C_{43}H_{47}N_3O_{10}$ | $4.76^a$ $6.94^b$ $12.33^c$ $8.79^d$ |

TABLE III-continued

Z Is Derived from 2,6-Dihydroxypyridine

| Code | Structures | M.W. | Formula | LogP |
|---|---|---|---|---|
| 10031 | 2-[(4-methoxybenzyl)(4-dimethylaminobenzyl)amino carbonyloxyethoxy], 6-[(4-methoxybenzyl)(4-dimethylaminobenzyl)amino carbonyloxyethoxy] pyridine | 791.93 | $C_{45}H_{53}N_5O_8$ | 4.98[a] 7.06[b] 12.92[c] 9.18[d] |
| 10032 | 2-[bis(thenyl)aminocarbonyloxyethoxyethoxy], 6-[bis(thenyl)aminocarbonyloxyethoxyethoxy] pyridine | 757.97 | $C_{35}H_{39}N_3O_8S_4$ | 3.66[a] 7.19[b] 6.47[c] |
| 10033 | 2-[bis(3-methoxybenzyl)aminocarbonyloxy ethoxyethoxy], 6-[bis(3-methoxybenzyl)aminocarbonyloxy ethoxyethoxy] pyridine | 853.95 | $C_{47}H_{55}N_3O_{12}$ | 4.98[a] 6.98[b] 11.36[c] |
| 10034 | 2-[(3-methoxybenzyl)(4-dimethylaminobenzyl) amino carbonyloxyethoxyethoxy], 6-[(3-methoxybenzyl)(4-dimethylaminobenzyl)amino carbonyloxyethoxyethoxy] pyridine | 880.04 | $C_{46}H_{61}N_5O_{10}$ | 5.20[a] 7.09[b] 12.79[c] |

TABLE III-continued

| | Z Is Derived from 2,6-Dihydroxypyridine | | | |
|---|---|---|---|---|
| Code | Structures | M.W. | Formula | LogP |
| 10035 | 2-[bis(4-methoxybenzyl)aminocarbonyloxy ethoxyethoxy], 6-[bis(4-methoxybenzyl)aminocarbonyloxy ethoxyethoxy] pyridine | 853.95 | $C_{47}H_{55}N_3O_{12}$ | 4.98[a]<br>6.98[b]<br>13.05[c] |
| 10036 | 2-[(4-methoxybenzyl)(4-dimethylaminobenzyl)amino carbonyloxyethoxyethoxy], 6-[(4-methoxybenzyl)(4-dimethylaminobenzyl)amino carbonyloxyethoxyethoxy] pyridine | 880.04 | $C_{46}H_{61}N_5O_{10}$ | 5.20[a]<br>7.09[b]<br>13.64[c] |
| 10037 | 6-(9H-Carbazol-9-ylcarbonyloxy)-2-pyridyl 9H-carbazole-9-carboxylate | 497.50 | $C_{31}H_{19}N_3O_4$ | 4.10[a]<br>7.39[b]<br>6.32[c]<br>9.05[d] |
| 10038 | 6-(3,6-Dimethoxy-9H-carbazol-9-ylcarbonyloxy)-2-pyridyl 3,6-dimethoxy-9H-carbazole-9-carboxylate | 617.60 | $C_{35}H_{27}N_3O_8$ | 4.10[a]<br>7.43[b]<br>5.98[c]<br>8.71[d] |

TABLE III-continued

Z Is Derived from 2,6-Dihydroxypyridine

| Code | Structures | M.W. | Formula | LogP |
|---|---|---|---|---|
| 10039 | 2-{6-[2-(9H-carbazol-9-ylcarbonyloxy)ethoxy]-2-pyridyloxy}ethyl 9H-carbazole-9-carboxylate | 585.60 | $C_{35}H_{27}N_3O_6$ | $4.32^a$ $7.43^b$ $7.74^c$ $9.52^d$ |
| 10040 | 2-{6-[2-(3,6-dimethoxy-9H-carbazol-9-ylcarbonyloxy)ethoxy]-2-pyridyloxy}ethyl 3,6-dimethoxy-9H-carbazole-9-carboxylate | 705.71 | $C_{39}H_{35}N_3O_{10}$ | $4.32^a$ $7.46^b$ $7.40^c$ $9.18^d$ |
| 10041 | 2-[2-(6-{2-[2-(9-carbazolylcarbonyloxy) ethoxy]ethoxy}-2-pyridyloxy)ethoxy]ethyl 9-carbazolecarboxylate | 673.71 | $C_{39}H_{35}N_3O_8$ | $4.54^a$ $7.46^b$ $8.45^c$ |
| 10042 | 2-[2-(6-{2-[2-(3,6-dimethoxy-9-carbazolylcarbonyloxy)ethoxy]ethoxy}-2-pyridyloxy)ethoxy]ethyl 3,6-dimethoxy-9-carbazolecarboxylate | 793.81 | $C_{43}H_{43}N_3O_{12}$ | $4.54^a$ $7.49^b$ $8.11^c$ |

Example 10—Synthesis of Integrin Agonists of Formula (IVa&b)

The following generalized synthetic schemes were used to prepare integrin agonists of the general Formula (IVa):

Q-R$^a$—Z—R$^a$-Q  (IVa)

wherein:
the Q groups comprise $R^1R^2NC(=O)$—,
the $R^1$ and $R^2$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof, the Z group is derived 2,6-dimethanolpyridine;
the $R^a$ groups comprise $(OCH_2CH_2)_n$;
n is an integers having a value between 0 and 6, or

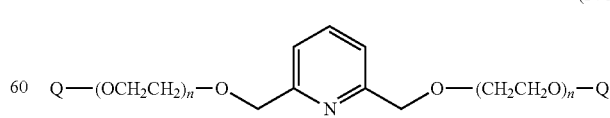

(IVb)

the Q groups comprise $R^1R^2NC(=O)$—;
the $R^1$ and $R^2$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof; and n is an integer having a value between 0 and 6.

The synthetic procedure of Example 8 is used to prepare the integrin activating compounds or agonists of Formula (IVa&b), 10043-10063, by reacting the head group intermediates 2-3a, 2-6a, 2-9a, 2-12a, 2-15a, 2-16, or 2-17 with starting materials or intermediates 1-15, 2-22, or 2-24.

Alternatively, the agonists 10022-10042 may be synthesized by reacting 2-3b, 2-6b, 2-9b, 2-12b, 2-15b, and the acid chloride of carbazole and 3,6-dimethoxycarbazole with starting materials or intermediates 1-15, 2-22, or 2-24.

Table IV includes a list of integrin activating compounds or agonists of Formula (IVa&b), wherein n=0, 1, or 2, for brevity, the same synthetic procedure may be used for preparing integrin activating compounds or agonists of Formula (IV), wherein n=3, 4, 5, or 6.

TABLE IV

Z Is Derived from 2,6-Dimethanol Pyridine

| Code | Structures | M.W. | Formula | LogP |
|---|---|---|---|---|
| 10043 | 2-({bis[(2-thienyl)methyl]aminocarbonyloxy}methyl)-6-({bis[(2-thienyl)methyl]aminocarbonyloxy}methyl) pyridine | 609.81 | $C_{29}H_{27}N_3O_4S_4$ | $3.44^a$ $7.09^b$ $3.00^c$ $6.45^d$ |
| 10044 | 2-({bis(3-methoxybenzyl)aminocarbonyloxy}methyl)-6-({bis(3-methoxybenzyl)aminocarbonyloxy}methyl) pyridine | 703.79 | $C_{41}H_{43}N_3O_8$ | $4.76^a$ $6.88^b$ $7.89^c$ $7.40^d$ |
| 10045 | 2-(3-methoxybenzyl,4-dimethylaminobenzyl)amino carbonyloxy}methyl)-6-(3-methoxybenzyl,4-dimethylaminobenzyl)amino carbonyloxy}methyl) pyridine | 731.88 | $C_{43}H_{49}N_5O_6$ | $4.98^a$ $7.00^b$ $9.32^c$ $7.79^d$ |

TABLE IV-continued

Z Is Derived from 2,6-Dimethanol Pyridine

| Code | Structures | M.W. | Formula | LogP |
|---|---|---|---|---|
| 10046 | 2-({bis(4-methoxybenzyl)aminocarbonyloxy}methyl)-6-({bis(4-methoxybenzyl)aminocarbonyloxy}methyl) pyridine | 705.79 | $C_{41}H_{43}N_3O_8$ | $4.76^a$<br>$6.88^b$<br>$9.58^c$<br>$7.40^d$ |
| 10047 | 2-(4-methoxybenzyl,4-dimethylaminobenzyl)amino carbonyloxy}methyl)-6-(4-methoxybenzyl,4-dimethylaminobenzyl)amino carbonyloxy}methyl) pyridine | 731.88 | $C_{43}H_{49}N_5O_6$ | $4.98^a$<br>$7.00^b$<br>$10.16^c$<br>$7.79^d$ |
| 10048 | 2-{bis[(2-thienyl)methyl]amino carbonyloxy}ethoxy)methyl]-6-{bis[(2-thienyl)methyl]amino carbonyloxy}ethoxy)methyl] pyridine | 697.92 | $C_{33}H_{35}N_3O_6S_4$ | $3.66^a$<br>$7.13^b$<br>$3.89^c$<br>$7.06^d$ |
| 10049 | 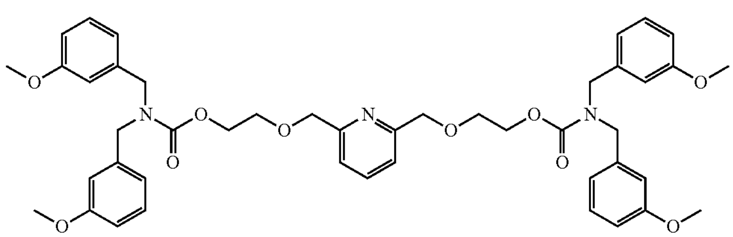 | 793.90 | $C_{45}H_{51}N_3O_{10}$ | $4.98^a$<br>$6.92^b$<br>$8.78^c$<br>$8.00^d$ |

TABLE IV-continued

Z Is Derived from 2,6-Dimethanol Pyridine

| Code | Structures | M.W. | Formula | LogP |
|---|---|---|---|---|
| | 2-{bis(3-methoxybenzyl)amino carbonyloxy}ethoxy)methyl]-6-{bis(3-methoxybenzyl)amino carbonyloxy}ethoxy)methyl] pyridine | | | |
| 10050 | 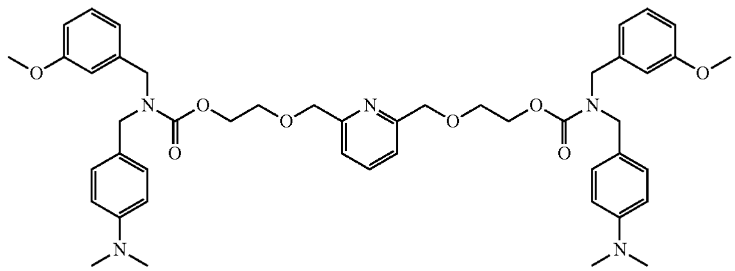 | 819.98 | $C_{47}H_{57}N_5O_8$ | 5.20$^a$<br>7.03$^b$<br>10.21$^c$<br>8.39$^d$ |
| | 2-(3-methoxybenzyl,4-dimethylaminobenzyl)amino carbonyloxy}ethoxy)methyl]-6-(3-methoxybenzyl,4-dimethylaminobenzyl)amino carbonyloxy}ethoxy)methyl] pyridine | | | |
| 10051 | 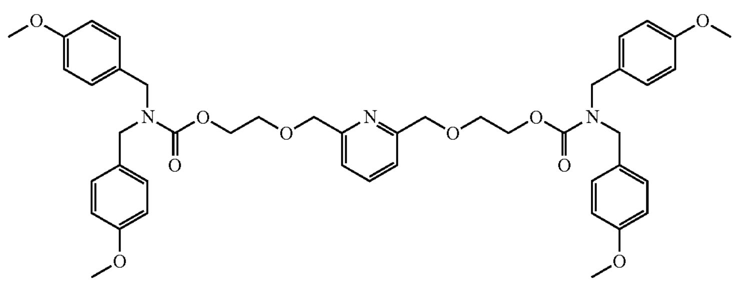 | 793.90 | $C_{45}H_{51}N_3O_{10}$ | 4.98$^a$<br>6.92$^b$<br>10.47$^c$<br>8.00$^d$ |
| | 2-{bis(4-methoxybenzyl)amino carbonyloxy}ethoxy)methyl]-6-{bis(4-methoxybenzyl)amino carbonyloxy}ethoxy)methyl] pyridine | | | |
| 10052 | 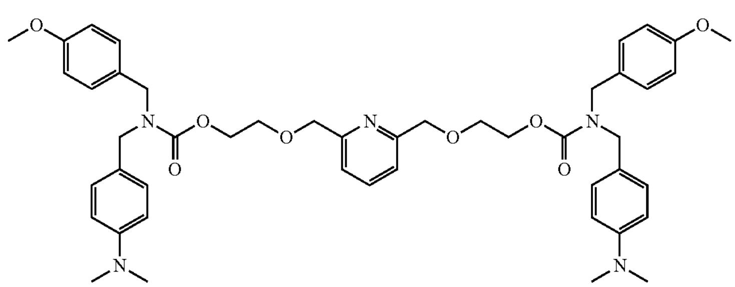 | 819.98 | $C_{47}H_{57}N_5O_8$ | 5.20$^a$<br>7.03$^b$<br>11.05$^c$<br>8.39$^d$ |
| | 2-(4-methoxybenzyl,4-dimethylaminobenzyl)amino carbonyloxy}ethoxy)methyl]-6-(4-methoxybenzyl,4-dimethylaminobenzyl)amino carbonyloxy}ethoxy)methyl] pyridine | | | |
| 10053 | 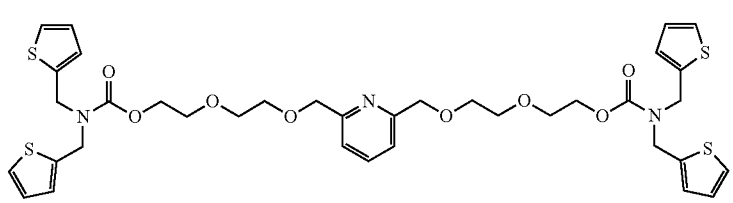 [SMILES: O=C(OCCOCCOCc1cccc(COCCOCCOC(=O)N(Cc2cccs2)Cc2cccs2)n1)N(Cc1cccs1)Cc1cccs1] | 786.02 | $C_{37}H_{43}N_3O_8S_4$ | 3.88<br>7.16<br>4.78<br>6.17$^d$ |

TABLE IV-continued

Z Is Derived from 2,6-Dimethanol Pyridine

| Code | Structures | M.W. | Formula | LogP |
|---|---|---|---|---|
| | 2-{bis[(2-thienyl)methyl]amino carbonyloxy}ethoxyethoxy)methyl]-6-{bis[(2-thienyl)methyl]amino carbonyloxy}ethoxyethoxy)methyl] pyridine | | | |
| 10054 | 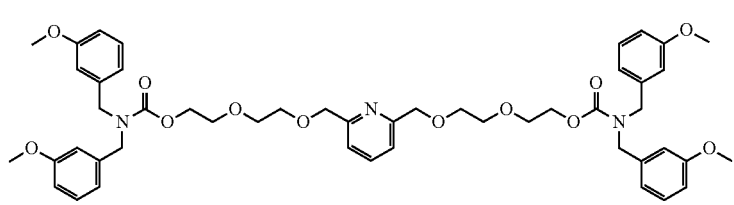 2-{bis(3-methoxybenzyl)amino carbonyloxy}ethoxyethoxy)methyl]-6-{bis(3-methoxybenzyl)amino carbonyloxy}ethoxyethoxy)methyl] pyridine | 882.00 | $C_{49}H_{59}N_3O_{12}$ | 5.20<br>6.50<br>9.67<br>7.12[d] |
| 10055 | 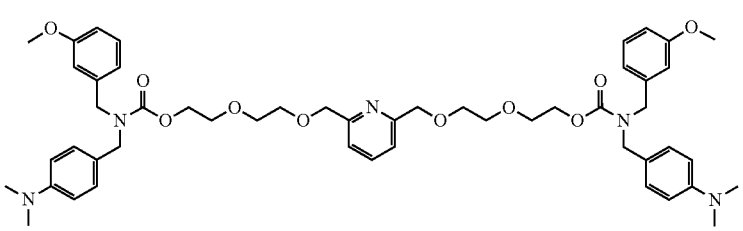 2-(3-methoxybenzyl,4-dimethylaminobenzyl)amino carbonyloxy}ethoxyethoxy)methyl]-6-(3-methoxybenzyl,4-dimethylaminobenzyl)amino carbonyloxy}ethoxyethoxy)methyl] pyridine | 908.09 | $C_{51}H_{65}N_5O_{10}$ | 5.42<br>7.06<br>10.93<br>7.51[d] |
| 10056 | 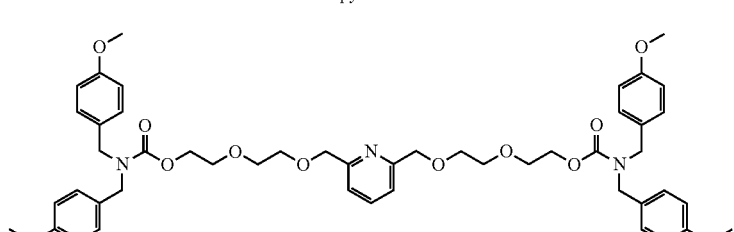 2-{bis(4-methoxybenzyl)amino carbonyloxy}ethoxyethoxy)methyl]-6-{bis(4-methoxybenzyl)amino carbonyloxy}ethoxyethoxy)methyl] pyridine | 882.00 | $C_{49}H_{59}N_3O_{12}$ | 5.20<br>6.95<br>11.01<br>7.12[d] |
| 10057 | 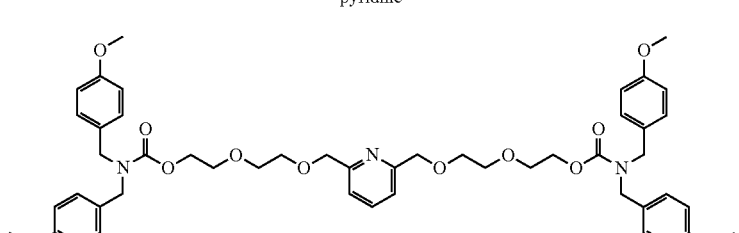 2-(4-methoxybenzyl,4-dimethylaminobenzyl)amino carbonyloxy}ethoxyethoxy)methyl]-6-(4-methoxybenzyl,4-dimethylaminobenzyl)amino carbonyloxy}ethoxyethoxy)methyl] pyridine | 908.09 | $C_{51}H_{65}N_5O_{10}$ | 5.42<br>7.06<br>11.77<br>7.51[d] |

TABLE IV-continued

Z Is Derived from 2,6-Dimethanol Pyridine

| Code | Structures | M.W. | Formula | LogP |
|---|---|---|---|---|
| 10058 | {6-[(9H-Carbazol-9-ylcarbonyloxy)methyl]-2-pyridyl}methyl 9H-carbazole-9-carboxylate | 525.55 | $C_{33}H_{23}N_3O_4$ | $4.32^a$ $7.36^b$ $4.98^c$ $7.99^d$ |
| 10059 | {6-[(3,6-Dimethoxy-9H-carbazol-9-ylcarbonyloxy)methyl]-2-pyridyl}methyl 3,6-dimethoxy-9H-carbazole-9-carboxylate | 645.66 | $C_{37}H_{31}N_3O_8$ | $4.32^a$ $7.40^b$ $4.64^c$ $7.65^d$ |
| 10060 | 2-[(6-{[2-(9H-carbazol-9-ylcarbonyloxy)ethoxy]methyl}-2-pyridyl)methoxy]ethyl 9H-carbazole-9-carboxylate | 585.60 | $C_{35}H_{27}N_3O_6$ | $4.32^a$ $7.43^b$ $7.74^c$ $8.73^d$ |
| 10061 | 2-[(6-{[2-(3,6-dimethoxy-9H-carbazol-9-ylcarbonyloxy)ethoxy]methyl}-2-pyridyl)methoxy]ethyl 3,6-dimethoxy-9H-carbazole-9-carboxylate | 705.71 | $C_{39}H_{35}N_3O_{10}$ | $4.32^a$ $7.46^b$ $7.40^c$ $8.39^d$ |
| 10062 | 2-(2-{[6-({2-[2-(9H-carbazolyl carbonyloxy)ethoxy]ethoxy}methyl)-2-pyridyl]methoxy}ethoxy)ethyl 9-carbazolecarboxylate | 701.76 | $C_{41}H_{39}N_3O_8$ | 4.76 7.43 6.59 |

TABLE IV-continued

Z Is Derived from 2,6-Dimethanol Pyridine

| Code | Structures | M.W. | Formula | LogP |
|------|------------|------|---------|------|
| 10063 | 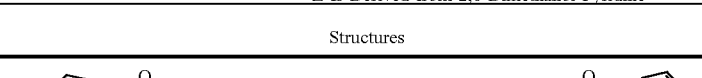 2-(2-{[6-({2-[2-(3,6-dimethoxy-9H-carbazolyl carbonyloxy)ethoxy]ethoxy}methyl)-2-pyridyl]methoxy}ethoxy)ethyl 3,6-dimethoxy-9-carbazolecarboxylate | 821.87 | $C_{45}H_{47}N_3O_{12}$ | 4.76<br>7.46<br>6.25 |

Example 11—Synthesis of Integrin Agonists of Formula (Va&b)

The following generalized synthetic schemes were used to prepare integrin agonists of the general Formula (Va):

$$Q\text{-}R^a\text{—}Z\text{—}R^a\text{-}Q \quad (Va)$$

wherein:
the Q groups comprise $R^1R^2NC(\!=\!O)\text{—}$,
 the $R^1$ and $R^2$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof;
the Z group is derived 3,5-dihydroxypyridine;
the $R^a$ groups comprise $(OCH_2CH_2)_n$;
n is an integers having a value between 0 and 6, or

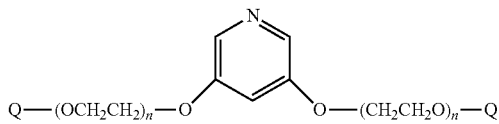
(Vb)

the Q groups comprise $R^1R^2NC(\!=\!O)\text{—}$;
 the $R^1$ and $R^2$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof; and
n is an integer having a value between 0 and 6.

The synthetic procedure of Example 8 is used to prepare the integrin activating compounds or agonists of Formula (Va&b), 10064-10084, by reacting the head group intermediates 2-3a, 2-6a, 2-9a, 2-12a, 2-15a, 2-16, or 2-17 with starting materials or intermediates 1-14, 2-19, or 2-21. Alternatively, the agonists 10022-10042 may be synthesized by reacting 2-3b, 2-6b, 2-9b, 2-12b, 2-15b, and the acid chloride of carbazole and 3,6-dimethoxycarbazole with starting materials or intermediates 1-14, 2-19, or 2-21.

Table V includes a list of integrin activating compounds or agonists of Formula (Va&b), wherein n=0, 1, or 2, for brevity, the same synthetic procedure may be used for preparing integrin activating compounds or agonists of Formula (V), wherein n=3, 4, 5, or 6.

TABLE V

Z Is Derived from 3,5-Dihydroxy Pyridine

| Code | Structures | M.W. | Formula | LogP |
|------|------------|------|---------|------|
| 10064 | 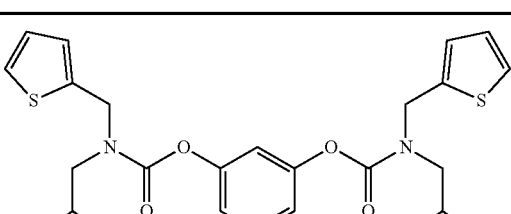 3-[bis(thenyl)aminocarbonyloxy], 5-[bis(thenyl)aminocarbonyloxy] pyridine | 581.76 | $C_{27}H_{23}N_3O_4S_4$ | $3.22^a$<br>$7.12^b$<br>$2.88^c$<br>$5.87^d$ |

TABLE V-continued

Z Is Derived from 3,5-Dihydroxy Pyridine

| Code | Structures | M.W. | Formula | LogP |
|---|---|---|---|---|
| 10065 | 3-[bis(3-methoxybenzyl)aminocarbonyloxy], 5-[bis(3-methoxybenzyl)aminocarbonyloxy] pyridine | 677.74 | $C_{39}H_{39}N_3O_8$ | 4.540[a]<br>6.911[b]<br>7.770[c]<br>6.83[d] |
| 10066 | 3-[(3-methoxybenzyl)(4-dimethylaminobenzyl)aminocarbonyloxy], 5-[(3-methoxybenzyl)(4-dimethylaminobenzyl)aminocarbonyloxy] pyridine | 703.82 | $C_{41}H_{45}N_5O_6$ | 4.76[a]<br>7.03[b]<br>9.20[c]<br>7.21[d] |
| 10067 | 3-[bis(4-methoxybenzyl)aminocarbonyloxy], 5-[bis(4-methoxybenzyl)aminocarbonyloxy] pyridine | 677.74 | $C_{39}H_{39}N_3O_8$ | 4.54[a]<br>6.91[b]<br>9.46[c]<br>6.83[d] |

TABLE V-continued

Z Is Derived from 3,5-Dihydroxy Pyridine

| Code | Structures | M.W. | Formula | LogP |
|---|---|---|---|---|
| 10068 | 3-[(4-methoxybenzyl)(4-dimethylaminobenzyl) aminocarbonyloxy], 5-[(4-methoxybenzyl)(4-dimethylaminobenzyl) aminocarbonyloxy] pyridine | 703.82 | $C_{41}H_{45}N_5O_6$ | $4.76^a$ $7.03^b$ $10.05^c$ $7.21^d$ |
| 10069 | 3-[bis(thenyl)aminocarbonyloxyethoxy], 5-[bis(thenyl)aminocarbonyloxyethoxy] pyridine | 669.87 | $C_{31}H_{31}N_3O_6S_4$ | $3.44^a$ $7.16^b$ $4.30^c$ $7.35^d$ |
| 10070 | 3-[bis(3-methoxybenzyl)aminocarbonyloxyethoxy], 5-[bis(3-methoxybenzyl)aminocarbonyloxyethoxy] pyridine | 765.85 | $C_{43}H_{47}N_3O_{10}$ | $4.76^a$ $6.94^b$ $9.19^c$ $8.30^d$ |
| 10071 | 3-[(3-methoxybenzyl)(4-dimethylaminobenzyl)amino carbonyloxyethoxy], 5-[(3-methoxybenzyl)(4-dimethylaminobenzyl)amino carbonyloxyethoxy] pyridine | 791.93 | $C_{45}H_{53}N_5O_8$ | $4.98^a$ $7.06^b$ $10.62^c$ $8.68^d$ |

TABLE V-continued

Z Is Derived from 3,5-Dihydroxy Pyridine

| Code | Structures | M.W. | Formula | LogP |
|---|---|---|---|---|
| 10072 | 3-[bis(4-methoxybenzyl)aminocarbonyloxyethoxy], 5-[bis(4-methoxybenzyl)aminocarbonyloxyethoxy] pyridine | 765.85 | $C_{43}H_{47}N_3O_{10}$ | $4.76^a$ $6.94^b$ $10.88^c$ $8.30^d$ |
| 10073 | 3-[(4-methoxybenzyl)(4-dimethylaminobenzyl)amino carbonyloxyethoxy], 5-[(4-methoxybenzyl)(4-dimethylaminobenzyl)amino carbonyloxyethoxy]pyridine | 791.93 | $C_{45}H_{53}N_5O_8$ | $4.98^a$ $7.06^b$ $11.46^c$ $8.68^d$ |
| 10074 | 3-[bis(thenyl)amino carbonyloxyethyoxyethoxy], 5-[bis(thenyl)amino carbonyloxyoxyethyethoxy]pyridine | 757.97 | $C_{35}H_{39}N_3O_8S_4$ | $3.66^a$ $7.19^b$ $5.02^c$ |
| 10075 | 3-[bis(3-methoxybenzyl)amino carbonyloxyethoxyethoxy], 5-[bis(3-methoxybenzyl)amino carbonyloxyethoxyethoxy]pyridine | 853.95 | $C_{47}H_{55}N_3O_{12}$ | $4.98^a$ $6.98^b$ $9.90^c$ |

TABLE V-continued

| | Z Is Derived from 3,5-Dihydroxy Pyridine | | | |
|---|---|---|---|---|
| Code | Structures | M.W. | Formula | LogP |
| 10076 | 3-[(4-methoxybenzyl)(4-dimethylaminobenzyl)amino carbonyloxyethoxyethoxy], 5-[(4-methoxybenzyl)(4-dimethylaminobenzyl)amino carbonyloxyethoxyethoxy]pyridine | 880.04 | $C_{49}H_{61}N_5O_{10}$ | $5.20^a$ $7.09^b$ $11.34^c$ |
| 10077 | 3-[bis(3-methoxybenzyl)amino carbonyloxyethoxyethoxy], 5-[bis(3-methoxybenzyl)amino carbonyloxyethoxyethoxy]pyridine | 853.95 | $C_{47}H_{55}N_3O_{12}$ | $4.98^a$ $6.98^b$ $11.59^c$ |
| 10078 | 3-[(4-methoxybenzyl)(4-dimethylaminobenzyl)amino carbonyloxyethoxyethoxy], 5-[(4-methoxybenzyl)(4-dimethylaminobenzyl)amino carbonyloxyethoxyethoxy]pyridine | 880.04 | $C_{49}H_{61}N_5O_{10}$ | $5.20^a$ $7.09^b$ $12.18^c$ |
| 10079 | 5-(9H-carbazol-9-ylcarbonyloxy)-3-pyridyl 9H-carbazole-9-carboxylate | 497.50 | $C_{31}H_{19}N_3O_4$ | $4.10^a$ $7.39^b$ $4.86^c$ $8.81^d$ |

TABLE V-continued

Z Is Derived from 3,5-Dihydroxy Pyridine

| Code | Structures | M.W. | Formula | LogP |
|---|---|---|---|---|
| 10080 | 5-(3,6-Dimethoxy-9H-carbazol-9-ylcarbonyloxy)-3-pyridyl 3,6-dimethoxy-9H-carbazole-9-carboxylate | 617.60 | $C_{35}H_{27}N_3O_8$ | 4.10[a]<br>7.43[b]<br>4.52[c]<br>8.47[d] |
| 10081 | 2-{5-[2-(9H-carbazol-9-ylcarbonyloxy)ethoxy]-3-pyridyloxy}ethyl 9H-carbazole-9-carboxylate | 585.60 | $C_{35}H_{27}N_3O_6$ | 4.32[a]<br>7.43[b]<br>6.28[c]<br>9.02[d] |
| 10082 | 2-{5-[2-(3,6-dimethoxy-9H-carbazol-9-ylcarbonyloxy)ethoxy]-3-pyridyloxy}ethyl 3,6-dimethoxy-9H-carbazole-9-carboxylate | 705.71 | $C_{39}H_{35}N_3O_{10}$ | 4.32[a]<br>7.46[b]<br>5.94[c]<br>8.68[d] |
| 10083 | 2-[2-(5-{2-[2-(9-carbazolylcarbonyloxy) ethoxy]ethoxy}-3-pyridyloxy)ethoxy]ethyl 9-carbazolecarboxylate | 673.71 | $C_{39}H_{35}N_3O_8$ | 4.54[a]<br>7.46[b]<br>7.00[c] |
| 10084 | 2-[2-(5-{2-[2-(3,6-dimethoxy-9-carbazolylcarbonyloxy)ethoxy]ethoxy}-3-pyridyloxy)ethoxy]ethyl 3,6-dimethoxy-9-carbazolecarboxylate | 793.81 | $C_{43}H_{43}N_3O_{12}$ | 4.54[a]<br>7.49[b]<br>6.66[c] |

Example 12—Synthesis of Integrin Agonists of Formula (VIa&b)

The following generalized synthetic schemes were used to prepare integrin agonists of the general Formula (VIa):

Q-R$^a$—Z—R$^a$-Q  (VIa)

wherein:
the Q groups comprise R$^1$R$^2$NC(=O)—,
the R$^1$ and R$^2$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof;
the Z group is derived 3,5-dimethanolpyridine;
the R$^a$ groups comprise (OCH$_2$CH$_2$)$_n$;
n is an integers having a value between 0 and 6, or (VIb)

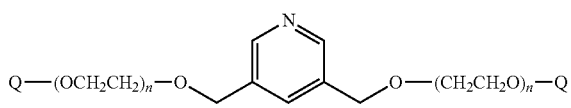

wherein:
the Q groups comprise R$^1$R$^2$NC(=O)—;
the R$^1$ and R$^2$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof; and
n is an integer having a value between 0 and 6.

The synthetic procedure of Example 8 is used to prepare the integrin activating compounds or agonists of Formula (VIa&b), 10085-10105, by reacting the head group intermediates 2-3a, 2-6a, 2-9a, 2-12a, 2-15a, 2-16, or 2-17 with starting materials or intermediates 1-16, 2-23, or 2-25. Alternatively, the agonists 10085-10105 may be synthesized by reacting 2-3b, 2-6b, 2-9b, 2-12b, 2-15b, and the acid chloride of carbazole and 3,6-dimethoxycarbazole with starting materials or intermediates 1-16, 2-23, or 2-25.

Table VI includes a list of integrin activating compounds or agonists of Formula (VIa&b), wherein n=0, 1, or 2, for brevity, the same synthetic procedure may be used for preparing integrin activating compounds or agonists of Formula (VI), wherein n=3, 4, 5, or 6.

TABLE VI

Z Derived from 3,5-Dimenthanol Pyridine

| Code | Structures | M.W. | Formula | LogP |
|---|---|---|---|---|
| 10085 | <br>3-({bis[(2-thienyl)methyl]aminocarbonyloxy}methyl)-<br>5-({bis[(2-thienyl)methyl]aminocarbonyloxy}methyl) pyridine | 609.81 | C$_{29}$H$_{27}$N$_3$O$_4$S$_4$ | 3.44[a]<br>7.09[b]<br>3.59[c]<br>6.45[d] |
| 10086 | <br>3-({bis(3-methoxybenzyl)aminocarbonyloxy}methyl)-<br>5-({bis(3-methoxybenzyl)aminocarbonyloxy}methyl) pyridine | 703.79 | C$_{41}$H$_{43}$N$_3$O$_8$ | 4.76[a]<br>6.88[b]<br>8.48[c]<br>7.40[d] |

TABLE VI-continued

Z Derived from 3,5-Dimenthanol Pyridine

| Code | Structures | M.W. | Formula | LogP |
|------|-----------|------|---------|------|
| 10087 | 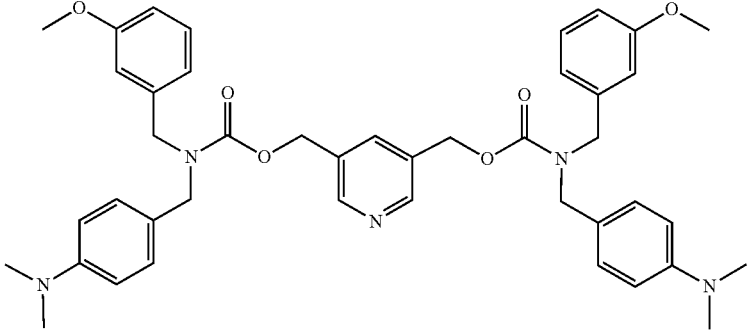<br>3-(3-methoxybenzyl,4-dimethylaminobenzyl)amino carbonyloxy}methyl)-<br>5-(3-methoxybenzyl,4-dimethylaminobenzyl)amino carbonyloxy}methyl)pyridine | 731.37 | $C_{43}H_{49}N_5O_6$ | $4.98^a$<br>$7.00^b$<br>$9.91^c$<br>$7.79^d$ |
| 10088 | 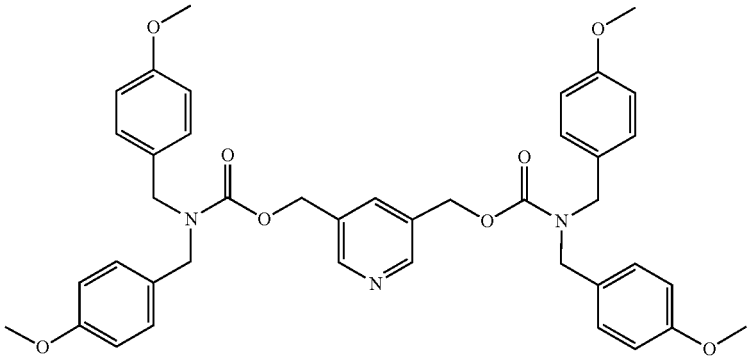<br>3-({bis(4-methoxybenzyl)aminocarbonyloxy}methyl)-<br>5-({bis(4-methoxybenzyl)aminocarbonyloxy}methyl) pyridine | 703.79 | $C_{41}H_{43}N_3O_8$ | $4.76^a$<br>$6.88^b$<br>$10.17^c$<br>$7.40^d$ |
| 10089 | 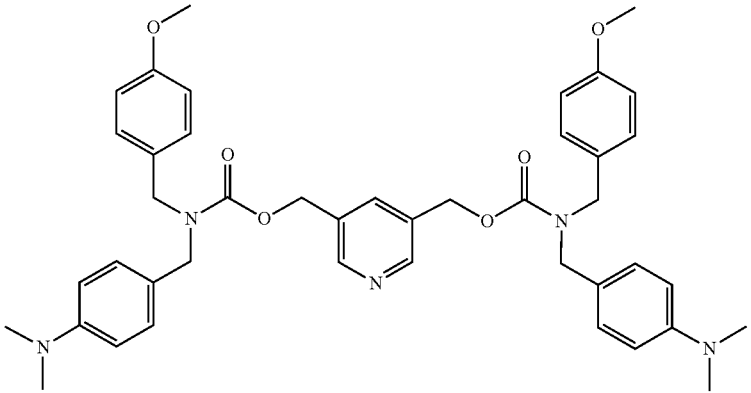<br>3-(4-methoxybenzyl,4-dimethylaminobenzyl)amino carbonyloxy}methyl)-<br>5-(4-methoxybenzyl,4-dimethylaminobenzyl)amino carbonyloxy}methyl)pyridine | 731.37 | $C_{43}H_{49}N_5O_6$ | $4.98^a$<br>$7.00^b$<br>$10.76^c$<br>$7.79^d$ |

TABLE VI-continued

Z Derived from 3,5-Dimenthanol Pyridine

| Code | Structures | M.W. | Formula | LogP |
|---|---|---|---|---|
| 10090 | 3-{bis[(2-thienyl)methyl]amino carbonyloxy}ethoxy)methyl]-5-{bis[(2-thienyl)methyl]amino carbonyloxy}ethoxy)methyl]pyridine | 697.92 | $C_{33}H_{35}N_3O_6S_4$ | $3.66^a$ $7.13^b$ $4.31^c$ $7.06^d$ |
| 10091 | 3-{bis(3-methoxybenzyl)amino carbonyloxy}ethoxy)methyl]-5-{bis(3-methoxybenzyl)amino carbonyloxy}ethoxy)methyl]pyridine | 793.90 | $C_{45}H_{51}N_3O_{10}$ | $4.98^a$ $6.92^b$ $9.20^c$ $8.00^d$ |
| 10092 | 3-(3-methoxybenzyl,4-dimethylaminobenzyl)amino carbonyloxy}ethoxy)methyl]-5-(3-methoxybenzyl,4-dimethylaminobenzyl)amino carbonyloxy}ethoxy)methyl]pyridine | 819.98 | $C_{47}H_{57}N_5O_8$ | $5.20^a$ $7.03^b$ $10.63^c$ $8.39^d$ |
| 10093 | 3-{bis(4-methoxybenzyl)amino carbonyloxy}ethoxy)methyl]-5-{bis(4-methoxybenzyl)amino carbonyloxy}ethoxy)methyl]pyridine | 793.90 | $C_{45}H_{51}N_3O_{10}$ | $4.98^a$ $6.92^b$ $10.88^c$ $8.00^d$ |

TABLE VI-continued

Z Derived from 3,5-Dimenthanol Pyridine

| Code | Structures | M.W. | Formula | LogP |
|---|---|---|---|---|
| 10094 | 3-(4-methoxybenzyl,4-dimethylaminobenzyl)amino carbonyloxy}ethoxy)methyl]-5-(4-methoxybenzyl,4-dimethylaminobenzyl)amino carbonyloxy}ethoxy)methyl]pyridine | 819.98 | $C_{47}H_{57}N_5O_8$ | 5.20[a]<br>7.03[b]<br>10.47[c]<br>8.39[d] |
| 10095 | 3-{bis[(2-thienyl)methyl]amino carbonyloxy}ethoxy ethoxy)methyl]-5-{bis[(2-thienyl)methyl]amino carbonyloxy}ethoxy ethoxy)methyl]pyridine | 786.02 | $C_{37}H_{45}N_3O_8S_4$ | 3.88<br>7.16<br>5.02 |
| 10096 | 3-{bis(3-methoxybenzyl)amino carbonyloxy}ethoxyethoxy)methyl]-5-{bis(3-methoxybenzyl)amino carbonyloxy}ethoxyethoxy)methyl]pyridine | 882.00 | $C_{49}H_{59}N_3O_{12}$ | 5.20<br>6.95<br>9.91 |
| 10097 | 3-(3-methoxybenzyl,4-dimethylaminobenzyl)amino carbonyloxy}ethoxyethoxy)methyl]-5-(3-methoxybenzyl,4-dimethylaminobenzyl)amino carbonyloxy}ethoxyethoxy)methyl]pyridine | 908.09 | $C_{51}H_{65}N_5O_{10}$ | 5.42<br>7.06<br>11.34 |
| 10098 | 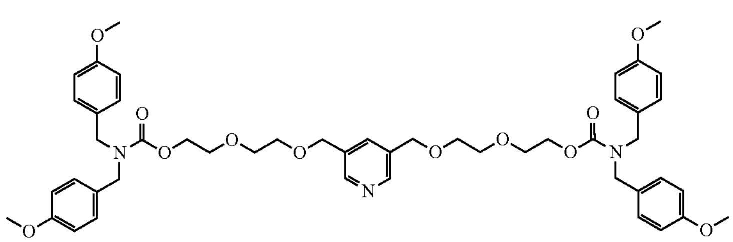 | 882.00 | $C_{49}H_{59}N_3O_{12}$ | 5.20<br>6.95<br>11.60 |

TABLE VI-continued

Z Derived from 3,5-Dimenthanol Pyridine

| Code | Structures | M.W. | Formula | LogP |
|---|---|---|---|---|
| | 3-{bis(4-methoxybenzyl)amino carbonyloxy}ethoxyethoxy)methyl]-5-{bis(4-methoxybenzyl)amino carbonyloxy}ethoxyethoxy)methyl]pyridine | | | |
| 10099 | 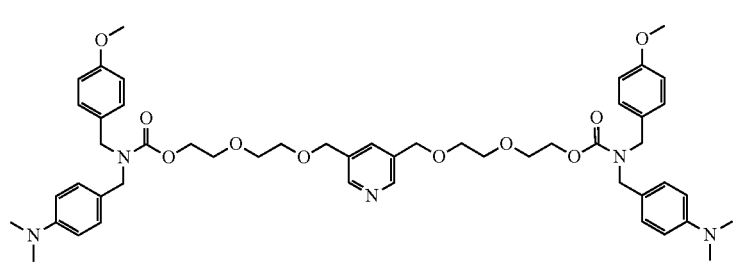 | 908.09 | $C_{51}H_{65}N_5O_{10}$ | 5.42<br>70.6<br>12.19 |
| | 3-(4-methoxybenzyl,4-dimethylaminobenzyl)amino carbonyloxy}ethoxyethoxy)methyl]-5-(4-methoxybenzyl,4-dimethylaminobenzyl)amino carbonyloxy}ethoxyethoxy)methyl]pyridine | | | |
| 10100 | 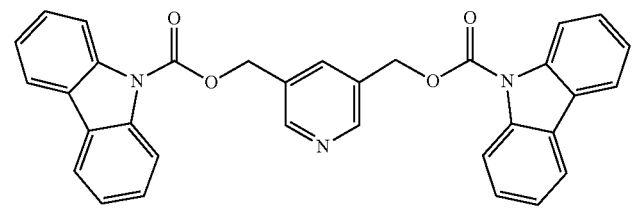 [SMILES: O=C(OCc1cncc(COC(=O)n2c3ccccc3c3ccccc32)c1)n1c2ccccc2c2ccccc21] | 525.55 | $C_{33}H_{23}N_3O_4$ | 4.32[a]<br>7.36[b]<br>5.57[c]<br>7.99[d] |
| | {5-[(9H-Carbazol-9-ylcarbonyloxy)methyl]-3-pyridyl}methyl 9H-carbazole-9-carboxylate | | | |
| 10101 | 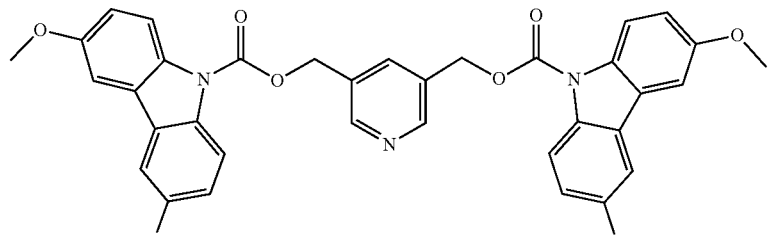 | 645.66 | $C_{37}H_{31}N_3O_8$ | 4.32[a]<br>7.40[b]<br>5.23[c]<br>7.62[d] |
| | {5-[(3,6-Dimethoxy-9H-carbazol-9-ylcarbonyloxy)methyl]-3-pyridyl}methyl 3,6-dimethoxy-9H-carbazole-9-carboxylate | | | |
| 10102 | 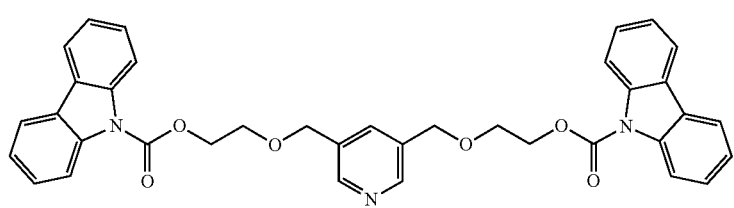 [SMILES: O=C(OCCOCc1cncc(COCCOC(=O)n2c3ccccc3c3ccccc32)c1)n1c2ccccc2c2ccccc21] | 585.60 | $C_{35}H_{27}N_3O_6$ | 4.32[a]<br>7.43[b]<br>6.28[c]<br>8.73[d] |
| | 2-[(5-{[2-(9H-Carbazol-9-ylcarbonyloxy)ethoxy]methyl}-3-pyridyl)methoxy]ethyl 9H-carbazole-9-carboxylate | | | |

TABLE VI-continued

Z Derived from 3,5-Dimenthanol Pyridine

| Code | Structures | M.W. | Formula | LogP |
|---|---|---|---|---|
| 10103 | 2-[(5-{[2-(3,6-Dimethoxy-9H-carbazol-9-ylcarbonyloxy)ethoxy]methyl}-3-pyridyl)methoxy]ethyl 3,6-dimethoxy-9H-carbazole-9-carboxylate | 733.76 | $C_{41}H_{39}N_3O_{10}$ | $4.32^a$ $7.46^b$ $5.94^c$ $8.39^d$ |
| 10104 | 2-(2-{[5-({2-[2-(9-carbazolylcarbonyloxy)ethoxy]ethoxy}methyl)-3-pyridyl]methoxy}ethoxy)ethyl 9-carbazolecarboxylate | 701.76 | $C_{41}H_{39}N_3O_8$ | $4.76^a$ $7.43^b$ $7.00^c$ |
| 10105 | 2-(2-{[5-({2-[2-(3,6-dimethoxy-9-carbazolylcarbonyloxy)ethoxy]ethoxy}methyl)-3-pyridyl]methoxy}ethoxy)ethyl 3,6-dimethoxy-9-carbazolecarboxylate | 821.87 | $C_{45}H_{47}N_3O_{12}$ | $4.76^a$ $7.46^b$ $6.66^c$ |

Example 13—Synthesis of Integrin Agonists of Formula (VIIa&b)

The following generalized synthetic schemes were used to prepare integrin agonists of the general Formula (VIIa):

Q-R$^a$—Z—R$^a$-Q         (VIIa)

wherein:

the Q groups comprise $R^1R^2NC(=O)$—;

the $R^1$ and $R^2$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof;

the Z group is derived 4-dimethylamino-3,5-dihydroxybenzene;

the R$^a$ groups comprise $(OCH_2CH_2)_n$; and n is an integers having a value between 0 and 6, or

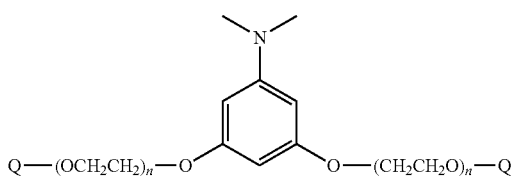

(VIIb)

the Q groups comprise $R^1R^2NC(=O)$—;

the $R^1$ and $R^2$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof; and n is an integer having a value between 0 and 6.

The synthetic procedure of Example 8 is used to prepare the integrin activating compounds or agonists of Formula (VIIa&b), 10106-10126, by reacting the head group intermediates 2-3a, 2-6a, 2-9a, 2-12a, 2-15a, 2-16, or 2-17 with starting materials or intermediates 1-17, 2-26, or 2-27. Alternatively, the agonists 10106-10126 may be synthesized by reacting 2-3b, 2-6b, 2-9b, 2-12b, 2-15b, and the acid chloride of carbazole and 3,6-dimethoxycarbazole with starting materials or intermediates 1-17, 2-26, or 2-27.

Table VII includes a list of integrin activating compounds or agonists of Formula (VIIa&b), wherein n=0, 1, or 2, for brevity, the same synthetic procedure may be used for preparing integrin activating compounds or agonists of Formula (VIIa&b), wherein n=3, 4, 5, or 6.

TABLE VII

Z Derived from 4-Dimethylamino-3,5-Dihydroxy Benzene

| Code | Structures | M.W. | Formula | LogP |
|---|---|---|---|---|
| 10106 | 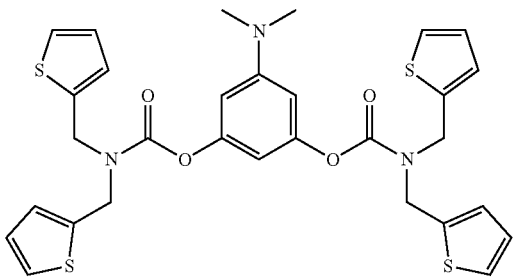 [SMILES: CN(C)c1cc(OC(=O)N(Cc2cccs2)Cc2cccs2)cc(OC(=O)N(Cc2cccs2)Cc2cccs2)c1] 3-[bis(thenyl)aminocarbonyloxy], 5-[bis(thenyl)aminocarbonyloxy], dimethylamino benzene | 623.84 | $C_{30}H_{29}N_3O_4S_4$ | $3.55^a$ $7.79^b$ $4.34^c$ $7.25^d$ |
| 10107 | 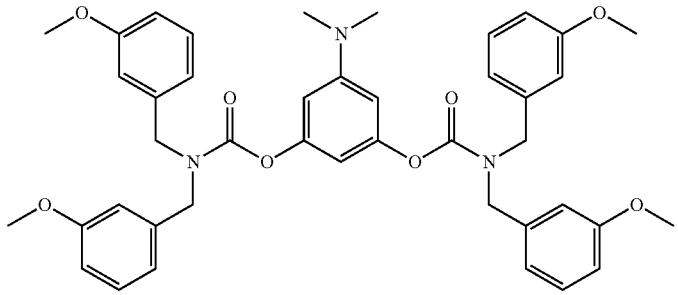 3-[bis(3-methoxybenzyl)aminocarbonyloxy], 5-[bis(3-methoxybenzyl)aminocarbonyloxy] dimethylamino benzene | 719.82 | $C_{42}H_{45}N_3O_8$ | $4.87^a$ $7.58^b$ $9.23^c$ $8.20^d$ |
| 10108 | 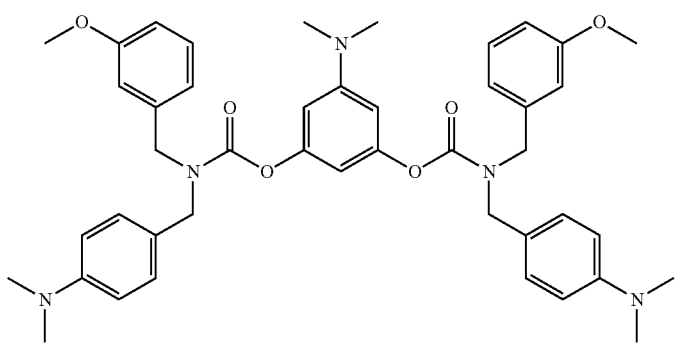 3-[(3-methoxybenzyl)(4-dimethylaminobenzyl)amino carbonyloxy], 5-[(3-methoxybenzyl)(4-dimethylaminobenzyl)amino carbonyloxy] dimethylamino benzene | 745.90 | $C_{44}H_{51}N_5O_6$ | $5.09^a$ $7.70^b$ $10.66^c$ $8.59^d$ |

TABLE VII-continued

Z Derived from 4-Dimethylamino-3,5-Dihydroxy Benzene

| Code | Structures | M.W. | Formula | LogP |
|---|---|---|---|---|
| 10109 | 3-[bis(4-methoxybenzyl)aminocarbonyloxy], 5-[bis(4-methoxybenzyl)aminocarbonyloxy] dimethylamino benzene | 719.82 | $C_{42}H_{45}N_3O_8$ | $4.87^a$ $7.58^b$ $10.92^c$ $8.20^d$ |
| 10110 | 3-[(4-methoxybenzyl)(4-dimethylaminobenzyl) aminocarbonyloxy], 5-[(4-methoxybenzyl)(4-dimethylaminobenzyl) aminocarbonyloxy]dimethylamino benzene | 745.90 | $C_{44}H_{51}N_5O_6$ | $5.09^a$ $7.70^b$ $11.51^c$ $8.59^d$ |
| 10111 | 3-[bis(thenyl)aminocarbonyloxyethoxy], 5-[bis(thenyl)aminocarbonyloxyethoxy] dimethylaminobenzene | 711.94 | $C_{34}H_{37}N_3O_6S_4$ | $3.77^a$ $7.83^b$ $5.76^c$ $8.05^d$ |
| 10112 | 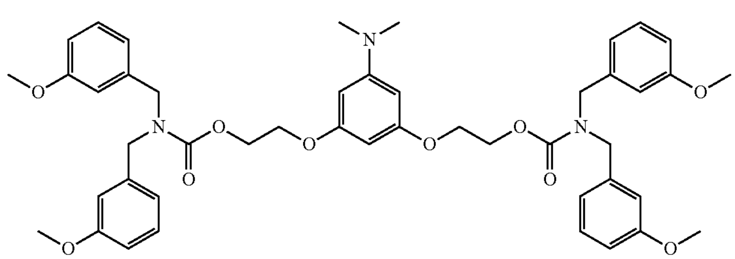 | 807.93 | $C_{46}H_{53}N_3O_{10}$ | $5.09^a$ $7.62^b$ $10.65^c$ $9.00^d$ |

TABLE VII-continued

Z Derived from 4-Dimethylamino-3,5-Dihydroxy Benzene

| Code | Structures | M.W. | Formula | LogP |
|---|---|---|---|---|
| 10113 | 3-[bis(3-methoxybenzyl)aminocarbonyloxyethoxy], 5-[bis(3-methoxybenzyl)aminocarbonyloxyethoxy] dimethylaminobenzene | 834.01 | $C_{48}H_{59}N_5O_8$ | $5.31^a$ $7.73^b$ $12.08^c$ $9.39^d$ |
| 10114 | 3-[(3-methoxybenzyl)(4-dimethylaminobenzyl) aminocarbonyloxyethoxy], 5-[(3-methoxybenzyl)(4-dimethylaminobenzyl) aminocarbonyloxyethoxy]dimethylaminobenzene | 807.93 | $C_{46}H_{53}N_3O_{10}$ | $5.09^a$ $7.62^b$ $12.34^c$ $9.00^d$ |
| 10115 | 3-[bis(4-methoxybenzyl)aminocarbonyloxyethoxy], 5-[bis(4-methoxybenzyl)aminocarbonyloxyethoxy] dimethylaminobenzene | 834.01 | $C_{48}H_{59}N_5O_8$ | $5.31^a$ $7.73^b$ $12.93^c$ $9.39^d$ |
| 10116 | 3-[(4-methoxybenzyl)(4-dimethylaminobenzyl)amino carbonyloxyethoxy], 5-[(4-methoxybenzyl)(4-dimethylaminobenzyl)amino carbonyloxyethoxy] dimethylaminobenzene | 800.05 | $C_{38}H_{45}N_3O_8S_4$ | $3.99^a$ $7.86^b$ $6.48^c$ |

TABLE VII-continued

Z Derived from 4-Dimethylamino-3,5-Dihydroxy Benzene

| Code | Structures | M.W. | Formula | LogP |
|---|---|---|---|---|
| | 3-[bis(thenyl)aminocarbonyloxyethoxyethoxy],<br>5-[bis(thenyl)aminocarbonyloxyethoxyethoxy]<br>dimethylaminobenzene | | | |
| 10117 | 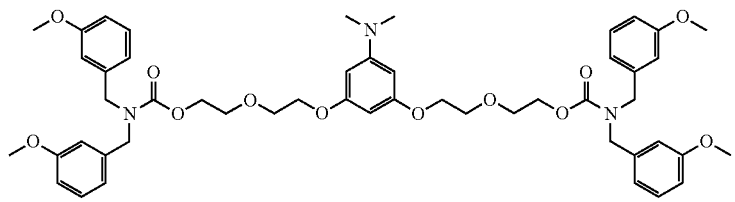 | 896.03 | $C_{50}H_{61}N_3O_{12}$ | 5.13[a]<br>7.65[b]<br>11.37[c] |
| | 3-[bis(3-methoxybenzyl)amino<br>carbonyloxyethoxyethoxy],<br>5-[bis(3-methoxybenzyl)amino<br>carbonyloxyethoxyethoxy]<br>dimethylaminobenzene | | | |
| 10118 | 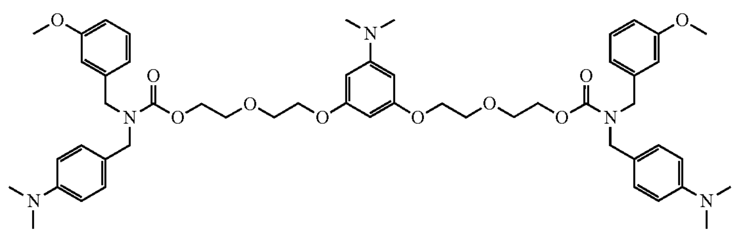 | 922.11 | $C_{52}H_{67}N_5O_{10}$ | 5.53[a]<br>7.76[b]<br>12.80[c] |
| | 3-[(3-methoxybenzyl)(4-dimethylaminobenzyl)amino<br>carbonyloxyethoxyethoxy],<br>5-[(3-methoxybenzyl)(4-dimethylaminobenzyl)amino<br>carbonyloxyethoxyethoxy]<br>dimethylaminobenzene | | | |
| 10119 | 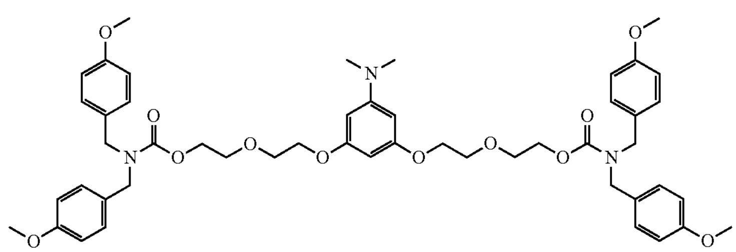 | 896.03 | $C_{50}H_{61}N_3O_{12}$ | 5.31[a]<br>7.65[b]<br>13.05[c] |
| | 3-[bis(4-methoxybenzyl)amino<br>carbonyloxyethoxy ethoxy],<br>5-[bis(4-methoxybenzyl)amino<br>carbonyloxyethoxy ethoxy]<br>dimethylaminobenzene | | | |
| 10120 | 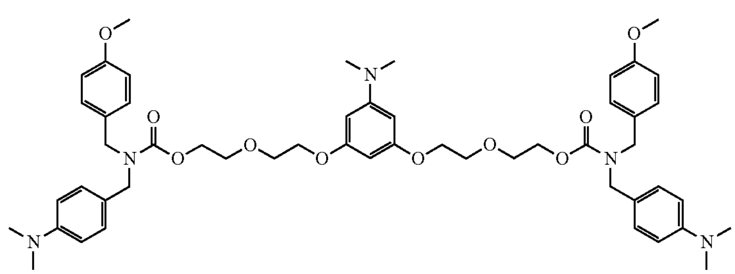 | 922.11 | $C_{52}H_{67}N_5O_{10}$ | 5.53[a]<br>7.76[b]<br>13.64[c] |
| | 3-[(4-methoxybenzyl)(4-dimethylaminobenzyl)amino<br>carbonyloxyethoxyethoxy],<br>5-[(4-methoxybenzyl)(4-dimethylaminobenzyl)amino<br>carbonyloxyethoxyethoxy]<br>dimethylaminobenzene | | | |

TABLE VII-continued

Z Derived from 4-Dimethylamino-3,5-Dihydroxy Benzene

| Code | Structures | M.W. | Formula | LogP |
|---|---|---|---|---|
| 10121 | 3-(9H-Carbazol-9-ylcarbonyloxy)-5-(dimethylamino)phenyl 9H-carbazole-9-carboxylate | 539.58 | $C_{34}H_{25}N_3O_4$ | $4.43^a$ $8.06^b$ $6.32^c$ $9.85^d$ |
| 10122 | 3-(3,6-Dimethoxy-9H-carbazol-9-ylcarbonyloxy)-5-(dimethylamino)phenyl 3,6-dimethoxy-9H-carbazole-9-carboxylate | 659.68 | $C_{38}H_{33}N_3O_8$ | $4.43^a$ $8.10^b$ $5.98^c$ $9.52^d$ |
| 10123 | 2-{3-[2-(9H-Carbazol-9-ylcarbonyloxy)ethoxy]-5-(dimethylamino)phenoxy}ethyl 9H-carbazole-9-carboxylate | 627.68 | $C_{38}H_{33}N_3O_6$ | $4.65^a$ $8.10^b$ $7.74^c$ $9.72^d$ |
| 10124 | 2-{3-[2-(3,6-Dimethoxy-9H-carbazol-9-ylcarbonyloxy)ethoxy]-5-(dimethylamino)phenoxy}ethyl 3,6-dimethoxy-9H-carbazole-9-carboxylate | 747.79 | $C_{42}H_{41}N_3O_{10}$ | $4.65^a$ $8.13^b$ $7.40^c$ $9.38^d$ |

TABLE VII-continued

Z Derived from 4-Dimethylamino-3,5-Dihydroxy Benzene

| Code | Structures | M.W. | Formula | LogP |
|---|---|---|---|---|
| 10125 | 2-[2-(3-{2-[2-(9-carbazolylcarbonyloxy) ethoxy]ethoxy}-5-(dimethylamino)phenoxy) ethoxy]ethyl 9-carbazolecarboxylate | 715.79 | $C_{42}H_{41}N_3O_8$ | 4.87[a] 8.13[b] 8.46[c] |
| 10126 | 2-[2-(3-{2-[2-(3,6-dimethoxy-9-carbazolylcarbonyloxy)ethoxy]ethoxy}-5-(dimethylamino)phenoxy)ethoxy]ethyl 3,6-dimethoxy-9-carbazolecarboxylate | 835.89 | $C_{46}H_{49}N_3O_{12}$ | 4.87[a] 8.16[b] 8.12[c] |

Example 14—Synthesis of Integrin Agonists of Formula (VIIIa&b)

The following generalized synthetic schemes were used to prepare integrin agonists of the general Formula (VIIIa):

$$Q\text{-}R^a\text{—}Z\text{—}R^a\text{-}Q \quad (\text{VIIIa})$$

wherein:

the Q groups comprise $R^1R^2NC(=O)$—, the $R^1$ and $R^2$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof;

the Z group is derived 3,5-dihydroxy-dimethyl benzylamine;

the $R^a$ groups comprise $(OCH_2CH_2)_n$;

n is an integers having a value between 0 and 6, or

(VIIIb)

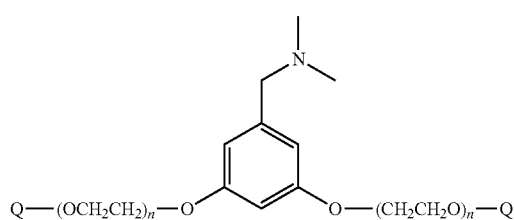

the Q groups comprise $R^1R^2NC(=O)$—;

the $R^1$ and $R^2$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof; and n is an integer having a value between 0 and 6.

The synthetic procedure of Example 8 is used to prepare the integrin activating compounds or agonists of Formula (VIIIa&b), 10127-10147, by reacting the head group intermediates 2-3a, 2-6a, 2-9a, 2-12a, 2-15a, 2-16, or 2-17 with starting materials or intermediates 1-18b, 2-28, or 2-29. Alternatively, the agonists 10127-10147 may be synthesized by reacting 2-3b, 2-6b, 2-9b, 2-12b, 2-15b, and the acid chloride of carbazole and 3,6-dimethoxycarbazole with starting materials or intermediates 1-18b, 2-28, or 2-29.

Table VIII includes a list of integrin activating compounds or agonists of Formula (VIIIa&b), wherein n=0, 1, or 2, for brevity, the same synthetic procedure may be used for preparing integrin activating compounds or agonists of Formula (VIIIa&b), wherein n=3, 4, 5, or 6.

TABLE VIII

Z Is Derived from 3,5-Dihydroxy-Dimethyl Benzylamine

| Code | Structures | M.W. | Formula | LogP |
|---|---|---|---|---|
| 10127 | 3-[bis(thenyl)aminocarbonyloxy], 5-[bis(thenyl)aminocarbonyloxy], dimethylamino benzylamine | 637.87 | $C_{31}H_{31}N_3O_4S_4$ | 3.66[a]<br>7.64[b]<br>3.89[c]<br>6.26[d] |
| 10128 | 3-[bis(3-methoxybenzyl)aminocarbonyloxy], 5-[bis(3-methoxybenzyl)aminocarbonyloxy] dimethylamino benzylamine | 733.85 | $C_{43}H_{47}N_3O_8$ | 4.98[a]<br>7.43[b]<br>8.77[c]<br>7.21[d] |
| 10129 | 3-[(3-methoxybenzyl)(4-dimethylaminobenzyl) aminocarbonyloxy], 5-[(3-methoxybenzyl)(4-dimethylaminobenzyl) aminocarbonyloxy] dimethylamino benzylamine | 759.93 | $C_{45}H_{53}N_5O_6$ | 5.20[a]<br>7.54[b]<br>10.21[c]<br>7.60[d] |

TABLE VIII-continued

Z Is Derived from 3,5-Dihydroxy-Dimethyl Benzylamine

| Code | Structures | M.W. | Formula | LogP |
|---|---|---|---|---|
| 10130 | 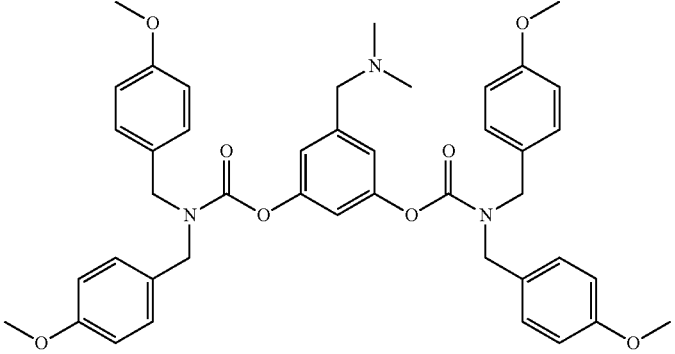 3-[bis(4-methoxybenzyl)aminocarbonyloxy], 5-[bis(4-methoxybenzyl)aminocarbonyloxy] dimethylaminobenzylamine | 733.85 | $C_{43}H_{47}N_3O_8$ | 4.98$^a$ 7.43$^b$ 10.46$^c$ 7.21$^d$ |
| 10131 | 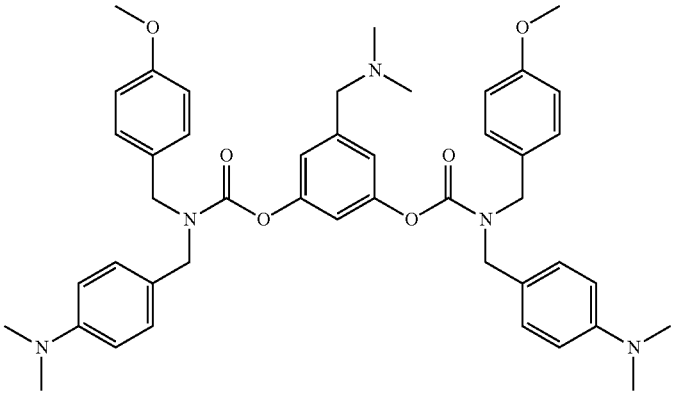 3-[(4-methoxybenzyl)(4-dimethylaminobenzyl) aminocarbonyloxy], 5-[(4-methoxybenzyl)(4-dimethylaminobenzyl) aminocarbonyloxy] dimethylaminobenzylamine | 759.93 | $C_{45}H_{53}N_5O_6$ | 5.20$^a$ 7.54$^b$ 11.05$^c$ 7.60$^d$ |
| 10132 | 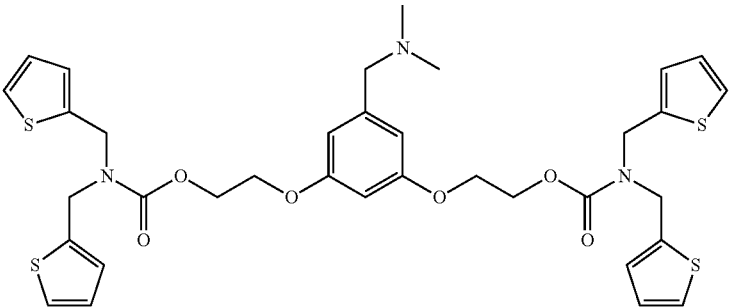 3-[bis(thenyl)aminocarbonyloxyethoxy], 5-[bis(thenyl)aminocarbonyloxyethoxy] dimethylaminobenzylamine | 725.97 | $C_{35}H_{39}N_3O_6S_4$ | 3.88$^a$ 7.67$^b$ 5.30$^c$ 7.73$^d$ |

TABLE VIII-continued

Z Is Derived from 3,5-Dihydroxy-Dimethyl Benzylamine

| Code | Structures | M.W. | Formula | LogP |
|---|---|---|---|---|
| 10133 | 3-[bis(3-methoxybenzyl)aminocarbonyloxyethoxy], 5-[bis(3-methoxybenzyl)aminocarbonyloxyethoxy] dimethylaminobenzylamine | 821.95 | $C_{47}H_{55}N_3O_{10}$ | $5.20^a$ $7.46^b$ $10.19^c$ $8.68^d$ |
| 10134 | 3-[(3-methoxybenzyl)(4-dimethylaminobenzyl) aminocarbonyloxyethoxy], 5-[(3-methoxybenzyl)(4-dimethylaminobenzyl) aminocarbonyloxyethoxy] dimethylaminobenzylamine | 848.04 | $C_{49}H_{61}N_5O_8$ | $5.42^a$ $7.57^b$ $11.62^c$ $9.07^d$ |
| 10135 | 3-[bis(4-methoxybenzyl)aminocarbonyloxyethoxy], 5-[bis(4-methoxybenzyl)aminocarbonyloxyethoxy] dimethylaminobenzylamine | 821.95 | $C_{47}H_{55}N_3O_{10}$ | $5.20^a$ $7.46^b$ $11.88^c$ $8.68^d$ |

TABLE VIII-continued

Z Is Derived from 3,5-Dihydroxy-Dimethyl Benzylamine

| Code | Structures | M.W. | Formula | LogP |
|---|---|---|---|---|
| 10136 | 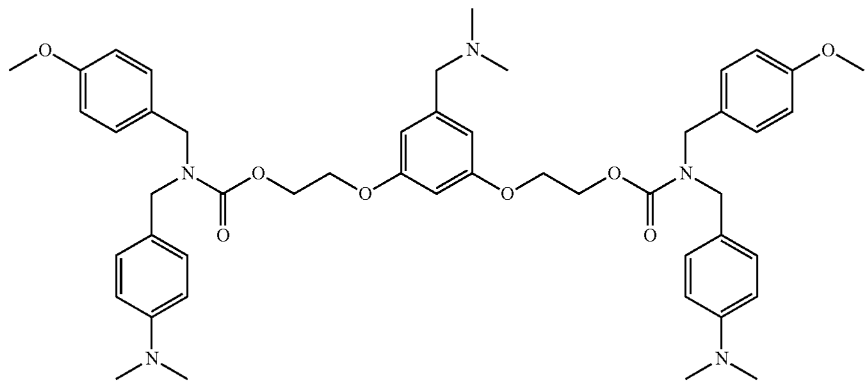 | 848.04 | $C_{49}H_{61}N_5O_8$ | $5.42^a$ $75.7^b$ $12.47^c$ $9.07^d$ |
| | 3-[(4-methoxybenzyl)(4-dimethylaminobenzyl) aminocarbonyloxyethoxy], 5-[(4-methoxybenzyl)(4-dimethylaminobenzyl) aminocarbonyloxyethoxy] dimethylaminobenzylamine | | | |
| 10137 | 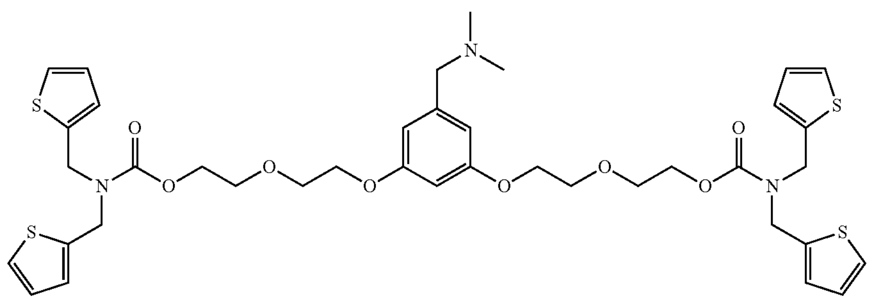 | 814.08 | $C_{39}H_{47}N_3O_8S_4$ | $4.10^a$ $7.70^b$ $6.02^c$ |
| | 3-[bis(thenyl)aminocarbonyloxyethoxyethoxy], 5-[bis(thenyl)aminocarbonyloxyethoxyethoxy] dimethylaminobenzylamine | | | |
| 10138 | 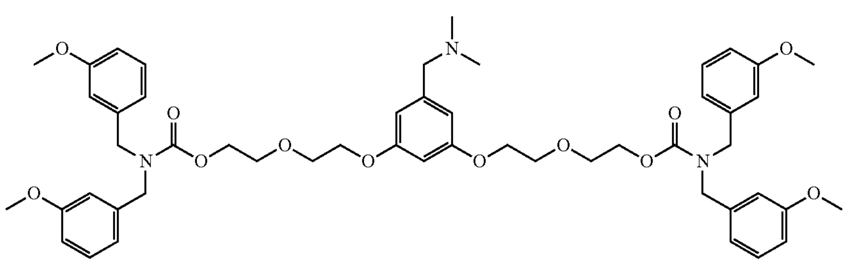 | 910.06 | $C_{51}H_{63}N_3O_{12}$ | $5.42^a$ $7.49^b$ $10.91^c$ |
| | 3-[bis(3-methoxybenzyl)amino- carbonyloxyethoxyethoxy], 5-[bis(3-methoxybenzyl]amino carbonyloxyethoxyethoxy] dimethylaminobenzylamine | | | |

TABLE VIII-continued

Z Is Derived from 3,5-Dihydroxy-Dimethyl Benzylamine

| Code | Structures | M.W. | Formula | LogP |
|---|---|---|---|---|
| 10139 | 3-[(3-methoxybenzyl)(4-dimethylaminobenzyl)aminocarbonyloxyethoxyethoxy], 5-[(3-methoxybenzyl)(4-dimethylaminobenzyl)aminocarbonyloxyethoxyethoxy] dimethylaminobenzylamine | 936.14 | $C_{53}H_{69}N_5O_{10}$ | 5.64[a] <br> 7.61[b] <br> 12.34[c] |
| 10140 | 3-[bis(4-methoxybenzyl)aminocarbonyloxyethoxy ethoxy], 5-[bis(4-methoxybenzyl)aminocarbonyloxyethoxyethoxy] dimethylaminobenzylamine | 910.06 | $C_{51}H_{63}N_3O_{12}$ | 5.42[a] <br> 7.49[b] <br> 12.60[c] |
| 10141 | 3-[(4-methoxybenzyl)(4-dimethylaminobenzyl)aminocarbonyloxyethoxyethoxy], 5-[(4-methoxybenzyl)(4-dimethylaminobenzyl)aminocarbonyloxyethoxyethoxy] dimethylaminobenzylamine | 936.14 | $C_{53}H_{69}N_5O_{10}$ | 5.64[a] <br> 7.61[b] <br> 13.18[c] |

TABLE VIII-continued

Z Is Derived from 3,5-Dihydroxy-Dimethyl Benzylamine

| Code | Structures | M.W. | Formula | LogP |
|---|---|---|---|---|
| 10142 | 3-(9H-Carbazol-9-ylcarbonyloxy)-5-[(methylamino)methyl]phenyl 9H-carbazole-9-carboxylate | 553.60 | $C_{35}H_{27}N_3O_4$ | $4.54^a$ $7.91^b$ $5.87^c$ $9.20^d$ |
| 10143 | 3-(3,6-Dimethoxy-9H-carbazol-9-ylcarbonyloxy)-5-[(dimethylamino)methyl]phenyl 3,6-dimethoxy-9H-carbazole-9-carboxylate | 673.71 | $C_{39}H_{35}N_3O_8$ | $4.54^a$ $7.94^b$ $5.53^c$ $8.86^d$ |
| 10144 | 2-{3-[2-(9H-Carbazol-9-ylcarbonyloxy)ethoxy]-5-[(dimethylamino)methyl]phenoxy}ethyl 9H-carbazole-9-carboxylate | 641.71 | $C_{39}H_{35}N_3O_6$ | $4.76^a$ $7.94^b$ $7.28^c$ $9.41^d$ |

TABLE VIII-continued

Z Is Derived from 3,5-Dihydroxy-Dimethyl Benzylamine

| Code | Structures | M.W. | Formula | LogP |
|---|---|---|---|---|
| 10145 | 2-{3-[2-(3,6-Dimethoxy-9H-carbazol-9-ylcarbonyloxy)ethoxy]-5-[(dimethylamino)methyl]phenoxy}ethyl 3,6-dimethoxy-9H-carbazole-9-carboxylate | 761.81 | $C_{43}H_{43}N_3O_{10}$ | 4.76[a]<br>7.97[b]<br>6.94[c]<br>9.07[d] |
| 10146 | 2-[2-(3-{2-[2-(9-carbazolylcarbonyloxy)ethoxy]ethoxy}-5-[(dimethylamino)methyl]phenoxy)ethoxy]ethyl 9-carbazolecarboxylate | 729.82 | $C_{44}H_{43}N_3O_8$ | 4.98[a]<br>7.97[b]<br>8.00[c] |
| 10147 | 2-[2-(3-{2-[2-(3,6-dimethoxy-9-carbazolylcarbonyloxy)ethoxy]ethoxy}-5-[(dimethylamino)methyl]phenoxy)ethoxy]ethyl 3,6-dimethoxy-9-carbazolecarboxylate | 849.92 | $C_{47}H_{51}N_3O_{12}$ | 4.98[a]<br>8.01[b]<br>7.66[c] |

Example 15—Synthesis of Integrin Agonists of Formula (IXa&b)

The following generalized synthetic schemes were used to prepare integrin agonists of the general Formula (IXa):

$$Q\text{-}R^a\text{—}Z\text{—}R^a\text{-}Q \quad \text{(IXa)}$$

wherein:

the Q groups comprise $R^1R^2NC(=O)$—;

the $R^1$ and $R^2$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof;

the Z group is derived 2,6-pyridine dicarboxylic acid;

the $R^a$ groups comprise $(OCH_2CH_2)_n$; and n is an integers having a value between 0 and 6, or

(IXb)

-continued

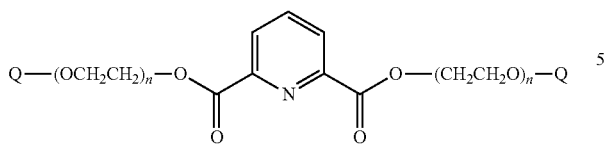

(IXc)

the Q groups comprise $R^1R^2NC(=O)$—;
the $R^1$ and $R^2$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof; and
n is an integer having a value between 0 and 6.

The synthetic procedure of Example 8 is used to prepare the integrin activating compounds or agonists of Formula (IXa&b), 10148-10162, by reacting the head group intermediates 2-3a, 2-6a, 2-9a, 2-12a, 2-15a, 2-16, or 2-17 with starting materials or intermediates 1-20, 2-30, or 2-31. Alternatively, the agonists 10148-10162 may be synthesized by reacting 2-3b, 2-6b, 2-9b, 2-12b, 2-15b, and the acid chloride of carbazole and 3,6-dimethoxycarbazole with starting materials or intermediates 1-20, 2-30, or 2-31.

Table IX includes a list of integrin activating compounds or agonists of Formula (IXa-c), wherein n=0, 1, or 2, for brevity, the same synthetic procedure may be used for preparing integrin activating compounds or agonists of Formula (IXa-c), wherein n=3, 4, 5, or 6.

TABLE IX
Z Is Derived from 2,6-Pyridine Dicarboxylic Acid
| Code | Structures | M.W. | Formula | LogP |
|---|---|---|---|---|
| 10148 | 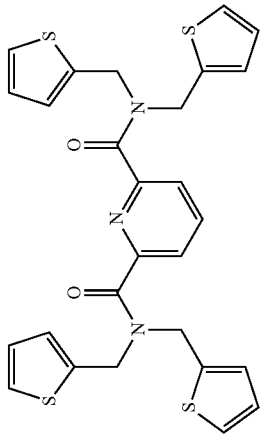<br>N,N,N,N-tetra(2-thienylmethyl)-2,6-pyridinedicarboxamide | 549.76 | $C_{27}H_{23}N_3O_2S_4$ | $3.44^a$<br>$6.41^b$<br>$2.67^c$ |
| 10149 | 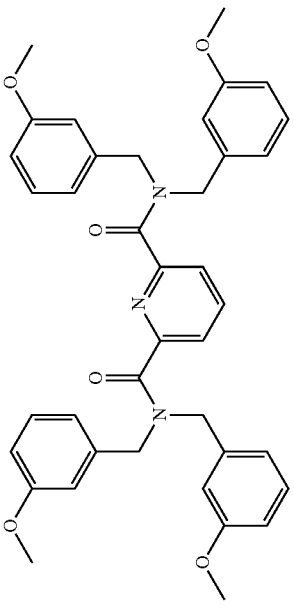<br>N,N,N,N-tetra(3-methoxybenzyl)-2,6-pyridinedicarboxamide | 645.74 | $C_{39}H_{39}N_3O_6$ | $4.76^a$<br>$6.19^b$<br>$7.91^c$ |

TABLE IX-continued
Z Is Derived from 2,6-Pyridine Dicarboxylic Acid
| Code | Structures | M.W. | Formula | LogP |
|---|---|---|---|---|
| 10150 | 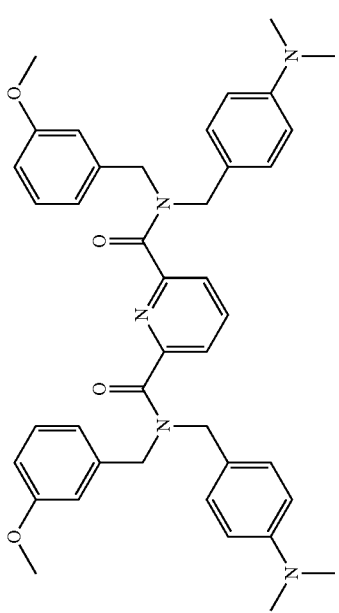 N,N-bis(3-methoxybenzyl)-N,N-bis(4-dimethylaminobenzyl)-2,6-pyridinedicarboxamide | 671.83 | $C_{41}H_{45}N_5O_4$ | $4.98^a$ $6.31^b$ $8.99^c$ |
| 10151 | 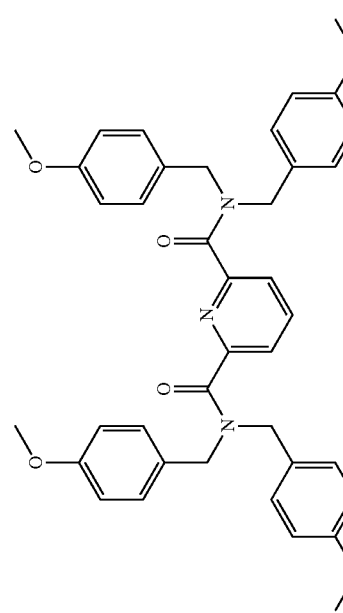 N,N,N,N-tetra(4-methoxybenzyl)-2,6-pyridinedicarboxamide | 645.74 | $C_{39}H_{39}N_3O_6$ | $4.76^a$ $6.19^b$ $9.42^c$ |

TABLE IX-continued
Z Is Derived from 2,6-Pyridine Dicarboxylic Acid
| Code | Structures | M.W. | Formula | LogP |
|---|---|---|---|---|
| 10152 | 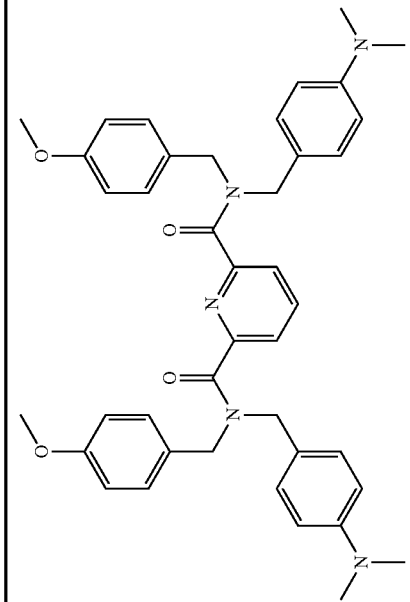<br>N,N-bis(4-methoxybenzyl)-N,N-bis(4-dimethylaminobenzyl)-2,6-pyridinedicarboxamide | 671.83 | $C_{41}H_{45}N_5O_4$ | 4.98[a]<br>6.31[b]<br>10.01[c] |
| 10153 | 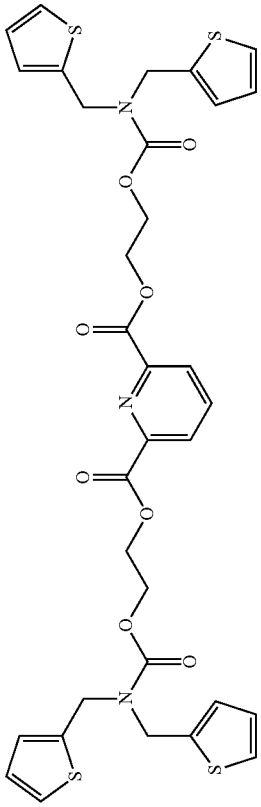<br>bis(2-{bis(2-thienylmethyl)amino-carbonyl)oxy}ethyl) 2,6-pyridinedicarboxylate | 725.89 | $C_{33}H_{31}N_3O_8S_4$ | 3.44[a]<br>6.71[b]<br>4.35[c]<br>7.22[d] |

TABLE IX-continued

Z Is Derived from 2,6-Pyridine Dicarboxylic Acid

| Code | Structures | M.W. | Formula | LogP |
|---|---|---|---|---|
| 10154 | bis(2-{bis[3-methoxybenzyl]amino-carbonyloxy}ethyl) 2,6-pyridinedicarboxylate | 821.87 | $C_{45}H_{47}N_3O_{12}$ | 4.76[a]<br>6.50[b]<br>9.23[c]<br>8.16[d] |
| 10155 | bis(2-{(3-methoxybenzyl)(4-dimethylamino benzyl)amino-carbonyloxy}ethyl) 2,6-pyridinedicarboxylate | 847.95 | $C_{47}H_{53}N_5O_{10}$ | 4.98[a]<br>6.62[b]<br>10.67[c]<br>8.55[d] |

TABLE IX-continued
Z Is Derived from 2,6-Pyridine Dicarboxylic Acid
| Code | Structures | M.W. | Formula | LogP |
|---|---|---|---|---|
| 10156 | 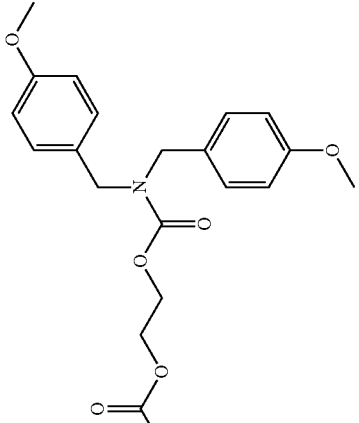 bis(2-{bis[4-methoxybenzyl]amino-carbonyloxy}ethyl) 2,6-pyridinedicarboxylate | 821.87 | $C_{45}H_{47}N_3O_{12}$ | 4.76[a]<br>6.50[b]<br>10.92[c]<br>8.16[d] |
| 10157 | 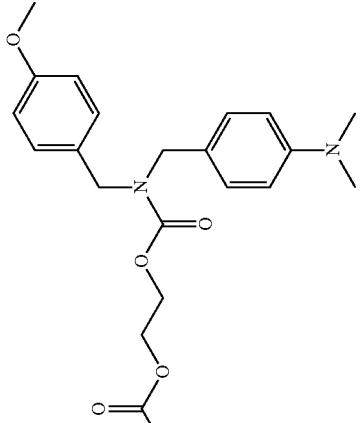 bis(2-{(4-methoxybenzyl)(4-dimethylaminobenzyl)amino-carbonyloxy}ethyl) 2,6-pyridinedicarboxylate | 847.95 | $C_{47}H_{53}N_5O_{10}$ | 4.98[a]<br>6.62[b]<br>11.51[c]<br>8.55[d] |

TABLE IX-continued

Z Is Derived from 2,6-Pyridine Dicarboxylic Acid

| Code | Structures | M.W. | Formula | LogP |
|---|---|---|---|---|
| 10158 | bis(2-{bis(2-thienylmethyl)amino-carbonyloxyethoxy}ethyl) 2,6-pyridinedicarboxylate | 813.99 | $C_{37}H_{39}N_3O_{10}S_4$ | 3.66[a]<br>6.75[b]<br>5.24[c]<br>6.38[d] |
| 10159 | bis(2-{bis[3-methoxybenzyl]amino-carbonyloxyethoxy}ethyl) 2,6-pyridinedicarboxylate | 909.97 | $C_{49}H_{55}N_3O_{14}$ | 4.98[a]<br>6.53[b]<br>9.78[c]<br>7.33[d] |

TABLE IX-continued

Z Is Derived from 2,6-Pyridine Dicarboxylic Acid

| Code | Structures | M.W. | Formula | LogP |
|---|---|---|---|---|
| 10160 | bis(2-{(4-methoxybenzyl)(4-dimethylaminobenzyl)aminocarbonyloxyethoxy}ethyl) 2,6-pyridinedicarboxylate | 936.06 | $C_{51}H_{61}N_5O_{12}$ | 5.20[a]<br>6.65[b]<br>11.38[c]<br>7.72[d] |
| 10161 | bis(2-{bis[4-methoxybenzyl]aminocarbonyloxyethoxy}ethyl) 2,6-pyridinedicarboxylate | 909.97 | $C_{49}H_{55}N_3O_{14}$ | 4.98[a]<br>6.53[b]<br>11.64[c]<br>7.33[d] |

TABLE IX-continued

Z Is Derived from 2,6-Pyridine Dicarboxylic Acid

| Code | Structures | M.W. | Formula | LogP |
|---|---|---|---|---|
| 10162 | bis(2-((4-methoxybenzyl)(4-dimethylaminobenzyl)amino-carbonyloxyethoxy}ethyl) 2,6-pyridinedicarboxylate | 936.06 | $C_{51}H_{61}N_5O_{12}$ | 5.20[b]<br>6.65[b]<br>12.23[c]<br>7.72[d] |

Example 16—Synthesis of Integrin Agonists of Formula (Xa&b)

The following generalized synthetic schemes were used to prepare integrin agonists of the general Formula (Xa):

Q-$R^a$—Z—$R^a$-Q    (Xa)

wherein:
the Q groups comprise $R^1R^2NC(=O)$—,
the $R^1$ and $R^2$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof;
the Z group is derived 3,5-pyridine dicarboxylic acid;
the $R^a$ groups comprise $(OCH_2CH_2)_n$;
n is an integers having a value between 0 and 6, or

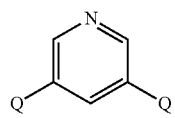

(Xb)

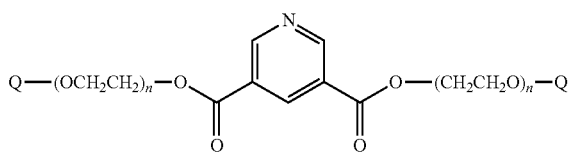

(Xc)

the Q groups comprise $R^1R^2NC(=O)$—;

the $R^1$ and $R^2$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof; and n is an integer having a value between 0 and 6.

The synthetic procedure of Example 8 is used to prepare the integrin activating compounds or agonists of Formula (Xa&b), 10163-10177, by reacting the head group intermediates 2-3a, 2-6a, 2-9a, 2-12a, 2-15a, 2-16, or 2-17 with starting materials or intermediates 1-22, 2-32, or 2-33. Alternatively, the agonists 10163-10177 may be synthesized by reacting 2-3b, 2-6b, 2-9b, 2-12b, 2-15b, and the acid chloride of carbazole and 3,6-dimethoxycarbazole with starting materials or intermediates 1-22, 2-32, or 2-33.

Table X includes a list of integrin activating compounds or agonists of Formula (Xa&b), wherein n=0, 1, or 2, for brevity, the same synthetic procedure may be used for preparing integrin activating compounds or agonists of Formula (Xa&b), wherein n=3, 4, 5, or 6.

TABLE X

Z Is Derived from 3,5-Pyridine Dicarboxylic Acid

| Code | Structures | M.W. | Formula | LogP |
|---|---|---|---|---|
| 10163 | N,N,N,N-tetra(2-thienylmethyl)-3,5-pyridinedicarboxamide | 549.76 | $C_{27}H_{23}N_3O_2S_4$ | 3.44[a]<br>6.41[b]<br>3.26[c] |
| 10164 | N,N,N,N-tetra(4-methoxybenzyl)-3,5-pyridinedicarboxamide | 645.74 | $C_{39}H_{39}N_3O_6$ | 4.76[a]<br>6.19[b]<br>8.15[c] |

TABLE X-continued

Z Is Derived from 3,5-Pyridine Dicarboxylic Acid

| Code | Structures | M.W. | Formula | LogP |
|---|---|---|---|---|
| 10165 | N,N-bis(3-methoxybenzyl)-N,N-bis(4-dimethylaminobenzyl)-3,5-pyridinedicarboxamide | 671.83 | $C_{41}H_{45}N_5O_4$ | 4.98[a]<br>6.31[b]<br>9.58[c] |
| 10166 | N,N,N,N-tetra(4-methoxybenzyl)-3,5-pyridinedicarboxamide | 645.74 | $C_{39}H_{39}N_3O_6$ | 4.76[a]<br>6.19[b]<br>9.84[c] |

TABLE X-continued
Z Is Derived from 3,5-Pyridine Dicarboxylic Acid
| Code | Structures | M.W. | Formula | LogP |
|---|---|---|---|---|
| 10167 | 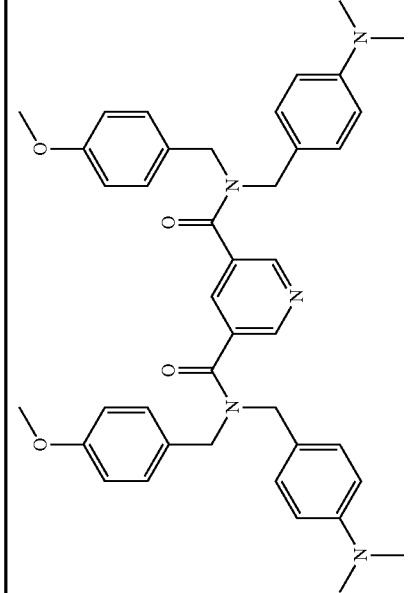 N,N-bis(4-methoxybenzyl)-N,N-bis(4-dimethylaminobenzyl)-3,5-pyridinedicarboxamide | 671.83 | $C_{41}H_{45}N_5O_4$ | $4.98^a$ $6.31^b$ $10.43^c$ |
| 10168 | 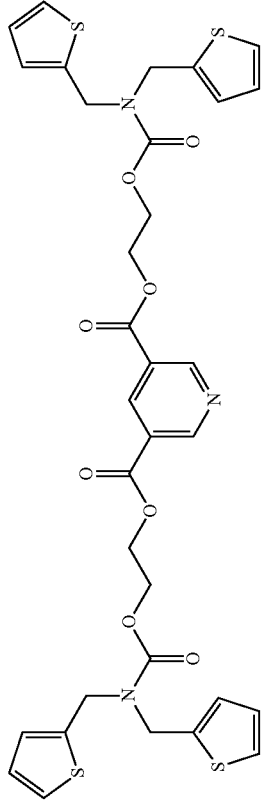 bis(2-{bis(2-thienylmethyl]amino-carbonyloxy}ethyl) 3,5-pyridinedicarboxylate | 725.89 | $C_{33}H_{31}N_3O_8S_4$ | $3.44^a$ $6.71^b$ $4.76^c$ $7.97^d$ |

TABLE X-continued
Z Is Derived from 3,5-Pyridine Dicarboxylic Acid
| Code | Structures | M.W. | Formula | LogP |
|---|---|---|---|---|
| 10169 | 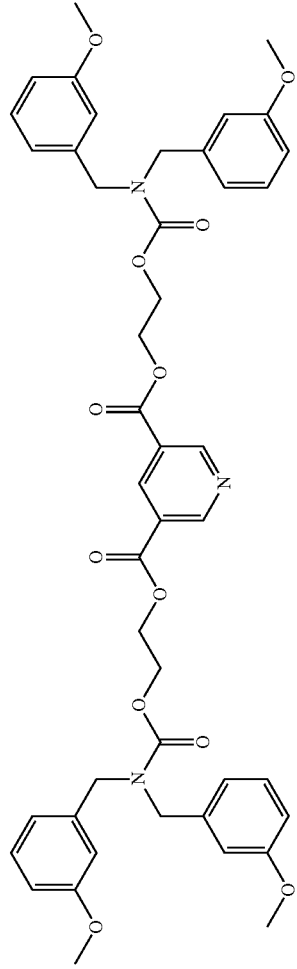 bis(2-{bis(3-methoxybenzyl)amino-carbonyloxy}ethyl) 3,5-pyridinedicarboxylate | 821.87 | $C_{45}H_{47}N_3O_{12}$ | $4.76^a$ $6.50^b$ $9.65^c$ $8.92^d$ |
| 10170 | 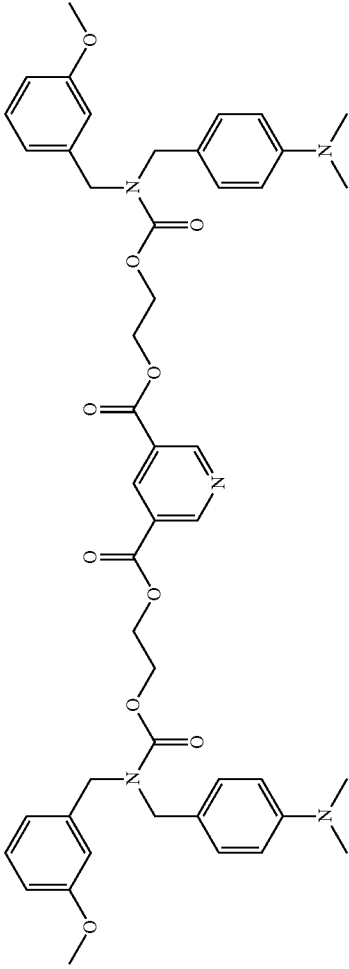 bis(2-{(3-methoxybenzyl) (4-methylaminobenzyl)amino-carbonyloxy}ethyl) 3,5-pyridinedicarboxylate | 847.95 | $C_{47}H_{53}N_5O_{10}$ | $4.98^a$ $6.62^b$ $11.08^c$ $9.31^d$ |

TABLE X-continued
Z Is Derived from 3,5-Pyridine Dicarboxylic Acid
| Code | Structures | M.W. | Formula | LogP |
|---|---|---|---|---|
| 10171 | 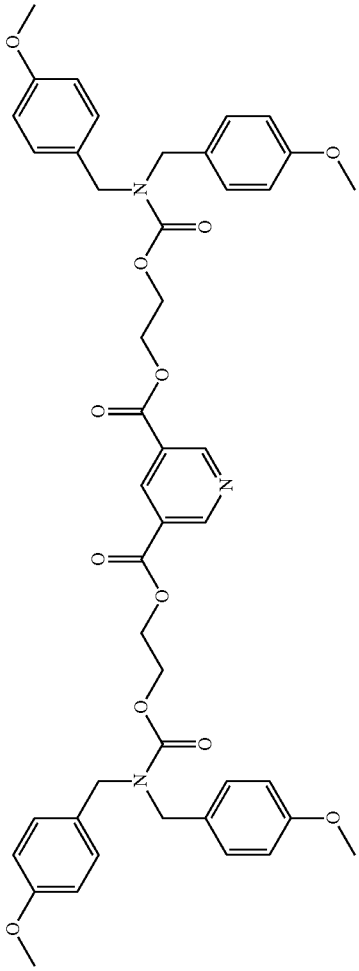<br>bis(2-{bis(4-methoxybenzyl)amino-carbonyloxy}ethyl) 3,5-pyridinedicarboxylate | 821.87 | $C_{45}H_{47}N_3O_{12}$ | $4.76^a$<br>$6.50^b$<br>$11.34^c$<br>$8.92^d$ |
| 10172 | 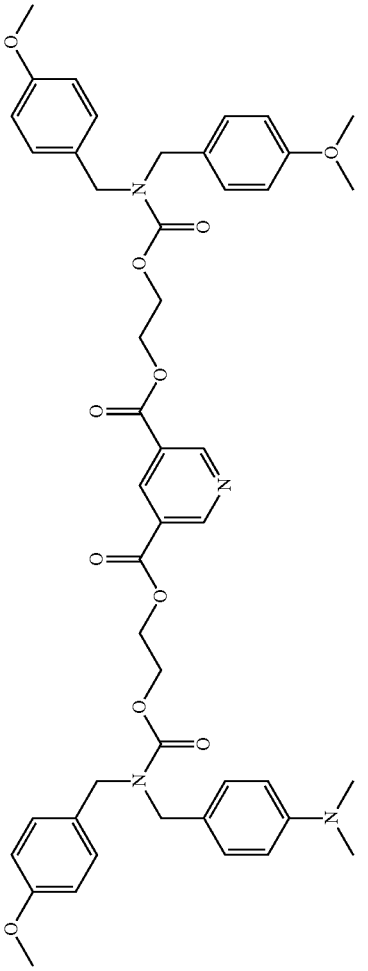<br>bis(2-{bis(4-methoxybenzyl)(4-methylaminobenzyl)amino-carbonyloxy}ethyl) 3,5-pyridinedicarboxylate | 847.95 | $C_{47}H_{53}N_5O_{10}$ | $4.98^a$<br>$6.62^b$<br>$11.93^c$<br>$9.31^d$ |

TABLE X-continued
Z Is Derived from 3,5-Pyridine Dicarboxylic Acid
| Code | Structures | M.W. | Formula | LogP |
|---|---|---|---|---|
| 10173 | 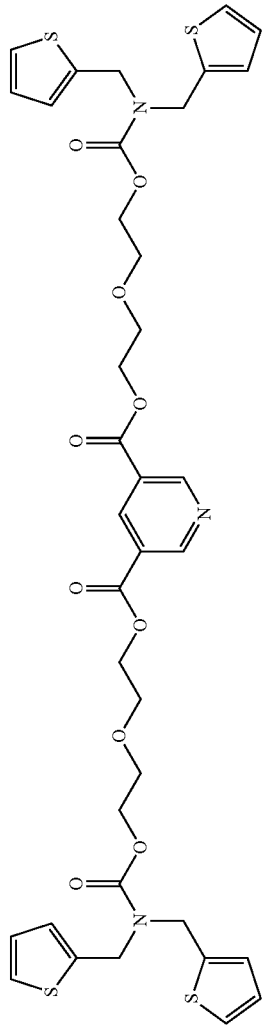 bis(2-{bis(2-thienylmethyl]amino-carbonyloxyethoxy}ethyl) 3,5-pyridinedicarboxylate | 813.99 | $C_{37}H_{39}N_3O_{10}S_4$ | 5.48[a] 6.75[b] 5.48[c] 7.14[d] |
| 10174 | 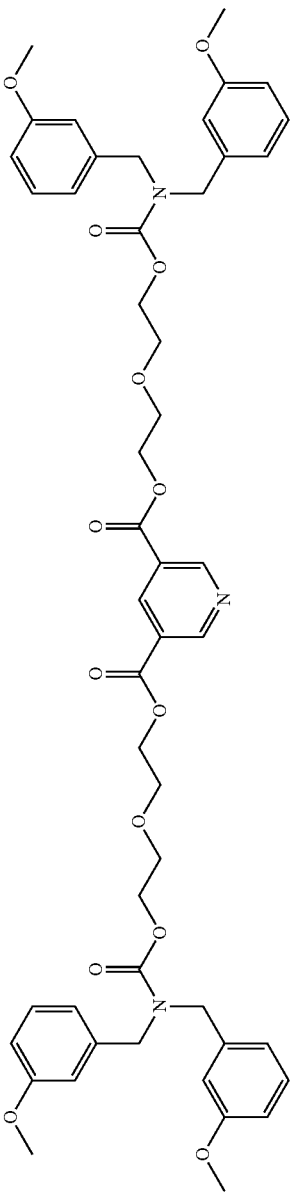 bis(2-{bis[3-methoxybenzyl]amino-carbonyloxyethoxy}ethyl) 3,5-pyridinedicarboxylate | 909.97 | $C_{49}H_5N_3O_{14}$ | 4.98[a] 6.53[b] 10.37[c] 8.09[d] |

TABLE X-continued

Z Is Derived from 3,5-Pyridine Dicarboxylic Acid

| Code | Structures | M.W. | Formula | LogP |
|---|---|---|---|---|
| 10175 | bis(2-{(3-methoxybenzyl)(4-dimethylaminobenzyl)aminocarbnyloxyethoxy}ethyl) 3,5-pyridinedicarboxylate | 936.06 | $C_{51}H_{61}N_5O_{12}$ | 5.20<br>6.65<br>11.80<br>8.48[d] |
| 10176 | bis(2-{bis[4-methoxybenzyl]aminocarbonyloxyethoxy}ethyl) 3,5-pyridinedicarboxylate | 909.97 | $C_{49}H_{55}N_3O_{14}$ | 4.98[a]<br>6.53[b]<br>12.06[c]<br>8.09[d] |

TABLE X-continued
Z Is Derived from 3,5-Pyridine Dicarboxylic Acid
| Code | Structures | M.W. | Formula | LogP |
|---|---|---|---|---|
| 10177 | 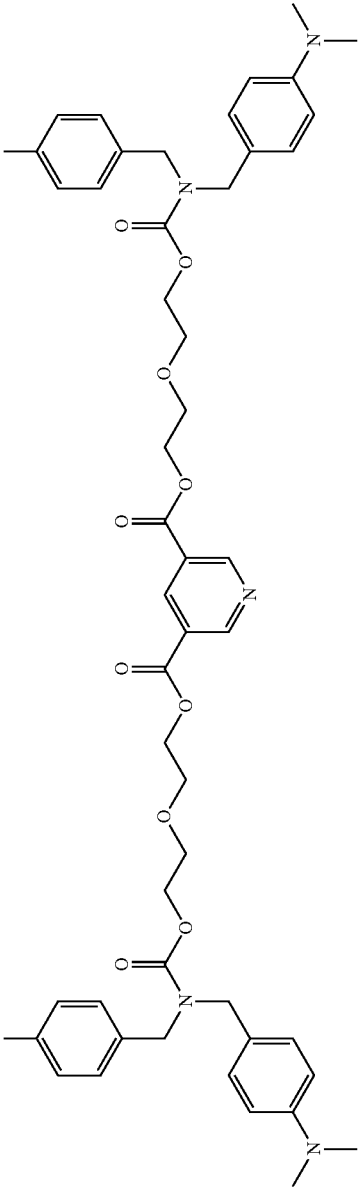 bis(2-((4-methoxybenzyl) (4-dimethylaminobenzyl)amino-carbonyloxyethoxy)ethyl) 3,5-pyridinedicarboxylate | 936.06 | $C_{51}H_{61}N_5O_{12}$ | 5.20[a] 6.65[b] 12.64[c] 8.48[d] |

Example 17—Synthesis of Integrin Agonists of Formula (XIa&b)

The following generalized synthetic schemes were used to prepare integrin agonists of the general Formula (XIa):

$$Q\text{-}R^a\text{—}Z\text{—}R^a\text{-}Q \quad (XIa)$$

wherein:
the Q groups comprise $R^1R^2NC(=O)$—,
the $R^1$ and $R^2$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof;
the Z group is derived 3-dimethylamino-1,5-pentanediol;
the $R^a$ groups comprise $(OCH_2CH_2)_n$;
n is an integers having a value between 0 and 6, or

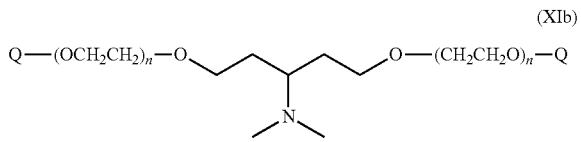

(XIb)

the Q groups comprise $R^1R^2NC(=O)$—;
the $R^1$ and $R^2$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof; and
n is an integer having a value between 0 and 6.

The synthetic procedure of Example 8 is used to prepare the integrin activating compounds or agonists of Formula (XIa&b), 10178-10192, by reacting the head group intermediates 2-3a, 2-6a, 2-9a, 2-12a, 2-15a, 2-16, or 2-17 with starting materials or intermediates 1-27, 2-34, or 2-35. Alternatively, the agonists 10163-10177 may be synthesized by reacting 2-3b, 2-6b, 2-9b, 2-12b, 2-15b, and the acid chloride of carbazole and 3,6-dimethoxycarbazole with starting materials or intermediates 1-27, 2-34, or 2-36.

Table XI includes a list of integrin activating compounds or agonists of Formula (XIa&b), wherein n=0, 1, or 2, for brevity, the same synthetic procedure may be used for preparing integrin activating compounds or agonists of Formula (XIa&b), wherein n=3, 4, 5, or 6.

TABLE XI

Z Is Derived From 3-Dimethylamino-1,5-Pentane Diol

| Code | Structures | M.W. | Formula | LogP |
|---|---|---|---|---|
| 10178 | 1-[bis(2-thienylmethyl)aminocarbonyloxy]-5-[bis(2-thienylmethyl)aminocarbonyloxy]-3-(dimethylamino)pentane | 617.88 | $C_{29}H_{35}N_3O_4S_4$ | 3.44[a]<br>7.01[b]<br>3.97[c] |
| 10179 | 1-[bis(3-methoxybenzyl)aminocarbonyloxy]-5-[bis(3-methoxybenzyl)aminocarbonyloxy]-3-(dimethylamino)pentane | 713.86 | $C_{41}H_{51}N_3O_8$ | 4.76[a]<br>6.80[b]<br>8.86[c] |

TABLE XI-continued

Z Is Derived From 3-Dimethylamino-1,5-Pentane Diol

| Code | Structures | M.W. | Formula | LogP |
|------|-----------|------|---------|------|
| 10180 | 1-[(3-methoxybenzyl),(4-dimethylaminobenzyl)aminocarbonyloxy]-5-[bis(3-methoxybenzyl),(4-dimethylaminobenzyl)aminocarbonyloxy]-3-(dimethylamino)pentane | 739.94 | $C_{43}H_{57}N_5O_6$ | $4.98^a$ $6.92^b$ $10.29^c$ |
| 10181 | 1-[bis(4-methoxybenzyl)aminocarbonyloxy]-5-[bis(4-methoxybenzyl)aminocarbonyloxy-3-(dimethylamino)pentane | 713.86 | $C_{41}H_{51}N_3O_8$ | $4.76^a$ $6.80^b$ $10.54^c$ |
| 10182 | 1-[(4-methoxybenzyl),(4-dimethylaminobenzyl)aminocarbonyloxy]-5-[bis(4-methoxybenzyl),(4-dimethyaminobenzyl)aminocarbonyloxy]-3-(dimethylamino)pentane | 739.94 | $C_{43}H_{57}N_5O_6$ | $4.98^a$ $6.92^b$ $11.13^c$ |

TABLE XI-continued

Z Is Derived From 3-Dimethylamino-1,5-Pentane Diol

| Code | Structures | M.W. | Formula | LogP |
|---|---|---|---|---|
| 10183 | 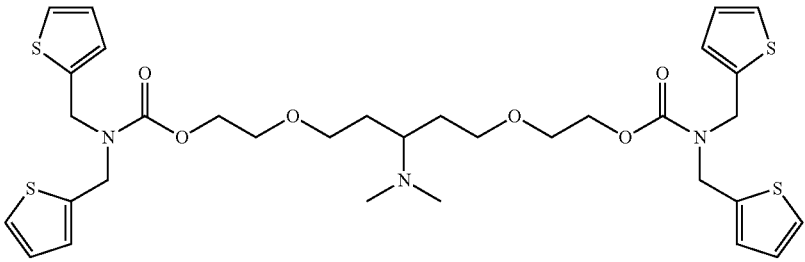<br>1-[bis(2-thienylmethyl)aminocarbonyloxyethoxy]-<br>5-[bis(2-thienylmethyl)aminocarbonyloxyethoxy]-<br>3-(dimethylamino)pentane | 705.98 | $C_{33}H_{43}N_3O_6S_4$ | 3.66[a]<br>7.05[b]<br>4.68[c] |
| 10184 | 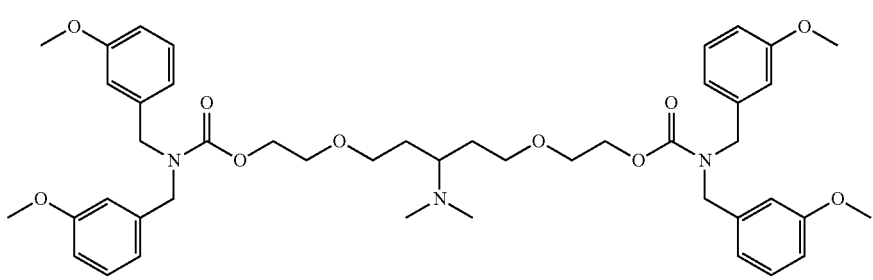<br>1-[bis(3-methoxybenzyl)aminocarbonyloxyethoxy]-<br>5-[bis(3-methoxybenzyl)aminocarbonyloxyethoxy]-<br>3-(dimethylamino)pentane | 801.96 | $C_{45}H_{59}N_3O_{10}$ | 4.98[a]<br>6.84[b]<br>9.57[c] |
| 10185 | 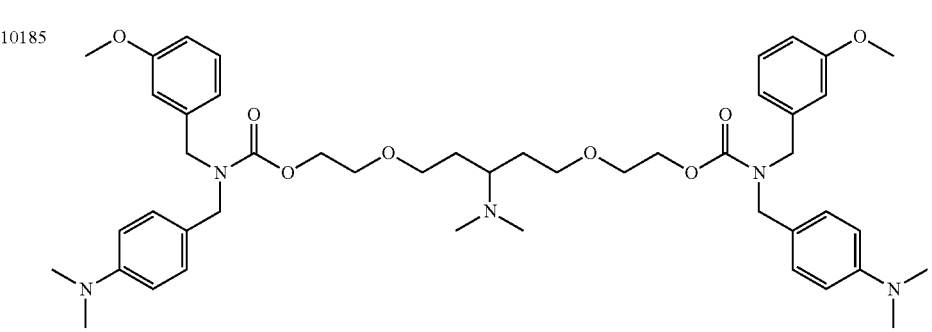<br>1-{[(3-methoxybenzyl)(4-dimethylaminobenzyl)<br>amino]carbonyloxyethoxy}-<br>5-{[(3-methoxybenzyl)(4-dimethylaminobenzyl)<br>amino]carbonyloxyethoxy}-<br>3-(dimethylamino)pentane | 828.05 | $C_{47}H_{65}N_5O_8$ | 5.20[a]<br>6.95[b]<br>11.00[c] |

TABLE XI-continued

Z Is Derived From 3-Dimethylamino-1,5-Pentane Diol

| Code | Structures | M.W. | Formula | LogP |
|------|------------|------|---------|------|
| 10186 | 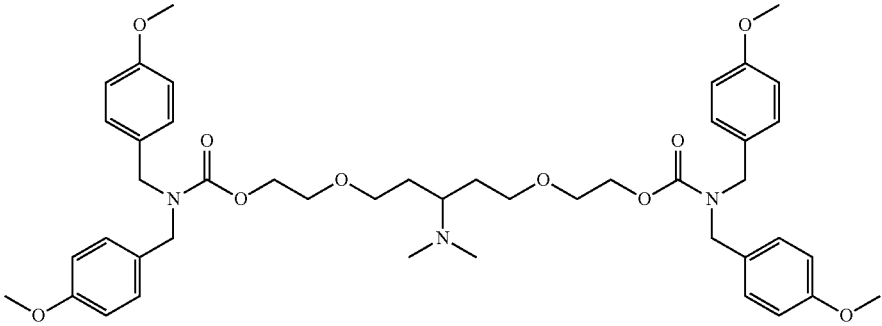<br>1-[bis(4-methoxybenzyl)aminocarbonyloxyethoxy]-<br>5-[bis(4-methoxybenzyl)aminocarbonyloxyethoxy]-<br>3-(dimethylamino)pentane | 801.96 | $C_{45}H_{59}N_3O_{18}$ | $4.98^a$<br>$6.84^b$<br>$11.26^c$ |
| 10187 | 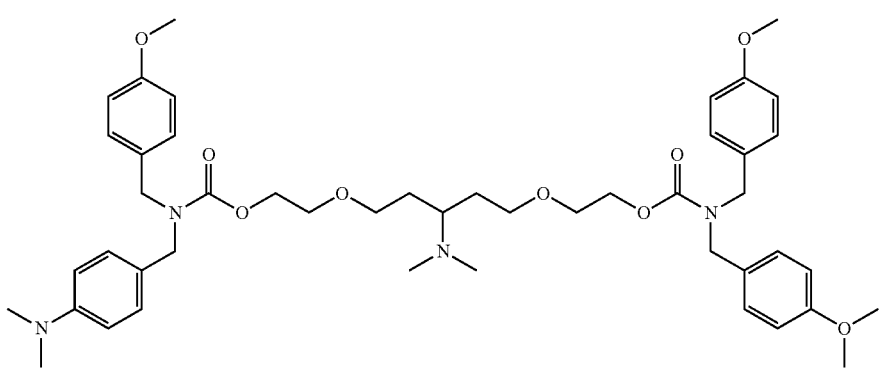<br>1-{[(4-methoxybenzyl)(4-dimethylaminobenzyl)<br>amino]carbonyloxyethoxy}-<br>5-{[(4-methoxybenzyl)(4-dimethylalminobenzyl)<br>amino]carbonyloxyethoxy}-<br>3-(dimethylamino)pentane | 828.05 | $C_{47}H_{65}N_5O_8$ | $5.20^a$<br>$6.95^b$<br>$11.85^c$ |
| 10188 | 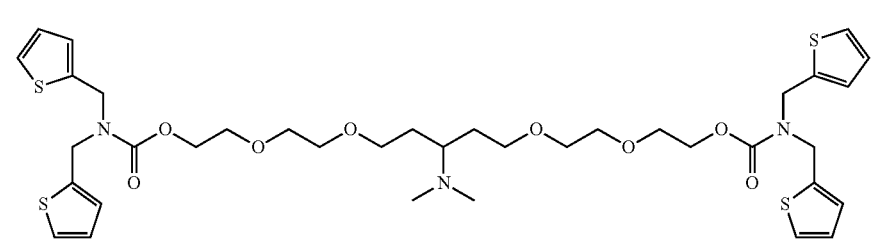<br>1-[bis(2-thienylmethyl)amino-<br>carbonyloxyethoxyethoxy]-<br>5-[bis(2-thienylmethyl)amino-<br>carbonyloxyethoxyethoxy]-<br>3-(dimethylamino)pentane | 794.09 | $C_{37}H_{51}N_3O_8S_4$ | $3.88^a$<br>$7.08^b$<br>$5.40^c$ |

TABLE XI-continued

Z Is Derived From 3-Dimethylamino-1,5-Pentane Diol

| Code | Structures | M.W. | Formula | LogP |
|---|---|---|---|---|
| 10189 | 1-[bis(3-methoxybenzyl)amino-carbonyloxyethoxyethoxy]-5-[bis(3-methoxybenzyl)amino-carbonyloxyethoxyethoxy]-3-(dimethylamino)pentane | 890.07 | $C_{49}H_{67}N_3O_{12}$ | $5.20^a$ $6.87^b$ $10.29^c$ |
| 10190 | 1-{[(3-methoxybenzyl)(4-dimethylaminobenzyl)amino]carbonyloxyethoxyethoxy}-5-{[(3-methoxybenzyl)(4-dimethylaminobenzyl)amino]carbonyloxyethoxyethoxy}-3-(dimethylamino)pentane | 916.15 | $C_{51}H_{73}N_5O_{10}$ | $5.42^a$ $6.98^b$ $11.72^c$ |
| 10191 | 1-[bis(4-methoxybenzyl)amino-carbonyloxyethoxyethoxy]-5-[bis(4-methoxybenzyl)amino-carbonyloxyethoxyethoxy]-3-(dimethylamino)pentane | 890.07 | $C_{49}H_{67}N_3O_{12}$ | $5.20^a$ $6.87^b$ $10.29^c$ |

TABLE XI-continued

Z Is Derived From 3-Dimethylamino-1,5-Pentane Diol

| Code | Structures | M.W. | Formula | LogP |
|---|---|---|---|---|
| 10192 | 1-{[(4-methoxybenzyl)(4-dimethylaminobenzyl)amino]carbonyloxyethoxyethoxy}-5-{[(4-methoxybenzyl)(4-dimethylaminobenzyl)amino]carbonyloxyethoxyethoxy}-3-(dimethylamino)pentane | 916.15 | $C_{51}H_{73}N_5O_{10}$ | 5.42[a]<br>6.98[b]<br>12.56[c] |

Example 18—Synthesis of Integrin Agonists of Formula (XIIa&b)

The following generalized synthetic schemes were used to prepare integrin agonists of the general Formula (XIIa):

$$Q\text{-}R^a\text{—}Z \quad (XIIa)$$

wherein:
the Q groups comprise $R^1R^2NC(=O)$—,
  the $R^1$ and $R^2$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof;
the Z group is derived PEGn-omega-dimethylamine;
the $R^a$ groups comprise $(OCH_2CH_2)_n$;
n is an integers having a value between 0 and 6, or $$Q\text{-}(OCH_2CH_2)_n N(CH_3)_2 \quad (XIIb)$$

the Q groups comprise $R^1R^2NC(=O)$—;
  the $R^1$ and $R^2$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof; and
n is an integer having a value between 2 and 6.

The synthetic procedure of Example 8 is used to prepare the integrin activating compounds or agonists of Formula (XIIa&b), 10193-10207, by reacting the head group intermediates 2-3a, 2-6a, 2-9a, 2-12a, 2-15a, 2-16, or 2-17 with starting materials or intermediates 1-23b, 1-24b, or 1-25b. Alternatively, the agonists 10193-10207 may be synthesized by reacting 2-3b, 2-6b, 2-9b, 2-12b, 2-15b, and the acid chloride of carbazole and 3,6-dimethoxycarbazole with starting materials or intermediates 1-23b, 1-24b, or 1-25b.

Table XII includes a list of integrin activating compounds or agonists of Formula (XIIa&b), wherein n=0, 1, or 2, for brevity, the same synthetic procedure may be used for preparing integrin activating compounds or agonists of Formula (XIIa&b), wherein n=3, 4, 5, or 6.

TABLE XII

Z Is Derived From Dimethylamine Terminated PEGs

| Code | Structures | M.W. | Formula | LogP |
|---|---|---|---|---|
| 10193 | 7-oxo-9-(2-thienyl)-8-(2-thienylmethyl)-3,6-dioxa-8-aza-nonanyl-N,N-dimethylamine | 368.52 | $C_{17}H_{24}N_2O_3S_2$ | 2.56[a]<br>3.22[b]<br>2.27[c] |

TABLE XII-continued

Z Is Derived From Dimethylamine Terminated PEGs

| Code | Structures | M.W. | Formula | LogP |
|---|---|---|---|---|
| 10194 | 7-oxo-9-(3-methoxyphenyl)-8-(3-methoxybenzyl)-3,6-dioxa-8-aza-nonanyl-N,N-dimethylamine | 416.51 | $C_{23}H_{32}N_2O_5$ | $3.220^a$ $3.117^b$ $4.715^c$ |
| 10195 | 7-oxo-9-(3-methoxyphenyl)-8-(4-dimethylaminobenzyl)-3,6-dioxa-8-aza-nonanyl-N,N-dimethylamine | 429.55 | $C_{24}H_{35}N_3O_4$ | $3.330^a$ $3.174^b$ $5.431^c$ |
| 10196 | 7-oxo-9-(4-methoxyphenyl)-8-(4-methoxybenzyl)-3,6-dioxa-8-aza-nonanyl-N,N-dimethylamine | 416.51 | $C_{23}H_{32}N_2O_5$ | $3.22^a$ $3.12^b$ $5.56^c$ |

TABLE XII-continued

Z Is Derived From Dimethylamine Terminated PEGs

| Code | Structures | M.W. | Formula | LogP |
|---|---|---|---|---|
| 10197 | 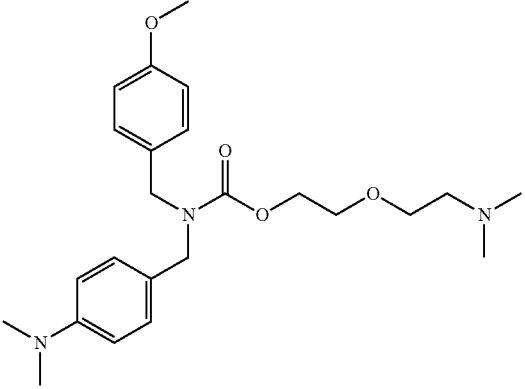<br>7-oxo-9-(4-methoxyphenyl)-<br>8-(4-dimethylaminobenzyl)-<br>3,6-dioxa-8-aza-nonanyl-<br>N,N-dimethylamine | 429.55 | $C_{24}H_{35}N_3O_4$ | 3.33[a]<br>3.17[b]<br>5.85[c] |
| 10198 | 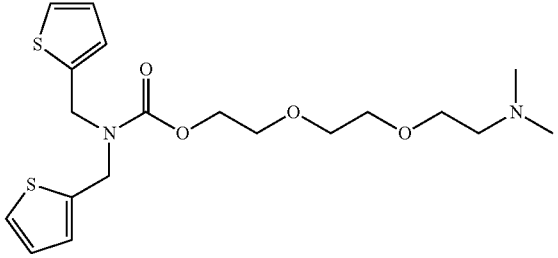<br>10-oxo-12-(2-thienyl)-<br>11-(2-thienylmethyl))-<br>3,6,9-trioxa-11-aza-dodecyl-<br>N,N-dimethylamine | 412.57 | $C_{19}H_{28}N_2O_4S_2$ | 2.67[a]<br>3.24[b]<br>2.63[c] |
| 10199 | 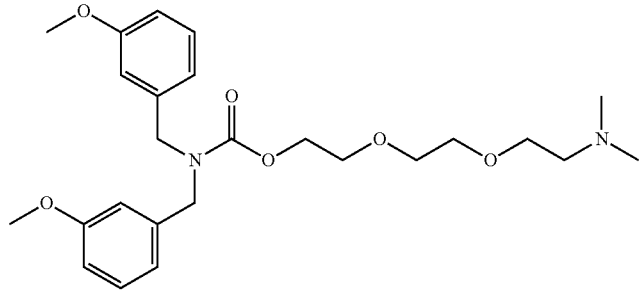<br>10-oxo-12-(3-methoxyphenyl)-<br>11-(3-methoxybenzyl)-<br>3,6,9-trioxa-11-aza-dodecyl-<br>N,N-dimethylamine | 460.56 | $C_{25}H_{36}N_2O_6$ | 3.33[a]<br>3.13[b]<br>5.07[c]<br>2.68[d] |

TABLE XII-continued

Z Is Derived From Dimethylamine Terminated PEGs

| Code | Structures | M.W. | Formula | LogP |
|---|---|---|---|---|
| 10200 | 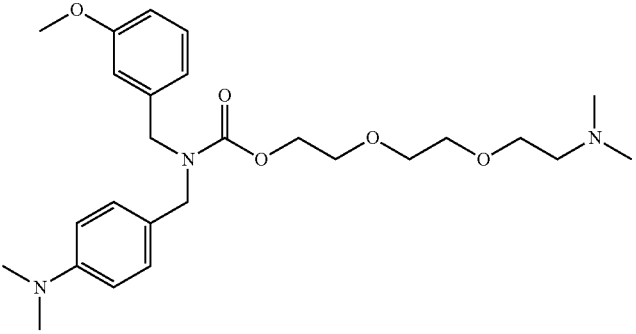<br>10-oxo-12-(3-methoxyphenyl)-<br>11-(4-dimethylaminobenzyl)-<br>3,6,9-trioxa-11-aza-dodecyl-<br>N,N-dimethylamine | 473.60 | $C_{26}H_{39}N_3O_5$ | $3.44^a$<br>$3.19^b$<br>$5.79^c$ |
| 10201 | 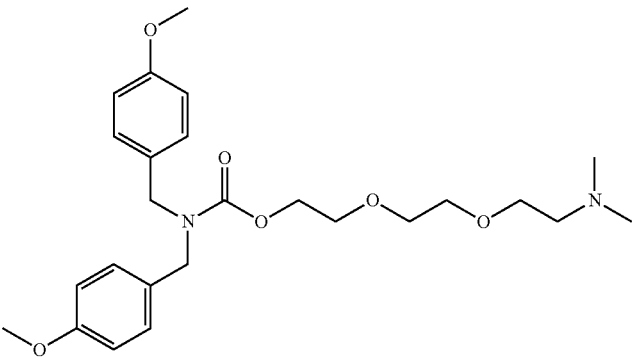<br>10-oxo-12-(3-methoxyphenyl)-<br>11-(3-methoxybenzyl)-<br>3,6,9-trioxa-11-aza-dodecyl-<br>N,N-dimethylamine | 460.56 | $C_{25}H_{36}N_2O_6$ | $3.44^a$<br>$7.09^b$<br>$3.00^c$<br>$2.68^d$ |
| 10202 | 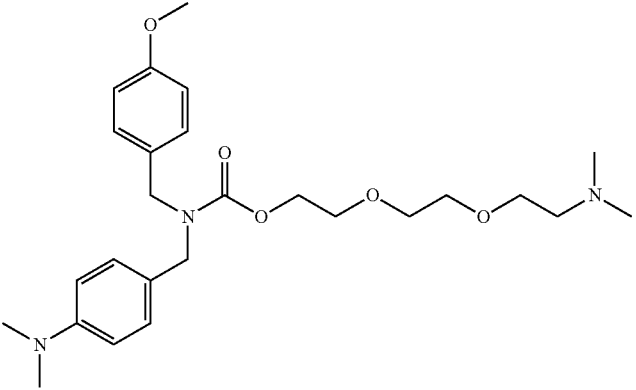<br>10-oxo-12-(3-methoxyphenyl)-<br>11-(4-dimethylaminobenzyl)-<br>3,6,9-trioxa-11-aza-dodecyl-<br>N,N-dimethylamine | 473.60 | $C_{26}H_{39}N_3O_5$ | $3.44^a$<br>$3.19^b$<br>$6.21^c$<br>$2.88^d$ |

TABLE XII-continued

Z Is Derived From Dimethylamine Terminated PEGs

| Code | Structures | M.W. | Formula | LogP |
|------|------------|------|---------|------|
| 10203 | 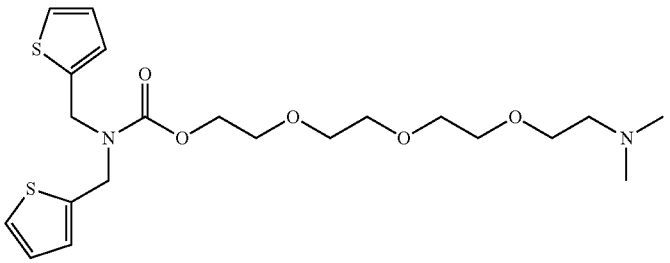<br>13-oxo-15-(2-thienyl)-<br>14-(2-thienylmethyl)-<br>3,6,9,12-tetraoxa-14-aza-pentadecyl-<br>N,N-dimethylamine | 456.62 | $C_{21}H_{32}N_2O_5S_2$ | 2.78[a]<br>3.27[b]<br>2.99[c] |
| 10204 | 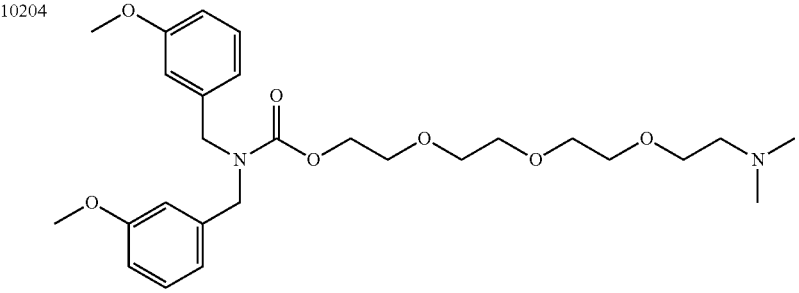<br>13-oxo-15-(3-methoxyphenyl)-<br>14-(3-methoxybenzyl)-<br>3,6,9,12-tetraoxa-14-aza-pentadecyl-<br>N,N-dimethylamine | 504.62 | $C_{27}H_{48}N_2O_7$ | 3.44[a]<br>3.15[b]<br>5.43[c] |
| 10205 | 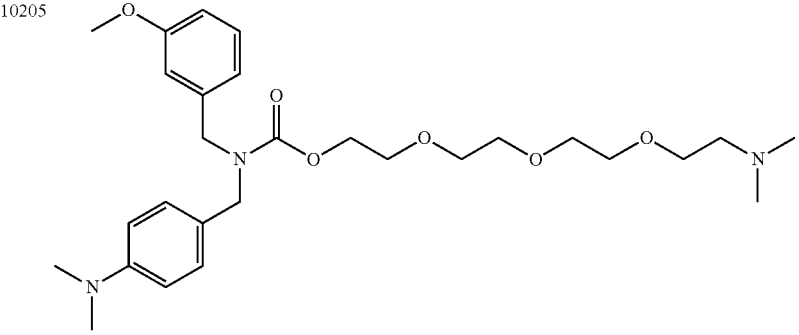<br>13-oxo-15-(3-methoxyphenyl)-<br>14-(4-dimethylaminobenzyl)-<br>3,6,9,12-tetraoxa-14-aza-pentadecyl-<br>N,N-dimethylamine | 517.66 | $C_{28}H_{43}N_3O_6$ | 3.55[a]<br>3.21[b]<br>6.15[c] |

TABLE XII-continued

Z Is Derived From Dimethylamine Terminated PEGs

| Code | Structures | M.W. | Formula | LogP |
|------|-----------|------|---------|------|
| 10206 | 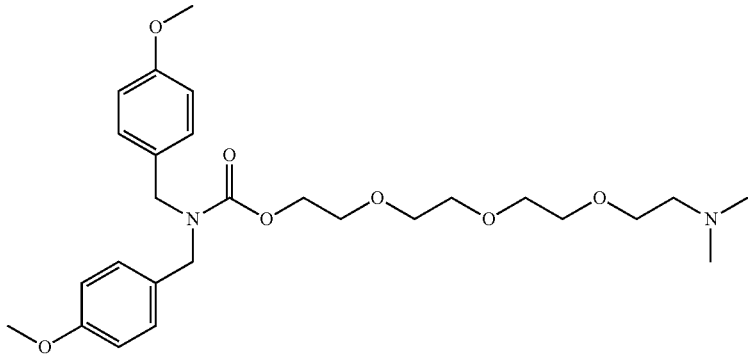<br>13-oxo-15-(4-methoxyphenyl)-<br>14-(4-methoxybenzyl)-<br>3,6,9,12-tetraoxa-14-aza-pentadecyl-<br>N,N-dimethylamine | 504.61 | $C_{27}H_{40}N_2O_7$ | 3.44[a]<br>3.15[b]<br>6.28[c] |
| 10207 | 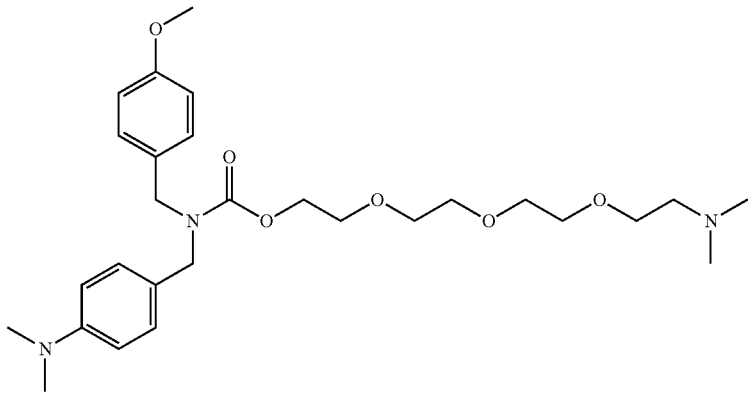<br>13-oxo-15-(3-methoxyphenyl)-<br>14-(4-dimethylaminobenzyl)-<br>3,6,9,12-tetraoxa-14-aza-pentadecyl-<br>N,N-dimethylamine | 517.66 | $C_8H_{43}N_3O_6$ | 3.55[a]<br>3.21[b]<br>6.57[c] |

Example 19—Generalized Synthetic Scheme 1B

Referring now to FIG. 14, a synthetic scheme for preparing integrin activators, wherein the Z group is derived from N-methyldiethanolamine reacted with 2 moles of ethylene oxide to from HOCH$_2$CH$_2$OCH$_2$CH$_2$N(CH$_3$)CH$_2$CH$_2$OCH$_2$CH$_2$H, which in turn is reacted with 2 equivalence of Ar$^1$Ar$^2$NC(=O)Cl, noting that any other N-alkyldialkenol amine may be used. The Ar$^1$ and Ar$^2$ groups may independently be any aryl, alkaryl, or hetero analogs thereof.

Example 20—Generalized Synthetic Scheme 1C

Referring now to FIG. 15, a synthetic scheme for preparing integrin activators, wherein the Z group is derived from triethanolamine reacted with 3 equivalence of Ar$^1$Ar$^2$NC(=O)Cl, noting that any trialkanolamine may be used. The Ar$^1$ and Ar$^2$ groups may independently be any aryl, alkaryl, or hetero analogs thereof. Additionally, the trialkanolamine may be reacted with ethylene oxide to form ethoxylated analogs as set forth herein.

Example 21—Generalized Synthetic Scheme 1D

Referring now to FIG. 16, a synthetic scheme for preparing integrin activators, wherein the Z group is derived from 2,6-dimethanolpyridine reacted with 2 equivalence of ethylene oxide to form 2,6-(HOCH$_2$CH$_2$OCH$_2$)pyridine, which is reacted with 2 moles of Ar$^1$Ar$^2$NC(=O)Cl. The Ar$^1$ and Ar$^2$ groups may independently be any aryl, alkaryl, or hetero analogs thereof.

Example 22—Generalized Synthetic Scheme 1E

Referring now to FIG. 17, a synthetic scheme for preparing integrin activators, wherein the Z group is derived from 3,5-dimethylaniline dicarboxylic acid chloride, which is reacted with 2 moles of Ar$^1$Ar$^2$N·HCl. The Ar$^1$ and Ar$^2$ groups may independently be any aryl, alkaryl, or hetero analogs thereof.

Example 23—Generalized Synthetic Scheme 1f

Referring now to FIG. 18, a synthetic scheme for preparing integrin activators, wherein the Z group is derived from 3,5-dimethylaniline dicarboxylic acid chloride, which is reacted with 2 moles of an ethoxylated $Ar^1Ar^2NC(=O)OCH_2CH_2OH$, formed by reacting $Ar^1Ar^2NC(=O)Cl$ with ethylene glycol, with 3,5-dimethylaniline dicarboxylic acid chloride. The $Ar^1$ and $Ar^2$ groups may independently be any aryl, alkaryl, or hetero analogs thereof. It should be understood that any glycol may be used in place of ethylene glycol such as methylene glycol, dimethylene glycol, polyemthylene glycols (3-6 ethylene units), diethylene glycol, polyethylene glycols (3-6 ethylene units), or higher analogs.

Example 24—Generalized Synthetic Scheme 1G

Referring now to FIG. 19, a synthetic scheme for preparing integrin activators, wherein the Z group is derived from 3,5-dimethylbenzylamine dicarboxylic acid chloride, which is reacted with 2 moles of $Ar^1Ar^2N \cdot HCl$. The $Ar^1$ and $Ar^2$ groups may independently be any aryl, alkaryl, or hetero analogs thereof.

Example 25—Generalized Synthetic Scheme 1H

Referring now to FIG. 20, a synthetic scheme for preparing integrin activators, wherein the Z group is derived from 3,5-dimethylbenyzlamine dicarboxylic acid chloride, which is reacted with 2 moles of an ethoxylated $Ar^1Ar^2NC(=O)OCH_2CH_2OH$, formed by reacting $Ar^1Ar^2NC(=O)Cl$ with ethylene glycol, with 3,5-dimethylaniline dicarboxylic acid chloride. The $Ar^1$ and $Ar^2$ groups may independently be any aryl, alkaryl, or hetero analogs thereof. It should be understood that any glycol may be used in place of ethylene glycol such as methylene glycol, dimethylene glycol, polyemthylene glycols (3-6 ethylene units), diethylene glycol, polyethylene glycols (3-6 ethylene units), or higher analogs.

Testing Experiments of the Disclosure

The compounds of this disclosure are designed to bind to integrin expressing cells. Cell adhesion assays are performed according to procedures previously described (Vanderslice, P., D G. Woodside, A. R. Caivano, E. R. Decker, C. L. Munsch, S. J. Sherwood, W. S. Lejeune, Y. J. Miyamoto, B. W. Mcintyre, R. G. Tilton, and R. A. Dixon. Potent in vivo suppression of inflammation by selectively targeting the high affinity conformation of integrin alpha4beta1. Biochem Biophys Res Commun 400:619-624.) Assays to evaluate enhanced cell binding mediated by Dv L and used K562-1 cells binding to CSl-BSA, K562 cells binding to fibronectin, HUVEC binding to vitronectin, HSB cells binding to ICAM-1, and K562-cells binding to MAdCAM-1, respectively. For each assay, the cells expressed the appropriate integrin receptor either in recombinant form (K562-u K562-1) or endogenously (K562-1, HUVEC-v.HSB). 96-well Pro-Bind plates were coated directly with adhesion substrate (fibronectin, vitronectin, CSl-BSA, VCAM-1, ICAM-1 or MAdCAM-1) at 4° C. overnight. The concentration of substrate protein added to the wells was a sub-optimal dose for cell adhesion (~EC10) as previously determined by dose dependent binding curves. Wells were blocked with 1% BSA at room temperature for 2 hours and then washed with binding buffer prior to the addition of cells. Integrin-expressing cells were labeled with calcein-AM (Molecular Probes) for 30 min at 37° C. HUVEC were trypsinized and resuspended in culture media prior to labeling. Cells were resuspended in binding buffer. Compounds were dissolved in DMSO to make a 100 mM stock solution. Serial dilutions were made in DMSO such that the working compound concentrations were at 100×. Compounds were then diluted 1:100 in binding buffer containing the cells to yield the desired working concentrations and a final DMSO concentration of 1%, and 2×105 cells dispensed into each well. The binding buffer was TBS, pH 7.4 with 1 mM MnCl2 for all assays. Following 30 min incubation at 37° C., the wells were washed with the appropriate binding buffer and the number of cells bound was quantitated on a TECAN Ultra384 or SAFIRE2 fluorescent plate reader. EC50 is defined as the concentration of compound required to achieve 50% of the maximal response.

The compounds of this disclosure are expected to have $EC_{50}$ values between less than 0.5 µM and greater the 30 µM, between about 0.5 µM and about 30 µM, between about 1 µM and about 20 µM, between about 5 µM and about 20 µM, or between about 5 µM and about 10 µM. The compounds of this disclosure are expected to have T-cell proliferation values as measured at an absorbance at 570 nm between about 0.200 and about 0.350 with a p value between about 0.01 and about 0.00001, between about 0.20 and about 0.325 with a p value between about 0.001 and about 0.00001, between about 0.200 and about 0.300 with a p value between about 0.01 and about 0.00001, or between about 0.200 and about 0.275 with a p value between about 0.01 and about 0.00001, including all subranges.

Human T cell isolation assays are carried out as follows: De-identified leukocyte enriched buffy coats were purchased from Gulf Coast Regional Blood Center (Houston, TX). The mononuclear cell fraction was enriched over a Ficoll gradient following standard procedures. In brief, cells were diluted 1:1 with PBS, 2% BSA and 25 mL was gently layered on top of 20 ml Ficoll. The gradient was centrifuged at 450 g for 40 min with no brake. The buffy coat was removed, diluted up to 50 mL with PBS, 2% BSA, and centrifuged at 300 g for 10 min with brake and the pellet was resuspended in 10 mL of PBS, 2% BSA. T cells were purified by negative selection using the MACS Pan T cell Isolation Kit (Miltenyi Biotec #130-096-535) as per manufacturer's instructions.

T cell proliferation assays are carried out as follows: in a 96 well plate, anti-CD3 antibody, clone OKT3, was added at 5 ng/well and incubated for 30 min at RT. ICAM-1 was then added at 200 ng/well and incubated overnight at 4° C. Plate was blocked with 0.5% BSA for 2 h at RT. Plate was washed with complete media and 100,000 T cells in 200 µL media containing either DMSO or 1 µM of compound (in DMSO) added to each well such that the final concentration of DMSO was 1% in all wells. The plate was incubated at 37° C. in cell culture incubator for 2 days. MTT (10 µL, Promega) was added and plate incubated for 4 h at 37° C. Following incubation, 100 uL of solubilization/stop solution was added and incubated for an additional 1 h. Absorbance at 570 nm was measured on a Tecan Safire² plate reader.

CLOSING PARAGRAPH

All references cited herein are incorporated by reference. Although the disclosure has been disclosed with reference to its preferred embodiments, from reading this description those of skill in the art may appreciate changes and modification that may be made which do not depart from the scope and spirit of the disclosure as described above and claimed hereafter.

Embodiment 1. An integrin agonist or integrin activating compound comprising one or more compounds of the general Formula (I):

$$Q^2\text{-}R^a\text{—}Z\text{—}R^b\text{-}Q^3 \qquad \text{(I)}$$

wherein:
the $Q^1$ and $Q^2$ groups may independently be an $R^1R^2N$— group, an $R^1R^2NC(=O)$— group, an $R^1R^2NC(=O)N(R^3)$— group, an $R^1R^2NC(=O)O$— group, or an $R^1R^2NSO_2$— group,
the $R^1$ and $R^2$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof, and
the $R^3$ group may be a hydrocarbyl group or a heterohydrocarbyl group;
the $R^a$ and $R^b$ groups may independently be a hydrocarbenyl linking group, wherein one or more carbon atoms may be replaced by oxygen atoms, e.g., an alkyleneoxide linking group such as a methlyeneoxide containing linking group or an ethyleneoxide containing linking group; and
the Z group may be a hydrocarbenyl linking group or a heterohydrocarbenyl linking group and includes one or more protonatable moieties.

Embodiment 2. The composition of Embodiment 1, wherein the integrin agonist or integrin activating compound comprises one or more compounds of the general Formula (XIII):

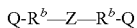 (XIII)

wherein:
the Q groups independently comprise $R^3R^4NC(=O)$—;
the $R^3$ and $R^4$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof;
the $R^a$ groups independently comprise $(OCH_2)_n$ or $(OCH_2CH_2)_n$;
n independently is an integer having a value between 1 and 6;
the Z group is N(R); and
the R group comprises a hydrocarbyl group or a heterohydrocarbyl group.

Embodiment 3. The composition of Embodiment 1, wherein the integrin agonist or integrin activating compound comprises one or more compounds of the general Formula (XIV):

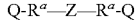 (XIV)

wherein:
the Q groups independently comprise $R^1R^2NC(=O)$—;
the $R^1$ and $R^2$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof;
the $R^a$ groups independently comprise $(OCH_2)_n$ or $(OCH_2CH_2)_n$;
n independently is an integer having a value between 0 and 6; and
the Z group is derived from 2,6-dihydroxypyridine; and.

Embodiment 4. The composition of Embodiment 1, wherein the integrin agonist or integrin activating compound comprises one or more compounds of the general Formula (XV):

 (XV)

wherein:
the Q groups independently comprise $R^1R^2NC(=O)$—,
the $R^1$ and $R^2$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof;
the $R^a$ groups independently comprise $(OCH_2)_n$ or $(OCH_2CH_2)_n$;
n independently is an integer having a value between 0 and 6; and
the Z group is derived 2,6-dimethanolpyridine.

Embodiment 5. The composition of Embodiment 1, wherein the integrin agonist or integrin activating compound comprises one or more compounds of the general Formula (XVI):

 (XVI)

wherein:
the Q groups independently comprise $R^1R^2NC(=O)$—,
the $R^1$ and $R^2$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof;
the $R^a$ groups independently comprise $(OCH_2)_n$ or $(OCH_2CH_2)_n$;
n independently is an integer having a value between 0 and 6; and
the Z group is derived 3,5-dihydroxypyridine.

Embodiment 6. The composition of Embodiment 1, wherein the integrin agonist or integrin activating compound comprises one or more compounds of the general Formula (XVII):

 (XVII)

wherein:
the Q groups independently comprise $R^1R^2NC(=O)$—,
the $R^1$ and $R^2$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof;
the $R^a$ groups independently comprise $(OCH_2)_n$ or $(OCH_2CH_2)_n$;
n independently is an integer having a value between 0 and 6; and
the Z group is derived 3,5-dimethanolpyridine.

Embodiment 7. The composition of Embodiment 1, wherein the integrin agonist or integrin activating compound comprises one or more compounds of the general Formula (XVIII):

 (XVIII)

wherein:
the Q groups independently comprise $R^1R^2NC(=O)-$,
the $R^1$ and $R^2$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof;
the $R^a$ groups independently comprise $(OCH_2)_n$ or $(OCH_2CH_2)_n$; and
n independently is an integer having a value between 0 and 6; and
the Z group is derived dimethyl-3,5-dihydroxyaniline.

Embodiment 8. The composition of Embodiment 1, wherein the integrin agonist or integrin activating compound comprises one or more compounds of the general Formula (XIX):

$$Q-R^a-Z-R^a-Q \quad (XIX)$$

wherein:
the Q groups independently comprise $R^1R^2NC(=O)-$,
the $R^1$ and $R^2$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof;
the $R^a$ groups independently comprise $(OCH_2)_n$ or $(OCH_2CH_2)_n$;
n independently is an integer having a value between 0 and 6; and
the Z group is derived dimethyl-3,5-dihydroxybenzylamine.

Embodiment 9. The composition of Embodiment 1, wherein the integrin agonist or integrin activating compound comprises one or more compounds of the general Formula (XX):

$$Q-R^a-Z-R^a-Q \quad (XX)$$

wherein:
the Q groups independently comprise $R^1R^2NC(=O)-$,
the $R^1$ and $R^2$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof;
the $R^a$ groups independently comprise $(OCH_2)_n$ or $(OCH_2CH_2)_n$
n independently is an integer having a value between 0 and 6; and
the Z group is derived 2,6-pyridine dicarboxylic acid.

Embodiment 10. The composition of Embodiment 1, wherein the integrin agonist or integrin activating compound comprises one or more compounds of the general Formula (XXI):

$$Q-R^a-Z-R^a-Q \quad (XXI)$$

wherein:
the Q groups independently comprise $R^1R^2NC(=O)-$,
the $R^1$ and $R^2$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof;
the $R^a$ groups independently comprise $(OCH_2)_n$ or $(OCH_2CH_2)_n$;
n independently is an integer having a value between 0 and 6
the Z group is derived 3,5-pyridine dicarboxylic acid.

Embodiment 11. The composition of Embodiment 1, wherein the integrin agonist or integrin activating compound comprises one or more compounds of the general Formula (XXIIa&b):

$$Q-R^a-Z-R^a-Q \quad (XXII)$$

wherein:
the Q groups independently comprise $R^1R^2NC(=O)-$,
the $R^1$ and $R^2$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof;
the $R^a$ groups independently comprise $(OCH_2)_n$ or $(OCH_2CH_2)_n$;
n independently is an integer having a value between 0 and 6; and
the Z group is derived 3-dimethylamino-1,5-pentanediol.

Embodiment 12. The composition of Embodiment 1, wherein the integrin agonist or integrin activating compound comprises one or more compounds of the general Formula (XXIII):

$$Q-R^a-Z$$

wherein:
the Q group comprises $R^1R^2NC(=O)-$,
the $R^1$ and $R^2$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof;
the $R^a$ group comprises $(OCH_2)_n$ or $(OCH_2CH_2)_n$;
n is an integer having a value between 2 and 6; and
the Z group comprises derived PEGn-omega-dimethylamine group.

Embodiment 13. A vaccine composition comprising:
an antigen effective amount of an antigen containing composition comprising one or more antigens, and
an agonist effective amount of an integrin agonist composition comprising one or more integrin activating or agonist compounds of the general Formula (XII):

$$Q^1-R^a-Z-R^b-Q^2 \quad (I)$$

wherein:
the $Q^1$ and $Q^2$ groups independently comprise an $R^1R^2N-$ group, an $R^1R^2NC(=O)-$ group, an $R^1R^2NC(=O)N(R^3)-$ group, an $R^1R^2NC(=O)O-$ group, or an $R^1R^2NSO_2-$ group,
the $R^1$ and $R^2$ groups independently comprise a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl groups, a fused heterocyclic ring group, or any combination thereof, and the R³ group may be a hydrocarbyl group or a heterohydrocarbyl group;

the Rᵃ and Rᵇ groups independently comprise a hydrocarbenyl linking group, wherein one or more carbon atoms may be replaced by oxygen atoms; and the Z group comprises a hydrocarbenyl linking group or a heterohydrocarbenyl linking group and at least one protonatable moiety, the integrin agonist composition may be administered before, during, and/or after the administration of the antigen composition, the one or more integrin activating or agonist compounds activate one or more integrins and enhance interactions between the integrins and their ligands, and the integrin agonist composition enhances antigen presentation, B-cells and T-cell interactions, B-cells and T-cell activation, and B-cells and T-cell activity.

Embodiment 14. The composition of Embodiment 13, wherein:

the at least one protonatable moiety is protonated at biological pHs and/or the at least one protonatable moiety is protonated and includes a pharmaceutically acceptable counterion, the integrins include α4β1, α4β7, α5β1, and/or αLβ2, and the ligands include VCAM-1, fibronectin, MAdCAM-1, ICAM-1, and/or ICAM-2.

Embodiment 15. The composition of Embodiment 13, wherein the vaccine composition comprises an anti-cancer vaccine.

Embodiment 16. The composition of Embodiment 13, wherein the integrin agonist composition and/or the antigen composition each further comprise:

a pharmaceutically acceptable carrier, wherein the pharmaceutically acceptable carriers may include one or more adjuvant comprising non-specific adjuvant substances and/or specific adjuvant substances capable of enhancing an immune response to the one or more antigens.

Embodiment 17. A composition comprising:

an effector cell composition including an effector cell effective amount of one or more treated and/or untreated effector cells, and an integrin agonist composition including an agonist effective amount of one or more integrin agonists or activator of the general Formula (XII):

$$Q^1\text{-}R^a\text{—}Z\text{—}R^b\text{-}Q^2 \qquad (I)$$

wherein:

the Q¹ and Q² may independently be an R¹R²N— group, an R¹R²NC(=O)— group, an R¹R²NC(=O)N(R³)— group, an R¹R²NC(=O)O— group, or an R¹R²NSO₂— group, the R¹ and R² groups independently comprise a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl groups, a fused heterocyclic ring group, or any combination thereof, and the R³ group may be a hydrocarbyl group or a heterohydrocarbyl group;

the Rᵃ group may be a hydrocarbenyl linking group, wherein one or more carbon atoms may be replaced by oxygen atoms;

the Rᵇ group may be a hydrocarbenyl linking group, wherein one or more carbon atoms may be replaced by oxygen atoms; and the Z group may be a hydrocarbenyl linking group or a heterohydrocarbenyl linking group and at least one protonatable moiety, the integrin agonists are capable of enhancing integrin-mediated binding of integrins of a cell to their respective ligand, and the integrin agonist composition may be administered before, during, and/or after the administration of the effector cell composition.

Embodiment 18. The composition of Embodiment 17, wherein:

the at least one protonatable moiety is protonated at biological pHs and/or the at least one protonatable moiety is protonated and includes a pharmaceutically acceptable counterion, the integrins include α4β1, α4β7, α5β1, and/or αLβ2, and the ligands include VCAM-1, fibronectin, MAdCAM-1, ICAM-1, and/or ICAM-2.

Embodiment 19. The composition of Embodiment 17, wherein the integrin agonist composition and/or the effector cell composition each further comprise:

a pharmaceutically acceptable carrier, wherein the pharmaceutically acceptable carriers may include one or more adjuvant comprising non-specific adjuvant substances and/or specific adjuvant substances capable of enhancing an immune response to the one or more antigens.

Embodiment 20. A composition comprising:

an antibody composition including an antibody effective amount of one or more therapeutic antibodies, and an integrin agonist composition including an agonist effective amount of one or more integrin agonists or activator of the general Formula (XII):

$$Q\text{-}R^a\text{—}Z\text{—}R^b\text{-}Q^2 \qquad (I)$$

wherein:

the Q¹ and Q² may independently be an R¹R²N— group, an R¹R²NC(=O)— group, an R¹R²NC(=O)N(R³)— group, an R¹R²NC(=O)O— group, or an R¹R²NSO₂— group, the R¹ and R² groups independently comprise a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl groups, a fused heterocyclic ring group, or any combination thereof, and the R³ group may be a hydrocarbyl group or a heterohydrocarbyl group;

the Rᵃ group may be a hydrocarbenyl linking group, wherein one or more carbon atoms may be replaced by oxygen atoms;

the Rᵇ group may be a hydrocarbenyl linking group, wherein one or more carbon atoms may be replaced by oxygen atoms; and the Z group may be a hydrocarbenyl linking group or a heterohydrocarbenyl linking group and at least one protonatable moiety, the integrin agonists are capable of enhancing integrin-mediated binding of integrins of a cell to their respective ligand; and the integrin agonist composition may be administered before, during, and/or after the administration of the antibody composition.

Embodiment 21. The composition of Embodiment 20, wherein:
the Z group may also include one or more moieties that protonate at biological pHs and/or bear a charge in association with an acceptable counterion;
the integrins include α4β1, α4β7, α5β1, and/or αLβ2; and
the ligands include VCAM-1, fibronectin, MAdCAM-1, ICAM-1, and/or ICAM-2.

Embodiment 22. The composition of Embodiment 20, wherein the integrin agonist composition and/or the antibody composition each further comprise:
a pharmaceutically acceptable carrier,
wherein the pharmaceutically acceptable carriers may include one or more adjuvant comprising non-specific adjuvant substances and/or specific adjuvant substances capable of enhancing an immune response to the one or more antigens.

Embodiment 23. A composition comprising:
a checkpoint inhibitor composition including a checkpoint inhibitor effective amount of one or more checkpoint inhibitors, and
an integrin agonist composition including an agonist effective amount of one or more integrin agonists or activator of the general Formula (XII):

$$Q\text{-}R^a\text{---}Z\text{---}R^b\text{-}Q^2 \qquad (I)$$

wherein:
the $Q^1$ and $Q^2$ may independently be an $R^1R^2N$— group, an $R^1R^2NC(=O)$— group, an $R^1R^2NC(=O)N(R^3)$— group, an $R^1R^2NC(=O)O$— group, or an $R^1R^2NSO_2$— group,
the $R^1$ and $R^2$ groups independently comprise a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl groups, a fused heterocyclic ring group, or any combination thereof, and
the $R^3$ group may be a hydrocarbyl group or a heterohydrocarbyl group;
the $R^a$ group may be a hydrocarbenyl linking group, wherein one or more carbon atoms may be replaced by oxygen atoms;
the $R^b$ group may be a hydrocarbenyl linking group, wherein one or more carbon atoms may be replaced by oxygen atoms; and
the Z group may be a hydrocarbenyl linking group or a heterohydrocarbenyl linking group and at least one protonatable moiety,
the integrin agonists are capable of enhancing integrin-mediated binding of integrins of a cell to their respective ligand; and
the integrin agonist composition may be administered before, during, and/or after the administration of the antibody composition.

Embodiment 24. The composition of Embodiment 23, wherein:
the Z group may also include one or more moieties that protonate at biological pHs and/or bear a charge in association with an acceptable counterion;
the integrins include α4β1, α4β7, α5β1, and/or αLβ2; and
the ligands include VCAM-1, fibronectin, MAdCAM-1, ICAM-1, and/or ICAM-2.

Embodiment 25. The composition of Embodiment 23, wherein the integrin agonist composition and/or the checkpoint inhibitor composition each further comprise:
a pharmaceutically acceptable carrier,
wherein the pharmaceutically acceptable carriers may include one or more adjuvant comprising non-specific adjuvant substances and/or specific adjuvant substances capable of enhancing an immune response to the one or more antigens.

Embodiment 26. A composition comprising:
an immuno-therapeutic agent composition including an immuno-therapeutic agent effective amount of one or more immuno-therapeutic agents, and
an integrin agonist composition including an agonist effective amount of one or more integrin agonists or activator of the general Formula (XII):

$$Q\text{-}R^a\text{---}Z\text{---}R^b\text{-}Q^2 \qquad (I)$$

wherein:
the $Q^1$ and $Q^2$ may independently be an $R^1R^2N$— group, an $R^1R^2NC(=O)$— group, an $R^1R^2NC(=O)N(R^3)$— group, an $R^1R^2NC(=O)O$— group, or an $R^1R^2NSO_2$— group,
the $R^1$ and $R^2$ groups independently comprise a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl groups, a fused heterocyclic ring group, or any combination thereof, and
the $R^3$ group may be a hydrocarbyl group or a heterohydrocarbyl group;
the $R^a$ group may be a hydrocarbenyl linking group, wherein one or more carbon atoms may be replaced by oxygen atoms;
the $R^b$ group may be a hydrocarbenyl linking group, wherein one or more carbon atoms may be replaced by oxygen atoms; and
the Z group may be a hydrocarbenyl linking group or a heterohydrocarbenyl linking group and at least one protonatable moiety,
the integrin agonists are capable of enhancing integrin-mediated binding of integrins of a cell to their respective ligand; and
the integrin agonist composition may be administered before, during, and/or after the administration of the antibody composition.

Embodiment 27. The composition of Embodiment 26, wherein:
the Z group may also include one or more moieties that protonate at biological pHs and/or bear a charge in association with an acceptable counterion;
the integrins include α4β1, α4β7, α5β1, and/or αLβ2; and
the ligands include VCAM-1, fibronectin, MAdCAM-1, ICAM-1, and/or ICAM-2.

Embodiment 28. The composition of Embodiment 26, the integrin agonist composition and/or the immuno-therapeutic agent composition each further comprise:
a pharmaceutically acceptable carrier,
wherein the pharmaceutically acceptable carriers may include one or more adjuvant comprising non-specific adjuvant substances and/or specific adjuvant substances capable of enhancing an immune response to the one or more antigens.

Embodiment 29. The composition of any of the preceding Embodiments, wherein the one or more compounds or agonists comprise compounds of the general:

Formula (XIII):

$$Q\text{-}R^b\text{—}Z\text{—}R^b\text{-}Q \quad (XIII)$$

wherein:
the Q groups independently comprise $R^3R^4NC(=O)$—;
the $R^3$ and $R^4$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof;
the $R^a$ groups independently comprise $(OCH_2)_n$ or $(OCH_2CH_2)_n$;
n independently is an integer having a value between 1 and 6;
the Z group is N(R); and
the R group comprises a hydrocarbyl group or a heterohydrocarbyl group, or Formulas (XIIIa):

$$Q\text{-}R^a\text{—}Z\text{—}R^a\text{-}Q \quad (XIIIa)$$

wherein:
the Q group comprise $R^4R^5NC(=O)$—;
the $R^4$ and $R^5$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof;
the $R^aZR^a$ group comprises $(OCH_2CH_2)_nN(Me)(CH_2CH_2O)_n$; and
n is an integer having a value between 1 and 6, or Formula (XIIIb):

$$Q\text{-}(OCH_2CH_2)_nN(Me)(CH_2CH_2O)_n\text{-}Q \quad (XIIIb)$$

wherein:
the Q groups comprise $R^4R^5NC(=O)$—;
the $R^4$ and $R^5$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof; and
n is an integer having a value between 1 and 6.

Embodiment 30. The composition of any of the preceding Embodiments, wherein the one or more compounds or agonists comprise compounds of the general:

Formula (XIV):

$$Q\text{-}R^a\text{—}Z\text{—}R^a\text{-}Q \quad (XIV)$$

wherein:
the Q groups independently comprise $R^1R^2NC(=O)$—;
the $R^1$ and $R^2$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof;
the $R^a$ groups independently comprise $(OCH_2)_n$ or $(OCH_2CH_2)_n$;
n independently is an integer having a value between 0 and 6; and
the Z group is derived from 2,6-dihydroxypyridine, or Formula (XIVa):

$$Q\text{-}R^a\text{—}Z\text{—}R^a\text{-}Q \quad (XIVa)$$

wherein:
the Q group comprise $R^1R^2NC(=O)$—;
the $R^1$ and $R^2$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof; the Z group is derived from 2,6-dihydroxypyridine;
the $R^a$ groups comprise $(OCH_2CH_2)_n$; and
n is an integers having a value between 0 and 6, or Formula (XIVb)

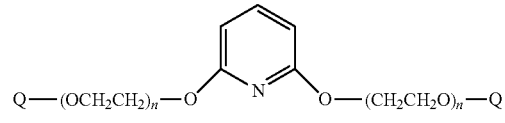

(XIVb)

$$Q\text{—}(OCH_2CH_2)_n\text{—}O\text{—[pyridine]—}O\text{—}(CH_2CH_2O)_n\text{—}Q$$

wherein:
the Q groups comprise $R^2R^3NC(=O)$—,
the $R^2$ and $R^3$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof; and
n is an integer having a value between 0 and 6.

Embodiment 31. The composition of any of the preceding Embodiments, wherein the one or more compounds or agonists comprise compounds of the general:

Formula (XV):

$$Q\text{-}R^a\text{—}Z\text{—}R^a\text{-}Q \quad (XV)$$

wherein:
the Q groups independently comprise $R^1R^2NC(=O)$—,
the $R^1$ and $R^2$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof;
the $R^a$ groups independently comprise $(OCH_2)_n$ or $(OCH_2CH_2)_n$;
n independently is an integer having a value between 0 and 6; and
the Z group is derived 2,6-dimethanolpyridine, or Formula (XVa):

Q-R$^a$—Z—R$^a$-Q  (XVa)

wherein:
the Q groups comprise R$^1$R$^2$NC(=O)—,
the R$^1$ and R$^2$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof;
the Z group is derived 2,6-dimethanolpyridine;
the R$^a$ groups comprise (OCH$_2$CH$_2$)$_n$;
n is an integers having a value between 0 and 6, or Formula (XVb)

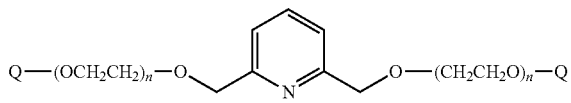

(XVb)

wherein:
the Q groups comprise R$^1$R$^2$NC(=O)—;
the R$^1$ and R$^2$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof; and
n is an integer having a value between 0 and 6.

Embodiment 32. The composition of any of the preceding Embodiments, wherein the one or more compounds or agonists comprise compounds of the general:

Formula (XVI):

Q-R$^a$—Z—R$^a$-Q  (XVI)

wherein:
the Q groups independently comprise R$^1$R$^2$NC(=O)—,
the R$^1$ and R$^2$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof;
the R$^a$ groups independently comprise (OCH$_2$)$_n$ or (OCH$_2$CH$_2$)$_n$;
n independently is an integer having a value between 0 and 6; and
the Z group is derived 3,5-dihydroxypyridine, or Formula (XVIa):

Q-R$^a$—Z—R$^a$-Q  (XVIa)

wherein:
the Q groups comprise R$^1$R$^2$NC(=O)—,
the R$^1$ and R$^2$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof;
the Z group is derived 3,5-dihydroxypyridine;
the R$^a$ groups comprise (OCH$_2$CH$_2$)$_n$;
n is an integers having a value between 0 and 6, or Formula (XVIb)

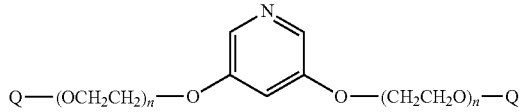

(XVIb)

wherein:
the Q groups comprise R$^1$R$^2$NC(=O)—;
the R$^1$ and R$^2$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof; and
n is an integer having a value between 0 and 6.

Embodiment 33. The composition of any of the preceding Embodiments, wherein the one or more compounds or agonists comprise compounds of the general:

Formula (XVII):

Q-R$^a$—Z—R$^a$-Q  (XVII)

wherein:
the Q groups independently comprise R$^1$R$^2$NC(=O)—,
the R$^1$ and R$^2$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof;
the R$^a$ groups independently comprise (OCH$_2$)$_n$ or (OCH$_2$CH$_2$)$_n$;
n independently is an integer having a value between 0 and 6; and
the Z group is derived 3,5-dimethanolpyridine, or Formula (XVIIa):

Q-R$^a$—Z—R$^a$-Q  (XVIIa)

wherein:
the Q groups comprise R$^1$R$^2$NC(=O)—,
the R$^1$ and R$^2$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof;
the Z group is derived 3,5-dimethanolpyridine;
the R$^a$ groups comprise (OCH$_2$CH$_2$)$_n$;
n is an integers having a value between 0 and 6, or Formula (XVIIb)

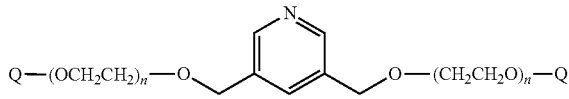
(XVIIb)

wherein:
- the Q groups comprise $R^1R^2NC(=O)-$;
  - the $R^1$ and $R^2$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof; and
- n is an integer having a value between 0 and 6.

Embodiment 34. The composition of any of the preceding Embodiments, wherein the one or more compounds or agonists comprise compounds of the general:

Formula (XVIII):

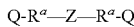
Q-R$^a$—Z—R$^a$-Q (XVIII)

wherein:
- the Q groups independently comprise $R^1R^2NC(=O)-$,
  - the $R^1$ and $R^2$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof;
- the R$^a$ groups independently comprise $(OCH_2)_n$ or $(OCH_2CH_2)_n$; and
  - n independently is an integer having a value between 0 and 6; and
- the Z group is derived 4-dimethylamino-3,5-dihydroxybenzene, or Formula (XVIIIa):

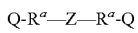
Q-R$^a$—Z—R$^a$-Q (XVIIIa)

wherein:
- the Q groups comprise $R^1R^2NC(=O)-$;
  - the $R^1$ and $R^2$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof;
- the Z group is derived 4-dimethylamino-3,5-dihydroxybenzene;
- the R$^a$ groups comprise $(OCH_2CH_2)_n$; and
- n is an integers having a value between 0 and 6, or Formula (XVIIIb)

(XVIIIb)

wherein:
- the Q groups comprise $R^1R^2NC(=O)-$;
  - the $R^1$ and $R^2$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof; and
- n is an integer having a value between 0 and 6.

Embodiment 35. The composition of any of the preceding Embodiments, wherein the one or more compounds or agonists comprise compounds of the general:

Formula (XIX):

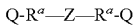
Q-R$^a$—Z—R$^a$-Q (XIX)

wherein:
- the Q groups independently comprise $R^1R^2NC(=O)-$,
  - the $R^1$ and $R^2$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof;
- the R$^a$ groups independently comprise $(OCH_2)_n$ or $(OCH_2CH_2)_n$;
  - n independently is an integer having a value between 0 and 6; and
- the Z group is derived 3,5-dihydroxy-dimethyl benzylamine, or Formula (XIXa):

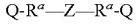
Q-R$^a$—Z—R$^a$-Q (XIXa)

wherein:
- the Q groups comprise $R^1R^2NC(=O)-$,
  - the $R^1$ and $R^2$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof;
- the Z group is derived 3,5-dihydroxy-dimethyl benzylamine;
- the R$^a$ groups comprise $(OCH_2CH_2)_n$;
- n is an integers having a value between 0 and 6, or Formula (XIXb)

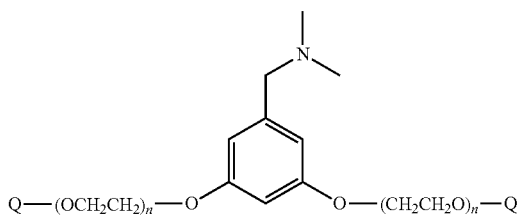
(XIXb)

wherein:
the Q groups comprise $R^1R^2NC(=O)—$;
the $R^1$ and $R^2$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof; and
n is an integer having a value between 0 and 6.

Embodiment 36. The composition of any of the preceding Embodiments, wherein the one or more compounds or agonists comprise compounds of the general:

Formula (XX):

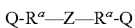 (XX)

wherein:
the Q groups independently comprise $R^1R^2NC(=O)—$,
the $R^1$ and $R^2$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof;
the $R^a$ groups independently comprise $(OCH_2)_n$ or $(OCH_2CH_2)_n$
n independently is an integer having a value between 0 and 6; and
the Z group is derived 2,6-pyridine dicarboxylic acid,
or Formula (XXa):

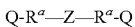 (XXa)

wherein:
the Q groups comprise $R^1R^2NC(=O)—$;
the $R^1$ and $R^2$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof;
the Z group is derived 2,6-pyridine dicarboxylic acid;
the $R^a$ groups comprise $(OCH_2CH_2)_n$; and
n is an integers having a value between 0 and 6,
or Formula (XXb & c)

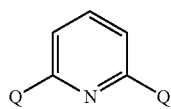
(XXb)

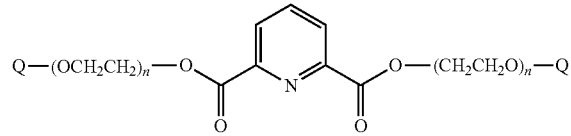
(XXc)

wherein:
the Q groups comprise $R^1R^2NC(=O)—$;
the $R^1$ and $R^2$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof; and
n is an integer having a value between 0 and 6.

Embodiment 37. The composition of any of the preceding Embodiments, wherein the one or more compounds or agonists comprise compounds of the general:

Formula (XXI):

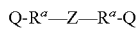 (XXI)

wherein:
the Q groups independently comprise $R^1R^2NC(=O)—$,
the $R^1$ and $R^2$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof;
the $R^a$ groups independently comprise $(OCH_2)_n$ or $(OCH_2CH_2)_n$;
n independently is an integer having a value between 0 and 6
the Z group is derived 3,5pyridine dicarboxylic acid,
or Formula (XXIa):

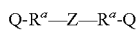 (XXIa)

wherein:
the Q groups comprise $R^1R^2NC(=O)—$,
the $R^1$ and $R^2$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof;
the Z group is derived 3,5pyridine dicarboxylic acid;
the $R^a$ groups comprise $(OCH_2CH_2)_n$;
n is an integers having a value between 0 and 6,
or Formula (XXIb & c)

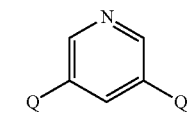
(XXIb)

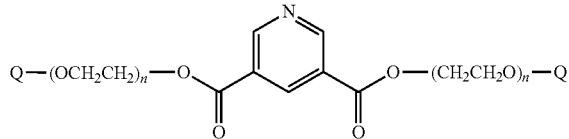
(XXIc)

wherein:
the Q groups comprise R¹R²NC(=O)—;
the R¹ and R² groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof; and
n is an integer having a value between 0 and 6.

Embodiment 38. The composition of any of the preceding Embodiments, wherein the one or more compounds or agonists comprise compounds of the general:

Formula (XXII):

Q-R$^a$—Z—R$^a$-Q     (XXII)

wherein:
the Q groups independently comprise R¹R²NC(=O)—,
the R¹ and R² groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof;
the R$^a$ groups independently comprise (OCH$_2$)$_n$ or (OCH$_2$CH$_2$)$_n$;
n independently is an integer having a value between 0 and 6; and
the Z group is derived 3-dimethylamino-1,5-pentanediol, or Formula (XXIIa):

Q-R$^a$—Z—R$^a$-Q     (XXIIa)

wherein:
the Q groups comprise R¹R²NC(=O)—,
the R¹ and R² groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof; the R$^a$ groups independently comprise (OCH$_2$)$_n$ or (OCH$_2$CH$_2$)$_n$;
n independently is an integer having a value between 0 and 6; and
the Z group is derived 3-dimethylamino-1,5-pentanediol, or

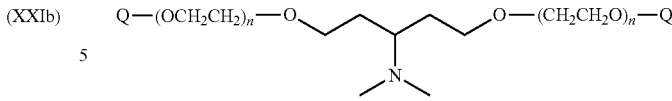
(XXIIb)

wherein:
the Q groups comprise R¹R²NC(=O)—;
the R¹ and R² groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof; and
n is an integer having a value between 0 and 6.

Embodiment 39. The composition of any of the preceding Embodiments, wherein the one or more compounds or agonists comprise compounds of the general:

Formula (XXIII):

Q-R$^a$—Z—R$^a$-Q     (XXIII)

wherein:
the Q groups comprise R¹R²NC(=O)—,
the R¹ and R² groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof;
the Z group is derived PEGn-omega-dimethylamine;
the R$^a$ groups comprise (OCH$_2$CH$_2$)$_n$;
n is an integers having a value between 2 and 6,
or Formula (XXIIIa):

Q-R$^a$—Z—R$^a$-Q     (XXIIIa)

wherein:
the Q groups comprise R¹R²NC(=O)—,
the R¹ and R² groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof;
the Z group is derived PEGn-omega-dimethylamine;
the R$^a$ groups comprise (OCH$_2$CH$_2$)$_n$;
n is an integers having a value between 2 and 6,
or Formula (XXIIIb):

Q-(OCH$_2$CH$_2$)$_n$N(CH$_3$)$_2$     (XXIIIb)

wherein:
the Q groups comprise R¹R²NC(=O)—;
the R¹ and R² groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof; and n is an integer having a value between 2 and 6.

Embodiment 40. The composition of any of the preceding Embodiments, wherein the one or more integrin activating compound or agonist comprises one or more compounds list below:

Class 1: (a) 3-oxo-1-(2-thienyl)-2-(2-thienylmethyl)-4-oxa-2,6-diaza-6-methyl-heptan-7-yl-bis(2-thienylmethyl) carbamate or 3,9-dioxo-1,11-bis(2-thienyl)-2,10-bis(2-thienylmethyl)-4,8-dioxa-2,6,10-triaza-6-methyl-undecane, (b) 3-oxo-1-(2-thienyl)-2-(2-thienylmethyl)-4,6,10-trioxa-2,8-diaza-8-methyl-undecan-11-yl-bis(2-thienylmethyl)carbamate or 3,13-dioxo-1,15-bis(2-thienyl)-2,14-bis(2-thienylmethyl)-4,6,10,12-tetraoxa-2,8,14-triaza-8-methyl-pentadecane, (c) 3-oxo-1-(2-thienyl)-2-(2-thienylmethyl)-4,6,8,12,14-pentaoxa-2,10-diaza-10-methyl-pentadecan-15-yl-bis(2-thienylmethyl)carbamate or 3,17-dioxo-1,19-bis(2-thienyl)-2,18-bis(2-thienylmethyl)-4,6,8,12,14,16-hexaoxa-2,10,18-triaza-10-methyl-nonadecane, (d) 3-oxo-1-(3-methoxyphenyl)-2-(3-methoxybenzyl)-4-oxa-2,6-diaza-6-methyl-heptan-7-yl-bis(3-methoxybenzyl)carbamate or 3,9-dioxo-1,11-bis(3-methoxyphenyl)-2,10-bis(3-methoxybenzyl)-4,8-dioxa-2,6,10-triaza-6-methyl-undecane, (e) 3-oxo-1-(3-methoxyphenyl)-2-(3-methoxybenzyl)-4,6,10-trioxa-2,8-diaza-8-methyl-undecan-11-yl-bis(3-methoxybenzyl)carbamate or 3,13-dioxo-1,15-bis(3-methoxyphenyl)-2,14-bis(3-methoxybenzyl)-4,6,10,12-tetraoxa-2,8,14-triaza-8-methyl-pentadecane, (f) 3-oxo-1-(3-methoxyphenyl)-2-(3-methoxybenzyl)-4,6,8,12,14-pentaoxa-2,10-diaza-10-methyl-pentadecan-15-yl-bis(3-methoxybenzyl) carbamate or 3,17-dioxo-1,19-bis(2-thienyl)-2,18-bis(3-methoxybenzyl)-4,6,8,12,14,16-hexaoxa-2,10,18-triaza-10-methyl-nonadecane, (g) 3-oxo-1-(3-methoxyphenyl)-2-(4-dimethylaminobenzyl)-4-oxa-2,6-diaza-6-methyl-heptan-7-yl-(3-methoxybenzyl)(4-dimethylaminobenzyl)carbamate or 3,9-dioxo-1,11-bis(3-methoxyphenyl)-2,10-bis(3-methoxybenzyl)-4,8-dioxa-2,6,10-triaza-6-methyl-undecane, (h) 3-oxo-1-(3-methoxyphenyl)-2-(4-dimethylaminobenzyl)-4,6,10-trioxa-2,8-diaza-8-methyl-undecan-11-yl-(3-methoxybenzyl)(4-dimethylaminobenzyl)carbamate or 3,13-dioxo-1,15-bis(3-methoxyphenyl)-2,14-bis(3-methoxybenzyl)-4,6,10,12-tetraoxa-2,8,14-triaza-8-methyl-pentadecane, (i) 3-oxo-1-(3-methoxyphenyl)-2-(4-dimethylaminobenzyl)-4,6,8,12,14-pentaoxa-2,10-diaza-10-methyl-pentadecan-15-yl-(3-methoxybenzyl)(4-dimethylaminobenzyl)carbamate or 3,17-dioxo-1,19-bis(2-thienyl)-2,18-bis(3-methoxybenzyl)-4,6,8,12,14,16-hexaoxa-2,10,18-triaza-10-methyl-nonadecane, (j) 3-oxo-1-(4-methoxyphenyl)-2-(4-methoxybenzyl)-4-oxa-2,6-diaza-6-methyl-heptan-7-yl-bis(4-methoxybenzyl)carbamate or 3,9-dioxo-1,11-bis(4-methoxyphenyl)-2,10-bis(4-methoxybenzyl)-4,8-dioxa-2,6,10-triaza-6-methyl-undecane, (k) 3-oxo-1-(4-methoxyphenyl)-2-(4-methoxybenzyl)-4,6,10-trioxa-2,8-diaza-8-methyl-undecan-11-yl-bis(4-methoxybenzyl)carbamate or 3,13-dioxo-1,15-bis(4-methoxyphenyl)-2,14-bis(4-methoxybenzyl)-4,6,10,12-tetraoxa-2,8,14-triaza-8-methyl-pentadecane, (l) 3-oxo-1-(4-methoxyphenyl)-2-(4-methoxybenzyl)-4,6,8,12,14-pentaoxa-2,10-diaza-10-methyl-pentadecan-15-yl-bis(4-methoxybenzyl)carbamate or 3,17-dioxo-1,19-bis(4-methoxyphenyl)-2,18-bis(4-methoxybenzyl)-4,6,8,12,14,16-hexaoxa-2,10,18-triaza-10-methyl-nonadecane, (m) 3-oxo-1-(4-methoxyphenyl)-2-(4-dimethylaminobenzyl)-4-oxa-2,6-diaza-6-methyl-heptan-7-yl-(4-methoxybenzyl)(4-dimethylaminobenzyl)carbamate or 3,9-dioxo-1,11-bis(4-methoxyphenyl)-2,10-bis(4-methoxybenzyl)-4,8-dioxa-2,6,10-triaza-6-methyl-undecane, (n) 3-oxo-1-(4-methoxyphenyl)-2-(4-dimethylaminobenzyl)-4,6,10-trioxa-2,8-diaza-8-methyl-undecan-11-yl-(4-methoxybenzyl)(4-dimethylaminobenzyl)carbamate or 3,13-dioxo-1,15-bis(4-methoxyphenyl)-2,14-bis(4-methoxybenzyl)-4,6,10,12-tetraoxa-2,8,14-triaza-8-methyl-pentadecane, (o) 3-oxo-1-(4-methoxyphenyl)-2-(4-dimethylaminobenzyl)-4,6,8,12,14-pentaoxa-2,10-diaza-10-methyl-pentadecan-15-yl-(4-methoxybenzyl)(4-dimethylaminobenzyl)carbamate or 3,17-dioxo-1,19-bis(2-thienyl)-2,18-bis(4-methoxybenzyl)-4,6,8,12,14,16-hexaoxa-2,10,18-triaza-10-methyl-nonadecane, (p) N-methylbis[(9-carbazolylcarbonyloxy) methyl]amine, (q) N-methylbis{[(9-carbazolylcarbonyloxy) methoxy]methyl}amine, (r) N-methylbis({[(9-carbazolylcarbonyloxy)methoxy]methoxy}methyl)amine, (s) N-methylbis[(3,6-dimethoxy-9-carbazolylcarbonyloxy)methyl] amine, (t) N-methylbis{[(3,6-dimethoxy-9-carbazolylcarbonyloxy)methoxy]methyl}amine, (u) N-methylbis({[(3,6-dimethoxy-9-carbazolylcarbonyloxy)methoxy]methoxy} methyl)amine, (v) higher analogs, or (w) mixtures and combinations thereof.

Embodiment 41. The composition of any of the preceding Embodiments, wherein the one or more integrin activating compound or agonist comprises one or more compounds list below:

Class 2: (a) 3-oxo-1-(2-thienyl)-2-(2-thienylmethyl)-4-oxa-2,7-diaza-7-methyl-nonan-9-yl-bis(2-thienylmethyl) carbamate or 3,11-dioxo-1,13-bis(2-thienyl)-2,11-bis(2-thienylmethyl)-4,10-dioxa-2,6,12-triaza-7-methyl-tridecane, (b) 3-oxo-1-(2-thienyl)-2-(2-thienylmethyl)-4,7,13-trioxa-2,10-diaza-10-methyl-pentadecan-15-yl-bis(2-thienylmethyl)carbamate, (c) 3-oxo-1-(2-thienyl)-2-(2-thienylmethyl)-4,7,10,16,19-pentaoxa-2,13-diaza-13-methyl-heneicosan-21-yl-bis(2-thienylmethyl)carbamate, (d) 3-oxo-1-(3-methoxyphenyl)-2-(3-methoxybenzyl)-4-oxa-2,7-diaza-7-methyl-nonan-9-yl-bis(3-methoxybenzyl)carbamate, (e) 3-oxo-1-(3-methoxyphenyl)-2-(3-methoxybenzyl)-4,7,13-trioxa-2,10-diaza-10-methyl-pentadecan-15-yl-bis(3-methoxybenzyl)carbamate, (f) 3-oxo-1-(3-methoxyphenyl)-2-(3-methoxybenzyl)-4,7,10,16,19-pentaoxa-2,13-diaza-13-methyl-heneicosan-21-yl-bis(3-methoxybenzyl)carbamate, (g) 3-oxo-1-(3-methoxyphenyl)-2-(4-dimethylaminobenzyl)-4-oxa-2,7-diaza-7-methyl-nonan-9-yl-(3-methoxybenzyl)(4-dimethylaminobenzyl)carbamate, (h) 3-oxo-1-(3-methoxyphenyl)-2-(4-dimethylaminobenzyl)-4,7,13-trioxa-2,10-diaza-10-methyl-pentadecan-15-yl-(3-methoxybenzyl)(4-dimethylaminobenzyl)carbamate, (i) 3-oxo-1-(3-methoxyphenyl)-2-(4-dimethylaminobenzyl)-4,7,10,16,19-pentaoxa-2,13-diaza-13-methyl-heneicosan-21-yl-(3-methoxybenzyl)(4-dimethylaminobenzyl)carbamate, (j) 3-oxo-1-(4-methoxyphenyl)-2-(4-methoxybenzyl)-4-oxa-2,7-diaza-7-methyl-nonan-9-yl-bis(4-methoxybenzyl)carbamate, (k) 3-oxo-1-(4-methoxyphenyl)-2-(4-methoxybenzyl)-4,7,13-trioxa-2,10-diaza-10-methyl-pentadecan-15-yl-bis(4-methoxybenzyl)carbamate, (l) 3-oxo-1-(4-methoxyphenyl)-2-(4-methoxybenzyl)-4,7,10,16,19-pentaoxa-2,13-diaza-13-methyl-heneicosan-21-yl-bis(4-methoxybenzyl)carbamate, (m) 3-oxo-1-(4-methoxyphenyl)-2-(4-dimethylaminobenzyl)-4-oxa-2,7-diaza-7-methyl-nonan-9-yl-(4-methoxybenzyl)(4-dimethylaminobenzyl) carbamate, (n) 3-oxo-1-(4-methoxyphenyl)-2-(4-dimethylaminobenzyl)-4,7,13-trioxa-2,10-diaza-10-methyl-pentadecan-15-yl-(4-methoxybenzyl)(4-dimethylaminobenzyl)carbamate, (o) 3-oxo-1-(4-methoxyphenyl)-2-(4-dimethylaminobenzyl)-4,7,10,16,19-pentaoxa-2,13-diaza-13-methyl-heneicosan-21-yl-(4-methoxybenzyl)(4-dimethylaminobenzyl)carbamate, (p) 2-{[2-(9H-carbazol-9-ylcarbonyloxy)ethyl]-N-methylamino}ethyl 9H-carbazole-9-carboxylate, (q) 2-[2-({2-[2-(9H-carbazol-9-ylcarbonyloxy)ethoxy]ethyl}-N-methylamino)ethoxy]ethyl 9H-carbazole-9-carboxylate, (r) 2-(2-

{2-[(2-{2-[2-(9-carbazolylcarbonyloxy)ethoxy]ethoxy}ethyl)-N-methylamino]ethoxy}ethoxy)ethyl 9-carbazolecarboxylate, (s) 2-{[2-(3,6-dimethoxy-9H-carbazol-9-ylcarbonyloxy)ethyl]-N-methylamino}ethyl 3,6-dimethoxy-9H-carbazole-9-carboxylate, (t) 2-[2-({2-[2-(3,6-dimethoxy-9H-carbazol-9-ylcarbonyloxy)ethoxy]ethyl}-N-methylamino)ethoxy]ethyl 3,6-dimethoxy-9H-carbazole-9-carboxylate, (u) 2-(2-{2-[(2-{2-[2-(3,6-dimethoxy-9-carbazolylcarbonyloxy)ethoxy]ethoxy}ethyl)-N-methylamino]ethoxy}ethoxy)ethyl 3,6-dimethoxy-9-carbazolecarboxylate, (v) higher analogs, or (w) mixtures and combinations thereof.

Embodiment 42. The composition of any of the preceding Embodiments, wherein the one or more integrin activating compound or agonist comprises one or more compounds list below:

Class 3: (a) 2-[bis(thenyl)aminocarbonyloxy],6-[bis(thenyl)aminocarbonyloxy]pyridine, (b) 2-[bis(3-methoxybenzyl)aminocarbonyloxy],6-[bis(3-methoxybenzyl)aminocarbonyloxy]pyridine, (c) 2-[(3-methoxybenzyl)(4-dimethylaminobenzyl)aminocarbonyloxy],6-[(3-methoxybenzyl)(4-dimethylaminobenzyl)aminocarbonyloxy]pyridine, (d) 2-[bis(4-methoxybenzyl)aminocarbonyloxy],6-[bis(4-methoxybenzyl)aminocarbonyloxy]pyridine, (e) 2-[(4-methoxybenzyl)(4-dimethylaminobenzyl)aminocarbonyloxy],6-[(4-methoxybenzyl)(4-dimethylaminobenzyl)aminocarbonyloxy]pyridine, (f) 6-(9H-carbazol-9-ylcarbonyloxy)-2-pyridyl 9H-carbazole-9-carboxylate, (g) 6-(3,6-dimethoxy-9H-carbazol-9-ylcarbonyloxy)-2-pyridyl 3,6-dimethoxy-9H-carbazole-9-carboxylate, or (h) mixtures and combinations thereof.

Embodiment 43. The composition of any of the preceding Embodiments, wherein the one or more integrin activating compound or agonist comprises one or more compounds list below:

Class 4: (a) 2-[bis(thenyl)aminocarbonyloxymethoxy],6-[bis(thenyl)amino carbonyloxymethoxy]pyridine, (b) 2-[bis(thenyl)aminocarbonyloxymethoxymethoxy], 6-[bis(thenyl)aminocarbonyloxymethoxymethoxy]pyridine, (c) 2-[bis(3-methoxybenzyl) aminocarbonyloxymethoxy],6-[bis(3-methoxybenzyl)aminocarbonyloxymethoxy]pyridine, (d) 2-[bis(3-methoxybenzyl)aminocarbonyloxymethoxymethoxy],6-[bis(3-methoxybenzyl)amino carbonyloxymethoxyemthyloxy] pyridine, (e) 2-[(3-methoxybenzyl)(4-dimethylaminobenzyl) aminocarbonyloxymethoxy],6-[(3-methoxybenzyl)(4-dimethylaminobenzyl)aminocarbonyloxy methoxy]pyridine, (f) 2-[(3-methoxybenzyl)(4-dimethylaminobenzyl) aminocarbonyloxymethoxy methoxy],6-[(3-methoxybenzyl)(4-dimethylaminobenzyl)aminocarbonyloxy methoxymethoxy]pyridine, (g) 2-[bis(4-methoxybenzyl)aminocarbonyloxymethoxy],6-[bis(4-methoxybenzyl)aminocarbonyloxymethoxy]pyridine, (h) 2-[bis(4-methoxybenzyl)aminocarbonyloxymethoxymethoxy],6-[bis(4-methoxybenzyl) aminocarbonyloxymethoxymethoxy] pyridine, (i) 2-[(4-methoxybenzyl)(4-dimethylaminobenzyl)aminocarbonyloxymethoxy],6-[(4-methoxybenzyl)(4-dimethylaminobenzyl)aminocarbonyloxymethoxy]pyridine, (j) 2-[(4-methoxybenzyl)(4-dimethylaminobenzyl)aminocarbonyloxymethoxymethoxy],6-[(4-methoxybenzyl)(4-dimethylaminobenzyl)aminocarbonyloxymethoxymethoxy]pyridine, (k) 2-{6-[2-(9H-carbazol-9-ylcarbonyloxy)methoxy]-2-pyridyloxy}methyl 9H-carbazole-9-carboxylate, (l) 2-[2-(6-{2-[2-(9-carbazolylcarbonyloxy)methoxy]methoxy}-2-pyridyloxy)methoxy]methyl 9-carbazolecarboxylate, (m) 2-{6-[2-(3,6-dimethoxy-9H-carbazol-9-ylcarbonyloxy)methoxy]-2-pyridyloxy}methyl 3,6-dimethoxy-9H-carbazole-9-carboxylate, (n) 2-[2-(6-{2-[2-(3,6-dimethoxy-9-carbazolylcarbonyloxy)methoxy]methoxy}-2-pyridyloxy)methoxy]methyl 3,6-dimethoxy-9-carbazolecarboxylate, (o) higher analogs, or (p) mixtures and combinations thereof.

Embodiment 44. The composition of any of the preceding Embodiments, wherein the one or more integrin activating compound or agonist comprises one or more compounds list below:

Class 5: (a) 2-[bis(thenyl)aminocarbonyloxyethoxy],6-[bis(thenyl)amino carbonyloxyethoxy]pyridine, (b) 2-[bis(thenyl)aminocarbonyloxyethoxyethoxy], 6-[bis(thenyl)aminocarbonyloxyethoxy ethoxy]pyridine, (c) 2-[bis(3-methoxybenzyl)aminocarbonyloxyethoxy],6-[bis(3-methoxybenzyl)aminocarbonyloxy ethoxy]pyridine, (d) 2-[bis(3-methoxybenzyl)aminocarbonyloxyethoxyethoxy], 6-[bis(3-methoxybenzyl)aminocarbonyloxyethoxyethoxy]pyridine, (e) 2-[(3-methoxybenzyl)(4-dimethylaminobenzyl) aminocarbonyloxyethoxy],6-[(3-methoxybenzyl)(4-dimethylaminobenzyl)aminocarbonyloxyethoxy]pyridine, (f) 2-[(3-methoxybenzyl)(4-dimethylaminobenzyl) aminocarbonyloxyethoxyethoxy],6-[(3-methoxybenzyl)(4-dimethylaminobenzyl)aminocarbonyloxyethoxyethoxy]pyridine, (g) 2-[bis(4-methoxybenzyl) aminocarbonyloxyethoxy],6-[bis(4-methoxybenzyl)aminocarbonyloxyethoxy]pyridine, (h) 2-[bis(4-methoxybenzyl)aminocarbonyloxyethoxyethoxy], 6-[bis(4-methoxybenzyl)aminocarbonyloxyethoxyethoxy]pyridine, (i) 2-[(4-methoxybenzyl)(4-dimethylaminobenzyl)aminocarbonyloxyethoxy],6-[(4-methoxybenzyl)(4-dimethylaminobenzyl)aminocarbonyloxyethoxy]pyridine, (j) 2-[(4-methoxybenzyl)(4-dimethylaminobenzyl)aminocarbonyloxyethoxyethoxy],6-[(4-methoxybenzyl)(4-dimethylaminobenzyl)aminocarbonyloxyethoxyethoxy]pyridine, (k) 2-{6-[2-(9H-carbazol-9-ylcarbonyloxy)ethoxy]-2-pyridyloxy}ethyl 9H-carbazole-9-carboxylate, (l) 2-[2-(6-{2-[2-(9-carbazolylcarbonyloxy) ethoxy]ethoxy}-2-pyridyloxy)ethoxy]ethyl 9-carbazolecarboxylate, (m) 2-{6-[2-(3,6-dimethoxy-9H-carbazol-9-ylcarbonyloxy)ethoxy]-2-pyridyloxy}ethyl 3,6-dimethoxy-9H-carbazole-9-carboxylate, (n) 2-[2-(6-{2-[2-(3,6-dimethoxy-9-carbazolylcarbonyloxy)ethoxy]ethoxy}-2-pyridyloxy)ethoxy]ethyl 3,6-dimethoxy-9-carbazolecarboxylate, (o) higher analogs, or (p) mixtures and combinations thereof.

Embodiment 45. The composition of any of the preceding Embodiments, wherein the one or more integrin activating compound or agonist comprises one or more compounds list below:

Class 6: (a) 2-({bis[(2-thienyl)methyl]aminocarbonyloxy}methyl)-6-({bis[(2-thienyl)methyl]aminocarbonyloxy}methyl)pyridine, (b) 2-({bis(3-methoxybenzyl)aminocarbonyloxy}methyl)-6-({bis(3-methoxybenzyl)aminocarbonyloxy}methyl)pyridine, (c) 2-(3-methoxybenzyl,4-dimethylaminobenzyl)aminocarbonyloxy}methyl)-6-(3-methoxybenzyl,4-dimethylamino benzyl)aminocarbonyloxy}methyl) pyridine, (d) 2-({bis(4-methoxybenzyl) aminocarbonyloxy}methyl)-6-({bis(4-methoxybenzyl) aminocarbonyloxy}methyl)pyridine, (e) 2-(4-methoxybenzyl,4-dimethylaminobenzyl)aminocarbonyloxy}methyl)-6-(4-methoxybenzyl,4-dimethylaminobenzyl) aminocarbonyloxy}methyl) pyridine, (f) {6-[(9H-carbazol-9-ylcarbonyloxy)methyl]-2-pyridyl}methyl 9H-carbazole-9-carboxylate, (g) {6-[(3,6-dimethoxy-9H-carbazol-9-ylcarbonyloxy)methyl]-2-pyridyl}methyl 3,6-dimethoxy-9H-carbazole-9-carboxylate, or (h) mixtures and combinations thereof.

Embodiment 46. The composition of any of the preceding Embodiments, wherein the one or more integrin activating compound or agonist comprises one or more compounds list below:

Class 7: (a) 2-{bis[(2-thienyl)methyl]aminocarbonyloxy}methoxy)methyl]-6-{bis[(2-thienyl)methyl]aminocarbonyloxy}methoxy)methyl]pyridine, (b) 2-{bis[(2-thienyl)methyl]aminocarbonyloxy}methoxymethoxy)methyl]-6-{bis[(2-thienyl)methyl]aminocarbonyloxy}methoxymethoxy)methyl]pyridine, (c) 2-{bis(3-methoxy benzyl)aminocarbonyloxy}methoxy)methyl]-6-{bis(3-methoxybenzyl)aminocarbonyloxy}methoxy)methyl]pyridine, (d) 2-{bis(3-methoxybenzyl)aminocarbonyloxy}methoxymethoxy)methyl]-6-{bis(3-methoxybenzyl)aminocarbonyloxy}methoxymethoxy) methyl]pyridine, (e) 2-(3-methoxybenzyl,4-dimethylaminobenzyl)aminocarbonyloxy}methoxy) methyl]-6-(3-methoxybenzyl,4-dimethylaminobenzyl)aminocarbonyloxy}methoxy)methyl]pyridine, (f) 2-(3-methoxybenzyl,4-dimethylaminobenzyl)aminocarbonyloxy}methoxymethoxy)methyl]-6-(3-methoxybenzyl,4-dimethylaminobenzyl)aminocarbonyloxy}methoxyemthoxy)methyl]pyridine, (g) 2-{bis(4-methoxybenzyl)aminocarbonyloxy}methoxy)methyl]-6-{bis(4-methoxybenzyl) aminocarbonyloxy}methoxy)methyl]pyridine, (h) 2-{bis(4-methoxybenzyl) aminocarbonyloxy}methoxymethoxy)methyl]-6-{bis(4-methoxybenzyl)aminocarbonyloxy}methoxymethoxy)methyl]pyridine, (i) 2-(4-methoxybenzyl,4-dimethylaminobenzyl) aminocarbonyloxy}methoxy)methyl]-6-(4-methoxybenzyl,4-dimethylaminobenzyl)amino carbonyloxy}methoxy)methyl]pyridine, (j) 2-(4-methoxybenzyl,4-dimethylaminobenzyl) amino carbonyloxy}methoxyemthoxy)methyl]-6-(4-methoxybenzyl,4-dimethylaminobenzyl)amino carbonyloxy}methoxymethoxy)methyl]pyridine, (k) 2-[(6-{[2-(9H-carbazol-9-ylcarbonyloxy)methoxy]methyl}-2-pyridyl)methoxy]ethyl 9H-carbazole-9-carboxylate, (l) 2-(2-{[6-({2-[2-(9H-carbazolyl carbonyloxy)methoxy]methoxy}methyl)-2-pyridyl]methoxy}ethoxy)ethyl 9-carbazolecarboxylate, (m) 2-[(6-{[2-(3,6-dimethoxy-9H-carbazol-9-ylcarbonyloxy)methoxy]methyl}-2-pyridyl)methoxy]ethyl 3,6-dimethoxy-9H-carbazole-9-carboxylate, (n) 2-(2-{[6-({2-[2-(3,6-dimethoxy-9H-carbazolylcarbonyloxy)methoxy]methoxy}methyl)-2-pyridyl]methoxy}methoxy)ethyl 3,6-dimethoxy-9-carbazolecarboxylate, (o) higher analogs, or (p) mixtures and combinations thereof.

Embodiment 47. The composition of any of the preceding Embodiments, wherein the one or more integrin activating compound or agonist comprises one or more compounds list below:

Class 8: (a) 2-{bis[(2-thienyl)methyl]aminocarbonyloxy}ethoxy)methyl]-6-{bis[(2-thienyl)methyl] aminocarbonyloxy} ethoxy)methyl]pyridine, (b) 2-{bis[(2-thienyl)methyl]aminocarbonyloxy}ethoxyethoxy)methyl]-6-{bis[(2-thienyl)methyl]aminocarbonyloxy}ethoxyethoxy)methyl]pyridine, (c) 2-{bis(3-methoxybenzyl)aminocarbonyloxy}ethoxy)methyl]-6-{bis(3-methoxybenzyl) amino carbonyloxy}ethoxy)methyl]pyridine, (d) 2-{bis(3-methoxybenzyl)aminocarbonyloxy}ethoxyethoxy)methyl]-6-{bis(3-methoxybenzyl)aminocarbonyloxy}ethoxyethoxy)methyl]pyridine, (e) 2-(3-methoxybenzyl,4-dimethylaminobenzyl)aminocarbonyloxy}ethoxy)methyl]-6-(3-methoxybenzyl,4-dimethylaminobenzyl)aminocarbonyloxy}ethoxy)methyl]pyridine, (f) 2-(3-methoxybenzyl,4-dimethylaminobenzyl)aminocarbonyloxy}ethoxyethoxy)methyl]-6-(3-methoxybenzyl,4-dimethylaminobenzyl)aminocarbonyloxy}ethoxyethoxy)methyl]pyridine, (g) 2-{bis(4-methoxybenzyl)aminocarbonyloxy}ethoxy)methyl]-6-{bis (4-methoxybenzyl) aminocarbonyloxy}ethoxy)methyl]pyridine, (h) 2-{bis(4-methoxybenzyl)aminocarbonyloxy}ethoxyethoxy)methyl]-6-{bis(4-methoxybenzyl) aminocarbonyloxy}ethoxyethoxy)methyl]pyridine, (i) 2-(4-methoxybenzyl,4-dimethylaminobenzyl)aminocarbonyloxy}ethoxy)methyl]-6-(4-methoxybenzyl,4-dimethylaminobenzyl)aminocarbonyloxy}ethoxy)methyl]pyridine, (j) 2-(4-methoxybenzyl,4-dimethylaminobenzyl)aminocarbonyloxy}ethoxyethoxy)methyl]-6-(4-methoxybenzyl,4-dimethylaminobenzyl)aminocarbonyloxy}ethoxyethoxy)methyl]pyridine, (k) 2-[(6-{[2-(9H-carbazol-9-ylcarbonyloxy)ethoxy]methyl}-2-pyridyl)methoxy]ethyl 9H-carbazole-9-carboxylate, (l) 2-(2-{[6-({2-[2-(9H-carbazolylcarbonyloxy)ethoxy]ethoxy}methyl)-2-pyridyl]methoxy}ethoxy)ethyl 9-carbazolecarboxylate, (m) 2-[(6-{[2-(3,6-dimethoxy-9H-carbazol-9-ylcarbonyloxy)ethoxy]methyl}-2-pyridyl)methoxy]ethyl 3,6-dimethoxy-9H-carbazole-9-carboxylate, (n) 2-(2-{[6-({2-[2-(3,6-dimethoxy-9H-carbazolyl carbonyloxy)ethoxy]ethoxy}methyl)-2-pyridyl]methoxy}ethoxy)ethyl 3,6-dimethoxy-9-carbazolecarboxylate, (o) higher analogs, or (p) mixtures and combinations thereof.

Embodiment 48. The composition of any of the preceding Embodiments, wherein the one or more integrin activating compound or agonist comprises one or more compounds list below:

Class 9: (a) 3-[bis(thenyl)aminocarbonyloxy],5-[bis(thenyl)aminocarbonyloxy]pyridine, (b) 3-[bis(3-methoxybenzyl)aminocarbonyloxy],5-[bis(3-methoxybenzyl)aminocarbonyloxy]pyridine, (c) 3-[(3-methoxybenzyl)(4-dimethylaminobenzyl)aminocarbonyloxy],5-[(3-methoxybenzyl)(4-dimethylaminobenzyl)aminocarbonyloxy]pyridine, (d) 3-[bis(4-methoxybenzyl)aminocarbonyloxy],5-[bis(4-methoxybenzyl)aminocarbonyloxy]pyridine, (e) 3-[(4-methoxybenzyl)(4-dimethylaminobenzyl)aminocarbonyloxy],5-[(4-methoxybenzyl)(4-dimethylaminobenzyl)aminocarbonyloxy]pyridine, (f) 5-(9H-carbazol-9-ylcarbonyloxy)-3-pyridyl 9H-carbazole-9-carboxylate, (g) 5-(3,6-dimethoxy-9H-carbazol-9-ylcarbonyloxy)-3-pyridyl 3,6-dimethoxy-9H-carbazole-9-carboxylate, or (h) mixtures and combinations thereof.

Embodiment 49. The composition of any of the preceding Embodiments, wherein the one or more integrin activating compound or agonist comprises one or more compounds list below:

Class 10: (a) 3-[bis(thenyl)aminocarbonyloxymethoxy],5-[bis(thenyl)amino carbonyloxymethoxy]pyridine, (b) 3-[bis(thenyl)aminocarbonyloxymethyoxymethoxy], 5-[bis(thenyl)aminocarbonyloxymethoxymethoxy]pyridine, (c) 3-[bis(3-methoxybenzyl)aminocarbonyloxymethoxy],5-[bis(3-methoxybenzyl)aminocarbonyloxy methoxy]pyridine, (d) 3-[bis(3-methoxybenzyl)aminocarbonyloxymethoxymethoxy],5-[bis(3-methoxybenzyl)aminocarbonyloxymethoxymethoxy]pyridine, (e) 3-[(3-methoxybenzyl)(4-dimethylaminobenzyl)aminocarbonyloxymethoxy],5-[(3-methoxybenzyl)(4-dimethylaminobenzyl)aminocarbonyloxymethoxy]pyridine, (f) 3-[(4-methoxybenzyl)(4-dimethylaminobenzyl)aminocarbonyloxymethoxymethoxy],5-[(4-methoxybenzyl)(4-dimethylaminobenzyl)aminocarbonyloxymethoxymethoxy]pyridine, (g) 3-[bis(4-methoxybenzyl)aminocarbonyloxymethoxy],5-[bis(4-methoxybenzyl)aminocarbonyloxy methoxy]pyridine, (h) 3-[bis(3-methoxybenzyl)aminocarbonyloxymethoxymethoxy],5-[bis(3-methoxybenzyl)aminocarbonyloxymethoxymethoxy] pyridine, (i) 3-[(4-methoxybenzyl)(4-dimethylaminobenzyl) aminocarbonyloxymethoxy],5-[(4-methoxybenzyl)(4-dimethylaminobenzyl)aminocarbonyloxymethoxy]pyridine, (j) 3-[(4-methoxybenzyl)(4-dimethylaminobenzyl)aminocarbonyloxymethoxymethoxy],5-[(4-methoxybenzyl)(4-dimethylaminobenzyl)aminocarbonyloxymethoxymethoxy] pyridine, (k) 2-{5-[2-(9H-carbazol-9-ylcarbonyloxy)

methoxy]-3-pyridyloxy}ethyl 9H-carbazole-9-carboxylate, (l) 2-[2-(5-{2-[2-(9-carbazolylcarbonyloxy)methoxy]methoxy}-3-pyridyloxy)ethoxy]ethyl 9-carbazolecarboxylate, (m) 2-{5-[2-(3,6-dimethoxy-9H-carbazol-9-ylcarbonyloxy)methoxy]-3-pyridyloxy}ethyl 3,6-dimethoxy-9H-carbazole-9-carboxylate, (n) 2-[2-(5-{2-[2-(3,6-dimethoxy-9H-carbazolylcarbonyloxy)methoxy]methoxy}-3-pyridyloxy)ethoxy]ethyl 3,6-dimethoxy-9-carbazolecarboxylate, (o) higher analogs, or (p) mixtures and combinations thereof.

Embodiment 50. The composition of any of the preceding Embodiments, wherein the one or more integrin activating compound or agonist comprises one or more compounds list below:

Class 11: (a) 3-[bis(thenyl)aminocarbonyloxyethoxy],5-[bis(thenyl)aminocarbonyloxy ethoxy]pyridine, (b) 3-[bis(thenyl)aminocarbonyloxyethyoxyethoxy],5-[bis(thenyl)aminocarbonyloxyethyoxyethoxy]pyridine, (c) 3-[bis(3-methoxybenzyl)amino carbonyloxyethoxy],5-[bis(3-methoxybenzyl)aminocarbonyloxyethoxy]pyridine, (d) 3-[bis(3-methoxybenzyl)aminocarbonyloxyethoxyethoxy],5-[bis(3-methoxybenzyl)aminocarbonyloxy ethoxyethoxy]pyridine, (e) 3-[(3-methoxybenzyl)(4-dimethylaminobenzyl)aminocarbonyloxy],5-[(3-methoxybenzyl)(4-dimethylaminobenzyl)aminocarbonyloxy]pyridine, (f) 3-[(3-methoxybenzyl)(4-dimethylaminobenzyl)aminocarbonyloxyethoxy],5-[(3-methoxybenzyl)(4-dimethylaminobenzyl)aminocarbonyloxyethoxy]pyridine, (g) 3-[(4-methoxybenzyl)(4-dimethylaminobenzyl)aminocarbonyloxyethoxyethoxy],5-[(4-methoxybenzyl)(4-dimethylaminobenzyl)aminocarbonyloxyethoxyethoxy]pyridine, (h) 3-[bis(4-methoxybenzyl)aminocarbonyloxyethoxy],5-[bis(4-methoxybenzyl)amino carbonyloxyethoxy]pyridine, (i) 3-[bis(3-methoxybenzyl)aminocarbonyloxy ethoxyethoxy],5-[bis(3-methoxybenzyl)aminocarbonyloxyethoxyethoxy]pyridine, (j) 3-[(4-methoxybenzyl)(4-dimethylaminobenzyl)aminocarbonyloxyethoxy],5-[(4-methoxybenzyl)(4-dimethylaminobenzyl)aminocarbonyloxyethoxy]pyridine, (k) 3-[(4-methoxybenzyl)(4-dimethylaminobenzyl)aminocarbonyloxyethoxyethoxy],5-[(4-methoxybenzyl)(4-dimethylaminobenzyl)aminocarbonyloxyethoxyethoxy]pyridine, (l) 2-{5-[2-(9H-carbazol-9-ylcarbonyloxy)ethoxy]-3-pyridyloxy}ethyl 9H-carbazole-9-carboxylate, (m) 2-[2-(5-{2-[2-(9-carbazolylcarbonyloxy)ethoxy]ethoxy}-3-pyridyloxy)ethoxy]ethyl 9-carbazolecarboxylate, (n) 2-{5-[2-(3,6-dimethoxy-9H-carbazol-9-ylcarbonyloxy)ethoxy]-3-pyridyloxy}ethyl 3,6-dimethoxy-9H-carbazole-9-carboxylate, (o) 2-[2-(5-{2-[2-(3,6-dimethoxy-9H-carbazolylcarbonyloxy)ethoxy]ethoxy}-3-pyridyloxy)ethoxy]ethyl 3,6-dimethoxy-9-carbazolecarboxylate, (p) higher analogs, or (q) mixtures and combinations thereof.

Embodiment 51. The composition of any of the preceding Embodiments, wherein the one or more integrin activating compound or agonist comprises one or more compounds list below:

Class 12: (a) 3-({bis[(2-thienyl)methyl]aminocarbonyloxy}methyl)-5-({bis[(2-thienyl)methyl]aminocarbonyloxy}methyl)pyridine, (b) 3-({bis(3-methoxybenzyl)aminocarbonyloxy}methyl)-5-({bis(3-methoxybenzyl)aminocarbonyloxy}methyl)pyridine, (c) 3-(3-methoxybenzyl,4-dimethyl aminobenzyl)aminocarbonyloxy}methyl)-5-(3-methoxybenzyl,4-dimethylaminobenzyl) aminocarbonyloxy}methyl)pyridine, (d) 3-({bis(4-methoxybenzyl)aminocarbonyloxy}methyl)-5-({bis(4-methoxybenzyl)aminocarbonyloxy}methyl)pyridine, (e) 3-(4-methoxybenzyl,4-dimethylaminobenzyl)aminocarbonyloxy}methyl)-5-(4-methoxybenzyl,4-dimethylaminobenzyl) aminocarbonyloxy}methyl)pyridine, (f) {5-[(9H-carbazol-9-ylcarbonyloxy)methyl]-3-pyridyl}methyl 9H-carbazole-9-carboxylate, (g) {5-[(3,6-dimethoxy-9H-carbazol-9-ylcarbonyloxy)methyl]-3-pyridyl}methyl 3,6-dimethoxy-9H-carbazole-9-carboxylate, or (h) mixtures and combinations thereof.

Embodiment 52. The composition of any of the preceding Embodiments, wherein the one or more integrin activating compound or agonist comprises one or more compounds list below:

Class 13: (a) 3-{bis[(2-thienyl)methyl]aminocarbonyloxy} methoxy)methyl]-5-{bis[(2-thienyl)methyl]aminocarbonyloxy}methoxy)methyl]pyridine, (b) 3-{bis[(2-thienyl)methyl]aminocarbonyloxy}methoxymethoxy)methyl]-5-{bis[(2-thienyl)methyl]aminocarbonyloxy}methoxymethoxy)methyl]pyridine, (c) 3-{bis(3-methoxybenzyl)amino carbonyloxy}methoxy)methyl]-5-{bis(3-methoxybenzyl)aminocarbonyloxy}methoxy) methyl]pyridine, (d) 3-{bis(3-methoxybenzyl)aminocarbonyloxy}methoxymethoxy)methyl]-5-{bis(3-methoxybenzyl)aminocarbonyloxy}methoxymethoxy)methyl]pyridine, (e) 3-(3-methoxybenzyl,4-dimethylaminobenzyl)aminocarbonyloxy}methoxy)methyl]-5-(3-methoxybenzyl,4-dimethylaminobenzyl)aminocarbonyloxy}methoxy)methyl]pyridine, (f) 3-(3-methoxybenzyl,4-dimethylaminobenzyl)aminocarbonyloxy}methoxymethoxy)methyl]-5-(3-methoxybenzyl,4-dimethylaminobenzyl)aminocarbonyloxy}methoxymethoxy)methyl]pyridine, (g) 3-{bis(4-methoxybenzyl)aminocarbonyloxy}methoxy)methyl]-5-{bis(4-methoxybenzyl) aminocarbonyloxy}methoxy)methyl]pyridine, (h) 3-{bis(4-methoxybenzyl)aminocarbonyloxy}methoxyethoxy)methyl]-5-{bis(4-methoxybenzyl)aminocarbonyloxy}methoxymethoxy) methyl]pyridine, (i) 3-(4-methoxybenzyl,4-dimethylaminobenzyl)aminocarbonyloxy}methoxy)methyl]-5-(4-methoxybenzyl,4-dimethylaminobenzyl)aminocarbonyloxy}methoxy) methyl]pyridine, (j) 3-(4-methoxybenzyl,4-dimethylaminobenzyl)aminocarbonyloxy} methoxymethoxy)methyl]-5-(4-methoxybenzyl,4-dimethylaminobenzyl)aminocarbonyloxy}methoxymethoxy)methyl] pyridine, (k) 2-[(5-{[2-(9H-carbazol-9-ylcarbonyloxy)methoxy]methyl}-3-pyridyl)methoxy]ethyl 9H-carbazole-9-carboxylate, (l) 2-(2-{[5-({2-[2-(9-carbazolylcarbonyloxy)methoxy]methoxy}methyl)-3-pyridyl]methoxy}ethoxy) ethyl 9-carbazolecarboxylate, (m) 2-[(5-{[2-(3,6-dimethoxy-9H-carbazol-9-ylcarbonyloxy)methoxy]methyl}-3-pyridyl)methoxy]ethyl 3,6-dimethoxy-9H-carbazole-9-carboxylate, (n) 2-(2-{[5-({2-[2-(3,6-dimethoxy-9-carbazolylcarbonyloxy)methoxy]methoxy}methyl)-3-pyridyl]methoxy}ethoxy)ethyl 3,6-dimethoxy-9-carbazolecarboxylate, (o) higher analogs, or (p) mixtures and combinations thereof.

Embodiment 53. The composition of any of the preceding Embodiments, wherein the one or more integrin activating compound or agonist comprises one or more compounds list below:

Class 14: (a) 3-{bis[(2-thienyl)methyl]aminocarbonyloxy}ethoxy)methyl]-5-{bis[(2-thienyl)methyl]aminocarbonyloxy}ethoxy)methyl]pyridine, (b) 3-{bis[(2-thienyl)methyl]aminocarbonyloxy}ethoxymethoxy)methyl]-5-{bis[(2-thienyl)methyl]aminocarbonyloxy}ethoxyethoxy)methyl]pyridine, (c) 3-{bis(3-methoxybenzyl)aminocarbonyloxy}ethoxy)methyl]-5-{bis(3-methoxybenzyl)aminocarbonyloxy}ethoxy)methyl]pyridine, (d) 3-{bis(3-methoxybenzyl) aminocarbonyloxy}ethoxyethoxy) methyl]-5-{bis(3-methoxybenzyl)aminocarbonyloxy}ethoxyethoxy)methyl]pyridine, (e) 3-(3-methoxybenzyl,4-dimethylaminobenzyl) aminocarbonyloxy}ethoxy)methyl]-5-

(3-methoxybenzyl,4-dimethylaminobenzyl)aminocarbonyloxy}ethoxy)methyl]pyridine, (f) 3-(3-methoxybenzyl,4-dimethylaminobenzyl)aminocarbonyloxy}ethoxymethoxy)methyl]-5-(3-methoxybenzyl,4-dimethylaminobenzyl)aminocarbonyloxy}ethoxyethoxy)methyl]pyridine, (g) 3-{bis(4-methoxybenzyl)aminocarbonyloxy}ethoxy)methyl]-5-{bis(4-methoxybenzyl)aminocarbonyloxy}ethoxy)methyl]pyridine, (h) 3-{bis(4-methoxybenzyl)aminocarbonyloxy}ethoxyethoxy)methyl]-5-{bis(4-methoxybenzyl)aminocarbonyloxy}ethoxyethoxy)methyl]pyridine, (i) 3-(4-methoxybenzyl,4-dimethylaminobenzyl)aminocarbonyloxy}ethoxy)methyl]-5-(4-methoxybenzyl,4-dimethylaminobenzyl)aminocarbonyloxy}ethoxy)methyl]pyridine, (j) 3-(4-methoxybenzyl,4-dimethylaminobenzyl)aminocarbonyloxy}ethoxyethoxy)methyl]-5-(4-methoxybenzyl,4-dimethylaminobenzyl)aminocarbonyloxy}ethoxyethoxy)methyl]pyridine, (k) 2-[(5-{[2-(9H-carbazol-9-ylcarbonyloxy)ethoxy]methyl}-3-pyridyl)methoxy]ethyl 9H-carbazole-9-carboxylate, (l) 2-(2-{[5-({2-[2-(9-carbazolylcarbonyloxy)ethoxy]ethoxy}methyl)-3-pyridyl]methoxy}ethoxy)ethyl 9-carbazolecarboxylate, (m) 2-[(5-{[2-(3,6-dimethoxy-9H-carbazol-9-ylcarbonyloxy)ethoxy]methyl}-3-pyridyl)methoxy]ethyl 3,6-dimethoxy-9H-carbazole-9-carboxylate, (n) 2-(2-{[5-({2-[2-(3,6-dimethoxy-9-carbazolylcarbonyloxy)ethoxy]ethoxy}methyl)-3-pyridyl]methoxy}ethoxy)ethyl 3,6-dimethoxy-9-carbazolecarboxylate, (o) higher analogs, or (p) mixtures and combinations thereof.

Embodiment 54. The composition of any of the preceding Embodiments, wherein the one or more integrin activating compound or agonist comprises one or more compounds list below:

Class 15: (a) 3-[bis(thenyl)aminocarbonyloxy],5-[bis(thenyl)aminocarbonyloxy]dimethylaminobenzene, (b) 3-[bis(3-methoxybenzyl)aminocarbonyloxy],5-[bis(3-methoxybenzyl)aminocarbonyloxy] dimethylaminobenzene, (c) 3-[(3-methoxybenzyl)(4-dimethylaminobenzyl)aminocarbonyloxy],5-[(3-methoxybenzyl)(4-dimethylaminobenzyl)aminocarbonyloxy]dimethylamino benzene, (d) 3-[bis(4-methoxybenzyl)aminocarbonyloxy],5-[bis(4-methoxybenzyl)aminocarbonyloxy]dimethylamino benzene, (e) 3-[(4-methoxybenzyl)(4-dimethylaminobenzyl)aminocarbonyloxy],5-[(4-methoxybenzyl)(4-dimethylaminobenzyl)aminocarbonyloxy]dimethylamino benzene, (f) 3-(9H-carbazol-9-ylcarbonyloxy)-5-(dimethylamino)phenyl 9H-carbazole-9-carboxylate, (g) 3-(3,6-dimethoxy-9H-carbazol-9-ylcarbonyloxy)-5-(dimethylamino)phenyl 3,6-dimethoxy-9H-carbazole-9-carboxylate, or (h) mixtures and combinations thereof.

Embodiment 55. The composition of any of the preceding Embodiments, wherein the one or more integrin activating compound or agonist comprises one or more compounds list below:

Class 16: (a) 3-[bis(thenyl)aminocarbonyloxymethoxy],5-[bis(thenyl)aminocarbonyloxymethoxy]dimethylaminobenzene, (b) 3-[bis(thenyl)aminocarbonyloxymethoxymethoxy], 5-[bis(thenyl)aminocarbonyloxymethoxymethoxy]dimethylaminobenzene, (c) 3-[bis(3-methoxybenzyl)aminocarbonyloxymethoxy],5-[bis(3-methoxybenzyl)aminocarbonyloxy methoxy]dimethylaminobenzene, (d) 3-[bis(3-methoxybenzyl)aminocarbonyloxy methoxymethoxy],5-[bis(3-methoxybenzyl)aminocarbonyloxymethoxymethoxy]dimethylaminobenzene, (e) 3-[(3-methoxybenzyl)(4-dimethylaminobenzyl)amino carbonyloxymethoxy],5-[(3-methoxybenzyl)(4-dimethylaminobenzyl)aminocarbonyloxy methoxy]dimethylaminobenzene, (f) 3-[(3-methoxybenzyl)(4-dimethylaminobenzyl) aminocarbonyloxymethoxymethoxy],5-[(3-methoxybenzyl)(4-dimethylaminobenzyl)amino carbonyloxymethoxymethoxy]dimethylaminobenzene, (g) 3-[bis(4-methoxybenzyl)aminocarbonyloxymethoxy],5-[bis(4-methoxybenzyl)amino carbonyloxymethoxy]dimethylaminobenzene, (h) 3-[bis(4-methoxybenzyl)aminocarbonyloxy methoxymethoxy],5-[bis(4-methoxybenzyl)aminocarbonyloxymethoxymethoxy]dimethylaminobenzene, (i) 3-[(4-methoxybenzyl)(4-dimethylaminobenzyl)aminocarbonyloxy methoxy],5-[(4-methoxybenzyl)(4-dimethylaminobenzyl)aminocarbonyloxymethoxy]dimethylaminobenzene, (j) 3-[(4-methoxybenzyl)(4-dimethylaminobenzyl)amino carbonyloxymethoxymethoxy],5-[(4-methoxybenzyl)(4-dimethylaminobenzyl)aminocarbonyloxy methoxymethoxy]dimethylaminobenzene, (k) 2-{3-[2-(9H-carbazol-9-ylcarbonyloxy)methoxy]-5-(dimethylamino)phenoxy}methyl 9H-carbazole-9-carboxylate, (l) 2-[2-(3-{2-[2-(9-carbazolylcarbonyloxy)methoxy]methoxy}-5-(dimethylamino)phenoxy)methoxy]ethyl 9-carbazolecarboxylate, (m) 2-{3-[2-(3,6-dimethoxy-9H-carbazol-9-ylcarbonyloxy)methoxy]-5-(dimethylamino)phenoxy}ethyl 3,6-dimethoxy-9H-carbazole-9-carboxylate, (n) 2-[2-(3-{2-[2-(3,6-dimethoxy-9-carbazolylcarbonyloxy)methoxy]methoxy}-5-(dimethylamino)phenoxy)methoxy]methyl 3,6-dimethoxy-9-carbazolecarboxylate, (o) higher analogs, or (p) mixtures and combinations thereof.

Embodiment 56. The composition of any of the preceding Embodiments, wherein the one or more integrin activating compound or agonist comprises one or more compounds list below:

Class 17: (a) 3-[bis(thenyl)aminocarbonyloxyethoxy],5-[bis(thenyl)aminocarbonyloxy ethoxy] dimethylaminobenzene, (b) 3-[bis(thenyl)aminocarbonyloxy ethoxyethoxy],5-[bis(thenyl)aminocarbonyloxyethoxyethoxy]dimethylaminobenzene, (c) 3-[bis(3-methoxybenzyl) aminocarbonyloxyethoxy],5-[bis(3-methoxybenzyl)aminocarbonyloxyethoxy]dimethylaminobenzene, (d) 3-[bis(3-methoxybenzyl)aminocarbonyloxyethoxyethoxy],5-[bis(3-methoxybenzyl)aminocarbonyloxyethoxyethoxy]dimethylaminobenzene, (e) 3-[(3-methoxybenzyl)(4-dimethylaminobenzyl)aminocarbonyloxyethoxy],5-[(3-methoxybenzyl)(4-dimethylaminobenzyl)aminocarbonyloxyethoxy] dimethylaminobenzene, (f) 3-[(3-methoxybenzyl)(4-dimethylaminobenzyl)aminocarbonyloxyethoxyethoxy],5-[(3-methoxybenzyl)(4-dimethylaminobenzyl)aminocarbonyloxyethoxyethoxy] dimethylaminobenzene, (g) 3-[bis(4-methoxybenzyl)aminocarbonyloxyethoxy],5-[bis(4-methoxybenzyl)aminocarbonyloxyethoxy]dimethylaminobenzene, (h) 3-[bis(4-methoxybenzyl)aminocarbonyloxyethoxyethoxy],5-[bis(4-methoxybenzyl)aminocarbonyloxy ethoxyethoxy]dimethylaminobenzene, (i) 3-[(4-methoxybenzyl)(4-dimethylaminobenzyl)aminocarbonyloxyethoxy],5-[(4-methoxybenzyl)(4-dimethylaminobenzyl)aminocarbonyloxyethoxy]dimethylaminobenzene, (j) 3-[(4-methoxybenzyl)(4-dimethylaminobenzyl)aminocarbonyloxyethoxyethoxy],5-[(4-methoxybenzyl)(4-dimethylaminobenzyl)aminocarbonyloxyethoxyethoxy] dimethylaminobenzene, (k) 2-{3-[2-(9H-carbazol-9-ylcarbonyloxy)ethoxy]-5-(dimethylamino)phenoxy}ethyl 9H-carbazole-9-carboxylate, (l) 2-[2-(3-{2-[2-(9-carbazolylcarbonyloxy)ethoxy]ethoxy}-5-(dimethylamino)phenoxy)ethoxy]ethyl 9-carbazolecarboxylate, (m) 2-{3-[2-(3,6-dimethoxy-9H-carbazol-9-ylcarbonyloxy)ethoxy]-5-(dimethylamino)phenoxy}ethyl 3,6-dimethoxy-9H-carbazole-9-carboxylate, (n) 2-[2-(3-{2-[2-(3,6-dimethoxy-9-carbazolylcarbonyloxy)ethoxy]ethoxy}-5-(dimethylamino)phenoxy)ethoxy]ethyl 3,6-dimethoxy-9-carbazolecarboxylate, (o) higher analogs, or (p) mixtures and combinations thereof.

Embodiment 57. The composition of any of the preceding Embodiments, wherein the one or more integrin activating compound or agonist comprises one or more compounds list below:

Class 18: (a) 3-[bis(thenyl)aminocarbonyloxy],5-[bis(thenyl)aminocarbonyloxy]dimethylamino benzylamine, (b) 3-[bis(3-methoxybenzyl)aminocarbonyloxy],5-[bis(3-methoxybenzyl)aminocarbonyloxy]dimethylamino benzylamine, (c) 3-[(3-methoxybenzyl)(4-dimethylaminobenzyl)aminocarbonyloxy],5-[(3-methoxybenzyl)(4-dimethylaminobenzyl)amino carbonyloxy]dimethylamino benzylamine, (d) 3-[bis(4-methoxybenzyl)aminocarbonyloxy],5-[bis(4-methoxybenzyl)aminocarbonyloxy]dimethylaminobenzylamine, (e) 3-[(4-methoxybenzyl)(4-dimethylaminobenzyl) aminocarbonyloxy],5-[(4-methoxybenzyl)(4-dimethylaminobenzyl)aminocarbonyloxy] dimethylaminobenzylamine, (f) 3-(9H-carbazol-9-ylcarbonyloxy)-5-[(methylamino)methyl]phenyl 9H-carbazole-9-carboxylate, (g) 3-(3,6-dimethoxy-9H-carbazol-9-ylcarbonyloxy)-5-[(dimethylamino)methyl]phenyl 3,6-dimethoxy-9H-carbazole-9-carboxylate, or (h) mixtures and combinations thereof.

Embodiment 58. The composition of any of the preceding Embodiments, wherein the one or more integrin activating compound or agonist comprises one or more compounds list below:

Class 19: (a) 3-[bis(thenyl)aminocarbonyloxymethoxy],5-[bis(thenyl)aminocarbonyloxy methoxy]dimethylaminobenzylamine, (b) 3-[bis(thenyl)aminocarbonyloxymethoxymethoxy], 5-[bis(thenyl)aminocarbonyloxymethoxymethoxy]dimethylaminobenzylamine, (c) 3-[bis(3-methoxybenzyl)aminocarbonyloxymethoxy],5-[bis(3-methoxybenzyl)aminocarbonyloxy methoxy]dimethylaminobenzylamine, (d) 3-[bis(3-methoxybenzyl)amino carbonyloxymethoxymethoxy],5-[bis(3-methoxybenzyl)aminocarbonyloxymethoxymethoxy]dimethylaminobenzylamine, (e) 3-[(3-methoxybenzyl)(4-dimethylaminobenzyl)aminocarbonyloxy methoxy],5-[(3-methoxybenzyl)(4-dimethylaminobenzyl)aminocarbonyloxymethoxy]dimethylaminobenzylamine, (f) 3-[(3-methoxybenzyl)(4-dimethylaminobenzyl)aminocarbonyloxy methoxymethoxy],5-[(3-methoxybenzyl)(4-dimethylaminobenzyl)aminocarbonyloxy methoxymethoxy], dimethylaminobenzylamine, (g) 3-[bis(4-methoxybenzyl)amino carbonyloxymethoxy],5-[bis(4-methoxybenzyl)aminocarbonyloxymethoxy]dimethylaminobenzylamine, (h) 3-[bis(4-methoxybenzyl)aminocarbonyloxymethoxymethoxy], 5-[bis(4-methoxybenzyl)aminocarbonyloxy ethoxymethoxy]dimethylaminobenzylamine, (i) 3-[(4-methoxybenzyl)(4-dimethylaminobenzyl)aminocarbonyloxymethoxy],5-[(4-methoxybenzyl)(4-dimethylaminobenzyl)aminocarbonyloxymethoxy]dimethylaminobenzylamine, (j) 3-[(4-methoxybenzyl)(4-dimethylaminobenzyl)aminocarbonyloxymethoxymethoxy],5-[(4-methoxybenzyl)(4-dimethylaminobenzyl)aminocarbonyloxymethoxymethoxy]dimethylaminobenzylamine, (k) 2-{3-[2-(9H-carbazol-9-ylcarbonyloxy)methoxy]-5-[(dimethylamino)methyl]phenoxy}methyl 9H-carbazole-9-carboxylate, (l) 2-[2-(3-{2-[2-(9-carbazolylcarbonyloxy)methoxy]methoxy}-5-[(dimethylamino)methyl]phenoxy)methoxy]methyl 9-carbazolecarboxylate, (m) 2-{3-[2-(3,6-dimethoxy-9H-carbazol-9-ylcarbonyloxy)ethoxy]-5-[(dimethylamino)methyl]phenoxy}methyl 3,6-dimethoxy-9H-carbazole-9-carboxylate, (n) 2-[2-(3-{2-[2-(3,6-dimethoxy-9-carbazolylcarbonyloxy)methoxy]methoxy}-5-[(dimethylamino)methyl]phenoxy)methoxy]methyl 3,6-dimethoxy-9-carbazolecarboxylate, (o) higher analogs, or (p) mixtures and combinations thereof.

Embodiment 59. The composition of any of the preceding Embodiments, wherein the one or more integrin activating compound or agonist comprises one or more compounds list below:

Class 20: (a) 3-[bis(thenyl)aminocarbonyloxyethoxy],5-[bis(thenyl)aminocarbonyloxyethoxy]dimethylaminobenzylamine, (b) 3-[bis(thenyl)aminocarbonyloxyethoxyethoxy], 5-[bis(thenyl)aminocarbonyloxyethoxyethoxy]dimethylaminobenzylamine, (c) 3-[bis(3-methoxybenzyl)aminocarbonyloxyethoxy],5-[bis(3-methoxybenzyl)aminocarbonyloxyethoxy]dimethylaminobenzylamine, (d) 3-[bis(3-methoxybenzyl)aminocarbonyloxyethoxy ethoxy],5-[bis(3-methoxybenzyl)aminocarbonyloxyethoxyethoxy]dimethylaminobenzylamine, (e) 3-[(3-methoxybenzyl)(4-dimethylaminobenzyl)aminocarbonyloxyethoxy],5-[(3-methoxybenzyl)(4-dimethylaminobenzyl)aminocarbonyloxyethoxy] dimethylaminobenzylamine, (f) 3-[(3-methoxybenzyl)(4-dimethylaminobenzyl)aminocarbonyloxyethoxyethoxy],5-[(3-methoxybenzyl)(4-dimethylaminobenzyl)aminocarbonyloxyethoxyethoxy], dimethylaminobenzylamine, (g) 3-[bis(4-methoxybenzyl)aminocarbonyloxyethoxy],5-[bis(4-methoxybenzyl)aminocarbonyloxyethoxy]dimethylaminobenzylamine, (h) 3-[bis(4-methoxybenzyl)aminocarbonyloxyethoxyethoxy],5-[bis(4-methoxybenzyl)aminocarbonyloxy ethoxyethoxy]dimethylaminobenzylamine, (i) 3-[(4-methoxybenzyl)(4-dimethylaminobenzyl)aminocarbonyloxyethoxy],5-[(4-methoxybenzyl)(4-dimethylaminobenzyl)aminocarbonyloxyethoxy]dimethylaminobenzylamine, (j) 3-[(4-methoxybenzyl)(4-dimethylaminobenzyl)aminocarbonyloxyethoxyethoxy],5-[(4-methoxybenzyl)(4-dimethylaminobenzyl)aminocarbonyloxyethoxyethoxy] dimethylaminobenzylamine, (k) 2-{3-[2-(9H-carbazol-9-ylcarbonyloxy)ethoxy]-5-[(dimethylamino)methyl]phenoxy}ethyl 9H-carbazole-9-carboxylate, (l) 2-[2-(3-{2-[2-(9-carbazolylcarbonyloxy)ethoxy]ethoxy}-5-[(dimethylamino)methyl]phenoxy)ethoxy]ethyl 9-carbazolecarboxylate, (m) 2-{3-[2-(3,6-dimethoxy-9H-carbazol-9-ylcarbonyloxy)ethoxy]-5-[(dimethylamino)methyl]phenoxy}ethyl 3,6-dimethoxy-9H-carbazole-9-carboxylate, (n) 2-[2-(3-{2-[2-(3,6-dimethoxy-9-carbazolylcarbonyloxy)ethoxy]ethoxy}-5-[(dimethylamino)methyl]phenoxy)ethoxy]ethyl 3,6-dimethoxy-9-carbazolecarboxylate, (o) higher analogs, or (p) mixtures and combinations thereof.

Embodiment 60. The composition of any of the preceding Embodiments, wherein the one or more integrin activating compound or agonist comprises one or more compounds list below:

Class 21: (a) N,N,N,N-tetra(2-thienylmethyl)-2,6-pyridinedicarboxamide, (b) N,N,N,N-tetra(3-methoxybenzyl)-2,6-pyridinedicarboxamide, (c) N,N-bis(3-methoxybenzyl)-N,N-bis(4-dimethylaminobenzyl)-2,6-pyridinedicarboxamide, (d) N,N,N,N-tetra(4-methoxybenzyl)-2,6-pyridinedicarboxamide, (e) N,N-bis(4-methoxybenzyl)-N,N-bis(4-dimethylaminobenzyl)-2,6-pyridinedicarboxamide, (f) or mixtures and combinations thereof.

Embodiment 61. The composition of any of the preceding Embodiments, wherein the one or more integrin activating compound or agonist comprises one or more compounds list below:

Class 22: (a) bis(2-{bis(2-thienylmethyl)aminocarbonyloxy}methyl) 2,6-pyridinedicarboxylate, (b) bis(2-{bis(2-thienylmethyl)aminocarbonyloxymethoxy}methyl) 2,6-pyridinedicarboxylate, (c) bis(2-{bis[3-methoxybenzyl]aminocarbonyloxy}methyl)2,6-pyridinedicarboxylate, (d)

bis(2-{bis[3-methoxybenzyl]aminocarbonyloxymethoxy}methyl)2,6-pyridinedicarboxylate, (e) bis(2-{(3-methoxybenzyl)(4-dimethylaminobenzyl)aminocarbonyloxy}methyl) 2,6-pyridinedicarboxylate, (f) bis(2-{(4-methoxybenzyl)(4-dimethylaminobenzyl)aminocarbonyloxymethoxy}methyl)2,6-pyridinedicarboxylate, (g) bis(2-{bis[4-methoxybenzyl]aminocarbonyloxy}methyl)2,6-pyridinedicarboxylate, (h) bis(2-{bis[4-methoxybenzyl]aminocarbonyloxymethoxy}methyl)2,6-pyridinedicarboxylate, (i) bis(2-{(4-methoxybenzyl)(4-dimethylaminobenzyl) aminocarbonyloxy}methyl)2,6-pyridinedicarboxylate, (j) bis(2-{(4-methoxybenzyl)(4-dimethylaminobenzyl)aminocarbonyloxymethoxy}methyl)2,6-pyridinedicarboxylate, (k) higher analogs, or (l) mixtures and combinations thereof.

Embodiment 62. The composition of any of the preceding Embodiments, wherein the one or more integrin activating compound or agonist comprises one or more compounds list below:

Class 23: (a) bis(2-{bis(2-thienylmethyl)aminocarbonyloxy}ethyl)2,6-pyridinedicarboxylate, (b) bis(2-{bis(2-thienylmethyl)aminocarbonyloxyethoxy}ethyl)2,6-pyridinedicarboxylate, (c) bis(2-{bis[3-methoxybenzyl]aminocarbonyloxy}ethyl)2,6-pyridinedicarboxylate, (d) bis(2-{bis[3-methoxybenzyl]aminocarbonyloxyethoxy}ethyl) 2,6-pyridinedicarboxylate, (e) bis(2-{(3-methoxybenzyl)(4-dimethylaminobenzyl)aminocarbonyloxy}ethyl) 2,6-pyridinedicarboxylate, (f) bis(2-{(4-methoxybenzyl)(4-dimethylaminobenzyl)amino carbonyloxyethoxy}ethyl)2,6-pyridinedicarboxylate, (g) bis(2-{bis[4-methoxybenzyl] amino carbonyloxy}ethyl)2,6-pyridinedicarboxylate, (h) bis(2-{bis[4-methoxybenzyl]aminocarbonyloxy ethoxy}ethyl)2,6-pyridinedicarboxylate, (i) bis(2-{(4-methoxybenzyl)(4-dimethylaminobenzyl)aminocarbonyloxy}ethyl)2,6-pyridinedicarboxylate, (j) bis(2-{(4-methoxybenzyl)(4-dimethylaminobenzyl)aminocarbonyloxyethoxy}ethyl) 2,6-pyridinedicarboxylate, (k) higher analogs, or (l) mixtures and combinations thereof.

Embodiment 63. The composition of any of the preceding Embodiments, wherein the one or more integrin activating compound or agonist comprises one or more compounds list below:

Class 24: (a) N,N,N,N-tetra(2-thienylmethyl)-3,5-pyridinedicarboxamide, (b) N,N,N,N-tetra(4-methoxybenzyl)-3,5-pyridinedicarboxamide, (c) N,N-bis(3-methoxybenzyl)-N,N-bis(4-dimethylaminobenzyl)-3,5-pyridinedicarboxamide, (d) N,N,N,N-tetra(4-methoxybenzyl)-3,5-pyridinedicarboxamide, (e) N,N-bis(4-methoxybenzyl)-N,N-bis(4-dimethylaminobenzyl)-3,5-pyridinedicarboxamide, or (f) mixture and combinations thereof.

Embodiment 64. The composition of any of the preceding Embodiments, wherein the one or more integrin activating compound or agonist comprises one or more compounds list below:

Class 25: (a) bis(2-{bis(2-thienylmethyl]aminocarbonyloxy}methyl) 3,5-pyridinedicarboxylate, (b) bis(2-{bis(2-thienylmethyl]aminocarbonyloxymethoxy}methyl) 3,5-pyridinedicarboxylate, (c) bis(2-{bis(3-methoxybenzyl)aminocarbonyloxy}methyl) 3,5-pyridinedicarboxylate, (d) bis(2-{bis[3-methoxybenzyl]aminocarbonyloxymethoxy}methyl) 3,5-pyridinedicarboxylate, (e) bis(2-{(3-methoxybenzyl)(4-methylaminobenzyl)aminocarbonyloxy}methyl) 3,5-pyridinedicarboxylate, (f) bis(2-{(3-methoxybenzyl)(4-dimethylaminobenzyl)aminocarbonyloxy methoxy}methyl)3,5-pyridinedicarboxylate, (g) bis(2-{bis(4-methoxybenzyl)aminocarbonyloxy}methyl)3,5-pyridinedicarboxylate, (h) bis(2-{bis[4-methoxybenzyl]aminocarbonyloxymethoxy}methyl)3,5-pyridinedicarboxylate, (i) bis(2-{bis(4-methoxybenzyl)(4-methylaminobenzyl)amino carbonyloxy}methyl)3,5-pyridinedicarboxylate, (j) bis(2-{(4-methoxybenzyl)(4-dimethylaminobenzyl)aminocarbonyloxymethoxy}methyl)3,5-pyridinedicarboxylate, (k) higher analogs, or (l) mixtures and combinations thereof.

Embodiment 65. The composition of any of the preceding Embodiments, wherein the one or more integrin activating compound or agonist comprises one or more compounds list below:

Class 26: (a) bis(2-{bis(2-thienylmethyl]aminocarbonyloxy}ethyl)3,5-pyridinedicarboxylate, (b) bis(2-{bis(2-thienylmethyl]aminocarbonyloxyethoxy}ethyl)3,5-pyridinedicarboxylate, (c) bis(2-{bis(3-methoxybenzyl)aminocarbonyloxy}ethyl)3,5-pyridinedicarboxylate, (d) bis(2-{bis[3-methoxybenzyl]aminocarbonyloxyethoxy}ethyl)2,6-pyridinedicarboxylate, (e) bis(2-{(3-methoxybenzyl)(4-methylaminobenzyl)aminocarbonyloxy}ethyl) 3,5-pyridinedicarboxylate, (f) bis(2-{(3-methoxybenzyl)(4-dimethylaminobenzyl)aminocarbonyloxy ethoxy}ethyl)2,6-pyridinedicarboxylate, (g) bis(2-{bis(4-methoxybenzyl)aminocarbonyloxy}ethyl)3,5-pyridinedicarboxylate (h) bis (2-{bis[4-methoxybenzyl]aminocarbonyloxyethoxy}ethyl) 3,5-pyridinedicarboxylate (i) bis(2-{bis(4-methoxybenzyl)(4-methylaminobenzyl)aminocarbonyloxy}ethyl)3,5-pyridinedicarboxylate, (j) bis(2-{(4-methoxybenzyl)(4-dimethylaminobenzyl)amino carbonyloxyethoxy}ethyl)2,6-pyridinedicarboxylate, (k) higher analogs, or (l) mixtures and combinations thereof.

Embodiment 66. The composition of any of the preceding Embodiments, wherein the one or more integrin activating compound or agonist comprises one or more compounds list below:

Class 27: (a) 1-[bis(2-thienylmethyl)aminocarbonyloxy]-5-[bis(2-thienylmethyl)aminocarbonyloxy]-3-(dimethylamino)pentane, (b) 1-[bis(3-methoxybenzyl)aminocarbonyloxy]-5-[bis(3-methoxybenzyl)aminocarbonyloxy]-3-(dimethylamino)pentane, (c) 1-[(3-methoxybenzyl),(4-dimethylaminobenzyl) aminocarbonyloxy]-5-[bis(3-methoxybenzyl),(4-dimethylaminobenzyl) aminocarbonyloxy]-3-(dimethylamino)pentane, (d) 1-[bis(4-methoxybenzyl)aminocarbonyloxy]-5-[bis(4-methoxybenzyl)aminocarbonyloxy]-3-(dimethylamino)pentane, (e) 1-[(4-methoxybenzyl),(4-dimethylaminobenzyl) aminocarbonyloxy]-5-[bis(4-methoxybenzyl),(4-dimethylaminobenzyl) aminocarbonyloxy]-3-(dimethylamino)pentane, or (f) mixtures and combinations thereof.

Embodiment 67. The composition of any of the preceding Embodiments, wherein the one or more integrin activating compound or agonist comprises one or more compounds list below:

Class 28: (a) 1-[bis(2-thienylmethyl)aminocarbonyloxymethoxy]-5-[bis(2-thienylmethyl)aminocarbonyloxymethoxy]-3-(dimethylamino)pentane, (b) 1-[bis(2-thienylmethyl)aminocarbonyloxymethoxymethoxy]-5-[bis(2-thienylmethyl)aminocarbonyloxymethoxymethoxy]-3-(dimethylamino)pentane, or (c) 1-[bis(3-methoxybenzyl)aminocarbonyloxymethoxy]-5-[bis(3-methoxybenzyl)aminocarbonyloxymethoxy]-3-(dimethylamino)pentane, (d) 1-[bis(3-methoxybenzyl)aminocarbonyloxymethoxymethoxy]-5-[bis(3-methoxybenzyl)aminocarbonyloxymethoxymethoxy]-3-(dimethylamino)pentane, (e) 1-{[(3-methoxybenzyl)(4-dimethylaminobenzyl)amino]carbonyloxymethoxy}-5-{[(3-methoxybenzyl)(4-dimethylaminobenzyl) amino] carbonyloxymethoxy}-3-(dimethylamino)pentane, (f) 1-{[(3-methoxybenzyl)(4-dimethylaminobenzyl) amino]

carbonyloxymethoxymethoxy}-5-{[(3-methoxybenzyl)(4-dimethylaminobenzyl) amino]carbonyloxymetho- xymethoxy}-3-(dimethylamino)pentane, (g) 1-[bis(4-methoxybenzyl)aminocarbonyloxymethoxy]-5-[bis(4-methoxybenzyl)aminocarbonyloxymethoxy]-3-(dimethylamino)pentane, (h) 1-[bis(4-methoxybenzyl)aminocarbonyloxymethoxymethoxy]-5-[bis(4-methoxybenzyl)aminocarbonyloxy methoxymethoxy]-3-(dimethylamino)pentane, (l) 1-{[(4-methoxybenzyl)(4-dimethylaminobenzyl) amino]carbonyloxymethoxy}-5-{[(4-methoxybenzyl)(4-dimethylaminobenzyl) amino]carbonyloxymethoxy}-3-(dimethylamino)pentane, (j) 1-{[(4-methoxybenzyl)(4-dimethylaminobenzyl) amino]carbonyloxymethoxymethoxy}-5-{[(4-methoxybenzyl)(4-dimethylaminobenzyl) amino]carbonyloxymethoxymethoxy}-3-(dimethylamino)pentane, (k) higher analogs, or (l) mixtures and combinations thereof.

Embodiment 68. The composition of any of the preceding Embodiments, wherein the one or more integrin activating compound or agonist comprises one or more compounds list below:

Class 29: (a) 1-[bis(2-thienylmethyl)aminocarbonyloxyethoxy]-5-[bis(2-thienylmethyl)aminocarbonyloxyethoxy]-3-(dimethylamino)pentane, (b) 1-[bis(2-thienylmethyl)aminocarbonyloxyethoxyethoxy]-5-[bis(2-thienylmethyl) aminocarbonyloxyethoxyethoxy]-3-(dimethylamino) pentane, or (c) 1-[bis(3-methoxybenzyl)aminocarbonyloxyethoxy]-5-[bis(3-methoxybenzyl)aminocarbonyloxyethoxy]-3-(dimethylamino)pentane, (d) 1-[bis(3-methoxybenzyl)aminocarbonyloxyethoxyethoxy]-5-[bis(3-methoxybenzyl)aminocarbonyloxyethoxyethoxy]-3-(dimethylamino)pentane, (e) 1-{[(3-methoxybenzyl)(4-dimethylaminobenzyl) amino]carbonyloxyethoxy}-5-{[(3-methoxybenzyl)(4-dimethylaminobenzyl) amino]carbonyloxyethoxy}-3-(dimethylamino)pentane, (f) 1-{[(3-methoxybenzyl)(4-dimethylaminobenzyl) amino]carbonyloxyethoxyethoxy}-5-{[(3-methoxybenzyl)(4-dimethylaminobenzyl) amino]carbonyloxyethoxyethoxy}-3-(dimethylamino)pentane, (g) 1-[bis(4-methoxybenzyl)aminocarbonyloxyethoxy]-5-[bis(4-methoxybenzyl)aminocarbonyloxyethoxy]-3-(dimethylamino)pentane, (h) 1-[bis(4-methoxybenzyl)aminocarbonyloxyethoxyethoxy]-5-[bis(4-methoxybenzyl)aminocarbonyloxy ethoxyethoxy]-3-(dimethylamino)pentane, (i) 1-{[(4-methoxybenzyl)(4-dimethylaminobenzyl) amino]carbonyloxyethoxy}-5-{[(4-methoxybenzyl)(4-dimethyl aminobenzyl) amino]carbonyloxyethoxy}-3-(dimethylamino)pentane, (j) 1-{[(4-methoxybenzyl)(4-dimethylaminobenzyl) amino]carbonyloxyethoxyethoxy}-5-{[(4-methoxybenzyl)(4-dimethylaminobenzyl) amino]carbonyloxyethoxyethoxy}-3-(dimethylamino)pentane, (k) higher analogs, or (l) mixtures and combinations thereof.

Embodiment 69. The composition of any of the preceding Embodiments, wherein the one or more integrin activating compound or agonist comprises one or more compounds list below:

Class 30: (a) 5-oxo-7-(2-thienyl)-6-(2-thienylmethyl)-2,4-dioxa-6-aza-heptanyl-N,N-dimethylamine, (b) 5-oxo-7-(3-methoxyphenyl)-6-(3-methoxybenzyl)-2,4-dioxa-6-aza-heptanyl-N,N-dimethylamine, (c) 5-oxo-7-(3-methoxyphenyl)-6-(4-dimethylaminobenzyl)-2,4-dioxa-6-aza-heptanyl-N,N-dimethylamine, (d) 5-oxo-7-(4-methoxyphenyl)-6-(4-methoxybenzyl)-2,4-dioxa-6-aza-heptanyl-N,N-dimethylamine, (e) 5-oxo-7-(4-methoxyphenyl)-6-(4-dimethylaminobenzyl)-2,4-dioxa-6-aza-heptanyl-N,N-dimethylamine, (f) 7-oxo-9-(2-thienyl)-8-(2-thienylmethyl)-2,4,6-trioxa-8-aza-nonayl-N,N-dimethylamine, (g) 7-oxo-9-(3-methoxyphenyl)-8-(3-methoxybenzyl)-2,4,6-trioxa-8-aza-undecyl-N,N-dimethylamine, (h) 7-oxo-9-(3-methoxyphenyl)-8-(4-dimethylaminobenzyl)-2,4,6-trioxa-8-aza-dodecyl-N,N-dimethylamine, (i) 7-oxo-9-(3-methoxyphenyl)-8-(3-methoxybenzyl)-2,4,6-trioxa-8-aza-dodecyl-N,N-dimethylamine, (j) 7-oxo-9-(3-methoxyphenyl)-8-(4-dimethylaminobenzyl)-2,4,6-trioxa-8-aza-dodecyl-N,N-dimethylamine, (k) 9-oxo-11-(2-thienyl)-10-(2-thienylmethyl)-2,4,6,8-tetraoxa-10-aza-undecyl-N,N-dimethylamine, (l) 9-oxo-11-(3-methoxyphenyl)-10-(3-methoxybenzyl)-2,4,6,8-tetraoxa-10-aza-pentadecyl-N,N-dimethylamine, (m) 9-oxo-11-(3-methoxyphenyl)-10-(4-dimethylaminobenzyl)-2,4,6,8-tetraoxa-10-aza-pentadecyl-N,N-dimethylamine, (n) 9-oxo-11-(4-methoxyphenyl)-10-(4-methoxybenzyl)-2,4,6,8-tetraoxa-10-aza-pentadecyl-N,N-dimethylamine, (o) 9-oxo-11-(3-methoxyphenyl)-10-(4-dimethylaminobenzyl)-2,4,6,8-tetraoxa-10-aza-pentadecyl-N,N-dimethylamine, (p) higher analogs, or (q) mixtures and combinations thereof.

Embodiment 70. The composition of any of the preceding Embodiments, wherein the one or more integrin activating compound or agonist comprises one or more compounds list below:

Class 31: (a) 7-oxo-9-(2-thienyl)-8-(2-thienylmethyl)-3,6-dioxa-8-aza-nonanyl-N,N-dimethylamine, (b) 7-oxo-9-(3-methoxyphenyl)-8-(3-methoxybenzyl)-3,6-dioxa-8-aza-nonanyl-N,N-dimethylamine, (c) 7-oxo-9-(3-methoxyphenyl)-8-(4-dimethylaminobenzyl)-3,6-dioxa-8-aza-nonanyl-N,N-dimethylamine, (d) 7-oxo-9-(4-methoxyphenyl)-8-(4-methoxybenzyl)-3,6-dioxa-8-aza-nonanyl-N,N-dimethylamine, (e) 7-oxo-9-(4-methoxyphenyl)-8-(4-dimethylaminobenzyl)-3,6-dioxa-8-aza-nonanyl-N,N-dimethylamine, or (f) mixtures and combinations thereof. (g) 10-oxo-12-(2-thienyl)-11-(2-thienylmethyl)-3,6,9-trioxa-11-aza-dodecyl-N,N-dimethylamine, (h) 10-oxo-12-(3-methoxyphenyl)-11-(3-methoxybenzyl)-3,6,9-trioxa-11-aza-dodecyl-N,N-dimethylamine, (i) 10-oxo-12-(3-methoxyphenyl)-11-(4-dimethylaminobenzyl)-3,6,9-trioxa-11-aza-dodecyl-N,N-dimethylamine, (j) 10-oxo-12-(3-methoxyphenyl)-11-(3-methoxybenzyl)-3,6,9-trioxa-11-aza-dodecyl-N,N-dimethylamine, (k) 10-oxo-12-(3-methoxyphenyl)-11-(4-dimethylaminobenzyl)-3,6,9-trioxa-11-aza-dodecyl-N,N-dimethylamine, (l) 13-oxo-15-(2-thienyl)-14-(2-thienylmethyl)-3,6,9,12-tetraoxa-14-aza-pentadecyl-N,N-dimethylamine, (m) 13-oxo-15-(3-methoxyphenyl)-14-(3-methoxybenzyl)-3,6,9,12-tetraoxa-14-aza-pentadecyl-N,N-dimethylamine, (n) 13-oxo-15-(3-methoxyphenyl)-14-(4-dimethylaminobenzyl)-3,6,9,12-tetraoxa-14-aza-pentadecyl-N,N-dimethylamine, (o) 13-oxo-15-(4-methoxyphenyl)-14-(4-methoxybenzyl)-3,6,9,12-tetraoxa-14-aza-pentadecyl-N,N-dimethylamine, (p) 13-oxo-15-(3-methoxyphenyl)-14-(4-dimethylaminobenzyl)-3,6,9,12-tetraoxa-14-aza-pentadecyl-N,N-dimethylamine, (q) higher analogs, or (r) mixtures and combinations thereof.

Embodiment 71. The composition of any of the preceding Embodiments, wherein the effective amount of the activators or agonists of the disclosure is between about 1 fM and about 300 µM or any subrange such as between about 1 fM and about 200 µM, between about 1 fM and about 100 µM, between about 1 fM and about 50 µM, between about 1 fM and about 25 µM, between about 1 fM and about 20 µM, between about 1 fM and about 15 µM, between about 1 fM and about 5 µM, between about 1 fM and about 1 µM, between about 1 fM and about 100 nM, between about 1 fM and about 75 nM, between about 1 fM and about 50 nM, between about 1 fM and about 25 nM, or any other subrange.

Embodiment 72. The composition of any of the preceding Embodiments, wherein the plasma concentration of the agonist(s) is(are) between about 1 nanogram/milliliter (ng/mL) and about 25 ng/mL or any subrange such as between about 1 ng/mL and about 20 ng/mL, between about 1 ng/mL and about 15 ng/mL, between about 1 ng/mL and about 5 ng/mL, between about 1 ng/mL and about 1 ng/mL, between about 1 ng/mL and about 100 ng/mL, between about 1 ng/mL and about 75 ng/mL, between about 1 ng/mL and about 50 ng/mL, between about 1 ng/kg and about 25 ng/mL, or any other subrange.

Embodiment 73. The composition of any of the preceding Embodiments, wherein the compounds have T-cell proliferation values as measured at an absorbance at 570 nm between about 0.200 and about 0.350 with a p value between about 0.01 and about 0.00001, between about 0.20 and about 0.325 with a p value between about 0.001 and about 0.00001, between about 0.200 and about 0.300 with a p value between about 0.01 and about 0.00001, or between about 0.200 and about 0.275 with a p value between about 0.01 and about 0.00001, including all subranges.

Embodiment 74. The composition of any of the preceding Embodiments, wherein the therapeutic effective amount of cells are between about $1 \times 10^4$ cells per kg and about $1 \times 10^9$ cells per kg of the animal, mammal, or human receiving the cells or any subrange such as between about $1 \times 10^4$ cells per kg and about $1 \times 10^8$ cells per kg, between about $1 \times 10^4$ cells per kg and about $1 \times 10^7$ cells per kg, or between about $1 \times 10^4$ cells per kg, about $1 \times 10^6$ cells per kg, between about $1 \times 10^4$ cells per kg and about $1 \times 10^5$ cells per kg, or any other subrange.

Embodiment 75. The composition of any of the preceding Embodiments, wherein the compounds enhance vaccine efficacies, enhance adoptive cell therapy efficacies, enhance immunotherapy efficacies, enhance therapeutic antibody therapy efficacies, enhance checkpoint inhibitor therapy efficacies, enhance effector cell therapy efficacies, and enhanced cell based transplant efficacies and wherein at protonatable moiety either protonate at biological pHs or bears a charge with associated pharmaceutically acceptable counterion making the compound water soluble to improve bioavailability Embodiment 76. A method of vaccinating a host comprising:
administering, to the host, an antigen effective amount of an antigen containing composition: comprising one or more antigens, and
administering, before, during, and/or after, the antigen containing composition administering
an integrin agonist effective amount of an agonist composition comprising:
one or more integrin activating or agonist compounds of the general including an antigen effective amount of one or more antigens, and of the general Formula (I):

   (I)

wherein:
the $Q^1$ and $Q^2$ groups independently comprise an $R^1R^2N$— group, an $R^1R^2NC(\!=\!O)$— group, an $R^1R^2NC(\!=\!O)N(R^3)$— group, an $R^1R^2NC(\!=\!O)$ O— group, or an $R^1R^2NSO_2$— group,
the $R^1$ and $R^2$ groups independently comprise a a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof, and
the $R^3$ group may be a hydrocarbyl group or a heterohydrocarbyl group;
the $R^a$ and $R^b$ groups independently comprise a hydrocarbenyl linking group, wherein one or more carbon atoms may be replaced by oxygen atoms; and
the Z group comprises a hydrocarbenyl linking group or a heterohydrocarbenyl linking group and at least one protonatable moiety,
the integrin agonist composition may be administered before, during, and/or after the administration of the antigen composition,
the one or more integrin activating or agonist compounds activate one or more integrins and enhance interactions between the integrins and their ligands, and
the integrin agonist composition enhances antigen presentation, B-cells and T-cell interactions, B-cells and T-cell activation, and B-cells and T-cell activity.

Embodiment 77. The method of Embodiment 74, wherein:
the at least one protonatable moiety is protonated at biological pHs and/or the at least one protonatable moiety is protonated and includes a pharmaceutically acceptable counterion, the integrins include α4β1, α4β7, α5β1, and/or αLβ2, and
the ligands include VCAM-1, fibronectin, MAdCAM-1, ICAM-1, and/or ICAM-2.

Embodiment 78. The method of Embodiment 74, wherein the vaccine composition comprises an anti-cancer vaccine.

Embodiment 79. The method of Embodiment 74, wherein the integrin agonist composition and/or the antigen composition each further comprise:
a pharmaceutically acceptable carrier,
wherein the pharmaceutically acceptable carriers may include one or more adjuvant comprising non-specific adjuvant substances and/or specific adjuvant substances capable of enhancing an immune response to the one or more antigens.

Embodiment 80. A method comprising:
administering, to a host, an effector cell composition including an effector cell effective amount of one or more treated and/or untreated effector cells, and
before, during, and/or after, administering, to the host, an integrin agonist composition including an agonist effective amount of one or more integrin agonists or activator of the general Formula (I):

   (I)

wherein:
the $Q^1$ and $Q^2$ groups independently comprise an $R^1R^2N$— group, an $R^1R^2NC(\!=\!O)$— group, an $R^1R^2NC(\!=\!O)N(R^3)$— group, an $R^1R^2NC(\!=\!O)$ O— group, or an $R^1R^2NSO_2$ group,
the $R^1$ and $R^2$ groups independently comprise a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof, and
the $R^3$ group may be a hydrocarbyl group or a heterohydrocarbyl group;

the $R^a$ and $R^b$ groups independently comprise a hydrocarbenyl linking group, wherein one or more carbon atoms may be replaced by oxygen atoms; and the Z group comprises a hydrocarbenyl linking group or a heterohydrocarbenyl linking group and at least one protonatable moiety, the integrin agonists are capable of enhancing integrin-mediated binding of integrins of a cell to their respective ligand.

Embodiment 81. The method of Embodiment 78, wherein:

the Z group may also include one or more moieties that protonate at biological pHs and/or bear a charge in association with an acceptable counterion;

the integrins include α4β1, α4β7, α5β1, and/or αLβ2; and the ligands include VCAM-1, fibronectin, MAdCAM-1, ICAM-1, and/or ICAM-2.

Embodiment 82. A method comprising:

administering, to a host, an antibody composition including an antibody effective amount of one or more therapeutic antibodies, and before, during, and/or after, administering, to the host, an integrin agonist composition including an agonist effective amount of one or more integrin agonists or activator of the general Formula (I):

$$Q^1\text{-}R^a\text{—}Z\text{—}R^b\text{-}Q^2 \qquad (I)$$

wherein:

the $Q^1$ and $Q^2$ groups independently comprise an $R^1R^2N$— group, an $R^1R^2NC(=O)$— group, an $R^1R^2NC(=O)N(R^3)$— group, an $R^1R^2NC(=O)O$— group, or an $R^1R^2NSO_2$— group, the $R^1$ and $R^2$ groups independently comprise a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof, and the $R^3$ group may be a hydrocarbyl group or a heterohydrocarbyl group;

the $R^a$ and $R^b$ groups independently comprise a hydrocarbenyl linking group, wherein one or more carbon atoms may be replaced by oxygen atoms; and the Z group comprises a hydrocarbenyl linking group or a heterohydrocarbenyl linking group and at least one protonatable moiety, the integrin agonists are capable of enhancing integrin-mediated binding of integrins of a cell to their respective ligand.

Embodiment 83. The method of Embodiment 80, wherein:

the Z group may also include one or more moieties that protonate at biological pHs and/or bear a charge in association with an acceptable counterion;

the integrins include α4β1, α4β7, α5β1, and/or αLβ2; and the ligands include VCAM-1, fibronectin, MAdCAM-1, ICAM-1, and/or ICAM-2.

Embodiment 84. A method comprising:

administering, to a host, a checkpoint inhibitor composition including a checkpoint inhibitor effective amount of one or more checkpoint inhibitors, and before, during, and/or after, administering, to the host, an integrin agonist composition including an agonist effective amount of one or more integrin agonists or activator of the general Formula (I):

$$Q^1\text{-}R^a\text{—}Z\text{—}R^b\text{-}Q^2 \qquad (I)$$

wherein:

the $Q^1$ and $Q^2$ groups independently comprise an $R^1R^2N$— group, an $R^1R^2NC(=O)$— group, an $R^1R^2NC(=O)N(R^3)$— group, an $R^1R^2NC(=O)O$— group, or an $R^1R^2NSO_2$— group, the $R^1$ and $R^2$ groups independently comprise a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof, and the $R^3$ group may be a hydrocarbyl group or a heterohydrocarbyl group;

the $R^a$ and $R^b$ groups independently comprise a hydrocarbenyl linking group, wherein one or more carbon atoms may be replaced by oxygen atoms; and the Z group comprises a hydrocarbenyl linking group or a heterohydrocarbenyl linking group and at least one protonatable moiety, the integrin agonists are capable of enhancing integrin-mediated binding of integrins of a cell to their respective ligand.

Embodiment 85. The method of Embodiment 82, wherein:

the Z group may also include one or more moieties that protonate at biological pHs and/or bear a charge in association with an acceptable counterion;

the integrins include α4β1, α4β7, α5β1, and/or αLβ2; and the ligands include VCAM-1, fibronectin, MAdCAM-1, ICAM-1, and/or ICAM-2.

Embodiment 86. A method comprising:

administering, to a host, an immuno-therapeutic agent composition including an immuno-therapeutic agent effective amount of one or more immuno-therapeutic agents, and before, during, and/or after, administering, to the host, an integrin agonist composition including an agonist effective amount of one or more integrin agonists or activator of the general Formula (I):

$$Q^1\text{-}R^a\text{—}Z\text{—}R^b\text{-}Q^2 \qquad (I)$$

wherein:

the $Q^1$ and $Q^2$ groups independently comprise an $R^1R^2N$— group, an $R^1R^2NC(=O)$— group, an $R^1R^2NC(=O)N(R^3)$— group, an $R^1R^2NC(=O)O$— group, or an $R^1R^2NSO_2$ group, the $R^1$ and $R^2$ groups independently comprise a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof, and the $R^3$ group may be a hydrocarbyl group or a heterohydrocarbyl group;

the $R^a$ and $R^b$ groups independently comprise a hydrocarbenyl linking group, wherein one or more carbon atoms may be replaced by oxygen atoms; and the Z group comprises a hydrocarbenyl linking group or a heterohydrocarbenyl linking group and at least one protonatable moiety, Embodiment 87. The method of Embodiment 84, wherein:
the Z group may also include one or more moieties that protonate at biological pHs and/or bear a charge in association with an acceptable counterion;
the integrins include α4β1, α4β7, α5β1, and/or αLβ2; and
the ligands include VCAM-1, fibronectin, MAdCAM-1, ICAM-1, and/or ICAM-2.

Embodiment 88. A method for anti-tumor activity comprising:
administering, to a host, an integrin agonist composition including an agonist effective amount of one or more integrin agonists or activator of the general Formula (I):

$$Q-R^a—Z—R^b-Q^2 \quad (I)$$

wherein:
the $Q^1$ and $Q^2$ may independently be an $R^1R^2N$— group, an $R^1R^2NC(=O)$— group, an $R^1R^2NC(=O)N(R^3)$— group, an $R^1R^2NC(=O)O$— group, or an $R^1R^2NSO_2$— group,
the $R^1$ and $R^2$ groups may independently be a hydrocarbyl group, a heterohydrocarbyl group, an aryl-containing hydrocarbyl group, a heteroaryl-containing hydrocarbyl group, an aryl-containing heterohydrocarbyl group, a heteroaryl-containing heterohydrocarbyl group, a fused heterocyclic ring group, or any combination thereof, and
the $R^3$ group may be a hydrocarbyl group or a heterohydrocarbyl group;
the $R^a$ group may be a hydrocarbenyl linking group, wherein one or more carbon atoms may be replaced by oxygen atoms;
the $R^b$ group may be a hydrocarbenyl linking group, wherein one or more carbon atoms may be replaced by oxygen atoms;
the Z group may be a hydrocarbenyl linking group or a heterohydrocarbenyl linking group;
the integrin agonists are capable of enhancing integrin-mediated binding of integrins of a cell to their respective ligand.

Embodiment 89. The method of Embodiment 86, wherein:
the Z group may also include one or more moieties that protonate at biological pHs and/or bear a charge in association with an acceptable counterion;
the integrins include α4β1, α4β7, α5β1, and/or αLβ2; and
the ligands include VCAM-1, fibronectin, MAdCAM-1, ICAM-1, and/or ICAM-2.

I claim:
1. A composition comprising:
one or more antigens, and
one or more integrin activating or agonist compounds of the general Formulas:

Formula (IIIb)

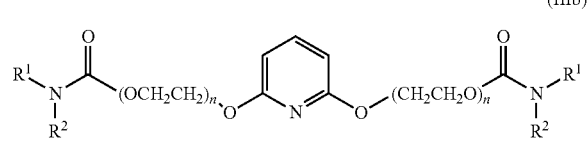

wherein:
the $R^1$ and $R^2$ groups are independently a —$(CH_2)$-aryl group, or a —$(CH_2)$-heterocyclylaryl group, or the $R^1$ and $R^2$ groups combine to form a fused heterocyclylaryl group including at least one nitrogen-containing aryl group, and
n independently is an integer having a value between 1 and 6;

Formula (IVb)

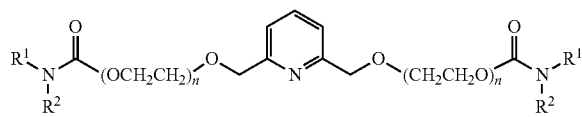

wherein:
the $R^1$ and $R^2$ groups are independently a —$(CH_2)$-aryl group, or a —$(CH_2)$-heterocyclylaryl group, or the $R^1$ and $R^2$ groups combine to form a fused heterocyclylaryl group including at least one nitrogen-containing aryl group, and
n independently is an integer having a value between 1 and 6;

Formula (Vb)

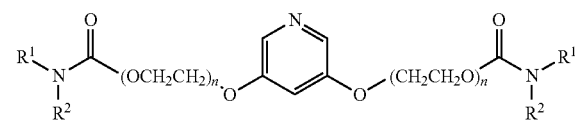

wherein:
the $R^1$ and $R^2$ groups are independently a —$(CH_2)$-aryl group, or a —$(CH_2)$-heterocyclylaryl group, or the $R^1$ and $R^2$ groups combine to form a fused heterocyclylaryl group including at least one nitrogen-containing aryl group, and
n independently is an integer having a value between 1 and 6;

Formula (VIb)

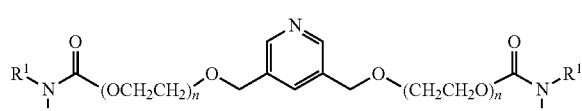

wherein:
the $R^1$ and $R^2$ groups are independently a —$(CH_2)$-aryl group, or a —$(CH_2)$-heterocyclylaryl group, or the $R^1$ and $R^2$ groups combine to form a fused heterocyclylaryl group including at least one nitrogen-containing aryl group, and
n independently is an integer having a value between 1 and 6;

Formula (VIIb)

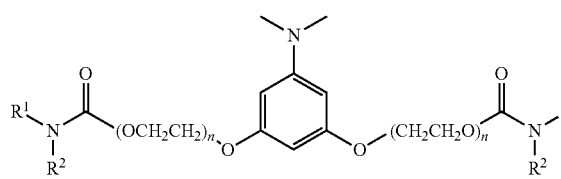
(VIIb)

wherein:
the $R^1$ and $R^2$ groups are independently a —$(CH_2)$-aryl group, or a —$(CH_2)$-heterocyclylaryl group, or the $R^1$ and $R^2$ groups combine to form a fused heterocyclylaryl group including at least one nitrogen-containing aryl group, and n independently is an integer having a value between 1 and 6;

Formula (VIIIb)

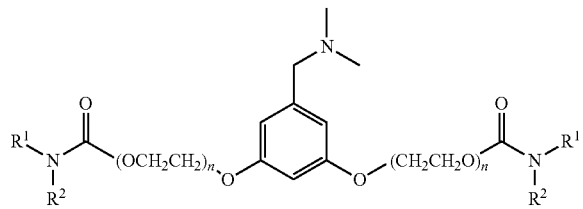
(VIIIb)

wherein:
the $R^1$ and $R^2$ groups are independently a —$(CH_2)$-aryl group, or a —$(CH_2)$-heterocyclylaryl group, or the $R^1$ and $R^2$ groups combine to form a fused heterocyclylaryl group including at least one nitrogen-containing aryl group, and n independently is an integer having a value between 1 and 6;

Formula (IXb)

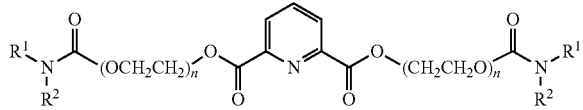
(IXb)

wherein:
the $R^1$ and $R^2$ groups are independently a —$(CH_2)$-aryl group, or a —$(CH_2)$-heterocyclylaryl group, or the $R^1$ and $R^2$ groups combine to form a fused heterocyclylaryl group including at least one nitrogen-containing aryl group, and n independently is an integer having a value between 1 and 6; and Formula (Xb)

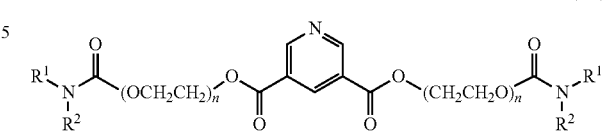
(Xb)

wherein:
the $R^1$ and $R^2$ groups are independently a —$(CH_2)$-aryl group, or a —$(CH_2)$-heterocyclylaryl group, or the $R^1$ and $R^2$ groups combine to form a fused heterocyclylaryl group including at least one nitrogen-containing aryl group, and n independently is an integer having a value between 1 and 6, wherein:
the one or more integrin activating or agonist compounds may be administered before, during, and/or after the administration of the one or more antigens, and the one or more integrin activating or agonist compounds activate one or more integrins.

2. The composition of claim 1, wherein the integrins are selected from the group consisting of α4β1, α4β7, α5β1, αLβ2, and combinations thereof.

3. The composition of claim 1, wherein the one or more antigens comprise one or more anti-cancer antigens.

4. The composition of claim 1, further comprising:
a pharmaceutically acceptable carrier.

5. The composition of claim 1, wherein the one or more integrin activating or agonist compounds are present in an agonist molar amount between about 1 femtomolar (fM) and about 300 micromolar (μM).

6. The composition of claim 1, wherein the one or more integrin activating or agonist compounds of Formula (IIIb) are selected from the group consisting of: (a) 2-[bis(thenyl) aminocarbonyloxyethoxy],6-[bis(thenyl)aminocarbonyl oxyethoxy]pyridine, (b) 2-[bis(thenyl)aminocarbonyloxyethoxyethoxy],6-[bis(thenyl) aminocarbonyloxyethoxyethoxy]pyridine, (c) 2-[bis(3-methoxybenzyl)aminocarbonyl oxyethoxy],6-[bis(3-methoxybenzyl) aminocarbonyloxy ethoxy]pyridine, (d) 2-[bis(3-methoxybenzyl)aminocarbonyloxyethoxyethoxy],6-[bis(3-methoxy benzyl)aminocarbonyloxyethoxyethoxy]pyridine, (e) 2-[(3-methoxybenzyl) (4-dimethylaminobenzyl) aminocarbonyloxyethoxy],6-[(3-methoxybenzyl)(4-dimethylaminobenzyl)aminocarbonyl oxyethoxy]pyridine, (f) 2-[(3-methoxybenzyl)(4-dimethylaminobenzyl)aminocarbonyloxy ethoxyethoxy], 6-[(3-methoxybenzyl)(4-dimethylaminobenzyl)aminocarbonyloxyethoxy ethoxy]pyridine, (g) 2-[bis(4-methoxybenzyl) aminocarbonyloxyethoxy],6-[bis(4-methoxy benzyl)aminocarbonyloxyethoxy]pyridine, (h) 2-[bis(4-methoxybenzyl)amino carbonyloxyethoxyethoxy],6-[bis(4-methoxybenzyl)aminocarbonyloxyethoxyethoxy]pyridine, (i) 2-[(4-methoxybenzyl)(4-dimethylaminobenzyl)aminocarbonyloxyethoxy], 6-[(4-methoxybenzyl)(4-dimethylaminobenzyl)aminocarbonyloxyethoxy]pyridine, (j) 2-[(4-methoxybenzyl)(4-dimethylaminobenzyl)aminocarbonyloxyethoxyethoxy], 6-[(4-methoxybenzyl)(4-dimethylaminobenzyl)aminocarbonyloxyethoxyethoxy]pyridine, (k) 2-{6-[2-(9H-carbazol-9-yl-carbonyloxy)ethoxy]-2-pyridyloxy} ethyl-9H-carbazole-9-carboxylate, (l) 2-[2-(6-{2-[2-(9-carbazolylcarbonyloxy)ethoxy]ethoxy}-2-pyridyloxy) ethoxy]ethyl 9-carbazolecarboxylate, (m) 2-{6-[2-(3,6- dimethoxy-9H-carbazol-9-yl carbonyloxy)ethoxy]-2-pyridyloxy}ethyl 3,6-dimethoxy-9H-carbazole-9-carboxylate, (n) 2-[2-(6-{2-[2-(3,6-dimethoxy-9-carbazolylcarbonyloxy)ethoxy]ethoxy}-2-pyridyloxy)ethoxy]ethyl 3,6-dimethoxy-9-carbazolecarboxylate, and (o) combinations thereof.

7. The composition of claim 1, wherein the one or more integrin activating or agonist compounds of Formula (IVb) are selected from the group consisting of: (a) 2-[({bis[(2-thienyl)methyl]aminocarbonyloxy} ethoxy)methyl]-6-[({bis [(2-thienyl)methyl]amino carbonyloxy} ethoxy)methyl]pyridine, (b) 2-[({bis[(2-thienyl)methyl]aminocarbonyloxy} ethoxyethoxy)methyl]-6-[({bis[(2-thienyl) methyl]aminocarbonyloxy} ethoxyethoxy)methyl]pyridine, (c) 2-[({bis(3-methoxybenzyl)aminocarbonyloxy} ethoxy)methyl]-6-[({bis(3-methoxybenzyl)amino carbonyloxy} ethoxy)methyl]pyridine, (d) 2-[({bis(3-methoxybenzyl)aminocarbonyloxy} ethoxyethoxy)methyl]-6-[({bis(3-methoxybenzyl)aminocarbonyloxy} ethoxyethoxy) methyl]pyridine, (e) 2-[({(3-methoxybenzyl,4-dimethylaminobenzyl)aminocarbonyl oxy} ethoxy)methyl]-6-[({(3-methoxybenzyl,4-dimethylaminobenzyl)aminocarbonyl oxy}ethoxy)methyl]pyridine, (f) 2-[({(3-methoxybenzyl,4-dimethylaminobenzyl)aminocarbonyloxy} ethoxyethoxy)methyl]-6-[({(3-methoxybenzyl,4-dimethylamino benzyl)aminocarbonyloxy} ethoxyethoxy)methyl]pyridine, (g) 2-[({bis(4-methoxybenzyl)aminocarbonyloxy} ethoxy)methyl]-6-[({bis(4-methoxybenzyl) aminocarbonyloxy} ethoxy)methyl]pyridine, (h) 2-[({{bis(4-methoxybenzyl)aminocarbonyloxy} ethoxyethoxy)methyl]-6-[({{bis(4-methoxybenzyl)aminocarbonyloxy} ethoxyethoxy)methyl] pyridine, (i) 2-[({(4-methoxybenzyl,4-dimethylaminobenzyl) aminocarbonyloxy} ethoxy)methyl]-6-[({(4-methoxybenzyl,4-dimethylaminobenzyl)amino carbonyloxy} ethoxy)methyl]pyridine, (j) 2-[({(4-methoxybenzyl,4-dimethylaminobenzyl)aminocarbonyloxy} ethoxyethoxy)methyl]-6-[({(4-methoxybenzyl,4-dimethylaminobenzyl) aminocarbonyloxy}ethoxyethoxy)methyl] pyridine, (k) 2-[(6-{[2-(9H-carbazol-9-ylcarbonyloxy)ethoxy]methyl}-2-pyridyl)methoxy]ethyl 9H-carbazole-9-carboxylate, (l) 2-(2-{[6-({2-[2-(9H-carbazolylcarbonyloxy)ethoxy]ethoxy} methyl)-2-pyridyl]methoxy} ethoxy)ethyl 9-carbazolecarboxylate, (m) 2-[(6-{[2-(3,6-dimethoxy-9H-carbazol-9-ylcarbonyloxy)ethoxy]methyl}-2-pyridyl)methoxy] ethyl 3,6-dimethoxy-9H-carbazole-9-carboxylate, (n) 2-(2-{[6-({2-[2-(3,6-dimethoxy-9H-carbazolylcarbonyloxy) ethoxy]ethoxy} methyl)-2-pyridyl]methoxy} ethoxy)ethyl 3,6-dimethoxy-9-carbazolecarboxylate, and (o) combinations thereof.

8. The composition of claim 1, wherein the one or more integrin activating or agonist compounds of Formula (IVb) are selected from the group consisting of: (a) 3-[bis(thenyl)aminocarbonyloxyethoxy],5-[bis(thenyl)aminocarbonyloxy ethoxy]pyridine, (b) 3-[bis(thenyl)aminocarbonyloxyethyoxyethoxy],5-[bis(thenyl) aminocarbonyloxyethyoxyethoxy]pyridine, (c) 3-[bis(3-methoxybenzyl)aminocarbonyloxyethoxy], 5-[bis(3-methoxybenzyl)aminocarbonyloxyethoxy]pyridine, (d) 3-[bis(3-methoxybenzyl)amino carbonyloxyethoxyethoxy],5-[bis(3-methoxybenzyl)aminocarbonyloxy ethoxyethoxy]pyridine, (e) 3-[(3-methoxybenzyl)(4-dimethylaminobenzyl)aminocarbonyloxy],5-[(3-methoxybenzyl)(4-dimethylaminobenzyl)aminocarbonyloxy]pyridine, (f) 3-[(3-methoxybenzyl)(4-dimethyl aminobenzyl)aminocarbonyloxyethoxy],5-[(3-methoxybenzyl)(4-dimethylaminobenzyl)amino carbonyloxyethoxy]pyridine, (g) 3-[(4-methoxybenzyl)(4-dimethylaminobenzyl)aminocarbonyloxy ethoxyethoxy],5-[(4-methoxybenzyl)(4-dimethylaminobenzyl) aminocarbonyloxy ethoxyethoxy]pyridine, (h) 3-[bis(4-methoxybenzyl)aminocarbonyloxyethoxy],5-[bis(4-methoxybenzyl)amino carbonyloxyethoxy]pyridine, (i) 3-[bis(3-methoxybenzyl)aminocarbonyloxy ethoxyethoxy],5-[bis(3-methoxybenzyl)aminocarbonyloxyethoxyethoxy]pyridine, (j) 3-[(4-methoxybenzyl)(4-dimethylaminobenzyl)aminocarbonyloxyethoxy],5-[(4-methoxybenzyl)(4-dimethylaminobenzyl)aminocarbonyloxyethoxyethoxy]pyridine, (k) 3-[(4-methoxybenzyl)(4-dimethylaminobenzyl)aminocarbonyloxyethoxyethoxy], 5-[(4-methoxybenzyl)(4-dimethylaminobenzyl) aminocarbonyloxyethoxyethoxy]pyridine, (l) 2-{5-[2-(9H-carbazol-9-ylcarbonyloxy)ethoxy]-3-pyridyloxy} ethyl 9H-carbazole-9-carboxylate, (m) 2-[2-(5-{2-[2-(9-carbazolylcarbonyloxy) ethoxy]ethoxy}-3-pyridyloxy)ethoxy]ethyl 9-carbazolecarboxylate, (n) 2-{5-[2-(3,6-dimethoxy-9H-carbazol-9-ylcarbonyloxy)ethoxy]-3-pyridyloxy} ethyl 3,6-dimethoxy-9H-carbazole-9-carboxylate, (0) 2-[2-(5-{2-[2-(3,6-dimethoxy-9H-carbazolylcarbonyloxy) ethoxy]ethoxy}-3-pyridyloxy)ethoxy]ethyl 3,6-dimethoxy-9-carbazolecarboxylate, and (p) combinations thereof.

9. The composition of claim 1, wherein the one or more integrin activating or agonist compounds of Formula (IVb) are selected from the group consisting of: (a) 3-{bis[(2-thienyl)methyl]aminocarbonyloxy}ethoxy)methyl]-5-{bis [(2-thienyl)methyl]aminocarbonyloxy} ethoxy)methyl]pyridine, (b) 3-{bis[(2-thienyl) methyl]aminocarbonyloxy}ethoxymethoxy)methyl]-5-{bis[(2-thienyl) methyl]aminocarbonyloxy} ethoxyethoxy)methyl]pyridine, (c) 3-{bis(3-methoxybenzyl)aminocarbonyloxy} ethoxy)methyl]-5-{bis(3-methoxybenzyl)amino carbonyloxy} ethoxy)methyl]pyridine, (d) 3-{bis(3-methoxybenzyl)aminocarbonyloxy} ethoxy ethoxy)methyl]-5-{bis(3-methoxy benzyl)aminocarbonyloxy} ethoxyethoxy)methyl]pyridine, (e) 3-(3-methoxybenzyl,4-dimethylaminobenzyl)aminocarbonyloxy} ethoxy)methyl]-5-(3-methoxy benzyl,4-dimethylaminobenzyl)aminocarbonyloxy} ethoxy)methyl]pyridine, (f) 3-(3-methoxybenzyl,4-dimethylaminobenzyl) aminocarbonyloxy} ethoxymethoxy)methyl]-5-(3-methoxybenzyl,4-dimethylaminobenzyl)aminocarbonyloxy} ethoxyethoxy)methyl]pyridine, (g) 3-{bis(4-methoxybenzyl)aminocarbonyloxy} ethoxy)methyl]-5-{bis(4-methoxybenzyl)amino carbonyloxy} ethoxy)methyl]pyridine, (h) 3-{bis(4-methoxybenzyl) amino carbonyloxy} ethoxyethoxy)methyl]-5-{bis(4-methoxybenzyl)aminocarbonyloxy} ethoxyethoxy)methyl]pyridine, (i) 3-(4-methoxybenzyl,4-dimethylaminobenzyl) aminocarbonyloxy}ethoxy)methyl]-5-(4-methoxybenzyl,4-dimethylaminobenzyl) amino carbonyloxy} ethoxy)methyl]pyridine, (j) 3-(4-methoxybenzyl,4-dimethylaminobenzyl)amino carbonyloxy} ethoxyethoxy)methyl]-5-(4-methoxybenzyl,4-dimethylaminobenzyl)amino carbonyloxy} ethoxyethoxy)methyl] pyridine, (k) 2-[(5-{[2-(9H-carbazol-9-ylcarbonyloxy) ethoxy]methyl}-3-pyridyl)methoxy]ethyl 9H-carbazole-9-carboxylate, (l) 2-(2-{[5-({2-[2-(9-carbazolylcarbonyloxy) ethoxy]ethoxy} methyl)-3-pyridyl]methoxy} ethoxy)ethyl 9-carbazolecarboxylate, (m) 2-[(5-{[2-(3,6-dimethoxy-9H-carbazol-9-ylcarbonyloxy)ethoxy]methyl}-3-pyridyl) methoxy]ethyl 3,6-dimethoxy-9H-carbazole-9-carboxylate, (n) 2-(2-{[5-({2-[2-(3,6-dimethoxy-9-carbazolylcarbonyloxy) ethoxy]ethoxy} methyl)-3-pyridyl]methoxy} ethoxy) ethyl 3,6-dimethoxy-9-carbazolecarboxylate, and (o) combinations thereof.

10. The composition of claim 1, wherein the one or more integrin activating or agonist compounds of Formula (IVb)

are selected from the group consisting of: (a) 3-[bis(thenyl)aminocarbonyloxyethoxy],5-[bis(thenyl)aminocarbonyloxyethoxy]dimethylamino benzene, (b) 3-[bis(thenyl)aminocarbonyloxy ethoxyethoxy],5-[bis(thenyl)amino carbonyloxyethoxyethoxy]dimethylaminobenzene, (c) 3-[bis(3-methoxybenzyl)aminocarbonyloxy ethoxy],5-[bis(3-methoxybenzyl)aminocarbonyloxyethoxy]dimethylaminobenzene, (d) 3-[bis(3-methoxybenzyl)aminocarbonyl oxyethoxyethoxy],5-[bis(3-methoxybenzyl)aminocarbonyloxyethoxyethoxy]dimethylaminobenzene, (e) 3-[(3-methoxybenzyl)(4-dimethylaminobenzyl)amino carbonyloxyethoxy],5-[(3-methoxybenzyl)(4-dimethylaminobenzyl)aminocarbonyloxyethoxy] dimethylaminobenzene, (f) 3-[(3-methoxybenzyl)(4-dimethylaminobenzyl)aminocarbonyloxy ethoxyethoxy],5-[(3-methoxybenzyl)(4-dimethylaminobenzyl)aminocarbonyloxyethoxyethoxy] dimethylaminobenzene, (g) 3-[bis(4-methoxybenzyl)aminocarbonyloxyethoxy],5-[bis(4-methoxy benzyl)aminocarbonyloxyethoxy]dimethylaminobenzene, (h) 3-[bis(4-methoxybenzyl)amino carbonyloxyethoxyethoxy], 5-[bis(4-methoxybenzyl) aminocarbonyloxyethoxyethoxy] dimethylaminobenzene, (i) 3-[(4-methoxybenzyl)(4-dimethylaminobenzyl)aminocarbonyloxy ethoxy],5-[(4-methoxybenzyl)(4-dimethylaminobenzyl)aminocarbonyloxyethoxy]dimethylamino benzene, (j) 3-[(4-methoxy benzyl)(4-dimethylaminobenzyl)aminocarbonyloxyethoxyethoxy],5-[(4-methoxybenzyl)(4-dimethylaminobenzyl)aminocarbonyloxyethoxyethoxy]dimethylaminobenzene, (k) 2-{3-[2-(9H-carbazol-9-ylcarbonyloxy)ethoxy]-5-(dimethylamino)phenoxy} ethyl 9H-carbazole-9-carboxylate, (1) 2-[2-(3-{2-[2-(9-carbazolylcarbonyloxy) ethoxy]ethoxy}-5-(dimethylamino)phenoxy)ethoxy]ethyl 9-carbazolecarboxylate, (m) 2-{3-[2-(3,6-dimethoxy-9H-carbazol-9-ylcarbonyloxy)ethoxy]-5-(dimethylamino)phenoxy} ethyl 3,6-dimethoxy-9H-carbazole-9-carboxylate, (n) 2-[2-(3-{2-[2-(3,6-dimethoxy-9-carbazolylcarbonyloxy)ethoxy] ethoxy}-5-(dimethylamino) phenoxy)ethoxy]ethyl 3,6-dimethoxy-9-carbazolecarboxylate, and (o) combinations thereof.

11. The composition of claim 1, wherein the one or more integrin activating or agonist compounds of Formula (IVb) are selected from the group consisting of: (a) 3-[bis(thenyl)aminocarbonyloxyethoxy],5-[bis(thenyl)aminocarbonyloxyethoxy]dimethyl benzylamine, (b) 3-[bis(thenyl)aminocarbonyloxyethoxyethoxy],5-[bis(thenyl)aminocarbonyloxyethoxyethoxy] dimethylbenzylamine, (c) 3-[bis(3-methoxybenzyl)aminocarbonyloxyethoxy],5-[bis(3-methoxy benzyl)aminocarbonyloxyethoxy]dimethylbenzylamine, (d) 3-[bis(3-methoxybenzyl)amino carbonyloxyethoxyethoxy],5-[bis(3-methoxybenzyl)aminocarbonyloxyethoxyethoxy] dimethylbenzyl amine, (e) 3-[(3-methoxybenzyl)(4-dimethylaminobenzyl)aminocarbonyloxyethoxy],5-[(3-methoxybenzyl)(4-dimethylaminobenzyl)amino carbonyloxyethoxy]dimethylbenzylamine, (f) 3-[(3-methoxybenzyl)(4-dimethylaminobenzyl) aminocarbonyloxyethoxyethoxy],5-[(3-methoxybenzyl)(4-dimethylaminobenzyl)aminocarbonyloxyethoxyethoxy], dimethylbenzylamine, (g) 3-[bis(4-methoxybenzyl)aminocarbonyloxyethoxy],5-[bis(4-methoxybenzyl)aminocarbonyloxyethoxy] dimethylbenzylamine, (h) 3-[bis(4-methoxybenzyl)aminocarbonyloxyethoxyethoxy],5-[bis(4-methoxybenzyl) aminocarbonyloxy ethoxyethoxy]dimethylbenzylamine, (i) 3-[(4-methoxybenzyl)(4-dimethyl aminobenzyl)aminocarbonyloxyethoxy],5-[(4-methoxybenzyl)(4-dimethylaminobenzyl) aminocarbonyloxyethoxy]dimethylbenzylamine, (j) 3-[(4-methoxybenzyl)(4-dimethylamino benzyl)aminocarbonyloxyethoxyethoxy],5-[(4-methoxybenzyl)(4-dimethylaminobenzyl)amino carbonyloxyethoxyethoxy]dimethylbenzylamine, (k) 2-{3-[2-(9H-carbazol-9-yl-carbonyloxy)ethoxy]-5-[(dimethylamino)methyl]phenoxy} ethyl 9H-carbazole-9-carboxylate, (1) 2-[2-(3-{2-[2-(9-carbazolyl carbonyloxy)ethoxy]ethoxy}-5-[(dimethylamino)methyl]phenoxy) ethoxy]ethyl 9-carbazole carboxylate, (m) 2-{3-[2-(3,6-dimethoxy-9H-carbazol-9-yl-carbonyloxy)ethoxy]-5-[(dimethyl amino)methyl]phenoxy} ethyl 3,6-dimethoxy-9H-carbazole-9-carboxylate, (n) 2-[2-(3-{2-[2-(3,6-dimethoxy-9-carbazolyl carbonyloxy)ethoxy]ethoxy}-5-[(dimethylamino)methyl]phenoxy) ethoxy]ethyl 3,6-dimethoxy-9-carbazolecarboxylate, and (o) combinations thereof.

12. The composition of claim 1, wherein the one or more integrin activating or agonist compounds of Formula (IVb) are selected from the group consisting of: (a) bis(2-{bis(2-thienyl methyl) aminocarbonyloxy} ethyl)2,6-pyridinedicarboxylate, (b) bis(2-{bis(2-thienylmethyl) aminocarbonyloxyethoxy} ethyl)2,6-pyridinedicarboxylate, (c) bis(2-{bis[3-methoxybenzyl]aminocarbonyloxy} ethyl)2,6-pyridinedicarboxylate, (d) bis(2-{bis[3-methoxybenzyl]aminocarbonyloxyethoxy}ethyl)2,6-pyridinedicarboxylate, (e) bis(2-{(3-methoxybenzyl)(4-dimethylaminobenzyl)aminocarbonyloxy}ethyl) 2,6-pyridine dicarboxylate, (f) bis(2-{(4-methoxybenzyl)(4-dimethylaminobenzyl)amino carbonyloxyethoxy} ethyl)2,6-pyridinedicarboxylate, (g) bis(2-{bis[4-methoxybenzyl]amino carbonyloxy} ethyl)2,6-pyridinedicarboxylate, (h) bis(2-{bis[4-methoxybenzyl] amino carbonyloxyethoxy} ethyl)2,6-pyridinedicarboxylate, (i) bis(2-{(4-methoxybenzyl)(4-dimethylaminobenzyl)aminocarbonyloxy} ethyl)2,6-pyridinedicarboxylate, (j) bis(2-{(4-methoxybenzyl)(4-dimethylaminobenzyl) aminocarbonyloxyethoxy} ethyl) 2,6-pyridinedicarboxylate, and (k) combinations thereof.

13. The composition of claim 1, wherein the one or more integrin activating or agonist compounds of Formula (IVb) are selected from the group consisting of: (a) bis(2-{bis(2-thienylmethyl]aminocarbonyloxy} ethyl)3,5-pyridinedicarboxylate, (b) bis(2-{bis(2-thienylmethyl]aminocarbonyloxyethoxy} ethyl) 3,5-pyridinedicarboxylate, (c) bis(2-{bis (3-methoxybenzyl)aminocarbonyloxy} ethyl)3,5-pyridinedicarboxylate, (d) bis(2-{bis[3-methoxybenzyl]aminocarbonyloxyethoxy} ethyl)2,6-pyridinedicarboxylate, (e) bis(2-{(3-methoxybenzyl)(4-methylaminobenzyl)aminocarbonyloxy} ethyl)3,5-pyridine dicarboxylate, (f) bis(2-{(3-methoxybenzyl)(4-dimethylaminobenzyl)aminocarbonyloxy ethoxy} ethyl)2,6-pyridinedicarboxylate, (g) bis(2-{bis (4-methoxybenzyl)aminocarbonyloxy} ethyl)3,5-pyridinedicarboxylate, (h) bis(2-{bis[4-methoxybenzyl] aminocarbonyloxyethoxy} ethyl)3,5-pyridinedicarboxylate, (i) bis(2-{bis(4-methoxybenzyl)(4-methylaminobenzyl) amino carbonyloxy} ethyl)3,5-pyridinedicarboxylate, (j) bis (2-{(4-methoxybenzyl)(4-dimethylaminobenzyl)aminocarbonyloxyethoxy} ethyl) 2,6-pyridinedicarboxylate, and (k) combinations thereof.

* * * * *